United States Patent
Charrier et al.

(10) Patent No.: US 7,652,153 B2
(45) Date of Patent: Jan. 26, 2010

(54) CASPASE INHIBITORS AND USES THEREOF

(75) Inventors: Jean Damien Charrier, Wantage (GB);
Steven Durrant, Abingdon (GB);
Michael Mortimore, Abingdon (GB);
Michael O'Donnell, Abingdon (GB);
Alistair Rutherford, Abingdon (GB);
Sharn Ramaya, Burghfield Common (GB); John Studley, Abingdon (GB);
Martin Trudeau, Shannon (CA); Adam Looker, Cambridge, MA (US)

(73) Assignee: Vertex Pharmaceuticals Incorporated

( * ) Notice: Subject to any disclaimer, the term of this patent is extended or adjusted under 35 U.S.C. 154(b) by 464 days.

(21) Appl. No.: 11/069,895

(22) Filed: Feb. 28, 2005

(65) Prior Publication Data
US 2005/0233979 A1 Oct. 20, 2005

Related U.S. Application Data

(60) Provisional application No. 60/548,610, filed on Feb. 27, 2004, provisional application No. 60/629,743, filed on Nov. 19, 2004, provisional application No. 60/629,661, filed on Nov. 19, 2004.

(51) Int. Cl.
*A61K 31/401* (2006.01)
*A61K 31/403* (2006.01)
*A61K 31/4025* (2006.01)
*C07D 207/09* (2006.01)
*C07D 209/02* (2006.01)

(52) U.S. Cl. ............ 548/567; 514/412; 514/414; 514/370; 514/422; 514/423; 548/190; 548/204; 548/467; 548/515

(58) Field of Classification Search ............ 548/567
See application file for complete search history.

(56) References Cited

U.S. PATENT DOCUMENTS

| 7,053,057 B2 | 5/2006 | Golec et al. |
| 7,109,357 B2 | 9/2006 | Wannamaker et al. |
| 2002/0045623 A1 | 4/2002 | Charrier et al. |
| 2002/0058630 A1 | 5/2002 | Charrier et al. |
| 2004/0019017 A1 | 1/2004 | Mortimore et al. |
| 2007/0010457 A1 | 1/2007 | Diu-Hercend et al. |

FOREIGN PATENT DOCUMENTS

| WO | 9535308 A1 | 12/1995 |
| WO | 9947545 A2 | 9/1999 |
| WO | 0190063 A2 | 11/2001 |

OTHER PUBLICATIONS

Karanewsky, Donald S, et al., "Conformationally Constrained Inhibitors of Caspase-1 (Interleukin-1β Converting Enzyme) and of The Human CED-3 Homologue Caspase-3 (CPP32, Appopain)," Bioorganic & Medicinal Chemistry Letters, Oxford, Great Britain, No. 8, 1998, pp. 2757-2767.

*Primary Examiner*—Laura L. Stockton
(74) *Attorney, Agent, or Firm*—Jennifer G. Che

(57) ABSTRACT

The present invention provides a compound of formula I:

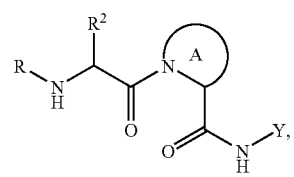

wherein the variables are as defined herein. The present invention also provides processes for preparing the compounds of formula I, and intermediates thereof, pharmaceutical compositions comprising those compounds, and methods of using the compounds and compositions.

19 Claims, No Drawings

CASPASE INHIBITORS AND USES THEREOF

CROSS REFERENCE TO RELATED APPLICATIONS

This present application claims the benefit, under 35 U.S.C. §119, to U.S. Provisional Application Nos. 60,548,610 filed Feb. 27, 2004; 60,629,743 filed Nov. 19, 2004; and 60,629,661 filed Nov. 19, 2004; the entire disclosures of which are incorporated herein by reference.

FIELD OF THE INVENTION

This invention relates to compounds, and compositions thereof, that are useful as caspase inhibitors.

This invention also relates to processes for preparing these compounds.

This invention further relates to pharmaceutical compositions comprising said compounds and to the use of the compounds and compositions thereof for the treatment of diseases and disorders related to caspase-mediated conditions.

BACKGROUND OF THE INVENTION

Caspases are a family of cysteine protease enzymes that are key mediators in inflammation. Caspase-1 (ICE) processes pre-IL-1β to produce the active form of IL-1β [WO 99/47545]. ICE has also been linked to the conversion of pro-IGIF to IGIF and/or to the production of IFN-γ [Id.]. Both IL-1β and IFN-γ contribute to the pathology associated with inflammatory, infectious, and autoimmune diseases (see, e.g., WO 99/47545; *J. Invest. Dermatology*, 120(1), pp. 164-167 (2003); *Br. J. Dermatology*, 141, pp. 739-746 (1999); *Science*, 282, pp. 490-493 (1998); *Schweiz. Med. Wochenschr.*, 130, pp. 1656-1661 (2000)].

Caspases are also key mediators in the signaling pathways for apoptosis and cell disassembly [N. A. Thornberry, *Chem. Biol.*, 5, pp. R97-R103 (1998)]. These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock [H. Yaoita et al., *Circulation*, 97, pp. 276-281 (1998); M. Endres et al., *J. Cerebral Blood Flow and Metabolism*, 18, pp. 238-247, (1998); Y. Cheng et al., *J. Clin. Invest.*, 101, pp. 1992-1999 (1998); A. G. Yakovlev et al., *J. Neurosci.*, 17, pp. 7415-7424 (1997); I. Rodriquez et al., *J. Exp. Med.*, 184, pp. 2067-2072 (1996); Grobmyer et al., *Mol. Med.*, 5, p. 585 (1999)].

However, due to their peptidic nature, such inhibitors are typically characterized by undesirable pharmacological properties, such as poor cellular penetration and cellular activity, poor oral absorption, poor stability and rapid metabolism [J. J. Plattner and D. W. Norbeck, in *Drug Discovery Technologies*, C. R. Clark and W. H. Moos, Eds. (Ellis Horwood, Chichester, England, 1990), pp. 92-126]. This has hampered their development into effective drugs. These and other studies with peptidic caspase inhibitors have demonstrated that an aspartic acid residue is involved in a key interaction with the caspase enzyme [K. P. Wilson et al., *Nature*, 370, pp. 270-275 (1994); Lazebnik et al., *Nature*, 371, p. 346 (1994)].

Accordingly, peptidyl and non-peptidyl aspartic acid compounds are useful as caspase inhibitors.

A need nevertheless exists for compounds that have the ability to act as caspase inhibitors, particularly with selective activity against certain caspases.

SUMMARY OF THE INVENTION

The present invention provides a compound of formula I:

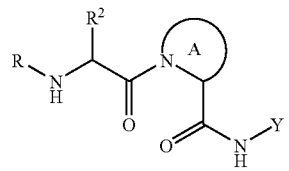

I wherein the variables are as defined herein.

The present invention also provides processes for preparing these compounds, compositions, pharmaceutical compositions, and methods of using such compounds and compositions for inhibiting caspases. These compounds are particularly useful as selective caspase-1/capase-8 inhibitors.

DETAILED DESCRIPTION OF THE INVENTION

The present invention provides a compound of formula I:

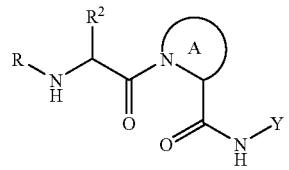

I wherein:
Y is

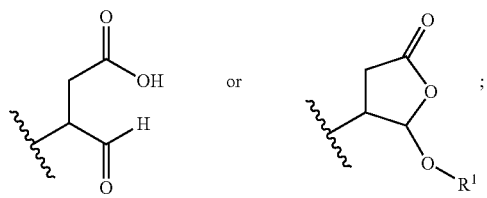

R is R³C(O)—, HC(O), R³SO₂—, R³OC(O), (R³)₂NC(O), (R³)(H)NC(O), R³C(O)C(O)—, R³—, (R³)₂NC(O)C(O), (R³)(H)NC(O)C(O), or R³OC(O)C(O)—;

R¹ is H, aliphatic, cycloaliphatic, aryl, heterocyclyl, heteroaryl, cycloalkyl-aliphatic-, cycloalkenyl-aliphatic-, aryl-aliphatic-, heterocyclyl-aliphatic-, or heteroaryl-aliphatic-, wherein any hydrogen atom is optionally and independently replaced by $R^8$ and any set of two hydrogen atoms bound to the same atom is optionally and independently replaced by carbonyl;

Ring A is:

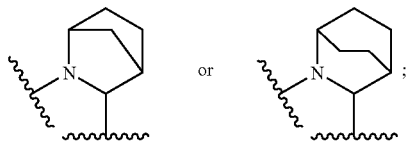

wherein, in each ring, any hydrogen atom is optionally and independently replaced by $R^4$ and any set of two hydrogen atoms bound to the same atom is optionally and independently replaced by carbonyl;

$R^3$ is aliphatic, cycloaliphatic, aryl, heterocyclyl, heteroaryl, cycloaliphatic-aliphatic-, aryl-aliphatic-, heterocyclyl-aliphatic-, or heteroaryl-aliphatic-; or two $R^3$ groups bound to the same atom form together with that atom a 3-10 membered aromatic or nonaromatic ring; wherein any ring is optionally fused to an aryl, heteroaryl, cycloalkyl, or heterocyclyl; wherein up to 3 aliphatic carbon atoms may be replaced by a group selected from O, N, $NR^9$, S, SO, and $SO_2$, wherein $R^3$ is substituted with up to 6 substituents independently selected from $R^8$;

$R^4$ is halogen, $-OR^9$, $-NO_2$, $-CN$, $-CF_3$, $-OCF_3$, $-R^9$, 1,2-methylenedioxy, 1,2-ethylenedioxy, $-N(R^9)_2$, $-SR^9$, $-SOR^9$, $-SO_2R^9$, $-SO_2N(R^9)_2$, $-SO_3R^9$, $-C(O)R^9$, $-C(O)C(O)R^9$, $-C(O)C(O)OR^9$, $-C(O)C(O)N(R^9)_2$, $-C(O)CH_2C(O)R^9$, $-C(S)R^9$, $-C(S)OR^9$, $-C(O)OR^9$, $-OC(O)R^9$, $-C(O)N(R^9)_2$, $-OC(O)N(R^9)_2$, $-C(S)N(R^9)_2$, $-(CH_2)_{0-2}NHC(O)R^9$, $-N(R^9)N(R^9)COR^9$, $-N(R^9)N(R^9)C(O)OR^9$, $-N(R^9)N(R^9)CON(R^9)_2$, $-N(R^9)SO_2R^9$, $-N(R^9)SO_2N(R^9)_2$, $-N(R^9)C(O)OR^9$, $-N(R^9)C(O)R^9$, $-N(R^9)C(S)R^9$, $-N(R^9)C(O)N(R^9)_2$, $-N(R^9)C(S)N(R^9)_2$, $-N(COR^9)COR^9$, $-N(OR^9)R^9$, $-C(=NH)N(R^9)_2$, $-C(O)N(OR^9)R^9$, $-C(=NOR^9)R^9$, $-OP(O)(OR^9)_2$, $-P(O)(R^9)_2$, $-P(O)(OR^9)_2$, or $-P(O)(H)(OR^9)$;

$R^2$ is $-C(R^5)(R^6)(R^7)$, aryl, heteroaryl, or $C_{3-7}$ cycloalkyl;

$R^5$ is H or a $C_{1-6}$ straight-chained or branched alkyl;

$R^6$ is H or a $C_{1-6}$ straight-chained or branched alkyl;

$R^7$ is $-CF_3$, $-C_{3-7}$cycloalkyl, aryl, heteroaryl, heterocycle, or a $C_{1-6}$ straight-chained or branched alkyl, wherein each carbon atom of the alkyl is optionally and independently substituted with $R^{10}$;

Or $R^5$ and $R^7$ taken together with the carbon atom to which they are attached form a 3-10 membered cycloaliphatic;

$R^8$ and $R^8$ are each independently halogen, $-OR^9$, $-NO_2$, $-CN$, $-CF_3$, $-OCF_3$, $-R^9$, 1,2-methylenedioxy, 1,2-ethylenedioxy, $-N(R^9)_2$, $-SR^9$, $-SOR^9$, $-SO_2R^9$, $-SO_2N(R^9)_2$, $-SO_3R^9$, $-C(O)R^9$, $-C(O)C(O)R^9$, $-C(O)C(O)OR^9$, $-C(O)C(O)N(R^9)_2$, $-C(O)CH_2C(O)R^9$, $-C(S)R^9$, $-C(S)OR^9$, $-C(O)OR^9$, $-OC(O)R^9$, $-C(O)N(R^9)_2$, $-OC(O)N(R^9)_2$, $-C(S)N(R^9)_2$, $-(CH_2)_{0-2}NHC(O)R^9$, $-N(R^9)N(R^9)COR^9$, $-N(R^9)N(R^9)C(O)OR^9$, $-N(R^9)N(R^9)CON(R^9)_2$, $-N(R^9)SO_2R^9$, $-N(R^9)SO_2N(R^9)_2$, $-N(R^9)C(O)OR^9$, $-N(R^9)C(O)R^9$, $-N(R^9)C(S)R^9$, $-N(R^9)C(O)N(R^9)_2$, $-N(R^9)C(S)N(R^9)_2$, $-N(COR^9)COR^9$, $-N(OR^9)R^9$, $-C(=NH)N(R^9)_2$, $-C(O)N(OR^9)R^9$, $-C(=NOR^9)R^9$, $-OP(O)(OR^9)_2$, $-P(O)(R^9)_2$, $-P(O)(OR^9)_2$, and $-P(O)(H)(OR^9)$;

$R^9$ is hydrogen, aliphatic, cycloaliphatic, aryl, heterocyclyl, heteroaryl, cycloaliphatic-aliphatic-, aryl-aliphatic-, heterocyclyl-aliphatic-, or heteroaryl-aliphatic-; wherein any hydrogen atom is optionally and independently replaced by $R^8$ and any set of two hydrogen atoms bound to the same atom is optionally and independently replaced by carbonyl;

$R^{10}$ is halogen, $-OR^{11}$, $-NO_2$, $-CN$, $-CF_3$, $-OCF_3$, $-R^{11}$, or $-SR^{11}$; wherein $R^{11}$ is $C_{1-4}$-aliphatic-.

The present invention also provides a compound of formula II:

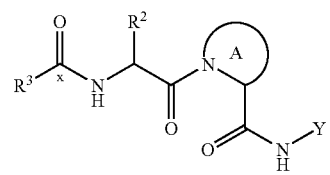

wherein:

Y is

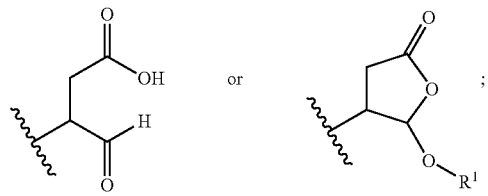

$R^1$ is H, aliphatic, cycloalkyl (e.g., cyclopentyl), cycloalkenyl, aryl, heterocyclyl, heteroaryl, cycloalkyl-aliphatic-cycloalkenyl-aliphatic-, aryl-aliphatic-, heterocyclyl-aliphatic-, or heteroaryl-aliphatic-, wherein any hydrogen atom is optionally and independently replaced by $R^8$ and any set of two hydrogen atoms bound to the same atom is optionally and independently replaced by carbonyl;

Ring A is:

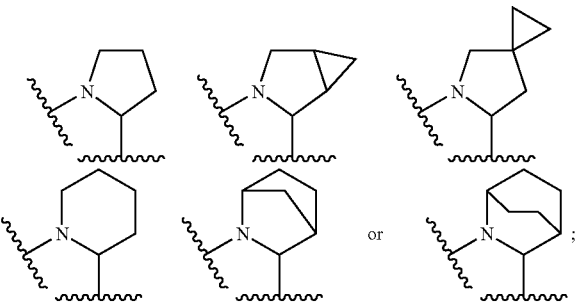

wherein, in each ring, any hydrogen atom is optionally and independently replaced by $R^4$ and any set of two hydrogen atoms bound to the same atom is optionally and independently replaced by carbonyl (or in an alternative embodiment, carbonyl or (C3-C6) spirocycle;)

$R^4$ is halogen, —$OR^9$, —$NO_2$, —CN, —$CF_3$, —$OCF_3$, —$R^9$, 1,2-methylenedioxy, 1,2-ethylenedioxy, —$N(R^9)_2$, —$SR^9$, —$SOR^9$, —$SO_2R^9$, —$SO_2N(R^9)_2$, —$SO_3R^9$, —$C(O)R^9$, —$C(O)C(O)R^9$, —$C(O)C(O)OR^9$, —$C(O)C(O)N(R^9)_2$, —$C(O)CH_2C(O)R^9$, —$C(S)R^9$, —$C(S)OR^9$, —$C(O)OR^9$, —$OC(O)R^9$, —$C(O)N(R^9)_2$, —$OC(O)N(R^9)_2$, —$C(S)N(R^9)_2$, —$(CH_2)_{0-2}NHC(O)R^9$, —$N(R^9)N(R^9)COR^9$, —$N(R^9)N(R^9)C(O)OR^9$, —$N(R^9)N(R^9)CON(R^9)_2$, —$N(R^9)SO_2R^9$, —$N(R^9)SO_2N(R^9)_2$, —$N(R^9)C(O)OR^9$, —$N(R^9)C(O)R^9$, —$N(R^9)C(S)R^9$, —$N(R^9)C(O)N(R^9)_2$, —$N(R^9)C(S)N(R^9)_2$, —$N(COR^9)COR^9$, —$N(OR^9)R^9$, —$C(=NH)N(R^9)_2$, —$C(O)N(OR^9)R^9$, —$C(=NOR^9)R^9$, —$OP(O)(OR^9)_2$, —$P(O)(R^9)_2$, —$P(O)(OR^9)_2$, or —$P(O)(H)(OR^9)$;

$R^2$ is —$C(R^5)(R^6)(R^7)$, aryl, heteroaryl, or —$C_{3-7}$ cycloalkyl;

$R^5$ is H or a $C_{1-6}$ straight-chained or branched alkyl;

$R^6$ is H or a $C_{1-6}$ straight-chained or branched alkyl;

$R^7$ is —$CF_3$, —$C_{3-7}$ cycloalkyl, aryl, heteroaryl, heterocycle, or a $C_{1-6}$ straight-chained or branched alkyl, wherein each carbon atom of the alkyl is optionally and independently substituted with $R^{10}$;

(or in an alternative embodiment, $R^5$ and $R^7$ taken together with the carbon atom to which they are attached form a 3-10 membered cycloaliphatic);

$R^3$ is phenyl, thiophene, or pyridine, wherein each ring is optionally substituted with up to 5 groups independently selected from $R^8$, and wherein at least one position on the phenyl, thiophene, or pyridine adjacent to bond x is substituted by $R^{12}$, wherein $R^{12}$ has no more than 5 straight-chained atoms;

$R^8$ and $R^8$ are each independently halogen, —$OR^9$, —$NO_2$, —CN, —$CF_3$, —$OCF_3$, —$R^9$, 1,2-methylenedioxy, 1,2-ethylenedioxy, —$N(R^9)_2$, —$SR^9$, —$SOR^9$, —$SO_2R^9$, —$SO_2N(R^9)_2$, —$SO_3R^9$, —$C(O)R^9$, —$C(O)C(O)R^9$, —$C(O)C(O)OR^9$, —$C(O)C(O)N(R^9)_2$, —$C(O)CH_2C(O)R^9$, —$C(S)R^9$, —$C(S)OR^9$, —$C(O)OR^9$, —$OC(O)R^9$, —$C(O)N(R^9)_2$, —$OC(O)N(R^9)_2$, —$C(S)N(R^9)_2$, —$(CH_2)_{0-2}NHC(O)R^9$, —$N(R^9)N(R^9)COR^9$, —$N(R^9)N(R^9)C(O)OR^9$, —$N(R^9)N(R^9)CON(R^9)_2$, —$N(R^9)SO_2R^9$, —$N(R^9)SO_2N(R^9)_2$, —$N(R^9)C(O)OR^9$, —$N(R^9)C(O)R^9$, —$N(R^9)C(S)R^9$, —$N(R^9)C(O)N(R^9)_2$, —$N(R^9)C(S)N(R^9)_2$, —$N(COR^9)COR^9$, —$N(OR^9)R^9$, —C(=NH)N($R^9)_2$, —$C(O)N(OR^9)R^9$, —$C(=NOR^9)R^9$, —$OP(O)(OR^9)_2$, —$P(O)(R^9)_2$, —$P(O)(OR^9)_2$, and —$P(O)(H)(OR^9)$;

$R^9$ is hydrogen, aliphatic, cycloalkyl, cycloalkenyl, aryl, heterocyclyl, heteroaryl, cycloaliphatic-aliphatic-, arylaliphatic-, heterocyclyl-aliphatic-, or heteroaryl-aliphatic-; (in certain embodiments, any hydrogen atom of $R^9$ is optionally and independently replaced by $R^8$ and any set of two hydrogen atoms bound to the same atom is optionally and independently replaced by carbonyl; provided that if $R^9$ is substituted with a $R^8$, wherein the $R^8$ comprises a $R^9$ substituent, then that $R^9$ substituent is not substituted with $R^8$);

$R^{10}$ is halogen, —$OR^{11}$, —$NO_2$, —CN, —$CF_3$, —$OCF_3$, —$R^{11}$, or —$SR^{11}$;

$R^{11}$ is $C_{1-4}$-aliphatic-; and $R^{12}$ is halogen, —$OR^{11}$, —$NO_2$, —CN, —$CF_3$, —$OCF_3$, —$R^{11}$, —$SR^9$.

As used in the definition of $R^{12}$, "straight-chained atoms" refers to atoms that are linearly bound, regardless of whether those atoms also have atoms bound in a branched fashion. According to this definition, an ethyl group and a trifluoromethoxy group each have three straight-chained atoms, and a methyl group has two straight-chained atoms. In the above embodiment, $R^{12}$ has no more than 5 straight-chained atoms. In two other embodiments, $R^{12}$ has no more than 4 straight-chained atoms and no more than 3 straight-chained atoms. In yet other embodiments, $R^{12}$ has 2 straight-chained atoms or 1 atom.

As used herein, a position adjacent to the bond x refers to a position which is located next to the position at which x is bound. In an aryl ring, this position is often called "the ortho position" or, in the case of a phenyl ring, it may be called "the 2-position". By way of example, in the structures immediately below, $R^{12}$ is bound to the phenyl, thiophene, and pyridine rings at "the position adjacent to bond x".

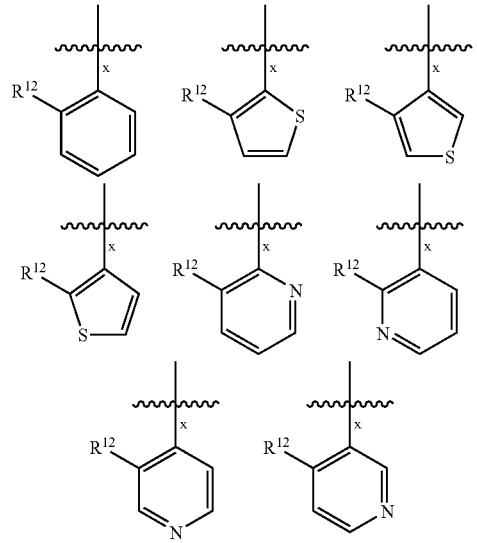

In one embodiment of this invention, R is $R^3C(O)$—.

In some embodiments, $R^3$ is optionally substituted $C_{6-10}$aryl or heteroaryl. In other embodiments $R^3$ is optionally substituted phenyl. In yet other embodiments, $R^3$ is a 8-10 membered optionally substituted heteroaryl (i.e. quinoline, isoquinoline, or quinazoline) In yet other embodiments, $R^3$ is an optionally substituted 5-6 membered heteroaryl (i.e., pyridyl, pyrimidyl, pyrazinyl, thiophenyl, furanyl, thiazolyl).

In some embodiments, $R^3$ is optionally and independently substituted by 0-5 $R^8$ groups.

In one embodiment, the compound of this invention is represented by formula II:

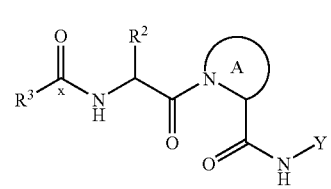

wherein:
a) $R^3$ is phenyl, thiophene, or pyridine;
b) each ring is optionally substituted with up to 5 groups independently selected from $R^8$; and
c) at least one position on the phenyl, thiophene, or pyridine adjacent to bond x is substituted by $R^{12}$, wherein $R^{12}$ has no more than 5 straight-chained atoms.

Another embodiment of this invention provides a compound wherein Y is:

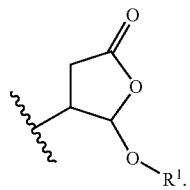

In one embodiment of this invention, $R^1$ is substituted with up to 3 groups selected independently from carbonyl and $R^8$.

In another embodiment, $R^1$ is $C_{1-12}$aliphatic or $C_{3-10}$cycloalkyl, wherein each $R^1$ is optionally substituted with 1-3 groups selected independently from $R^8$. In yet another embodiment, $R^1$ is a straight-chain or branched $C_{1-4}$ alkyl that is optionally substituted with 1-3 groups selected independently from $R^8$.

In one embodiment, $R^1$ is an unsubstituted, straight-chain or branched $C_{1-4}$ alkyl (e.g., ethyl, isopropyl, n-propyl, or n-butyl). In another embodiment, $R^1$ is ethyl.

In any of these embodiments, $R^8$ is halogen, $-OR^9$, $-CN$, $-CF_3$, $-OCF_3$, or $-R^9$. In another embodiment wherein $R^8$ is $-R^9$, that $R^9$ is benzyl.

In another embodiment, Y is

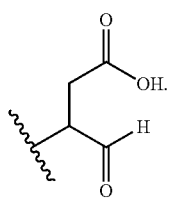

In another embodiment, Ring A is substituted with up to 3 groups (preferably, 1 group) selected independently from carbonyl and $R^4$.

In one embodiment, Ring A is:

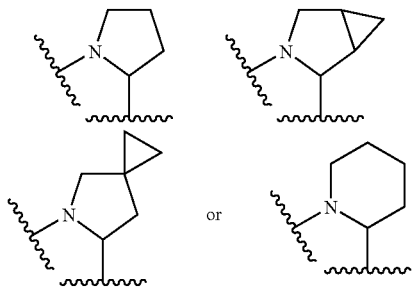

optionally substituted with $R^4$.

In yet another embodiment, Ring A is:

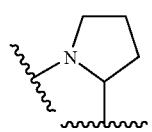

optionally substituted with $R^4$.

In another form of this embodiment, Ring A is unsubstituted proline (i.e., $R^4$ is hydrogen).

In yet another embodiment, Ring A is:

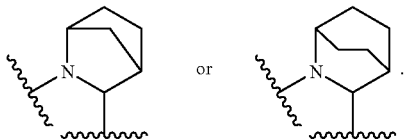

optionally substituted with R4.

In one embodiment, Ring A is

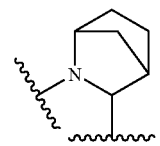

optionally substituted with $R^4$.

In any of these embodiments, $R^4$ is halogen, $-OR^9$, $-CF_3$, $-OCF_3$, $-R^9$, or $-SR^9$. In certain embodiments $R^4$ is H.

In one embodiment, $R^2$ is a $C_{3-4}$ branched alkyl group.

In another embodiment, $R^5$ is H or $-CH_3$, $R^6$ is $-CH_3$, and $R^7$ is $-CH_3$.

In another embodiment, $R^{12}$ is $-OCF_3$, $-OCH_3$, $-CF_3$, $-CH_3$, $-CH_2CH_3$, $-Cl$, or $-F$.

In yet another embodiment, $R^{12}$ is $-CF_3$, $-CH_3$, $-Cl$, or $-F$.

In yet another embodiment, $R^{12}$ is $-CH_3$, $-Cl$, or $-F$.

In another embodiment, each $R^{8'}$, if present, is independently halogen, $-OR^9$, $-NO_2$, $-CN$, $-CF_3$, $-OCF_3$, $-R^9$, 1,2-methylenedioxy, 1,2-ethylenedioxy, $-N(R^9)_2$, $-SR^9$, $-SOR^9$, $-SO_2R^9$, $-SO_2N(R^9)_2$, $-C(O)R^9$, $-C(O)C(O)N(R^9)_2$, $-C(O)N(R^9)_2$, $-OC(O)N(R^9)_2$, $-(CH_2)_{0-2}NHC(O)R^9$, $-N(R^9)SO_2R^9$, $-N(R^9)SO_2N(R^9)_2$, $-N(R^9)C(O)OR^9$, $-N(R^9)C(O)R^9$, or $-N(R^9)C(O)N(R^9)_2$.

In another embodiment, $R^{8'}$ is $-NH_2$, $-N(R^9)_2$, $-N(R^9)C(O)R^9$, $-OCF_3$, $-OR^9$, $-CF_3$, $-R^9$, $-SR^9$, or halo. In this embodiment, halo is, preferably, Cl or F and $R^9$ is, preferably, straight or branched $C_{1-4}$ alkyl.

According to one embodiment, this invention provides compounds of formula III:

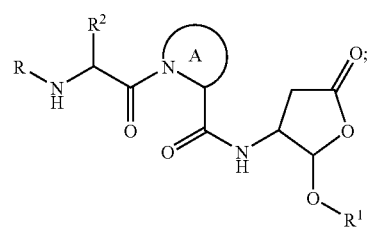

III wherein the variables are as defined in any of the embodiments herein.

In one form of this embodiment, the compound has the stereochemistry indicated below:

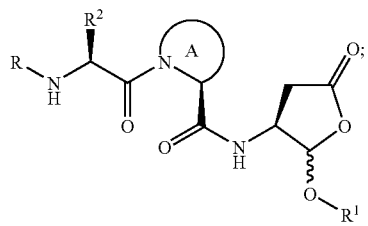

wherein the variables are as defined in any of the embodiments herein.

In other forms of this embodiment, the compound has the stereochemistry indicated below:

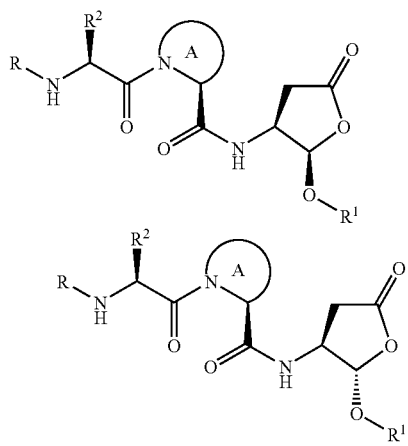

wherein the variables are as defined in any of the embodiments herein.

According to another embodiment, this invention provides compound of formula IV:

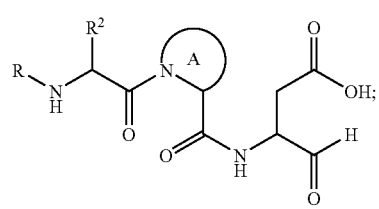

IV wherein the variables are as defined in any of the embodiments herein.

In one form of this embodiment, the compound has the stereochemistry indicated below:

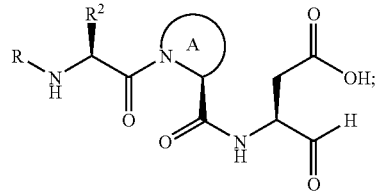

wherein the variables are as defined in any of the embodiments herein.

The embodiments herein may be combined to provide a compound according to this invention.

According to one embodiment, the present invention provides a compound selected from Table 1 below:

TABLE 1

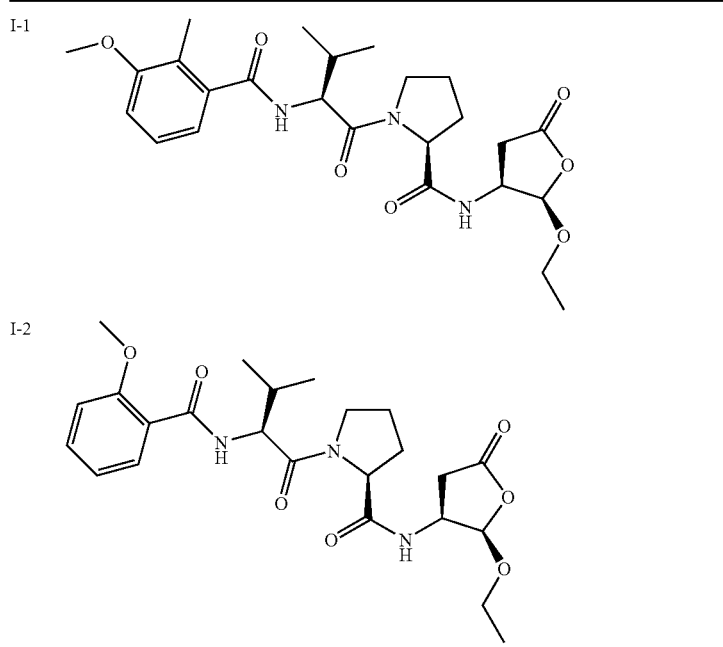

TABLE 1-continued
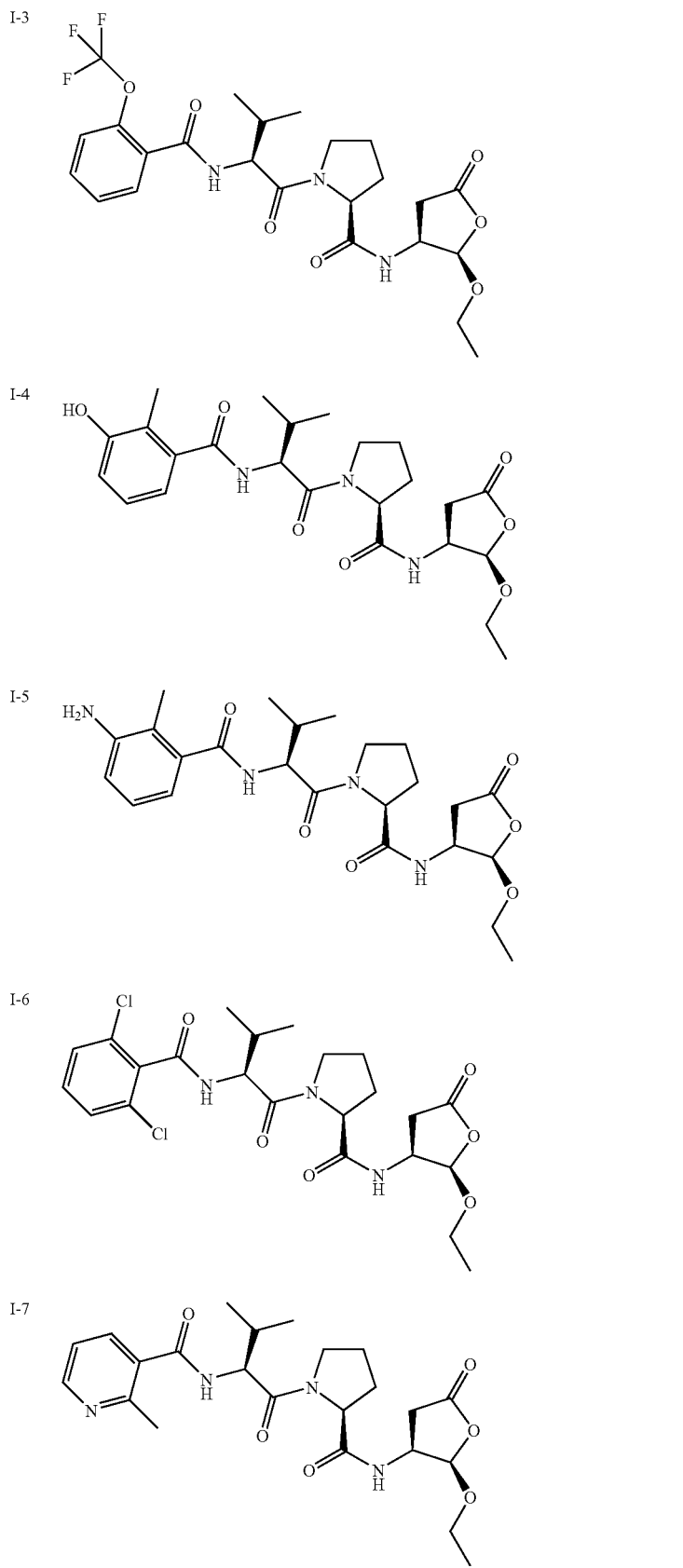

TABLE 1-continued
I-8 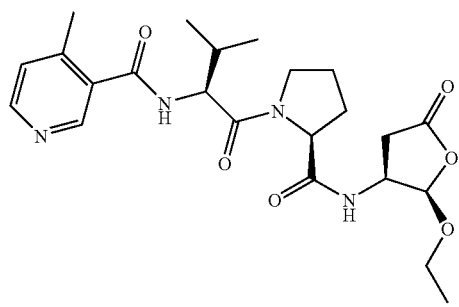
I-9 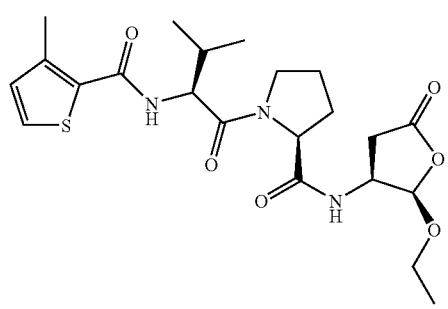
I-10 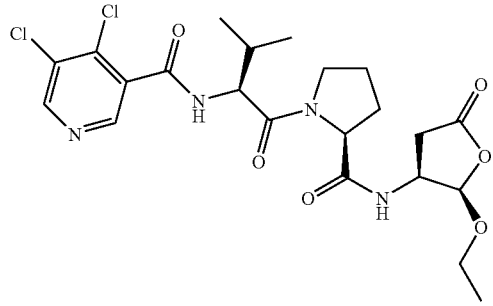
I-11 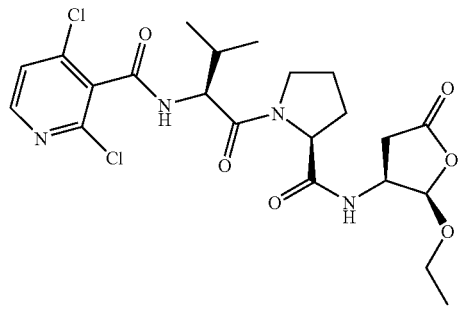
I-12 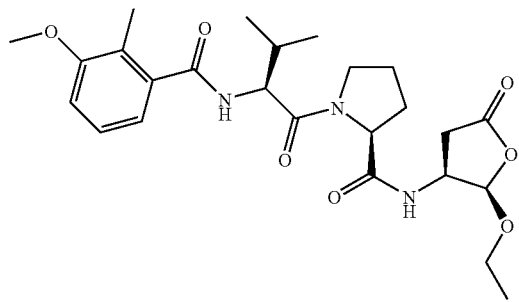

TABLE 1-continued
I-13
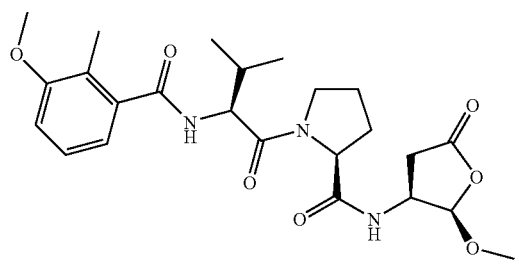
I-14
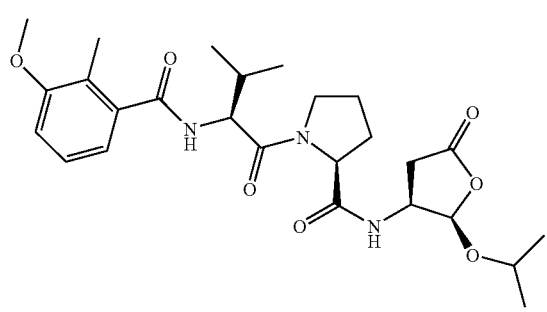
I-15
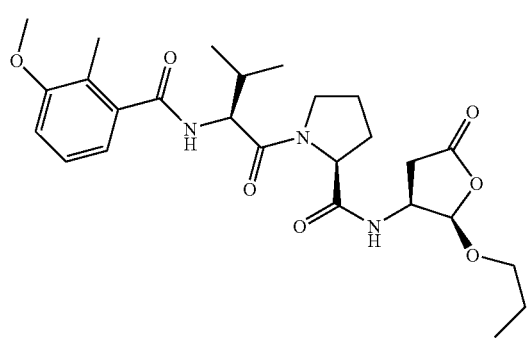
I-16
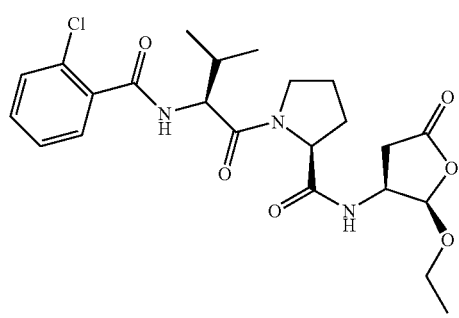
I-17
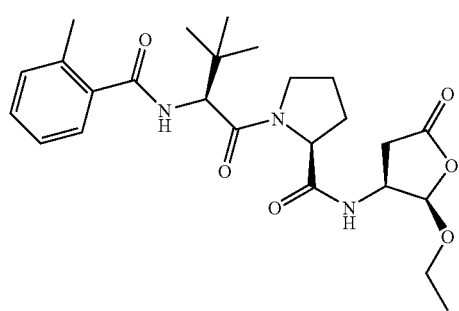

TABLE 1-continued
I-18 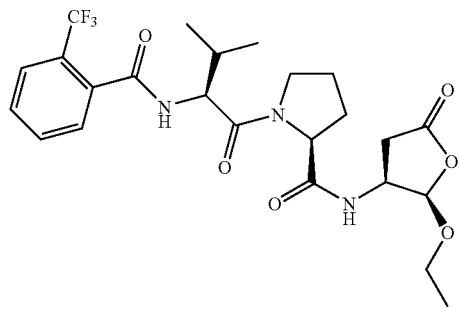
I-19 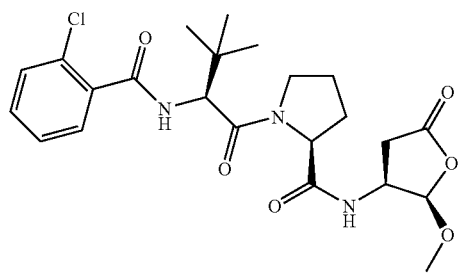
I-20 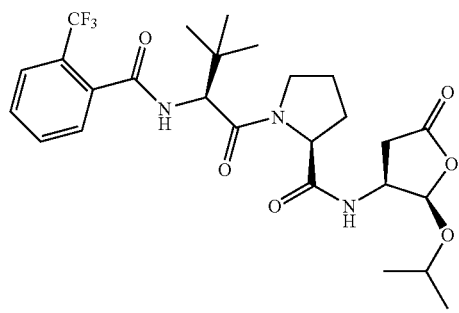
I-21 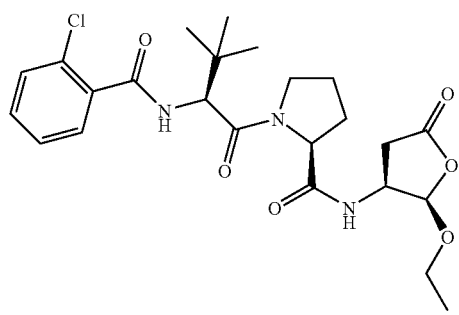
I-22 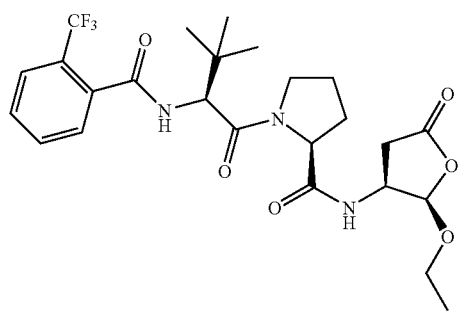

TABLE 1-continued
I-23 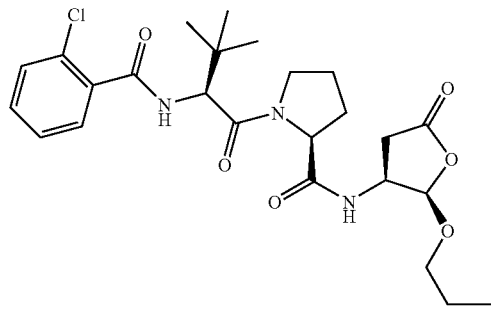
I-24 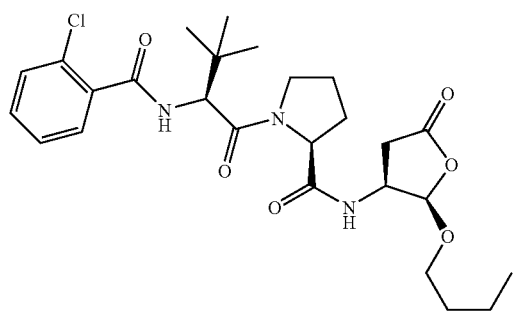
I-25 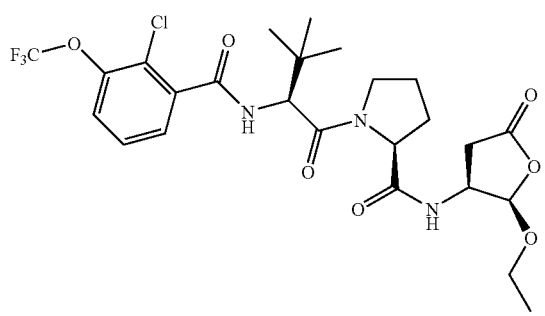
I-26 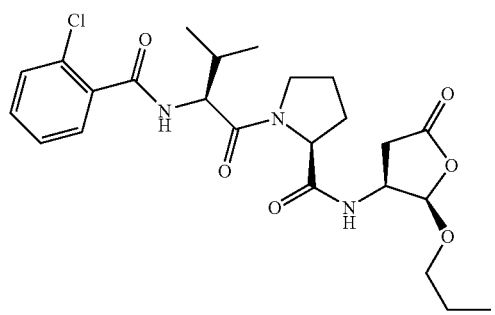
I-27 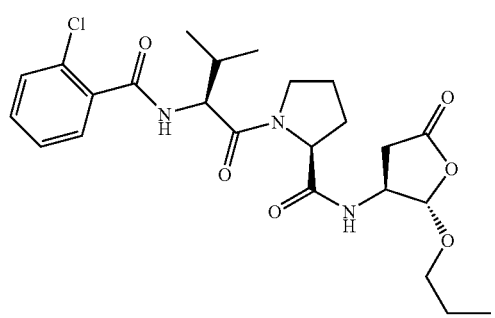

TABLE 1-continued
I-28 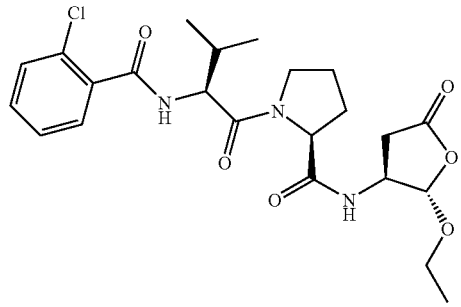
I-29 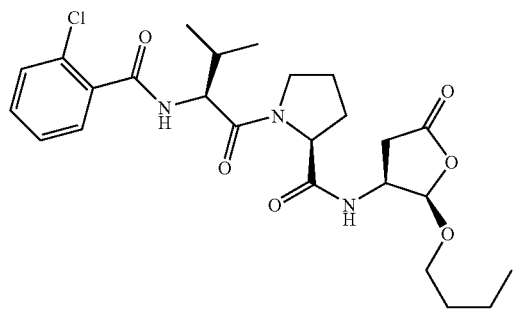
I-30 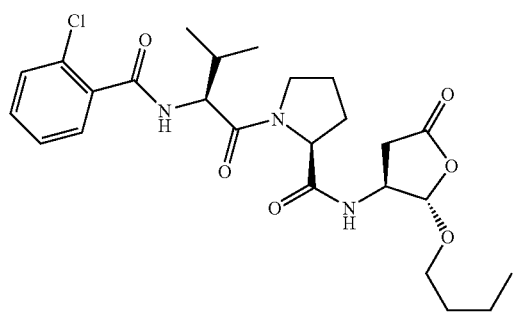
I-31 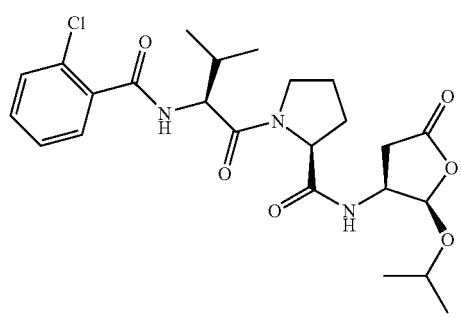
I-32 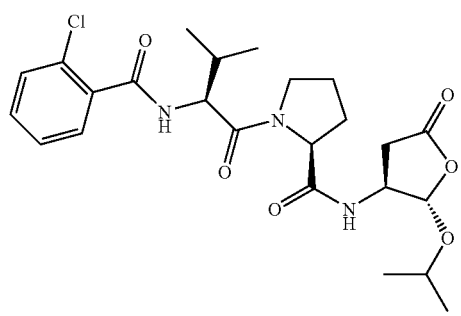

TABLE 1-continued
I-33 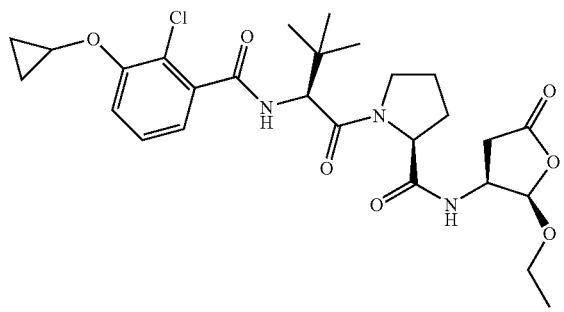
I-34 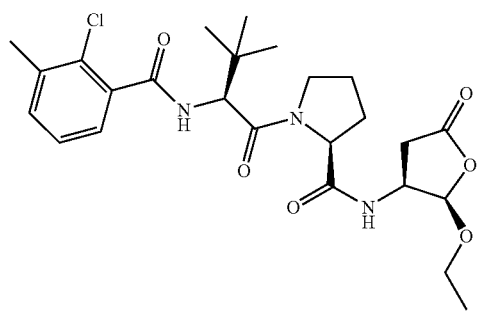
I-35 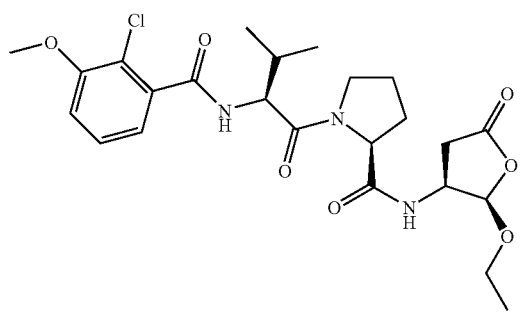
I-36 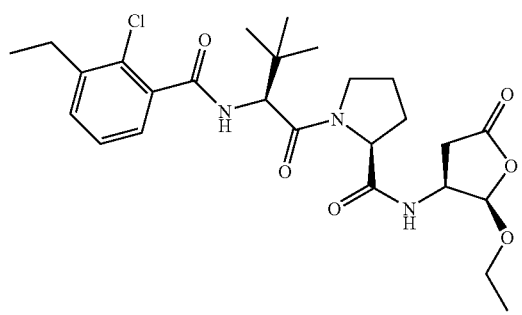
I-37 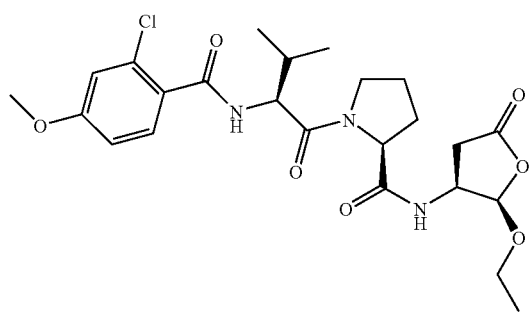

TABLE 1-continued
I-38 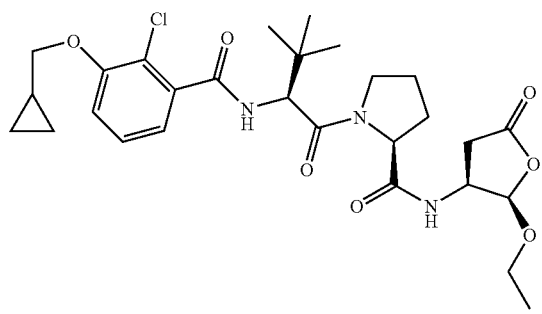
I-39 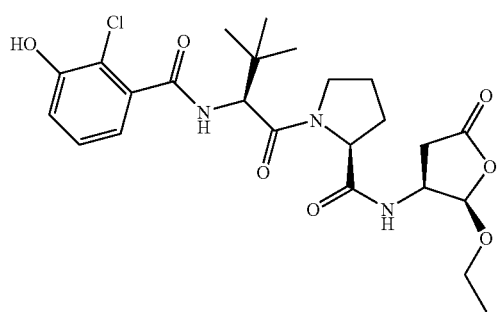
I-40 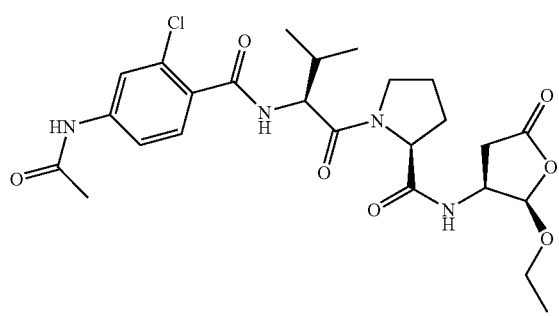
I-41 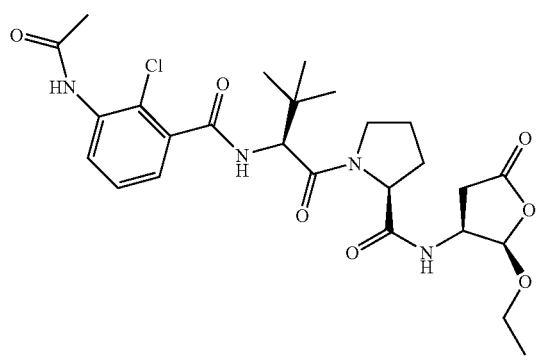
I-42 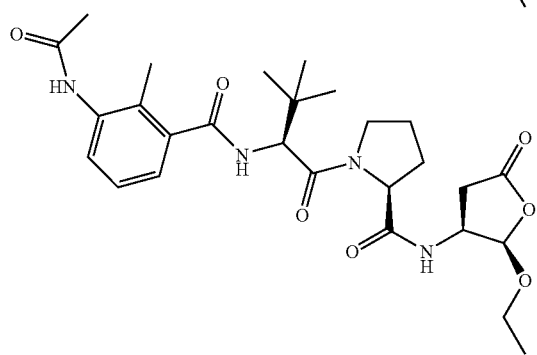

TABLE 1-continued
I-43 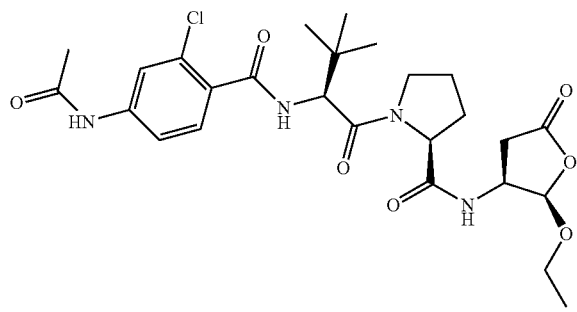
I-44 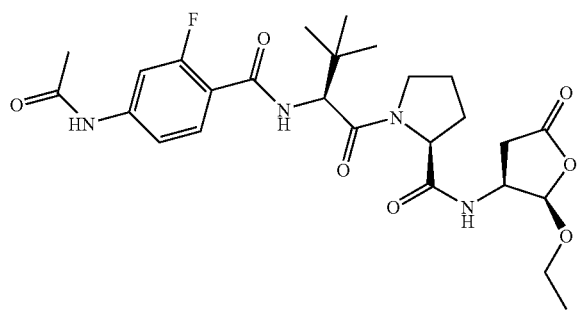
I-45 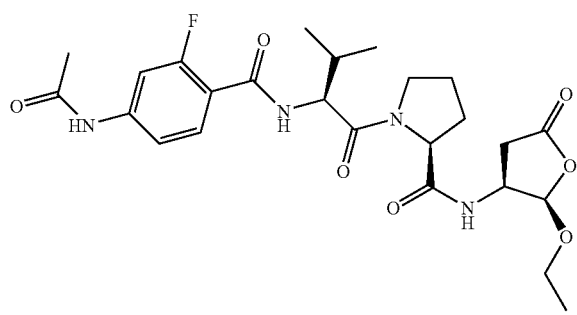
I-46 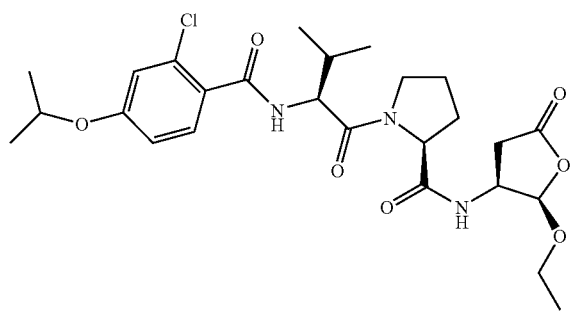
I-47 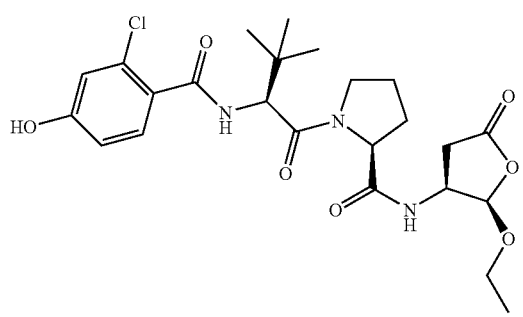

TABLE 1-continued
I-48 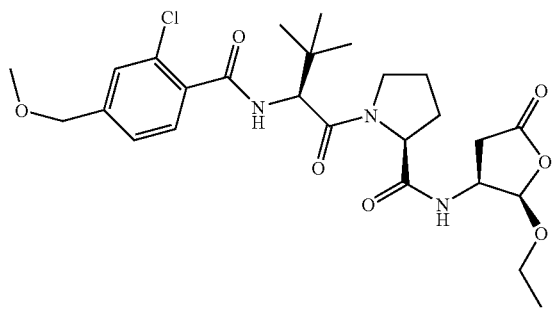
I-49 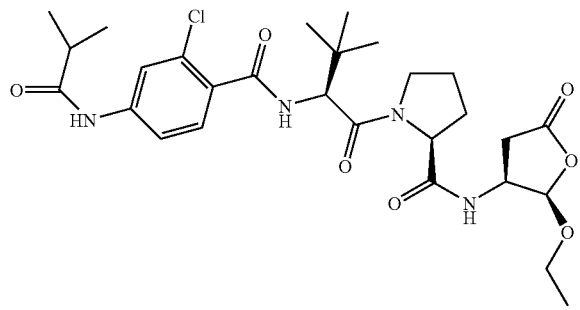
I-50 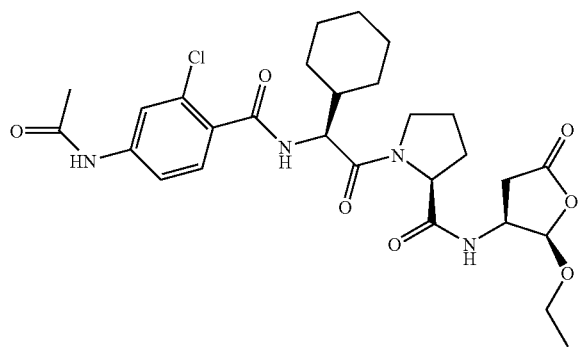
I-51 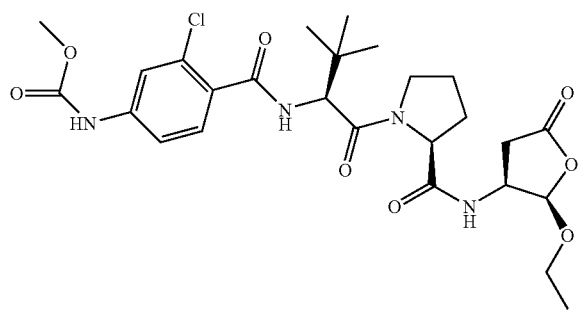
I-52 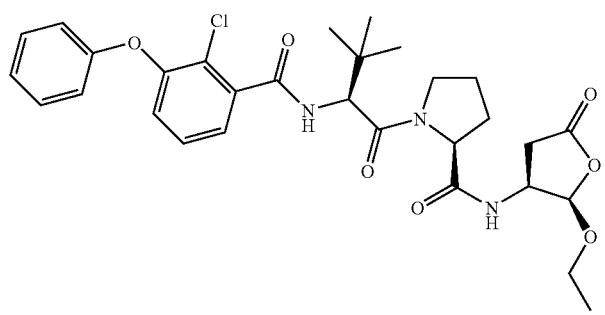

TABLE 1-continued
I-53 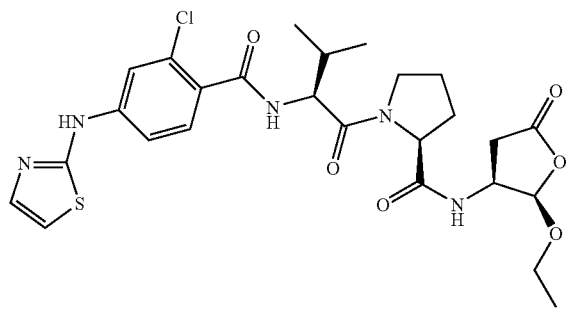
I-54 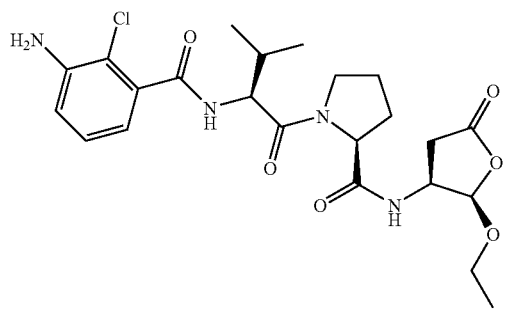
I-55 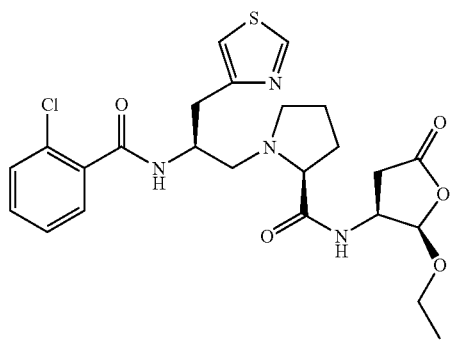
I-56 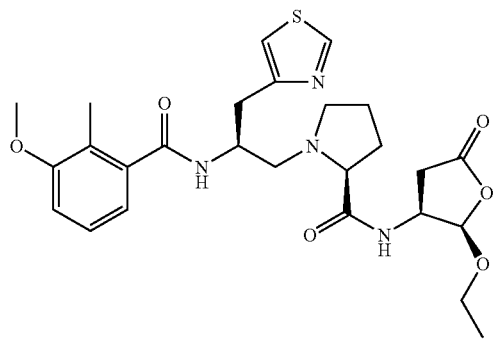
I-57 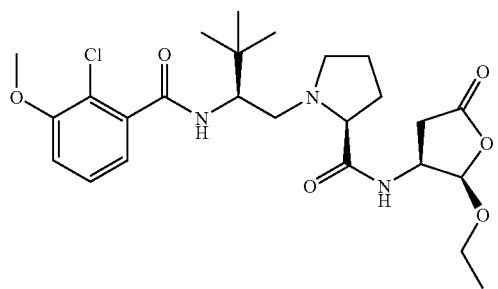

TABLE 1-continued
I-58
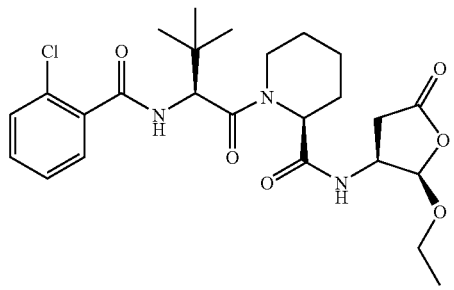
I-59
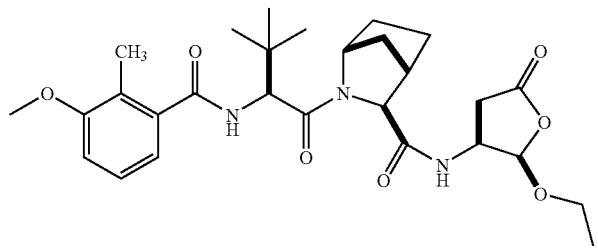
I-60
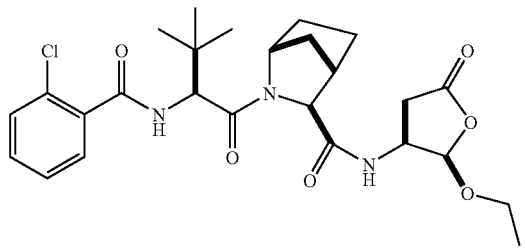
I-61
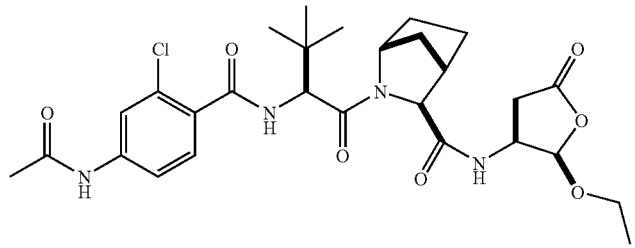
I-62
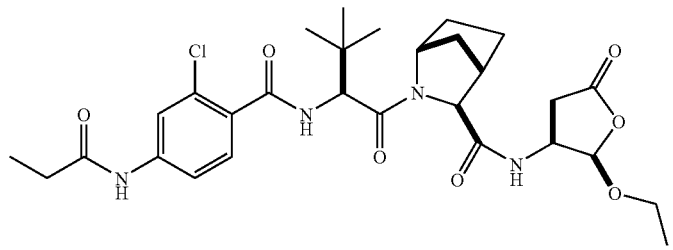
I-63
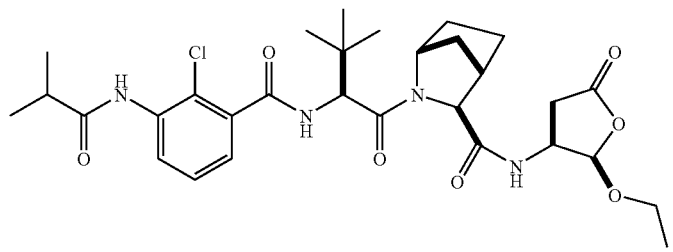

TABLE 1-continued
I-64
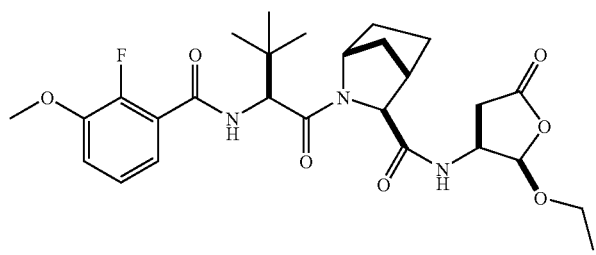
I-65
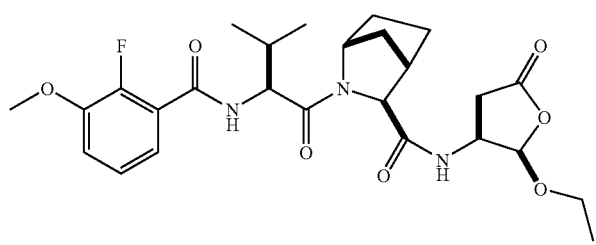
I-66
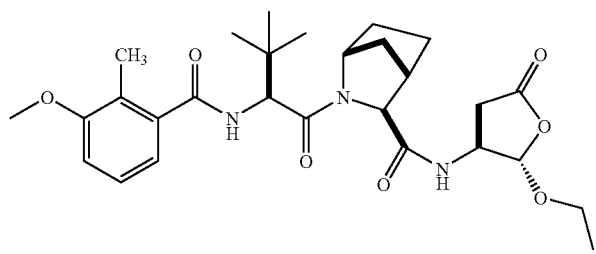
I-67
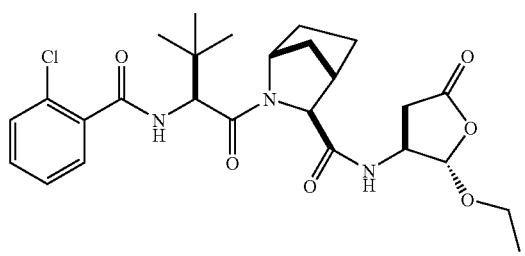
I-68
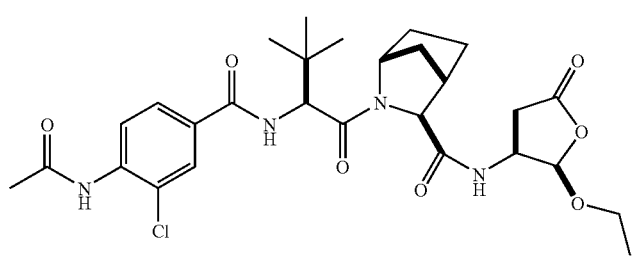
I-69
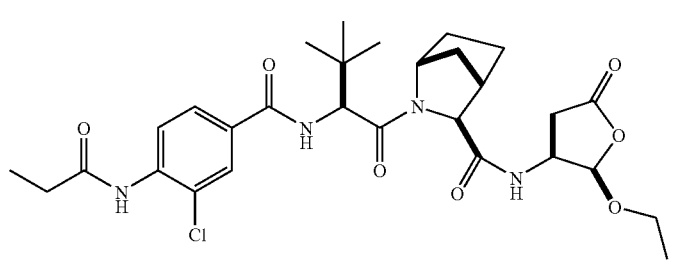

TABLE 1-continued
I-70 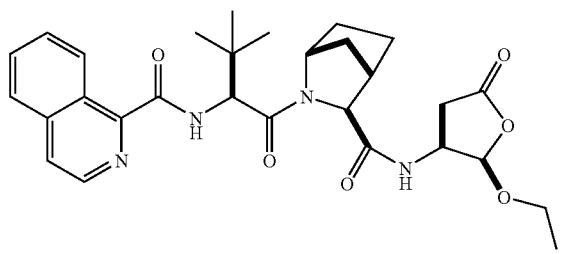
I-71 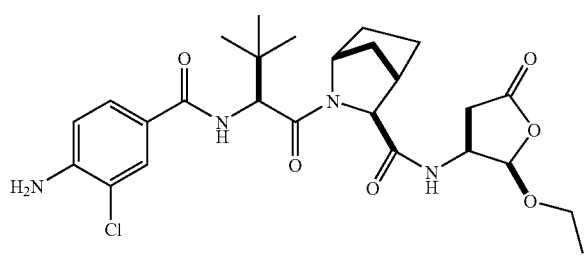
I-72 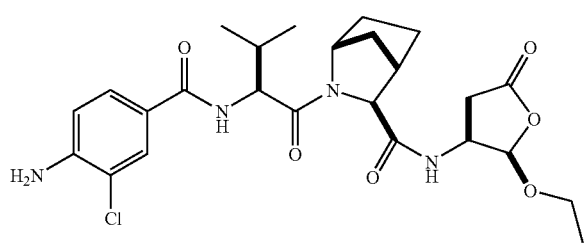
I-73 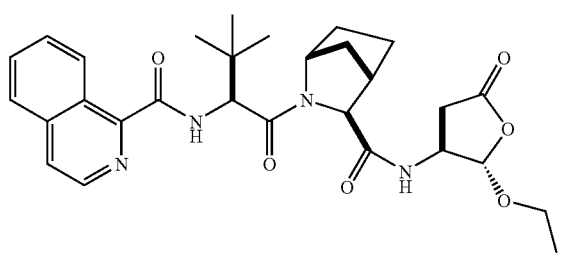
According to another embodiment, the present invention provides a compound of formula II selected from Table 2 below:
TABLE 2
II-1 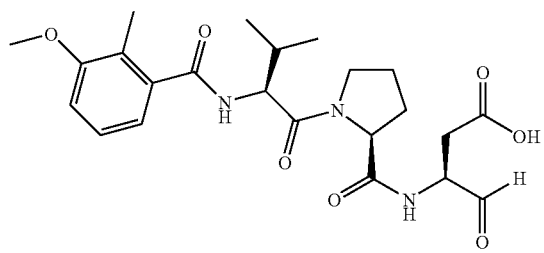

TABLE 2-continued
II-2 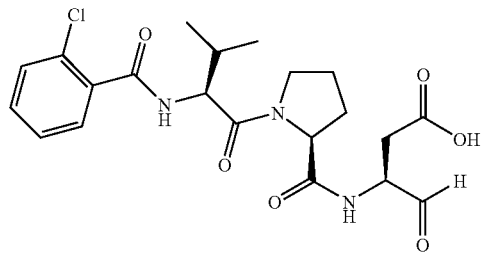
II-3 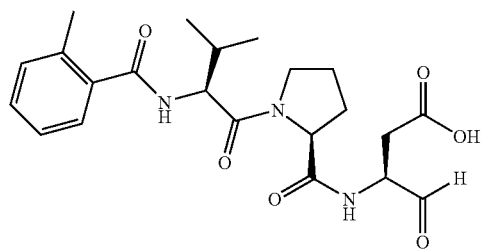
II-4 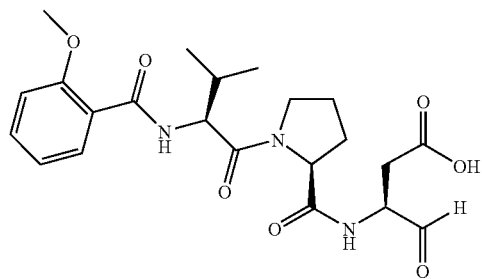
II-5 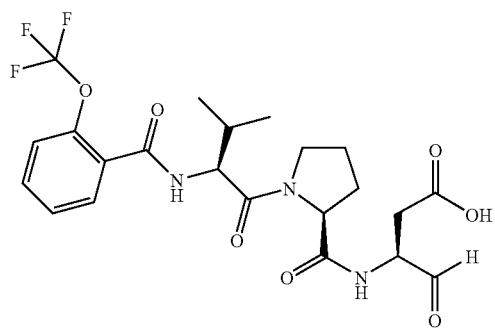
II-6 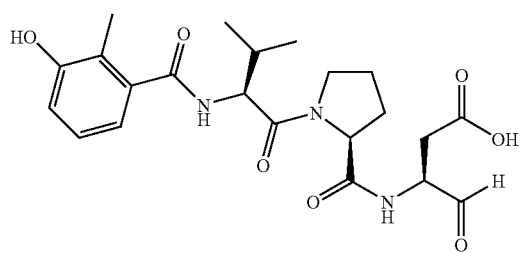

TABLE 2-continued
II-7 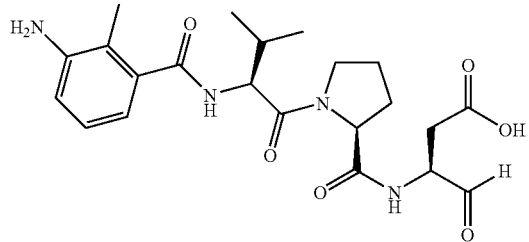
II-8 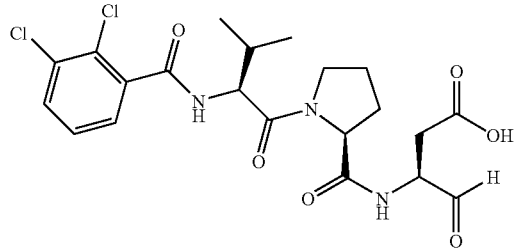
II-9 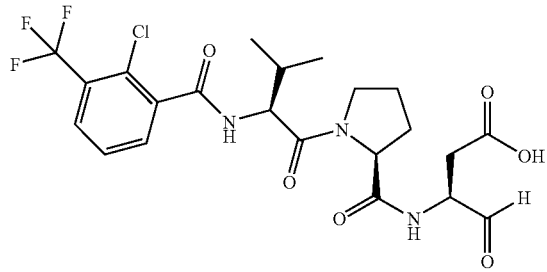
II-10 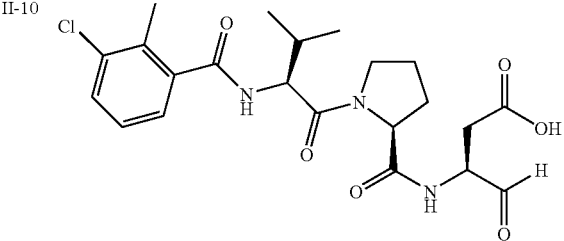
II-11 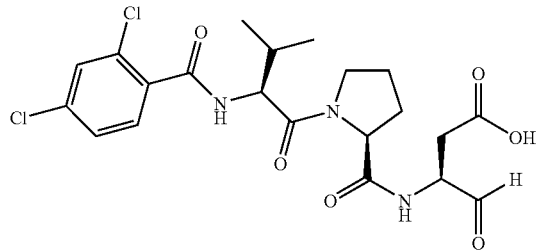
II-12 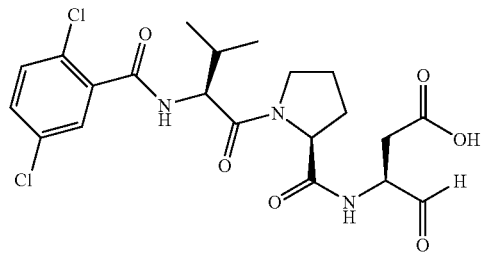

TABLE 2-continued
II-13
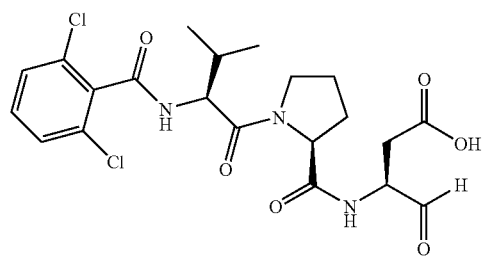
II-14
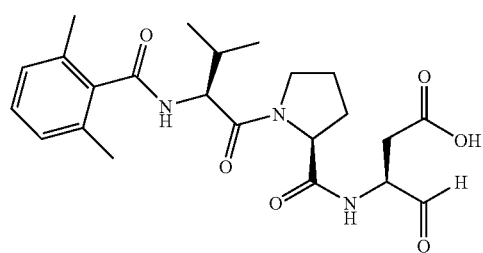
II-15
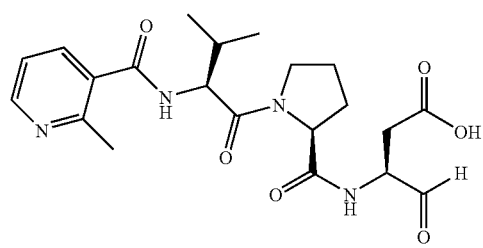
II-16
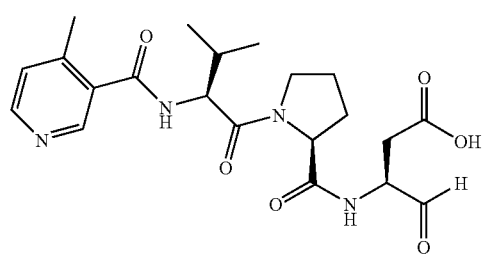
II-17
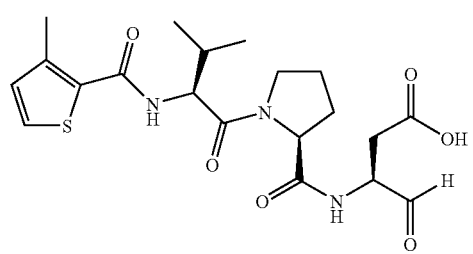
II-18
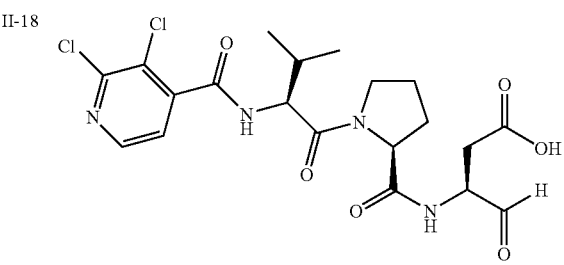

TABLE 2-continued
II-19 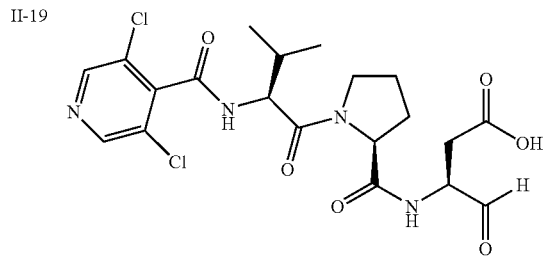
II-20 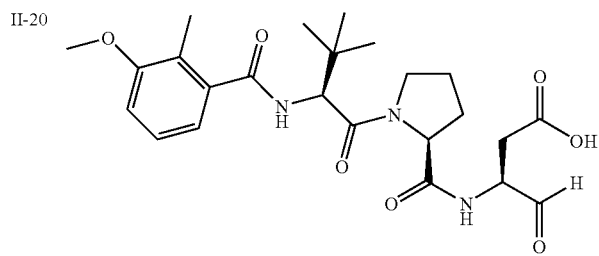
II-21 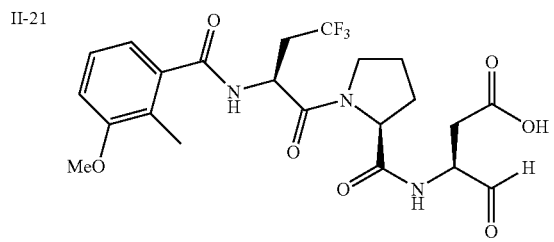
II-22 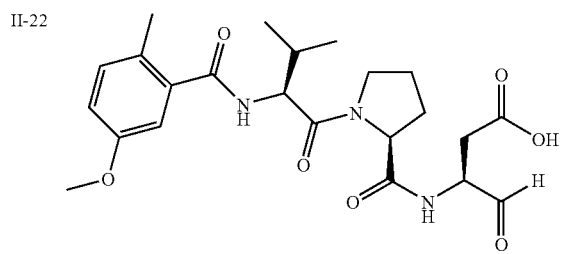
II-23 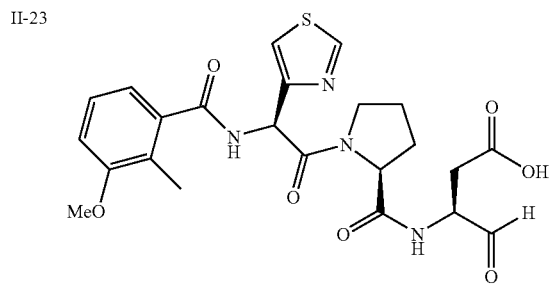
II-24 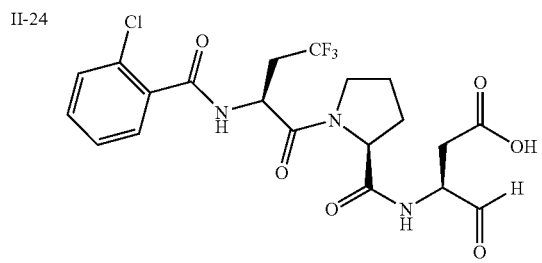

TABLE 2-continued
II-25 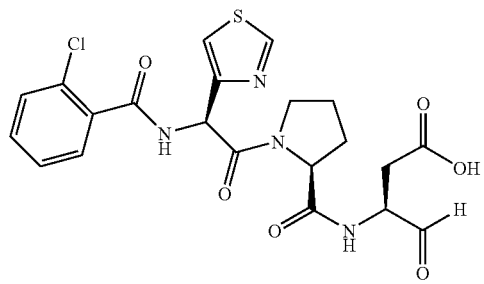
II-26 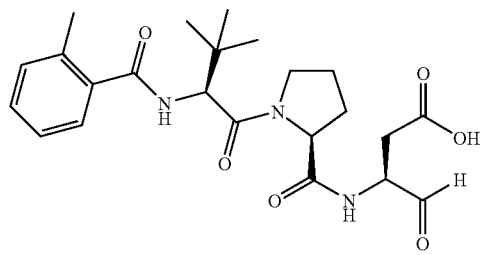
II-27 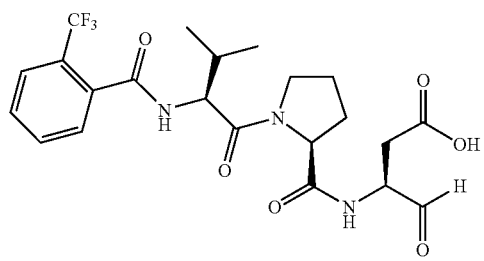
II-28 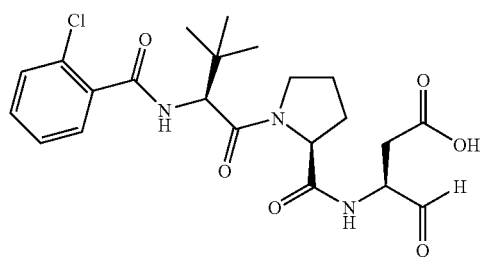
II-29 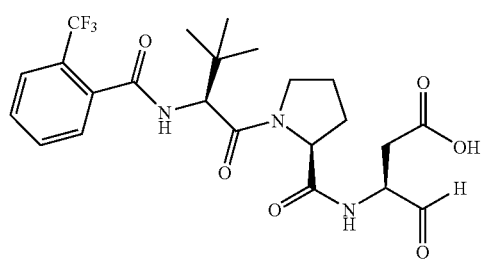
II-30 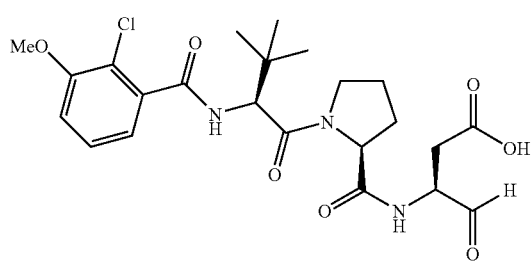

TABLE 2-continued
II-31 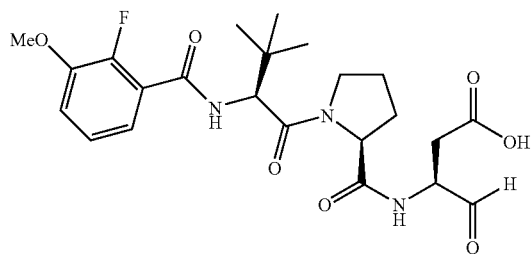
II-32 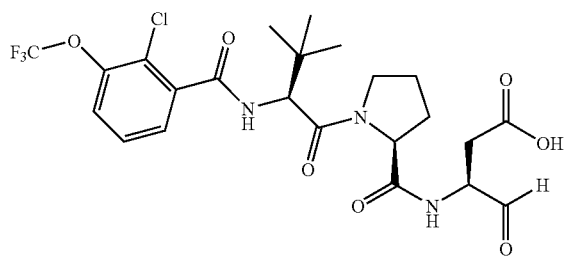
II-33 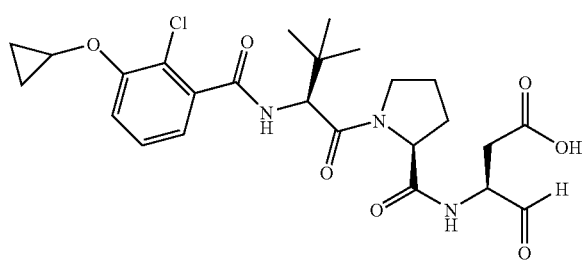
II-34 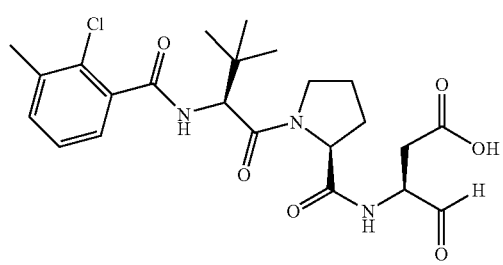
II-35 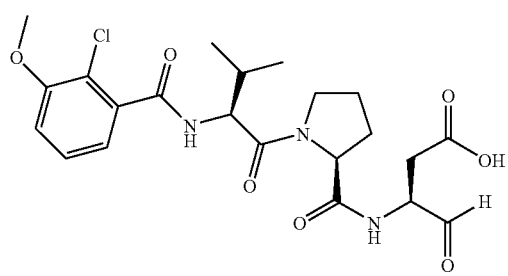
II-36 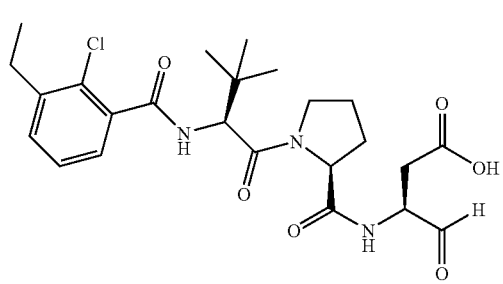

TABLE 2-continued
II-37 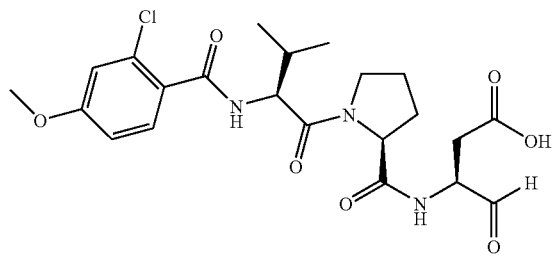
II-38 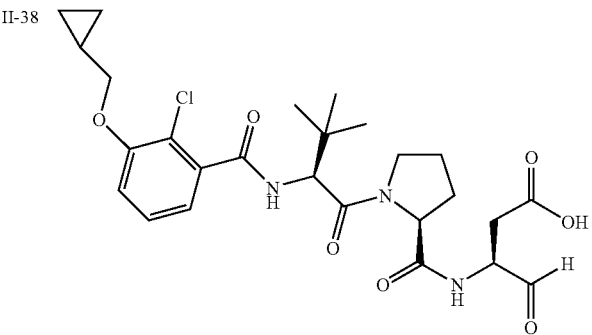
II-39 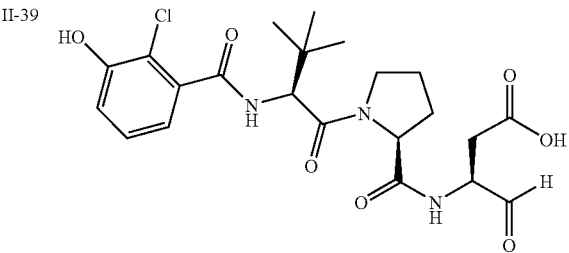
II-40 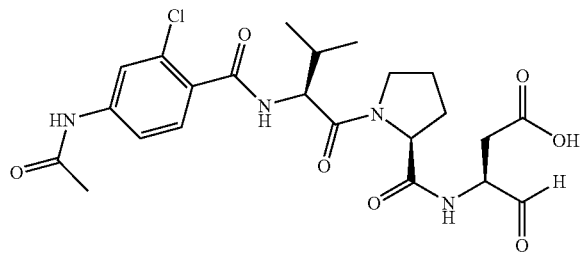
II-41 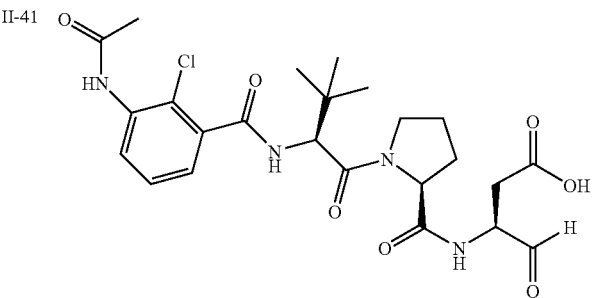

TABLE 2-continued
II-42 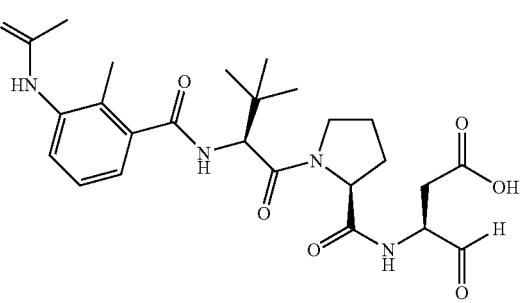
II-43 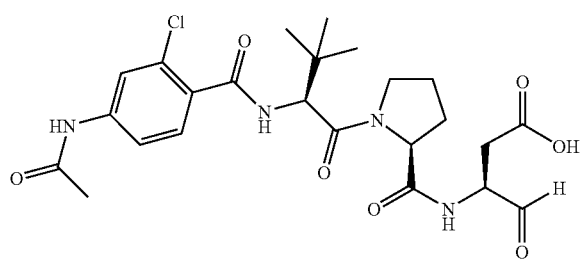
II-44 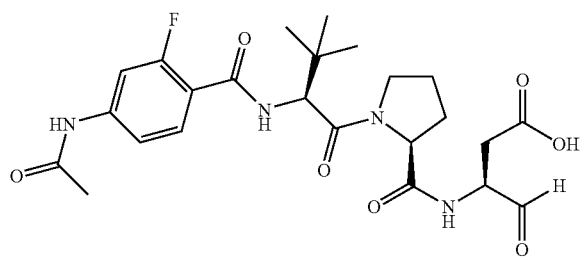
II-45 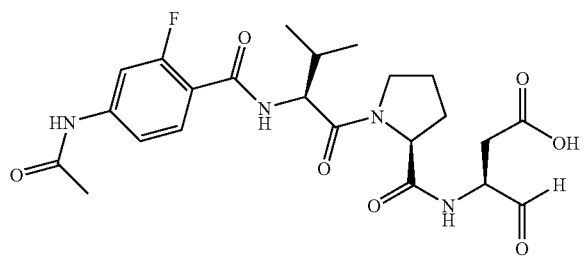
II-46 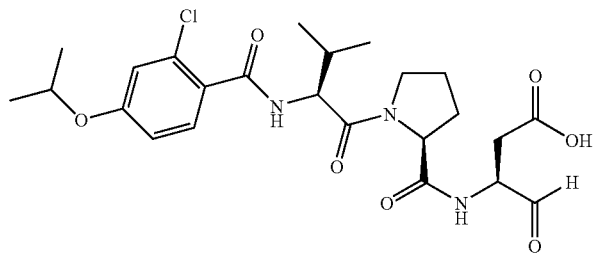
II-47 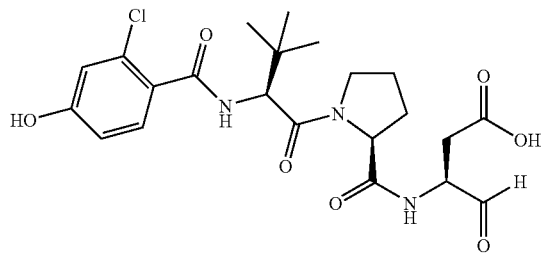

TABLE 2-continued
II-48 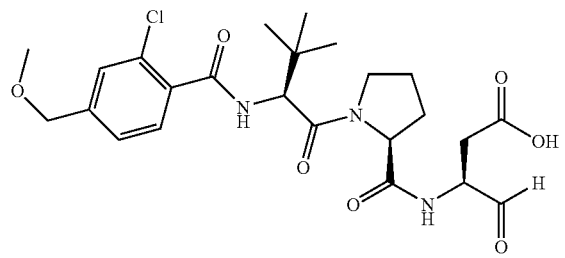
II-49 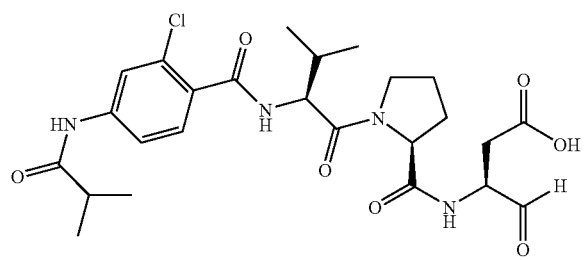
II-50 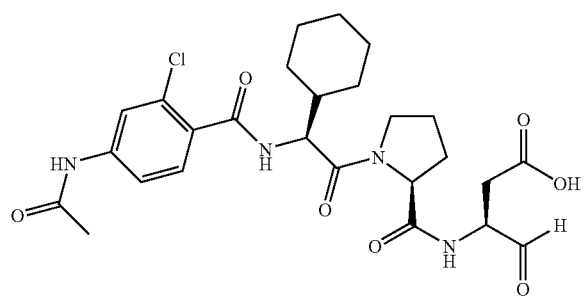
II-51 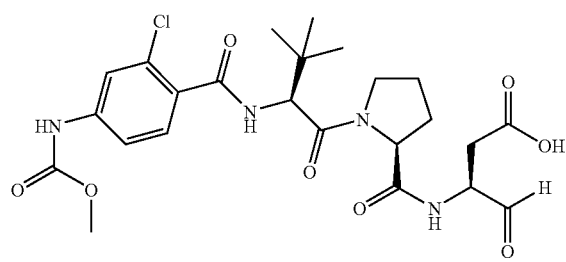
II-52 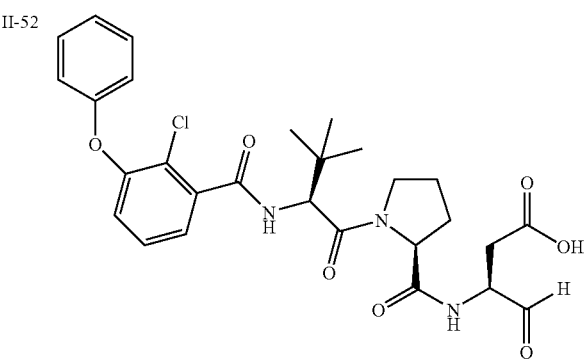

TABLE 2-continued
II-53
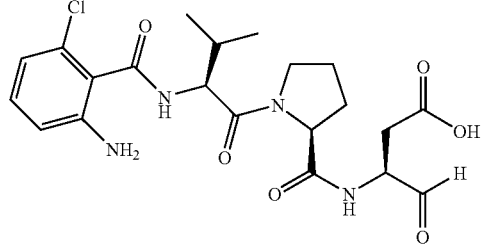
II-54
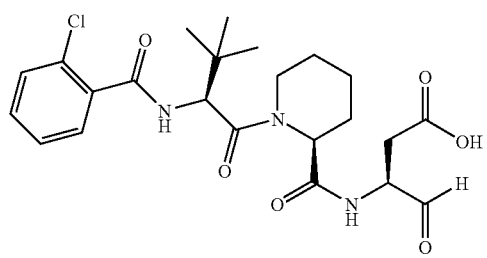
II-55
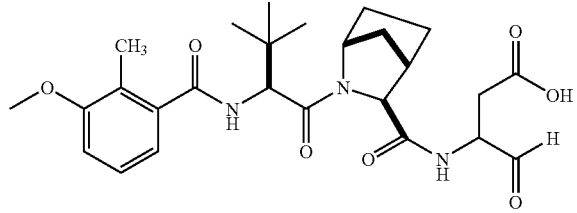
II-56
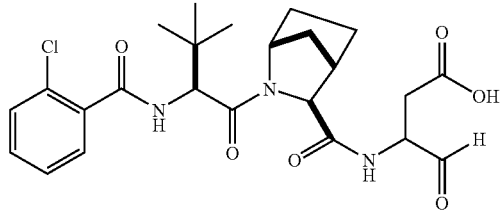
II-57
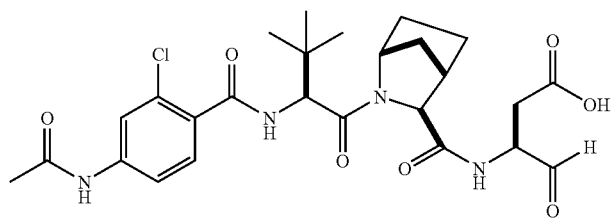
II-58
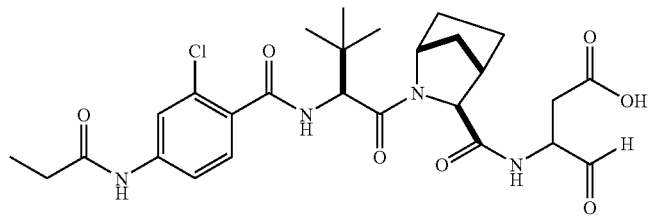

TABLE 2-continued
II-59 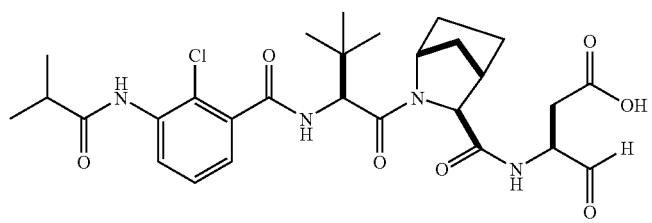
II-60 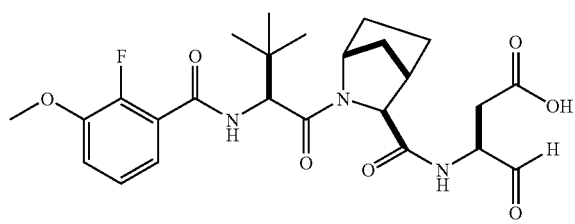
II-61 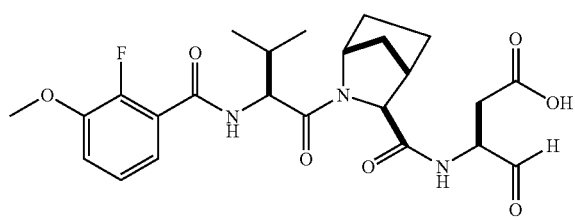
II-62 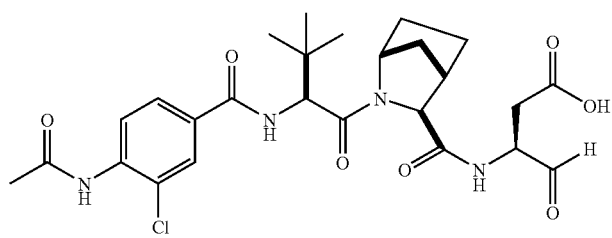
II-63 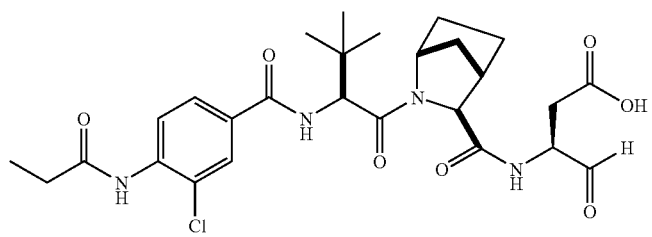
II-64 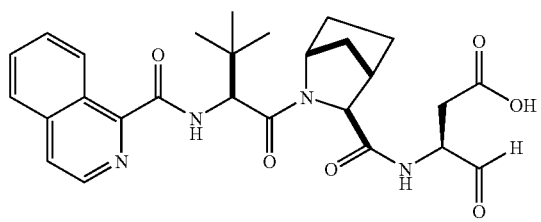
II-65 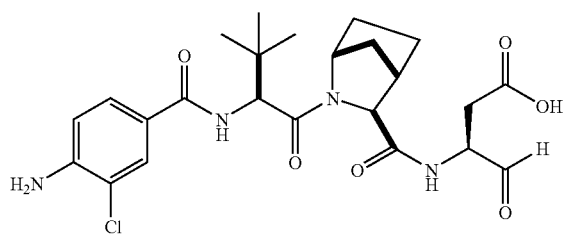

TABLE 2-continued

II-66

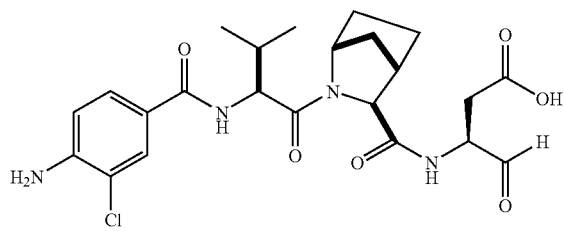

In certain embodiments of this invention, the variable definitions are selected from those depicted in the compounds of Table 1 and/or Table 2.

As used herein, a specified number atoms includes any integer therein. For example, a group having from 1-4 atoms, could have 1, 2, 3, or 4 atoms.

As used herein, an aliphatic group includes straight-chained and branched groups having the specified number of atoms. If the number of atoms is unspecified, the aliphatic group has from 1 to 12 carbon atoms. As would be understood, alkenyl and/or alkynyl aliphatic groups have a minimum of 2 carbon atoms. Preferred aliphatic groups are alkyl groups (preferably having from 1 to 6 atoms).

Cycloalkyl and cycloalkenyl groups have between 3 and 10 carbon atoms and are monocyclic or bicyclic, including linearly fused, bridged, or spirocyclic.

As used herein, "aromatic group" or "aryl" refers to a 6-10-membered ring system that contains at least one aromatic ring. Examples of aromatic rings include phenyl and naphthyl.

As used herein a "heteroaryl" refers to ring system having 5-10 members and 1, 2, or 3 heteroatoms independently selected from N, N($R^9$), O, S, SO, and $SO_2$., wherein at least one ring is heteroaromatic (e.g., pyridyl, thiophene, or thiazole).

As used herein a "heterocycle" refers to ring system having 3-10 members and 1, 2, or 3 heteroatoms independently selected from N, N($R^9$), O, S, SO, and $SO_2$, wherein no ring is aromatic (e.g., piperidine and morpholine).

Further examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

Further examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Each of the above aliphatic, aryl, cycloaliphatic, heteroaryl, and heterocyclyl may contain appropriate substituents (preferably up to 5) independently selected from, for example, carbonyl and $R^8$. Preferred substituents are halogen, —$OR^9$, —$NO_2$, —$CF_3$, —$OCF_3$, —$R^9$, oxo, —$OR^9$, —O-benzyl, —O-phenyl, 1,2-methylenedioxy, 1,2-ethylenedioxy, —N($R^9$)$_2$, —C(O)$R^9$, —COO$R^9$ or —CON($R^9$)$_2$, wherein $R^9$ is defined herein (and is preferably H, (C1-C6)-alkyl, or (C2-C6)-alkenyl and alkynyl), with (C1-C6)-alkyl being most preferred). It should be understood that this definition would include a perfluorinated alkyl group.

It will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

The compounds of this invention may be obtained by any method, including general, synthetic methods known to those skilled in the art for analogous compounds (see e.g., WO 99/47545). For the purposes of illustration, the following Schemes for the synthesis of the compounds of the present invention are provided.

The following abbreviations are used:
EDC is 1-(3-dimethylaminopropyl)-3-ethylcarbodiimide
HOBt is 1-hydroxybenzotriazole
THF is tetrahydrofuran
TFA is trifluoroacetic acid
DCM is dichloromethane
DMAP is 4-dimethylaminopyridine
DIPEA is diisopropylethylamine
DMF is dimethylformamide
TFA is trifluoroacetic acid
Z is benzyloxycarbonyl
$^1$H NMR is nuclear magnetic resonance
TLC is thin layer chromatography Scheme I. General scheme for the preparation of E and F

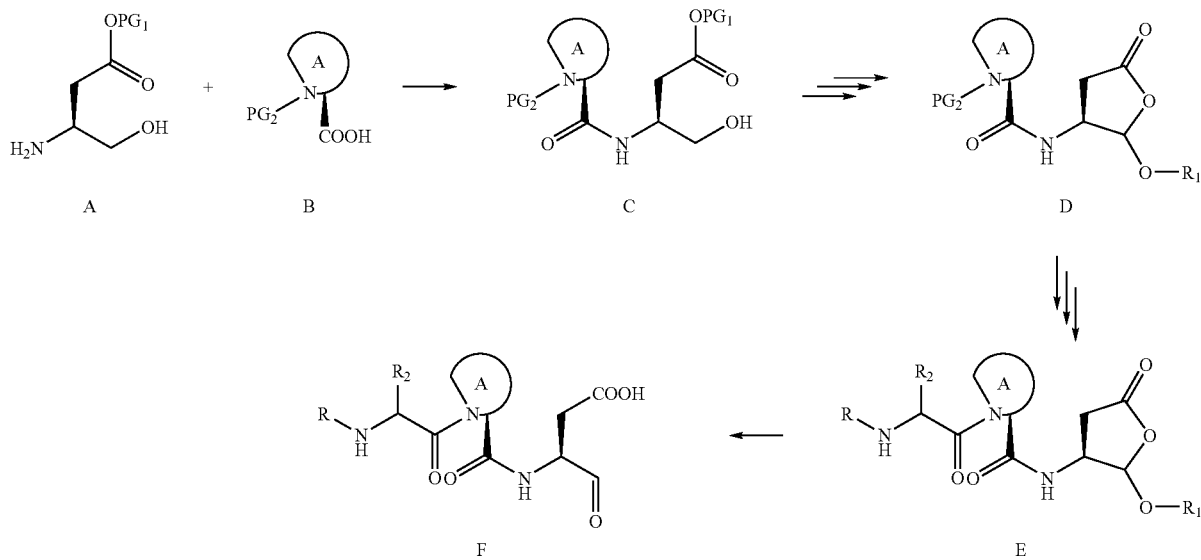

Scheme I depicts a general route to prepare the compounds E and F disclosed in this invention. The amino group of species A, readily obtained from reduction of the α-carboxylic group of aspartic acid (protected with $PG_1$ as an ester), is coupled to the carboxylic acid moiety of species B (N-protected with $PG_2$) to give species C. $PG_1$ and $PG_2$ are orthogonal protecting groups (i.e., protecting groups where a protecting group may be selectively removed in the presence of another protecting group. Ideally, $PG_1$ should be able to be removed without removing $PG_2$ and vice versa). Here, the aspartate part of the molecule is then manipulated in an oxidation/ketalisation/deprotection/cyclisation sequence to give species D. The Ring A portion of D is then functionalized further to give species E which is part of the disclosed invention. Deprotection of the ketal gives species F which represent the other part of the disclosed invention.

In various embodiments of this invention, $PG_2$ is a suitable amine protecting group, including but not limited to, the amine protecting groups described in T. W. Greene & P. G. M Wutz, "Protective Groups in Organic Synthesis", $3^{rd}$ Edition, John Wiley & Sons, Inc. (1999 and other editions) ("*Greene*"). A "Z" protecting group (benzyloxycarbonyl) is a particularly useful N-protecting group for use in connection with this invention. In compounds wherein $PG_2$ is protecting the nitrogen of a proline, $PG_2$ is preferably Z. It should be understood that modified Z groups ("Z-type protecting groups") employed in connection with the compounds and processes of this invention would also fall within the scope of this invention. For example, Z could be substituted at the $CH_2$ group or the phenyl group with $R^8$ (preferably halo or $C_{1-6}$ straight-chained or branched alkyl) to provide a Z-type protecting group.

In various embodiments of this invention, $PG_1$ is a suitable carboxylic acid protecting group, including but not limited to the acid protecting groups described in *Greene*. In certain embodiments, $PG_1$ is $C_{1-6}$ straight-chained or branched alkyl group. A t-butyl group is a particularly useful acid protecting group for use in connection with this invention.

In Scheme I, compound A is a modified aspartic acid residue. In addition to compound A, other modified aspartic acid residues, including the following, have been reported:

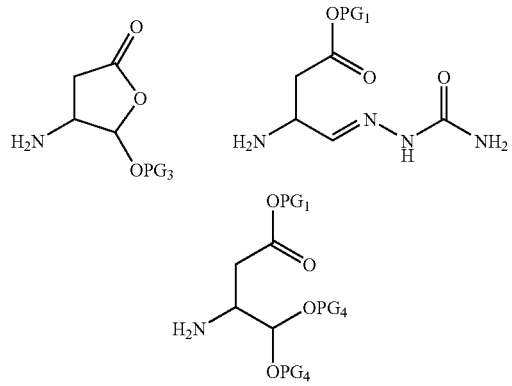

wherein, $PG_3$ and $PG_4$ are appropriate protecting groups. These modified aspartic acids may be prepared by methods known to skilled practitioners. See, for example, U.S. patent application Publication US 2002/0042376 (especially page 9, paragraph [0121] and pages 21-22, paragraph [0250] and the documents cited at paragraph [0123]) and U.S. Pat. No. 6,235,899. See also, C. Gros et al. "Stereochemical control in the preparation of a-amino N-methylthiazolidine Masked Aldehydes used for Peptide Aldehyde Synthesis" *Tetrahedron*, 58, pp. 2673-2680 (2002); K. T. Chapman, "Synthesis of a Potent Reversible Inhibitor of Interleukin-β Converting Enzyme" *Bioorg. Med. Chem. Letts.*, 2, pp. 613-618 (1982); M. D. Mullican et al. "The Synthesis and Evaluation of Peptidyl Aspartyl Aldehydes as Inhibitors of ICE'" 4, pp. 2359-2364 (1994); M. H. Chen, et al. "An Efficient Stereoselective Synthesis of [3S(1S,9S)]-3-[[[9-(Benzoylamino)octahydro-6,10-Dioxo-6H-pyridazino-(1,2-a)(1,2)-Diazepin-1-yl]-carbonyl]amino]-4-oxobutanoic acid, an interleukin converting enzyme (ICE) Inhibitor" 9, pp. 1587-1592 (1999). Accordingly, Scheme I (and also Scheme III below) could be modified to use these other aspartic acid residues.

Scheme II. Preparation of Compounds of Formulae I and II

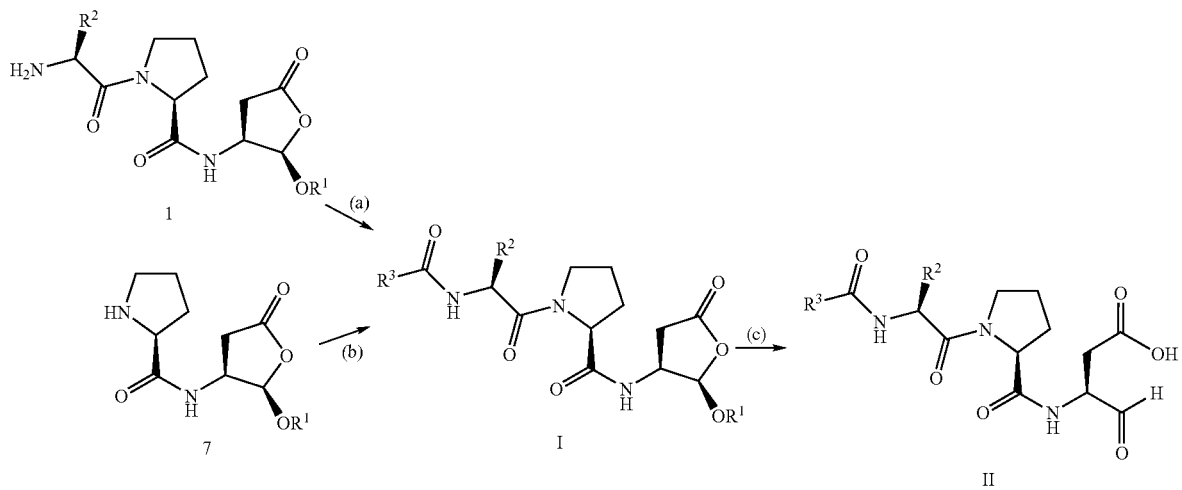

Reagent and conditions: (a) R³COOH, HOBt, DMAP, EDC, THF; (b) R³CONHCH(R²)COOH, HOBt, DMAP, EDC, THF; (c) 2M HCl, MeCN.

Scheme II depicts formation of compounds of formula I and II, wherein Ring A is unsubstituted proline. Here the cyclic acetal form of a compound of this invention is depicted as formula I and the aldehyde form is depicted as formula II. Compounds having a Ring A other than unsubstituted proline could be substituted in the methods depicted in Scheme I.

Scheme II depicts the routes utilized to prepare compounds of formulae I and II. Compounds I can be prepared from compounds 1 by condensation of the amino group in 1 with the suitably functionalized carboxylic acid (or derivative). In this step, standard coupling reagents to form amide bonds have been depicted; other conditions known in the art to form amide bonds can also be used.

As known to skilled practitioners, a carboxylic acid (—C(O)OH) can be coupled to the amine under appropriate conditions for coupling amines and carboxylic acids. Alternatively, in such couplings, a carboxylic acid derivative (—C(O)X) may be employed instead of the carboxylic acid. It should be understood that in the context of coupling an amine and a carboxylic acid derivative, the derivative would activate the acid to facilitate coupling to an amine. Appropriate X groups are essentially leaving groups and are known to skilled practitioners. "March's Advanced Organic Chemistry", 5$^{th}$ Ed., Ed.: Smith, M. B. and March, J., John Wiley & Sons, New York: 2001.

Typical conditions for coupling an amine and an acid include combining a suitable solvent, a carboxylic acid, a base, and a peptide-coupling reagent. Examples of suitable conditions are described in US2002/0042376 and WO 01/81330, the entireties of which are hereby incorporated by reference. In certain embodiments, the conditions are as described in the Schemes and Examples herein.

Examples of appropriate derivatives include, but are not limited to, compounds of the formula RX wherein X is Cl, F, OC(=O)R" (R" is aliphatic or aryl), SH, SR, SAr, or SeAr. In some embodiments R is C(=O). Suitable conditions for using these appropriate derivatives are known in the art.

Scheme III. Preparation of Compound 1

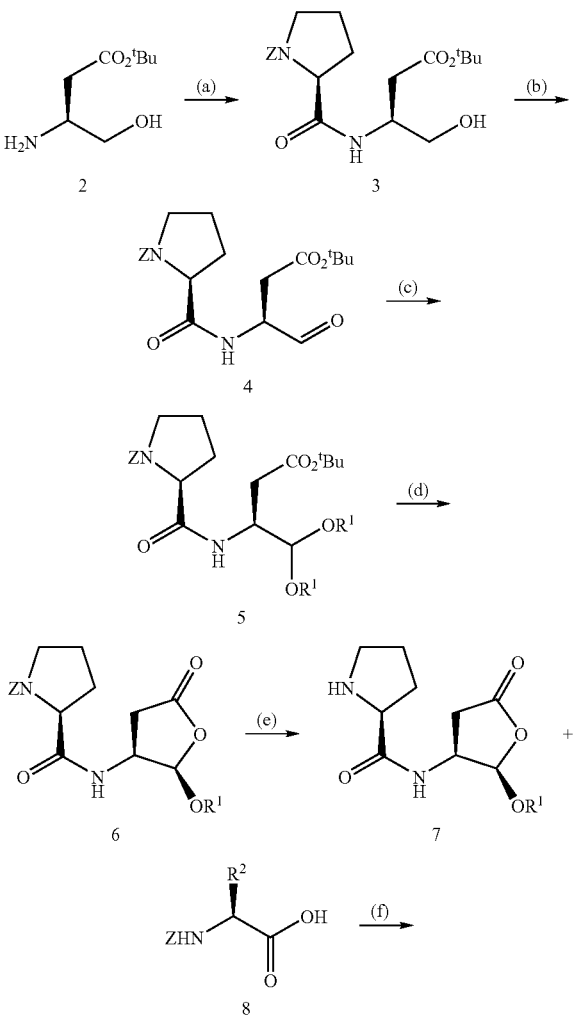

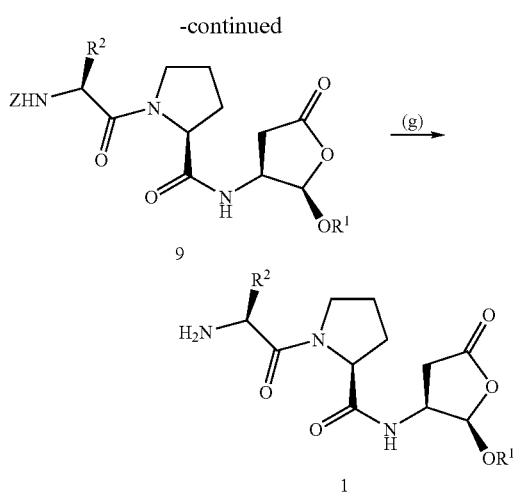

Reagent and conditions: (a) Cbz-Pro-OH, EDC, HOBt, DMAP, DIPEA, THF; (b) Swern; (c) $R^1OH$, 3 Å sieves, DCM, TsOH; (d) TFA, DCM; (e) $H_2$, Pd(OH)$_2$, EtOAc, DMF, Et$_3$N; (f) EDC, HOBt, Et$_3$N, EtOAc, DMF; (g) $H_2$, Pd/C, Citrate Acid.

Scheme III depicts a possible route to prepare compounds 7 and compounds 1 described in scheme I. Compound 2, readily obtained from reduction of the α-carboxylic group of aspartic acid, is coupled to N-protected proline (or other ring, wherein Ring A is other than unsubstituted proline) to form 3. Here, the proline is N-protected with a Z (benzyloxycarbonyl) group. Compounds 3 are then oxidized into the aldehydes 4 which are acetalized in situ to give the acetals 5. Acetals can be formed in the presence of $R^1$—OH (or a suitable acetal forming reagent), a protic acid (for example, TSOH), or a Lewis acid, and a suitable solvent. Examples of suitable acetal forming reagents that form compounds wherein $R^1$ is ethyl can be considered ethanol equivalents and include, but are not limited to, triethylorthoformate or a diethylacetal, such as a $(CH_3)_2C(OCH_2CH_3)_2$. Preferably, the solvent is $CH_2Cl_2$, toluene, or chlorobenzene. Appropriate protic acids include, but are not limited to, TFA, p-TsOH. Appropriate Lewis acids include, but are not limited to TiCl$_4$, MgBr$_2$, and ZnCl$_2$.

In Scheme III, the oxidation of compounds 3 to compounds 4 is depicted as being done under Swern conditions. Other oxidation conditions may also be employed to prepare compounds of this invention. Preferred oxidation conditions are those that a mild and relatively quick to minimize epimerization at the acid side chain of the modified aspartic acid residue. In one embodiment, the oxidation step is a TEMPO oxidation (see Example I-1, Method C, below). Other oxidation conditions include a Dess-Martin oxidation and a tetrapropylammonium perruthenate (TPAP) oxidation.

Aldehydes 4 may be isolated but are preferably carried through directly to 5 without isolation. Deprotection of the tert-butyl ester (in 5) is accompanied by spontaneous ring cyclization to give a mixture of diastereoisomers which were separated by column chromatography to give the enantiomerically pure syn ketals 6 and anti ketals (not represented in this scheme). The deprotection may be done under protic acid or Lewis acid conditions in an appropriate solvent. Appropriate solvents include, but are not limited to, toluene, chlorobenzene, and DCM. Appropriate protic acids include, but are not limited to, TFA, p-TsOH. Appropriate Lewis acids include, but are not limited to TiCl$_4$, MgBr$_2$, and ZnCl$_2$. For clarity of the scheme, only syn ketals are represented in the next steps to form compounds 7 and 1 but the same sequence may be used to form anti ketals. Compounds 6 are submitted to hydrogenolysis and the resulting compounds 7 are reacted with Z-protected aminoacids, using conditions known in the art to prepare amide bonds, to yield compounds 9. Compounds 7 may be generated and used in situ. If isolated, it is preferable to use compounds 7 relatively soon after generation. Compounds 9 are finally submitted to hydrogenolysis to give compounds 1, which can be used directly to prepare compounds I, as depicted in Scheme II.

Alternatively, compounds 7 can be used to prepare compounds I, as depicted in Scheme II. In this preparation, an amino acid residue and the desired N-terminal group is prepared in one step (see, Scheme II, reaction (b)).

As described in connection with Scheme I, aspartic acid derivatives other than compounds 2 can be employed to obtain compounds of this invention.

Scheme IV. Preparation of Compounds of Formulae III and IV

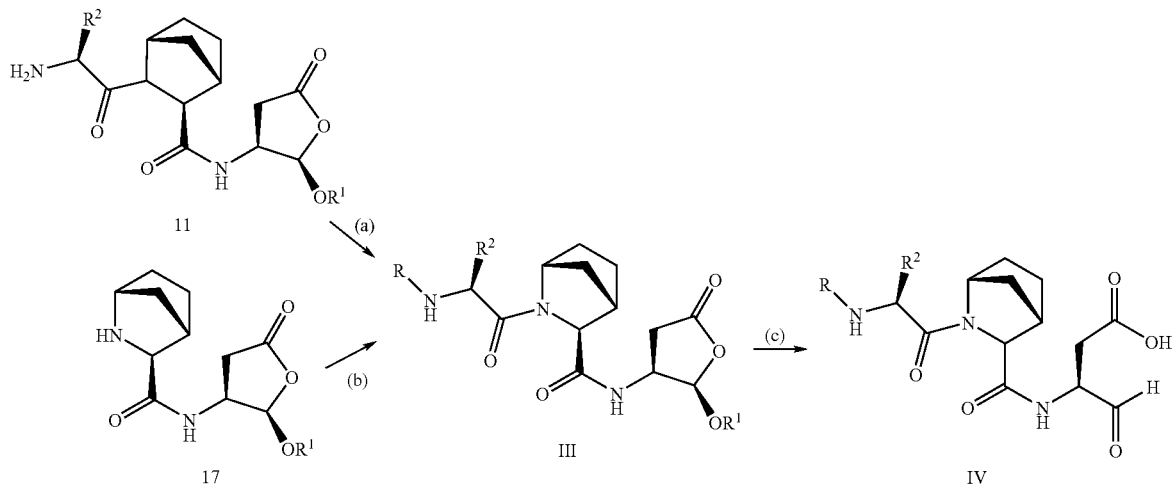

Reagent and conditions: (a) ROH/HOBt/DMAP/EDC/THF or RCl/Et₃N/DCM; (b) RNHCH(R²)COOH, HOBt, DMAP, EDC, THF; (c) 2M HCl, MeCN.

Scheme IV depicts formation of compounds of formula III and IV, wherein Ring A is 2-Aza-bicyclo[2.2.1]-heptane-3-carboxylic acid. Here the cyclic acetal form of a compound of this invention is depicted as formula III and the aldehyde form is depicted as formula IV. Scheme IV depicts the routes utilized to prepare compounds of formulae III and IV. Compounds III can be prepared from compounds 11 by condensation of the amino group in 11 under conditions to provide the desired R group, such as suitably functionalized carboxylic acid (or derivative), sulfonic acid (or derivative), chloroformate or carbamoyl chloride (or isocyanate), for example, under appropriate reaction condition. In this step, standard coupling reagents to form CO—NH bonds have been depicted; other conditions known in the art to form CO—NH (or alkyl-N, or SO₂—N) bonds can also be used to provide the desired compound comprising R—N. Alternatively, compounds I can be prepared from compounds 17 by condensation of the amino group in 17 with the suitably functionalized carboxylic acid (or derivative), sulfonic acid (or derivative), chloroformate or carbamoyl chloride (or isocyanate). In this step, standard coupling reagents to form CO—NH bonds have been depicted; other conditions known in the art to form CO—NH bonds can also be used.

Scheme V. Preparation of Compound 11

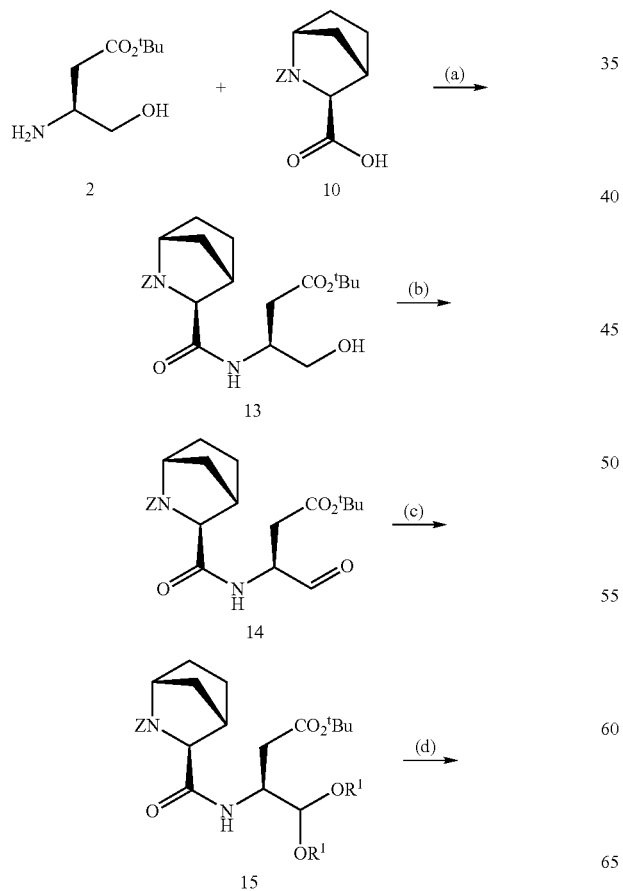

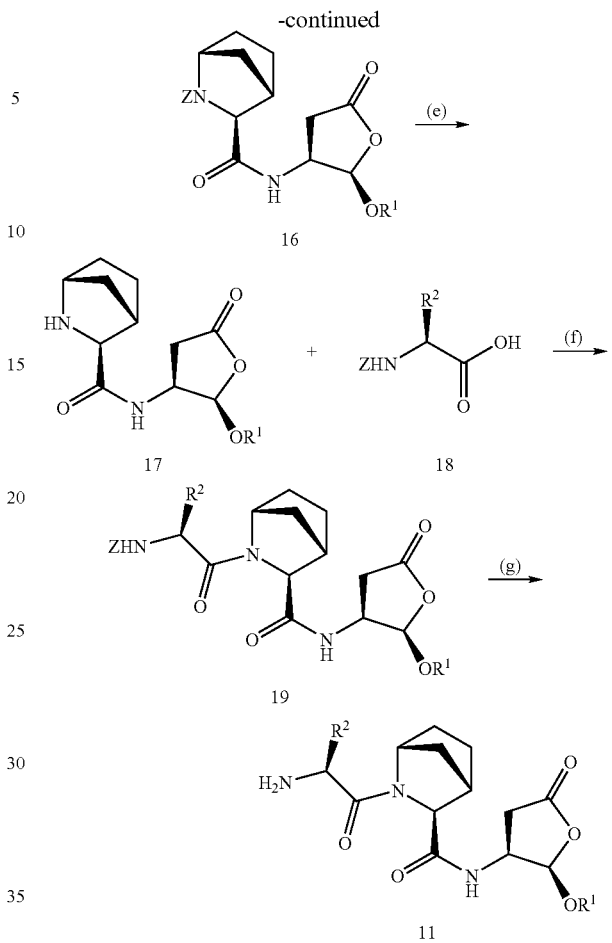

Reagent and conditions: (a) EDC, HOBt, DMAP, DIPEA, THF; (b) Swern; (c) R¹OH, 3 Å sieves, DCM, TsOH; (d) TFA, DCM; (e) H₂, Pd(OH)₂, EtOAC, DMF, Et₃N; (f) EDC, HOBt, Et₃N, EtOAc, DMF; (g) H₂, Pd/C, Citrate Acid.

Scheme V depicts a possible route to prepare compounds 17 and compounds 11 described in scheme III. Compound 2, readily obtained from reduction of the α-carboxylic group of aspartic acid, is coupled to N-protected 2-aza-bicyclo[2.2.1] heptane-3-carboxylic acid 10 (prepared as in *Tetrahedron: Asymmetry*, 13, 2002, 25-28) to form 13. Compound 13 is then oxidized into the aldehyde 14 which is acetalized in situ to give the acetals 15. Deprotection of the tert-butyl ester is accompanied by spontaneous ring cyclization to give a mixture of diastereoisomers which were separated by column chromatography to give the enantiomerically pure syn ketals 16 and anti ketals (not represented in this scheme). Alternative Ring A groups are either commercially available, reported in the literature, or may be prepared according to methods known in the literature.

For clarity of the scheme, only syn ketals are represented in the next steps to form compounds 17 and 11 but the same sequence may be used to form anti ketals. Compounds 16 are submitted to hydrogenolysis and the resulting compounds 17 are reacted with Z-protected aminoacids, using conditions known in the art to prepare amide bonds, to yield compounds 19.

Alternatively, compounds 17 can be used to prepare compounds III, as depicted in Scheme IV. Compounds 19 are finally submitted to hydrogenolysis to give compounds 11, which can be used directly to prepare compounds III, as depicted in Scheme IV.

The R³COOH used in Scheme II are either commercially available, reported in the literature, or prepared according to methods known in the literature. For compound II-30, 2-chloro-3-methoxybenzoic acid was prepared as in *J. Org. Chem*, 59, 1994, 2939-2944.

For compound II-32, 2-chloro-3-trifluoromethoxybenzoic acid was prepared from 2-amino-3-trifluoromethoxybenzoic acid (prepared as in *J. Org. Chem*, 68, 2003, 4693-4699) using a Sandmeyer replacement of the amino group by a chloro, according to a method substantially similar to the one reported in *J. Org. Chem*, 59, 1994, 2939-2944.

Accordingly, this invention also provides a process for preparing a compound of this invention.

In one embodiment is provided a process for preparing a compound of formula I:

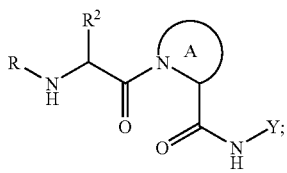

wherein Y is:

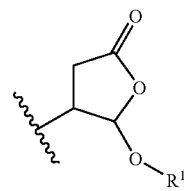

and the other variables are as defined in any of the embodiments herein;

comprising reacting a compound of formula 1:

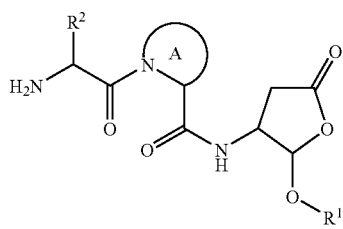

wherein the variables are as defined in any of the embodiments herein; and a compound of formula RX, wherein X is OH or an appropriate derivative (i.e., leaving group), in the presence of conditions for coupling an amine and an acid (when X is OH) or an amine and an appropriate acid derivative (when X is not OH (i.e., a leaving group; for example, Cl) to provide the compound of formula I.

Another embodiment provides a process for preparing a compound of formula I:

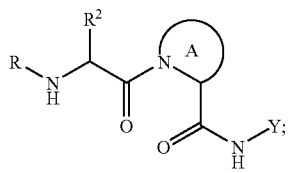

wherein Y is:

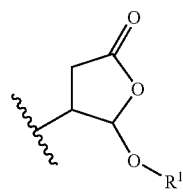

and the other variables are as defined in any of the embodiments herein;

comprising reacting a compound of formula 7:

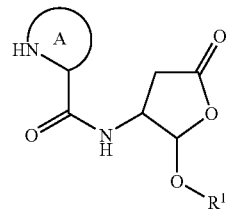

wherein the variables are as defined in any of the embodiments herein, and a compound of formula RNHCH(R²)C(O)X, wherein X is OH or an appropriate derivative, in the presence of conditions for coupling an amine and an acid (when X is OH) or an appropriate acid derivative (when X is not OH; for example, X is Cl) to provide the compound of formula I.

Yet another embodiment of this invention provides a process for preparing a compound of formula IV:

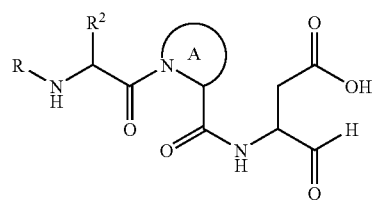

wherein the variables are as defined in any of the embodiments herein, comprising reacting a compound of formula I:

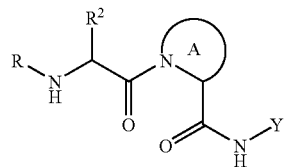

wherein Y is:

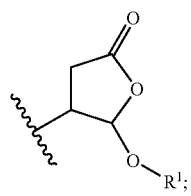

wherein R and $R^1$ are each independently as defined in any of the embodiments herein, under hydrolysis conditions, to provide the compound of formula II. In certain embodiments, R is $R^3C(=O)$. In yet other embodiments, when A is proline, R is $R^3C(=O)$. Hydrolysis conditions for converting I to II are well known to skilled practitioners (see e.g., Greene). Such conditions include an appropriate solvent (e.g., acetonitrile) and aqueous acid (e.g., 2M HCl).

Another embodiment provides a process for preparing a compound of formula 6-A:

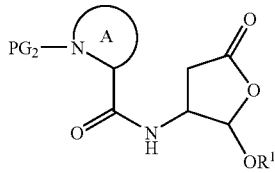

wherein $PG_2$ is a suitable nitrogen protecting group and $R^1$ is as defined in any of the embodiments herein, comprising reacting a compound of formula 5-A:

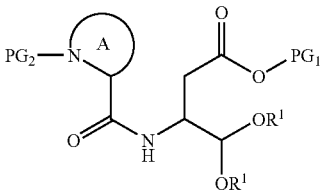

under suitable ring cyclization conditions, to provide the compound of formula 6-A. Suitable ring cyclization conditions include an acid and a suitable solvent; for example, TFA in DCM.

Another embodiment provides a process for preparing a compound of formula 5-A:

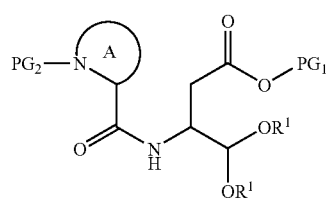

comprising reacting a compound of formula 4-A:

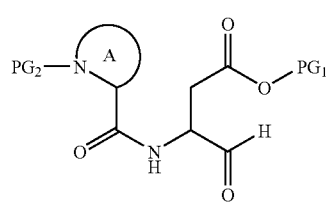

in the presence of $R^1$—OH (or a suitable acetal forming reagent), protic or Lewis acid (for example, TsOH), and a suitable solvent to provide the compound of formula 5-A.

Another embodiment provides a process for preparing a compound of formula 4-A:

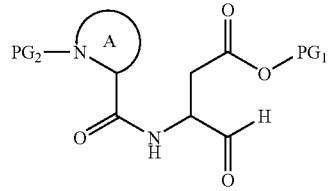

comprising reacting a compound of formula 3-A:

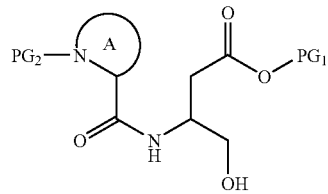

under suitable oxidation conditions (for example, a Swern oxidation: Mancuso, A. J.; Swern, D. Synthesis, 1981, 165-185) to provide the compound of formula 4-A. Preferred oxidation conditions include a TEMPO oxidation (see Example I-1, Method C, below).

Another embodiment provides a process for preparing a compound of formula 3-A:

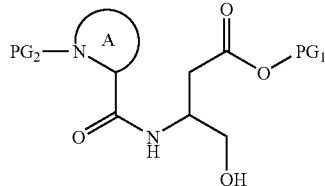
3-A comprising:
reacting a compound of formula 2:

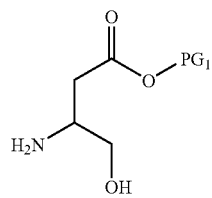
2 with a compound of formula 20-A:

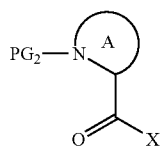
20-A under conditions for coupling an amine and a carboxylic acid (when X is OH), or an amine and an appropriate carboxylic acid (when X is not OH), to provide the compound of formula 3-A.

Another embodiment provides a process for preparing a compound of formula 6:

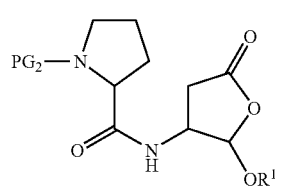
6 wherein $PG_2$ is a suitable nitrogen protecting group and $R^1$ is as defined in any of the embodiments herein, comprising reacting a compound of formula 5:

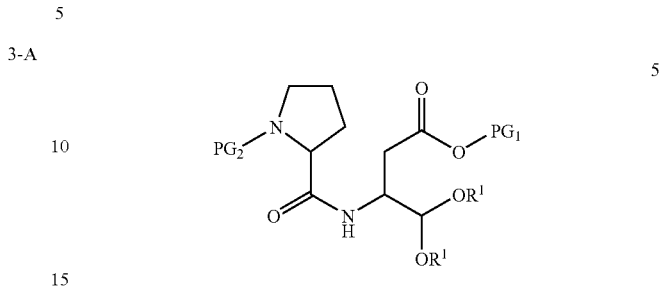
5 under suitable cyclization conditions, to provide the compound of formula 6.

Another embodiment provides a process for preparing a compound of formula 5:

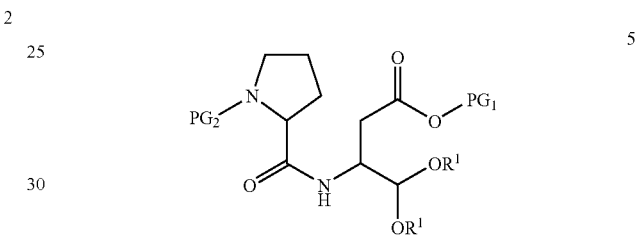
5 comprising reacting a compound of formula 4:

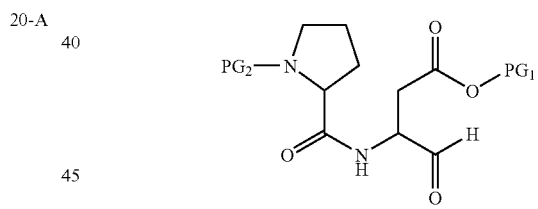
4 in the presence of $R^1$—OH (or a suitable acetal forming reagent), protic or Lewis acid (for example, TsOH), and a suitable solvent to provide the compound of formula 5. Preferably, the solvent is $CH_2Cl_2$, toluene, or chlorobenzene.

Another embodiment provides a process for preparing a compound of formula 4:

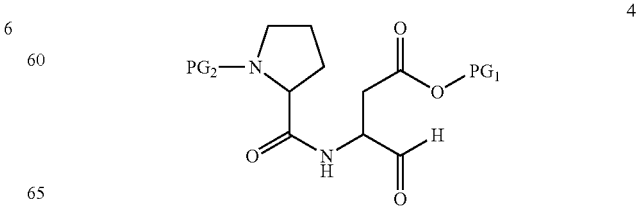
4 comprising reacting a compound of formula 3:

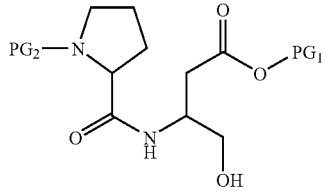

under suitable oxidation conditions (for example a Swern oxidation) to provide the compound of formula 4. Preferred oxidation conditions include a TEMPO oxidation (see Example I-1, Method C, below).

Another embodiment provides a process for preparing a compound of formula 3:

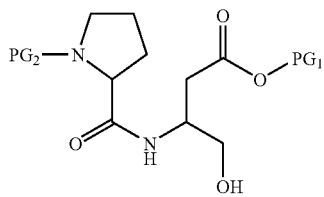

comprising:
reacting a compound of formula 2:

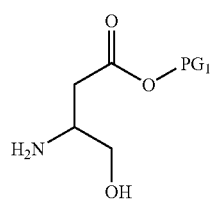

with a compound of formula 20:

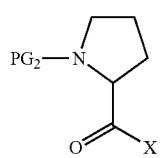

under conditions for coupling an amine and a carboxylic acid (when X is OH), or an amine and an appropriate carboxylic acid (when X is not OH), to provide the compound of formula 3.

Another embodiment provides a process for preparing a compound of formula 16:

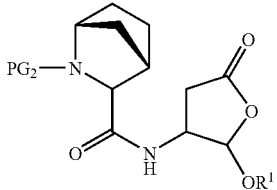

wherein $PG_2$ is a suitable nitrogen protecting group and $R^1$ is as defined in any of the embodiments herein, comprising reacting a compound of formula 15:

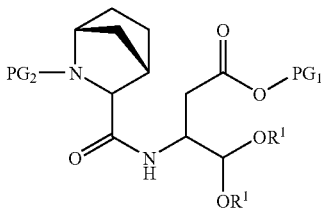

under suitable cyclization conditions, to provide the compound of formula 16.

Another embodiment provides a process for preparing a compound of formula 15:

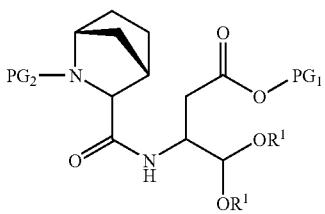

comprising reacting a compound of formula 14:

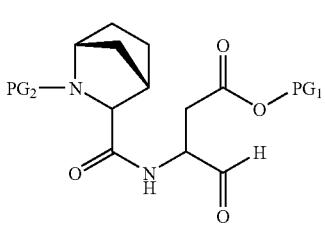

in the presence of $R^1$—OH (or a suitable acetal forming reagent), protic or Lewis acid (for example, TsOH), and a suitable solvent to provide the compound of formula 15.

Another embodiment provides a process for preparing a compound of formula 14:

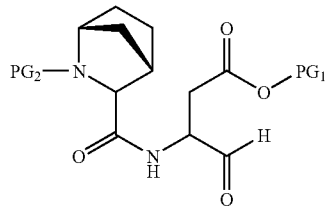

14 comprising reacting a compound of formula 13:

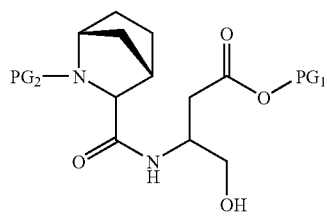

13 under suitable oxidation conditions (example, a Swern oxidation) to provide the compound of formula 14.

Another embodiment provides a process for preparing a compound of formula 13:

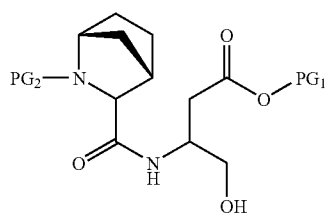

13 comprising reacting a compound of formula 2 with a compound of formula 21:

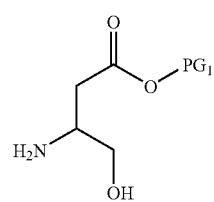

2

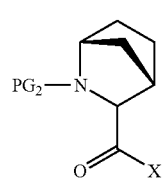

21 under conditions for coupling an amine and a carboxylic acid (when X is OH), or an amine and an appropriate carboxylic acid (when X is not OH), to provide the compound of formula 13.

Another embodiment provides a process for preparing a compound of formula 22:

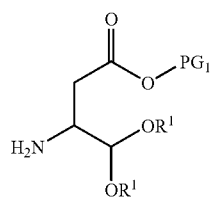

22 comprising reacting a compound of formula 23:

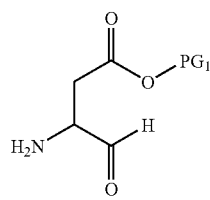

23 in the presence of $R^1$—OH (or a suitable acetal forming reagent), protic or Lewis acid (for example, TsOH), and a suitable solvent to provide the compound of formula 22. Acetal forming equivalents include, but are not limited to, triethylorthoformate, a diethylacetal, such as a $(CH_3)_2C(OCH_2CH_3)_2$. Preferably, the solvent is $CH_2Cl_2$, toluene, or chlorobenzene.

Another embodiment provides a process for preparing a compound of formula 23 comprising reacting a compound of formula 2:

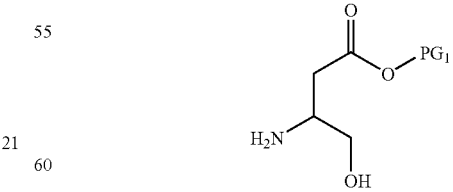

2 under suitable oxidation conditions (example Swern) to provide the compound of formula 23.

Another embodiment provides a process for preparing a compound of formula 5-A

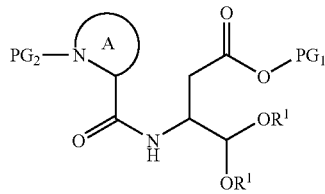

5-A wherein PG$_1$ is a suitable carboxylic acid protecting group, PG$_2$ is a suitable nitrogen-protecting group, and R$^1$ is as defined in any one of claims 1 or 5-9, comprising:
reacting a compound of formula 20-A:

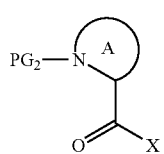

20-A with a compound of formula 22

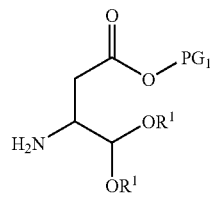

22 under conditions for coupling an amine and a carboxylic acid (when X is OH), or an amine and an appropriate carboxylic acid (when X is an appropriate leaving group), to provide the compound of formula 5-A.

Another embodiment provides a process for preparing a compound of formula 5:

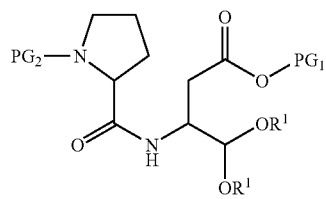

5 comprising reacting a compound of formula 20:

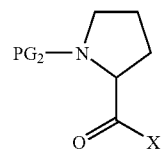

20 with a compound of formula 22

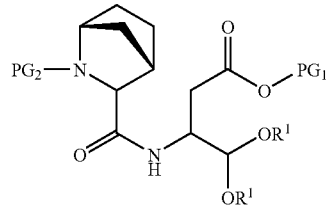

22 under conditions for coupling an amine and a carboxylic acid (when X is OH), or an amine and an appropriate carboxylic acid (when X is not OH), to provide the compound of formula 5.

Another embodiment provides a process for preparing a compound of formula 5-A:

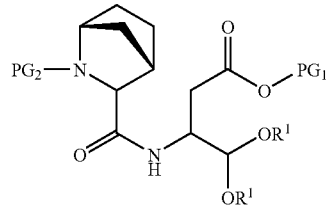

5-A comprising reacting a compound of formula 21:

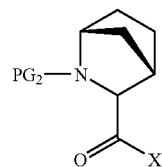

21 with a compound of formula 22

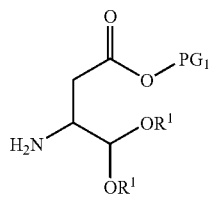

22 under conditions for coupling an amine and a carboxylic acid (when X is OH), or an amine and an appropriate carboxylic acid (when X is not OH), to provide the compound of formula 5-A.

In accordance with this invention, the processes may be used alone or in combination to provide a compound of this invention.

Certain specific embodiments of this invention provide processes for preparing compounds 4 from 3 (in embodiments where compounds 4 are isolated); 5 from 3 (in embodiments where compounds 4 is not isolated but carried on directly, e.g., generated in situ); 5 from 4; and 6 from 5 according to the methods disclosed herein. In a preferred embodiment, compounds 6 are prepared from compounds 5; compounds 5 are prepared from compounds 4 (whether isolated or not); and compounds 4 are prepared from 3. Preferably, compounds 6 are used in the preparation of proline containing caspase inhibitors. Such proline containing caspase inhibitors include, but are not limited to, those disclosed in WO 95/35308, WO 99/47545, WO 01/81330, and WO 01/90063 (which are all incorporated herein by reference). For example, compound IA (and stereoisomers thereof) of WO 01/90063 (which are specifically incorporated herein by reference) could be prepared as disclosed herein (see, e.g., page 13). For the avoidance of doubt, it should be understood that such proline containing compounds could be depicted by formula I except that Ring A is pyrrolidine

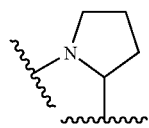

(i.e. is derived from proline).

The processes for converting compounds 6 to proline containing caspase inhibitors are preferably as disclosed herein. The processes for preparing compounds 3 are also preferably as disclosed herein. However other processes known to skilled practitioners could be used to convert compounds 6 to proline containing caspase inhibitors and/or to prepare compounds 3.

Other embodiments of this invention provide the compounds of formula 3 to 6, 3-A to 6-A, and 13-16.

One embodiment of this invention provides the compounds of formula 4A:

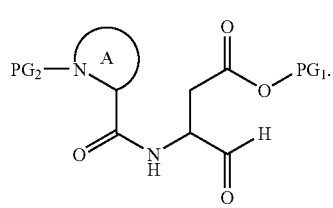

4A

Another embodiment of this invention provides the compounds of formula 4:

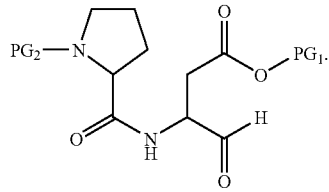

4

Another embodiment of this invention provides the compounds of formula 14:

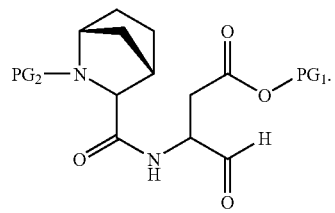

14

One embodiment of this invention provides the compounds of formula 5-A:

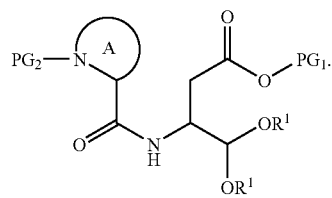

5-A

Another embodiment of this invention provides the compounds of formula 5:

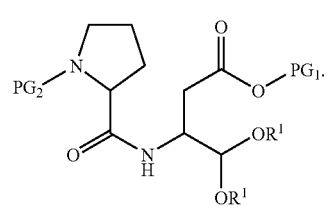

5

Another embodiment of this invention provides the compounds of formula 15:

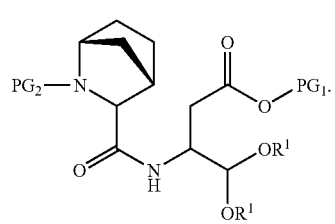

15

One embodiment of this invention provides the compounds of formula 3-A:

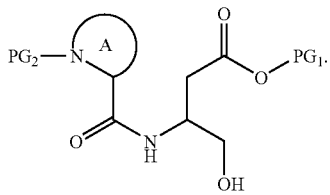

3-A

Another embodiment of this invention provides the compounds of formula 3:

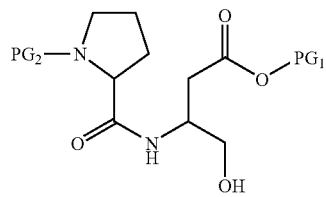

3

Another embodiment of this invention provides the compounds of formula 13:

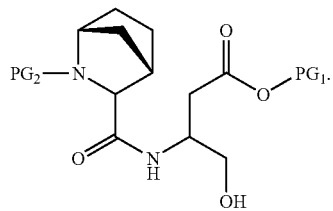

13

In all the above embodiments, the variables are as defined in any of the embodiments herein. In a preferred form of 3, $PG_2$ is Z and $PG_1$ is $C_{1-6}$ straight-chained or branched alkyl group (preferably a t-butyl group), either alone or in combination.

As would be realized by skilled practitioners certain process steps may be accomplished in discrete steps or in situ. For example, deprotection and subsequent reaction of an amine may be accomplished by step-wise (by isolating the amine) or in a one step procedure (without isolating the amine).

In certain embodiments, the above processes are conducted as described herein (e.g., in the schemes, examples, and accompanying description).

Compounds such as 3 could be used in processes for preparing proline containing compounds, such as caspase inhibitors. Proline containing caspase inhibitors include, but are not limited to, those disclosed in WO 95/35308, WO 99/47545, WO 01/81330, and WO 01/90063 (which are all incorporated herein by reference). For example, compound IA (and stereoisomers thereof) of WO 01/90063 (which are specifically incorporated herein by reference) could be prepared as disclosed herein (see, e.g., page 13).

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

For example, a carboxylic acid group in a compound of this invention may be derivatized as, for example, an ester. Preferred esters would be those derived from:

a $C_{1-6}$ straight-chained or branched alkyl, alkenyl, or alkynyl, wherein the alkyl, alkenyl, or alkynyl is optionally substituted with $C_{6-10}$aryl, $CF_3$, Cl, F, OMe, OEt, $OCF_3$, CN, or $NMe_2$;

a $C_{1-6}$ cycloalkyl, wherein 1-2 carbon atoms in the cycloalkyl is optionally replaced with —O— or —$NR^9$—.

Compounds of this invention having a carbonyl group may be similarly derivatized as, e.g., an acetal, ketal, oxime (=$NOR^9$), hydrazine (=$NN(R^9)_2$), thioacetal, or thioketal.

Appropriate derivatives of amines are known in the art and are also included within the scope of this invention.

Certain of the above derivatives would include the protective groups known to skilled practitioners (see, e.g., *Greene*). As would be recognized by a skilled practitioner, these protective groups may also be employed in the processes of this invention.

The compounds of this invention may be assayed for their ability to inhibit apoptosis, the release of IL-1β or caspase activity directly. Assays for each of the activities are known in the art. However, as would be recognized by a skilled practitioner, a prodrug compound of this invention should be active only in assays where the prodrug moiety would be cleaved, typically in in vivo assays.

Assays for caspase activity are described in WO 99/47545.

According to another embodiment, the present invention provides a pharmaceutical composition comprising:

a) a compound of the invention, as defined herein, or a pharmaceutically acceptable salt thereof; and b) a pharmaceutically acceptable carrier, adjuvant or vehicle.

It should be understood that compounds and pharmaceutically acceptable salts thereof are included within this invention are. If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum. In one embodiment, the compositions are as formulated in, e.g., U.S. Pat. No. 6,645,994 and/or U.S. Pat. No. 6,630,473.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compounds and compositions are particularly useful in therapeutic applications relating to an IL-1 mediated disease, an apoptosis mediated disease, an inflammatory disease, an autoimmune disease, a destructive bone disorder, a proliferative disorder, an infectious disease (e.g., bacterial infections, preferably, eye infections), a degenerative disease, a disease associated with cell death, an excess dietary alcohol intake disease, a viral mediated disease, retinal disorders, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs. host disease, organ transplant rejection, organ apoptosis after burn injury, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, hemorrhagic shock, sepsis, septic shock, burns, Shigellosis, Alzheimer's disease, Parkinson's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, Japanese encephalitis, various forms of liver disease, renal disease, polycystic kidney disease, *H. pylori*-associated gastric and duodenal ulcer disease, HIV infection, tuberculosis, meningitis, toxic epidermal necrolysis, pemphigus, and autoinflammatory diseases (sometimes referred to as autoinflammatory fever syndromes) and related syndromes such as Muckle-Wells Syndrome (MWS), Familial Cold Urticaria (FCU), Familial Mediterranean Fever (FMF), Chronic Infantile Neurological Cutaneous and Articular Syndrome (CINCAS), a.k.a. Neonatal Onset Multisystem Inflammatory Disease (NOMID), TNFR1-Associated Periodic Syndrome (TRAPS), and Hyper-IgD periodic fever Syndrome (HIDS). The compounds and compositions are also useful in treating complications associated with coronary artery bypass grafts. The compounds and compositions are also useful for decreasing IGIF (also known as IL-18) or IFN-γ production. The compounds and compositions are also useful in immunotherapy as a cancer treatment.

The compounds and compositions may also be used in methods for preserving cells. These methods would be useful for preserving organs, particularly those intended for transplant, or blood products.

The compounds of this invention are useful as dual caspase-1 and capase-8 inhibitors. Without being bound by theory, the $R^2$ and $R^3$ groups of the compounds of this invention appear to be related to this surprising activity. Bridged A groups of the compounds of this invention, such as

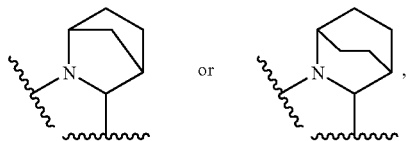

also appear to be related to this surprising activity. As such, the compounds and compositions of this invention are particularly useful in treating or preventing inflammatory conditions.

According to another embodiment, the compositions of this invention may further comprise another therapeutic agent (i.e., one or more additional agents). Such agents include, but are not limited to, thrombolytic agents such as tissue plasminogen activator and streptokinase. When an additional agent is used, the additional agent may be administered either as a separate dosage form or as part of a single dosage form with the compounds or compositions of this invention.

The amount of compound present in the compositions of this invention should be sufficient to cause a detectable decrease in the severity of the disease or in caspase activity and/or cell apoptosis, as measured by any of the assays known in the art.

Dosage levels of between about 0.01 and about 50 or about 100 mg/kg body weight per day, preferably between 0.5 and about 75 mg/kg body weight per day and most preferably between about 1 and about 25 or about 50 mg/kg body weight per day of the active ingredient compound are useful in a monotherapy.

Typically, a compound or composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of this invention and one or more additional therapeutic or prophylactic agents, both the compound and the additional agent should be present at dosage levels of between about 10% to about 100%, and more preferably between about 10% to about 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled practitioner will appreciate, lower or higher doses than those recited above may be required. It should be understood that a specific dosage and treatment regimens for any particular patient will depend upon a variety of factors, including the activity of the specific compound employed, the age, body weight, general health, sex, diet, time of administration, rate of excretion, drug combination, the severity and course of the particular disease, the patient's disposition to the disease being treated, and the judgment of the treating physician. The amount of active ingredients will also depend upon the particular compound and other therapeutic agent, if present, in the composition.

In a preferred embodiment, the invention provides a method of treating a patient, preferably a mammal, having one of the aforementioned diseases, comprising the step of administering to said patient a compound or a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

The compounds of this invention may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention and a carrier suitable for coating said implantable device. In still another aspect, the present invention includes an implantable device coated with a composition comprising a compound of the present invention and a carrier suitable for coating said implantable device.

Another aspect of the invention relates to inhibiting caspase activity in a biological sample, which method comprises contacting said biological sample with a compound of this invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of caspase activity in a biological sample is useful for a variety of purposes that are known to one of skill in the art. Examples of such purposes include, but are not limited to, blood transfusion, organ-transplantation, biological specimen storage, and biological assays.

The compounds of this invention are useful in methods for preserving cells, such as may be needed for an organ transplant or for preserving blood products. Similar uses for caspase inhibitors have been reported [Schierle et al., Nature Medicine, 5, 97 (1999)]. The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

Without being bound by theory, applicants' cyclic acetal compounds are believed to be prodrugs. That is, the acetal portion is cleaved in vivo to provide a corresponding acid-aldehyde compound. As would be recognized by a skilled practitioner, chemical compounds may be metabolized in vivo, e.g., at a site other than the prodrug cleavage site. Any such metabolites are included within the scope of this invention.

In order that this invention be more fully understood, the following preparative and testing examples are set forth. These examples are for the purpose of illustration only and are not to be construed as limiting the scope of the invention in any way.

EXAMPLE I-1

(S,S,S,R)-1-[(2S)-(3-Methoxy-2-methyl-benzoylamino)-3-methyl-butyryl]-pyrrolidine-(2S)-carboxylic acid [(2R)-ethoxy-5-oxo-tetrahydro-furan-(3S)-yl]-amide

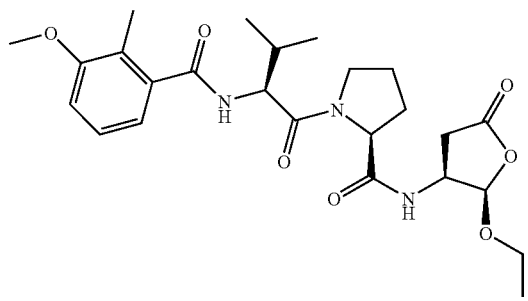

Method A (S)-3-Amino-4-hydroxy-butyric acid tert-butyl ester

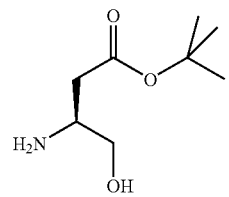

A solution of (S)-benzyloxycarbonylamino-4-hydroxybutyric acid tert-butyl ester (prepared as described in Michel etal, Helvetica Chimica Acta 1999, 1960)(0.94g) in ethyl acetate (15 ml) was hydrogenated over palladium hydroxide/carbon (20% w/w, 160 mg). The catalyst was removed via filtration through celite. Concentration of the filtrate in vacuo afforded the subtitle compound as a colorless oil (486 mg, 91%); $^1$H NMR (400 MHz, CDCl$_3$) δ 1.48 (9H, S), 1.95 (3H, brs), 2.28 (1H, dd), 2.46 (1H, dd), 3.29 (1H, brm), 3.42 (1H, m), 3.60 (1H, m).

Method B (1S)-2-((S)-2-tert-Butoxycarbonyl-1-hydroxymethyl-ethylcarbamoyl)-pyrrolidine-1-carboxylic acid benzyl ester

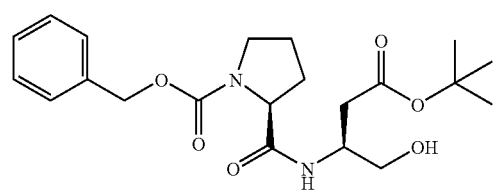

To a stirred solution of (S)-3-Amino-4-hydroxy-butyric acid Lert-butyl ester (800 mg, 4.57 mmol) and Z-Pro-OH (1.14 g, 4.57 mmol) in THF (30 ml) was added 2-hydroxybenzotriazole hydrate (741 mg, 1.2 eq,), DMAP (698 mg, 1.25 eq.), diisopropylethylamine (1.03 ml, 1.3 eq.) and 1-(3-dimethylaminopropyl)-3-ethylcarbodiimide hydrochloride (EDC, 1.05 g, 1.2 eq.). The resulting mixture was stirred at ambient temperature for 18 hours then diluted with ethyl acetate. The mixture was then washed with water, saturated aqueous sodium bicarbonate solution and brine, dried over magnesium sulfate, filtered and concentrated under reduced pressure. The residue was purified by flash chromatography (60% ethyl acetate/petrol) to afford the sub-title compound as a colorless solid (1.483 g, 90%); MS ES(+)407.3.

Method C (1S)-2-((S)-2-tert-Butoxycarbonyl-1-formyl-ethyl-carbamoyl)-pyrrolidine-1-carboxylic acid benzyl ester

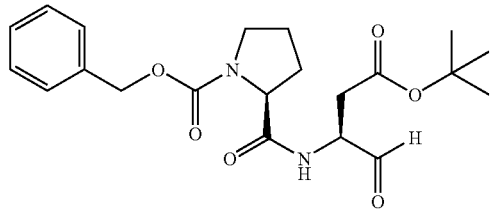

A solution of (1S)-2-((S)-2-tert-Butoxycarbonyl-1-hydroxymethyl-ethylcarbamoyl)-pyrrolidine-1-carboxylic acid benzyl ester (10 g) in DCM (100 ml) was cooled to 0° C. under nitrogen. 2,2,6,6-tetramethylpiperidinyloxy (TEMPO, 38 mg) was then added followed by trichloroisocyanuric acid (6 g) portionwise over 30 minutes. The mixture was stirred at ambient temperature for 2 hours, then filtered through celite. The filtrate was washed with water, 1M sodium thiosulfate solution and water. Drying over magnesium sulfate and concentration under reduced pressure gave the sub-title compound as a pale yellow oil (9.92 g, 99%); $^1$H NMR (400 MHz, d-6 DMSO) δ 1.38 (9H, d), 1.79-1.86 (3H, m), 2.08-2.23 (1H, m), 2.36-2.51 (1H, 2×dd), 2.61-2.86 (1H, 2×dd), 3.88-3.46 (2H, m), 4.24-4.30 (2H, m), 5.05 (2H, quin), 7.28-7.37 (5H, m), 8.59-8.64 (1H, 2×d), 9.21 (0.57H, s), 9.37 (0.43H, s).

Method D (1S)-2-((S)-1-tert-Butoxycarbonylmethyl-2,2-diethoxy-ethylcarbamoyl)-pyrrolidine-1-carboxylic acid benzyl ester

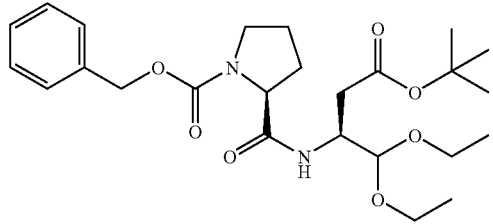

To a solution of (1S)-2-((S)-2-tert-Butoxycarbonyl-1-formyl-ethylcarbamoyl)-pyrrolidine-1-carboxylic acid benzyl ester (4.98 g) in dichloromethane (70 ml) was added triethyl orthoformate (6.2 mL) and p-toluenesulfonic acid monohydrate (47 mg). The resulting mixture was stirred at ambient temperature until no aldehyde remained by TLC. The mixture was concentrated in vacuo, the re-dissolved in dichloromethane (35 mL). Saturated aqueous sodium bicarbonate solution (35 mL) was then added and the organic phase removed. This was washed with water and brine, dried (magnesium sulfate), filtered and concentrated under reduced pressure. This gave the sub-title compound as a pale yellow oil (4.85 g, 82%); $^1$H NMR (400 MHz, d-6 DMSO) δ 1.04-1.11 (6H, m), 1.35-1.37 (9H, m), 1.73-1.89 (3H, m), 2.01-2.49 (3H, m), 3.43-3.52 (6H, m), 4.05-4.29 (3H, m), 4.96-5.06 (2H, m), 7.27-7.38 (5H, m), 7.80 (0.5H, d), 7.88 (0.5H, d).

Method E (1S)-2-((2R,3S)-2-Ethoxy-5-oxo-tetrahydro-furan-3-ylcarbamoyl)-pyrrolidine-1-carboxylic acid benzyl ester 6.1

(1S)-2-((2S,3S)-2-Ethoxy-5-oxo-tetrahydro-furan-3-ylcarbamoyl)-pyrrolidine-1-carboxylic acid benzyl ester 6.2

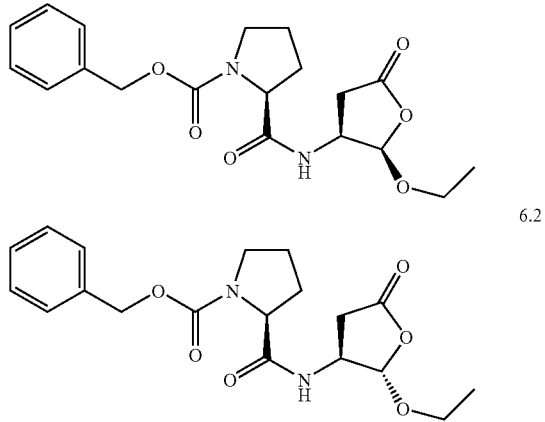

A solution of (1S)-2-((S)-1-tert-Butoxycarbonylmethyl-2,2-diethoxy-ethylcarbamoyl)-pyrrolidine-1-carboxylic acid benzyl ester (4.85 g) in dichloromethane (25 ml) was cooled to 0° C. under nitrogen. Trifluoroacetic acid (6 ml) was then added and the mixture stirred at 0° C. for 15 minutes, then warmed to ambient temperature and stirred until the reaction was complete by TLC. The mixture was then diluted with dichloromethane (90 ml) and saturated aqueous sodium bicarbonate solution (130 ml) and stirred for 15 minutes. The organic phase was then removed and washed with 1:1 saturated aqueous sodium bicarbonate/brine (100 ml), the combined aqueous washings was re-extracted with DCM (100 ml) and the combined organic layers dried (magnesium sulfate), filtered and concentrated under reduced pressure. This afforded the sub-title compound as a mixture of epimers at the ketal centre (C2). The epimers were separated on silica gel, eluting with 30% acetone/petrol. Syn-isomer 6.1 (white solid); $^1$H NMR (400 MHz, d-6 DMSO) δ 1.08-1.17 (3H, m), 1.78-2.01 (3H, m), 2.08-2.12 (1H, m), 2.37-2.57 (1H, 2×dd), 2.61-2.79 (1H, 2×dd), 3.35-3.51 (2H, m), 3.55-3.68 (1H, m), 3.71-3.82 (1H, d), 4.20-4.32 (1H, m), 4.52-4.61 (1H, m), 4.98-5.11 (2H, m), 5.53-5.58 (1H, m), 7.24-7.42 (5h, m), 8.25-8.31 (1H, m); MS ES+377.3 (100%), ES−375.3 (10%); Anti-isomer 6.2 (colorless oil); $^1$H NMR (400 MHz, d-6 DMSO) δ 1.08-1.19 (3H, m), 1.78-1.89 (3H, m), 2.10-2.34 (1H, m), 2.92-3.07 (1H, 2×dd), 3.36-3.51 (3H, m), 3.62-3.78 (2H, m), 4.12-4.21 (2H, m), 4.97-5.12 (3H, m), 7.28-7.40 (5H, m), 8.51-8.58 (1H, m); MS ES+377.4 (100%), ES−375.3 (10%).

(1S)-2-((2R,3S)-2-Methoxy-5-oxo-tetrahydro-furan-3-ylcarbamoyl)-pyrrolidine-1-carboxylic acid benzyl ester 6.3

(1S)-2-((2S,3S)-2-Methoxy-5-oxo-tetrahydro-furan-3-ylcarbamoyl)-pyrrolidine-1-carboxylic acid benzyl ester 6.4

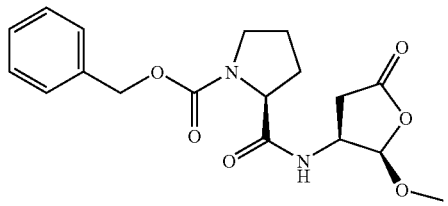

6.3

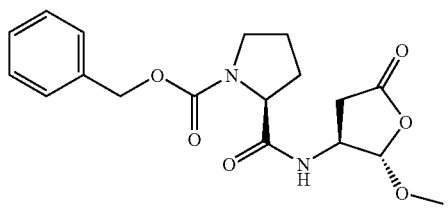

6.4

Prepared in a similar manner to that described in methods A-E, using trimethylorthoformate in step D, to afford the sub-title compounds as a mixture of epimers 6.3 and 6.4. The epimers were separated on silica gel eluting with 30% to 40% 2-Butanone/Petrol to 70% Acetone/Petrol. Syn-isomer 6.3 (viscous colorless oil); $^1$H NMR (400 MHz, d-6 DMSO) δ 1.77-1.89 (3H, m), 2.07-2.12 (1H, m), 2.32-2.43 (1H, 2×d), 2.55-2.61 (1H, 2×d), 2.71-2.81 (1H, 2×d), 3.39-3.62 (4H, m), 4.21-4.30 (1H, m), 4.57-4.64 (1H, m), 5.01-5.09 (2H, m), 5.42-5.47 (1H, m), 7.27-7.42 (5H, m), 8.24-8.31 (1H, m); Anti-isomer 6.4 (white solid); $^1$H NMR (400 MHz, d-6 DMSO) δ 1.79-1.90 (3H, m), 2.09-2.21 (1H, m), 2.23-41 (1H, 2×d), 2.91-3.05 (1H, 2×dd), 3.35-3.71 (5H, m), 4.09-4.21 (2H, m), 4.98-5.19 (3H, m), 7.28-7.41 (5H, m), 8.51-8.58 (1H, m).

(1S)-2-((2R,3S)-2-Isopropoxy-5-oxo-tetrahydro-furan-3-ylcarbamoyl)-pyrrolidine-1-carboxylic acid benzyl ester 6.5

(1S)-2-((2S,3S)-2-Isopropoxy-5-oxo-tetrahydro-furan-3-ylcarbamoyl)-pyrrolidine-1-carboxylic acid benzyl ester 6.6

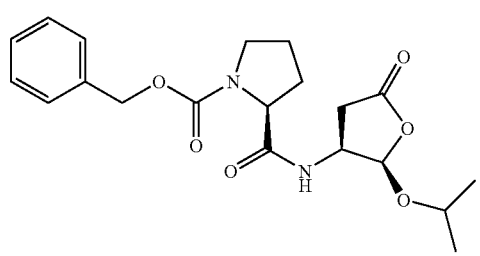

6.5

-continued

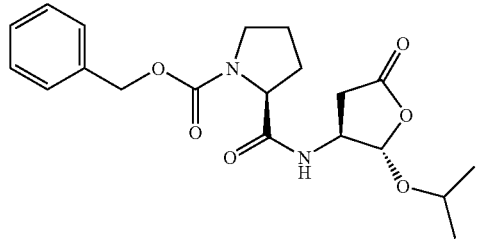

6.6

Prepared in a similar manner to that described in Methods A-E, using triisopropylorthoformate in step D, to afford the sub-title compound as a mixture of epimers 6.5 and 6.6. The epimers were separated on silica gel eluting with 30% to 40% 2-Butanone/Petrol. Syn-isomer 6.5 (colorless gum); $^1$H NMR (400 MHz, d-6 DMSO) δ 1.07-1.16 (6H, m), 1.81-1.86 (2H, m), 2.37-2.71 (2H, m), 3.35-3.53 (2H, m), 3.86-3.90 (1H, m), 4.18-4.24 (1H, m), 4.46-4.55 (1H, m), 4.95-5.10. (2H, m), 5.63 (1H, d), 7.27-7.38 (5H, m), 8.22-8.30 (1H, m); MS ES+391.3 (100%); Anti-isomer 6.6 (white solid); $^1$H NMR (400 MHz, d-6 DMSO) δ 1.07-1.15 (6H, m), 1.78-1.82 (3H, m), 2.07-2.41 (2H, m), 2.87-3.01 (1H, m), 3.35-3.50 (2H, m), 3.74-3.96 (1H, m), 4.07-4.18 (2H, m), 4.95-5.11 (2H, m), 5.22 (1H, 2×s), 7.24-7.39 (5H, m), 8.48-8.53 (1H, m); MS ES+391.4 (100%).

(1S)-2-((2R,3S)-2-Propoxy-5-oxo-tetrahydro-furan-3-ylcarbamoyl)-pyrrolidine-1-carboxylic acid benzyl ester 6.7

(1S)-2-((2S,3S)-2-Propoxy-5-oxo-tetrahydro-furan-3-ylcarbamoyl)-pyrrolidine-1-carboxylic acid benzyl ester 6.8

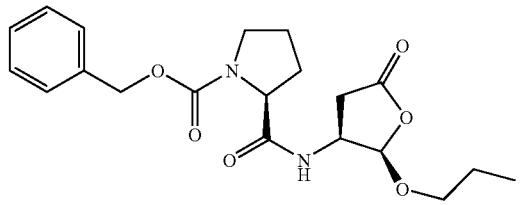

6.7

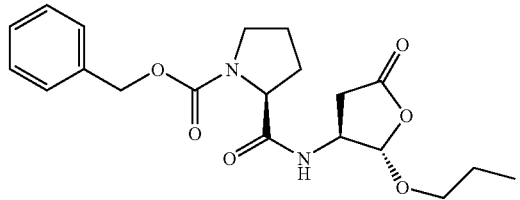

6.8

Prepared in a similar manner to that described in methods A-E, using tripropylorthoformate in step D, to afford the sub-title compounds as a mixture of epimers 6.7 and 6.8. The epimers were separated on silica gel eluting with 30% to 40% 2-Butanone/Petrol. Syn-isomer 6.7 (colorless gum); ¹H NMR (400 MHz, d-6 DMSO) δ 0.84-0.93 (3H, m), 1.55 (2H, m), 1.81-1.89 (3H, m), 2.08-2.22 (1H, m), 2.37-2.61 (1H, 2×dd), 2.71-2.80 (1H, 2×dd), 3.31-3.53 (2H, m), 3.60-3.69 (1H, m), 4.20-4.29 (1H, m), 4.52-4.61 (1H, m), 4.95-5.11 (2H, m), 5.50 (1H, m), 7.27-7.36 (5H, m), 8.27 (1H, m); Anti-isomer 6.8 (colorless oil); ¹H NMR (400 MHz, d-6 DMSO) δ 0.82-0.90 (3H, m), 1.46-1.57 (2H, m), 1.77-1.89 (3H, m), 2.06-2.41 (1H, m), 2.90-3.05 (1H, 2×dd), 3.33-3.66 (5H, m), 4.11-4.20 (2H, m), 4.94-5.10 (3H, m), 7.28-7.37 (5H, m), 8.51 (1H, m).

(1S)-2-((2R,3S)-2-Butoxy-5-oxo-tetrahydro-furan-3-ylcarbamoyl)-pyrrolidine-1-carboxylic acid benzyl ester 6.9

(1S)-2-((2S,3S)-2-Butoxy-5-oxo-tetrahydro-furan-3-ylcarbamoyl)-pyrrolidine-1-carboxylic acid benzyl ester 6.10

6.9

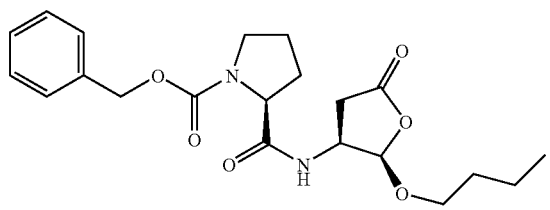

6.10

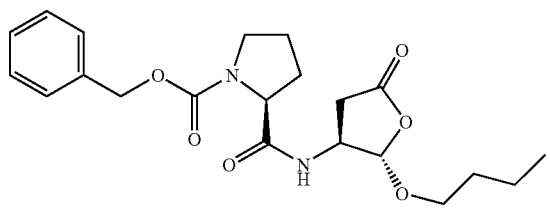

Prepared in a similar manner to that described in methods A-E, using tributylorthoformate in step D, to afford the sub-title compounds as a mixture of epimers 6.9 and 6.10. The epimers were separated on silica gel eluting with 30% to 40% 2-Butanone/Petrol. Syn-isomer 6.9 (colorless gum); ¹H NMR (400 MHz, d-6 DMSO) δ 0.86-0.92 (3H, m), 1.28-1.37 (2H, m), 1.45-1.54 (2H, m), 1.79-1.88 (3H, m), 2.07-2.21 (1H, m), 2.35-2.78 (2H, m), 3.31-3.54 (2H, m), 3.63-3.70 (1H, m), 4.21-4.29 (1H, m), 4.51-4.61 (1H, m), 4.95-5.09 (2H, m), 5.50 (1H, m), 7.27-7.37 (5H, m), 8.25 (1H, m); Anti-isomer 6.10 (colorless oil); ¹H NMR (400 MHz, d-6 DMSO) δ 0.85-0.93 (3H, m), 1.26-1.36 (2H, m), 1.44-1.56 (2H, m), 1.77-1.90 (3H, m), 2.08-2.40 (1H, m), 2.89-3.05 (1H, 2×dd), 3.34-3.70 (5H, m), 4.08-4.19 (2H, m), 4.95-5.10 (3H, m), 7.28-7.39 (5H, m), 8.53 (1H, m).

Method F

{(S)-1-[(1R,3S,4S)-3-((2R,3S)-2-Ethoxy-5-oxo-tetrahydro-furan-3ylcarbamoyl)-2-pyrrolidine-2-carbonyl]-2,2-dimethyl-propyl}-carbamic acid benzyl ester

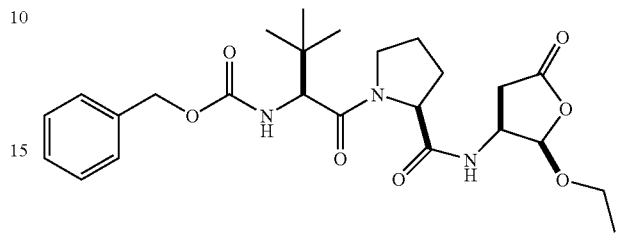

To a solution of (1S)-2-((2R,3S)-2-Ethoxy-5-oxo-tetrahydro-furan-3-ylcarbamoyl)-pyrrolidine-1-carboxylic acid benzyl ester 6.1 (4.68 g) in ethyl acetate (160 ml) and DMF (25 ml) was added triethylamine (2.5 g) followed by palladium hydroxide/carbon (20% w/w, 1 g). The mixture was stirred under an atmosphere of hydrogen until no starting material was present by TLC. The catalyst was removed by filtration through celite. To the filtrate was added (S)-2-benzyloxycarbonylamino-3,3-dimethyl-butyric acid (4.93 g), hydroxybenzotriazole hydrate (2.01 g) and 1-(3-dimethylaminopropyl)-3-ethylcarbodiimide hydrochloride (EDC, 2.85 g). The resulting mixture was stirred at ambient temperature overnight. Saturated aqueous sodium bicarbonate solution (180 ml) was then added and the organic phase removed. This was washed with saturated aqueous ammonium chloride (180 ml), then brine (180 ml), dried (magnesium sulfate), filtered and concentrated under reduced pressure. The crude product was purified on silica gel, eluting with 40-75% ethyl acetate/petrol. The sub-title compound was obtained as a white foam (4.02 g, 66%); ¹H NMR (400 MHz, CDCl₃) δ 0.97 (9H, s), 1.14 (3H, t), 1.79-1.94 (3H, m), 2.02-2.10 (1H, m), 2.44 (1H, dd), 2.75 (1H, dd), 3.52-3.66 (2H, m), 3.70-3.79 (2H, m), 4.22 (1H, d), 4.38-4.41 (1H, m), 4.48-4.58 (1H, m), 5.03 (2H, q), 5.56 (1H, d), 7.26 (1H, d), 7.29-7.40 (5H, m), 8.24 (1H, d); MS ES+490.6 (100%), ES−488.8 (10%).

Method G (S,S,S,R)-1-[(2S)-(3-Methoxy-2-methyl-benzoylamino)-3-methyl-butyryl]-pyrrolidine-(2S)-carboxylic acid [(2R)-ethoxy-5-oxo-tetrahydro-furan-(3S)-yl]-amide

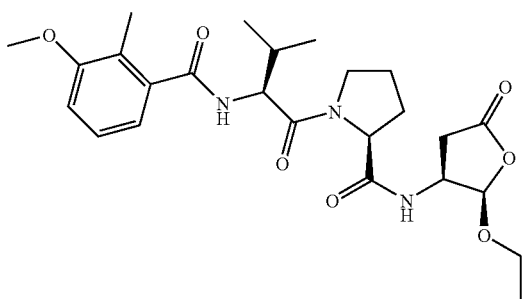

To a solution of {(S)-1-[(1R,3S,4S)-3-((2R,3S)-2-Ethoxy-5-oxo-tetrahydro-furan-3ylcarbamoyl)-2-pyrrolidine-2-carbonyl]-2,2-dimethyl-propyl}-carbamic acid benzyl ester (344 mg) in ethyl acetate (20 ml) was added palladium hydroxide/carbon (20% w/w, 74 mg). The mixture was stirred under an atmosphere of hydrogen until no starting material was present by TLC. The catalyst was removed by filtration through celite and the filtrate concentrated under reduced pressure to give the amine as a brown foam (260 mg). A portion of this material (153 mg) was dissolved in THF and 3-methoxy-2-methyl benzoic acid (146 mg), diisopropylamine (191 µl), hydroxybenzotriazole hydrate (77 mg) and 1-(3-dimethylaminopropyl)-3-ethylcarbodiimide hydrochloride (EDC, 109 mg) were added. The resulting mixture was stirred at ambient temperature for 24 hours then diluted with saturated aqueous sodium bicarbonate. The organic phase was removed and washed with saturated aqueous ammonium chloride, then brine, dried (magnesium sulfate), filtered and concentrated under reduced pressure. The crude product was purified on silica gel, eluting with ethyl acetate. This gave the sub-title compound as a white solid (138 mg, 62%); analytical data summarized in Table 3.

Compounds of formula I-2 to I-58 have been prepared by methods substantially similar to those described in Example I-1.

EXAMPLE I-2

(S,S,S,R)-1-[(2S)-(2-Methoxy-benzoylamino)-3-methyl-butyryl]-pyrrolidine-(2S)-carboxylic acid [(2R)-ethoxy-5-oxo-tetrahydro-furan-(3S)-yl]-amide

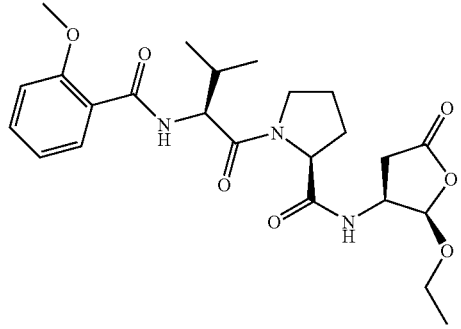

EXAMPLE I-3

(S,S,S,R)-1-[3-Methyl-(2S)-(2-trifluoromethoxy-benzoylamino)-butyryl]-pyrrolidine-(2S)-carboxylic acid [(2R)-ethoxy-5-oxo-tetrahydro-furan-(3S)-yl]-amide

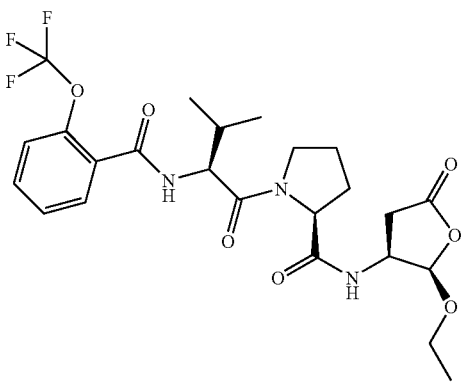

EXAMPLE I-4

(S,S,S,R)-1-[(2S)-(3-Hydroxy-2-methyl-benzoylamino)-3-methyl-butyryl]-pyrrolidine-(2S)-carboxylic acid [(2R)-ethoxy-5-oxo-tetrahydro-furan-(3S)-yl]-amide

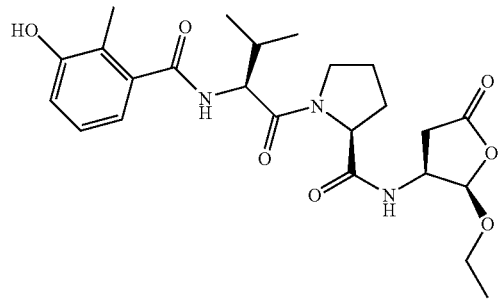

EXAMPLE I-5

(S,S,S,R)-1-[(2S)-(3-Amino-2-methyl-benzoylamino)-3-methyl-butyryl]-pyrrolidine-(2S)-carboxylic acid [(2R)-ethoxy-5-oxo-tetrahydro-furan-(3S)-yl]-amide

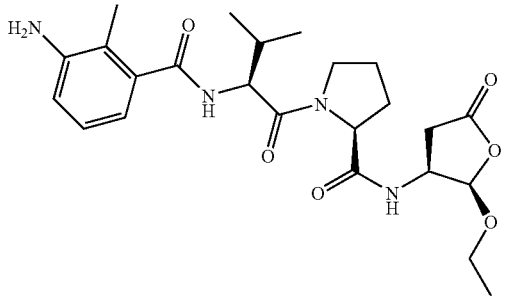

EXAMPLE I-6

(S,S,S,R)-1-[(2S)-(2,6-Dichloro-benzoylamino)-3-methyl-butyryl]-pyrrolidine-(2S)-carboxylic acid [(2R)-ethoxy-5-oxo-tetrahydro-furan-(3S)-yl]-amide

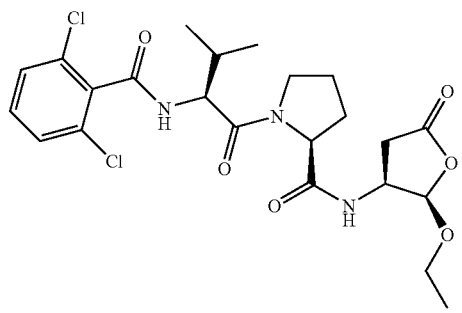

EXAMPLE I-7

(S,S,S,R)—N-{(1S)-[(2S)-((2R)-Ethoxy-5-oxo-tetrahydro-furan-(3S)-ylcarbamoyl)-pyrrolidine-1-carbonyl]-2-methyl-propyl}-2-methyl-nicotinamide

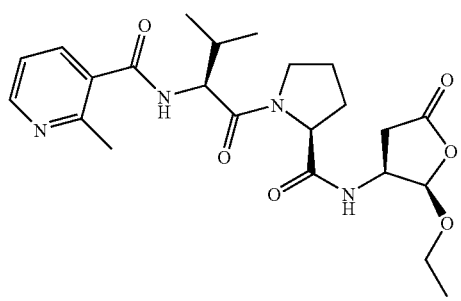

EXAMPLE I-8

(S,S,S,R)—N-{(1S)-[(2S)-((2R)-Ethoxy-5-oxo-tetrahydro-furan-(3S)-ylcarbamoyl)-pyrrolidine-1-carbonyl]-2-methyl-propyl}-4-methyl-nicotinamide

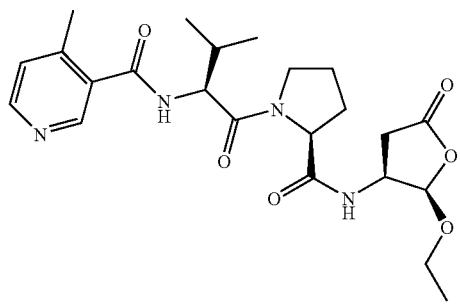

EXAMPLE I-9

(S,S,S,R)-1-{3-Methyl-(2S)-[(3-methyl-thiophene-2-carbonyl)-amino]-butyryl}-pyrrolidine-(2S)-carboxylic acid [(2R)-ethoxy-5-oxo-tetrahydro-furan-(3S)-yl]-amide

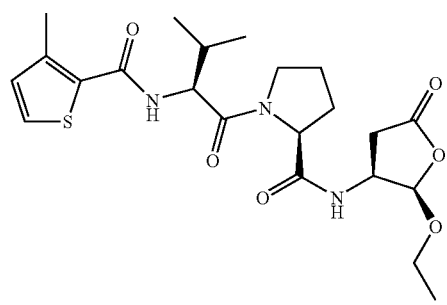

EXAMPLE I-10

(S,S,S,R)-2,3-Dichloro-N-{(1S)-[(2S)-((2R)-ethoxy-5-oxo-tetrahydro-furan-(3S)-ylcarbamoyl)-pyrrolidine-1-carbonyl]-2-methyl-propyl}-isonicotinamide

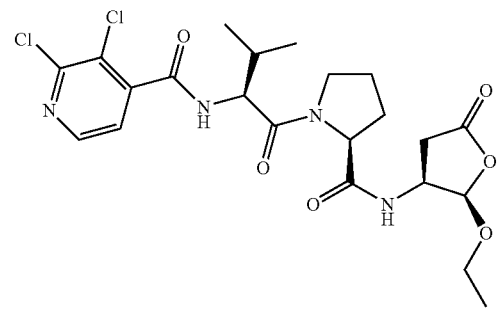

EXAMPLE I-11

(S,S,S,R)-3,5-Dichloro-N-{(1S)-[(2S)-((2R)-ethoxy-5-oxo-tetrahydro-furan-(3S)-ylcarbamoyl)-pyrrolidine-1-carbonyl]-2-methyl-propyl}-isonicotinamide

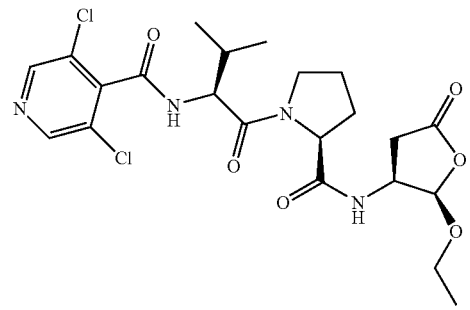

EXAMPLE I-12

(S,S,S,R)-1-[(2S)-(3-Methoxy-2-methyl-benzoylamino)-3,3-dimethyl-butyryl]-pyrrolidine-(2S)-carboxylic acid [(2R)-ethoxy-5-oxo-tetrahydro-furan-(3S)-yl]-amide

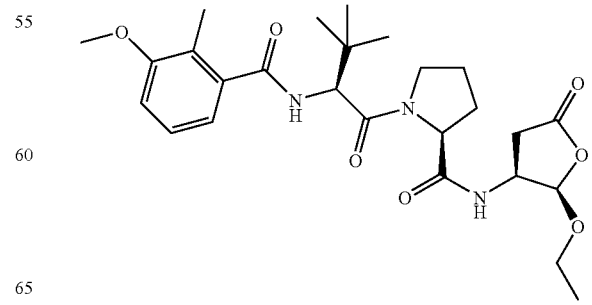

EXAMPLE I-13

(S,S,S,R)-1-[(2S)-(3-Methoxy-2-methyl-benzoylamino)-3-methyl-butyryl]-pyrrolidine-(2S)-carboxylic acid [(2R)-methoxy-5-oxo-tetrahydro-furan-(3S)-yl]-amide

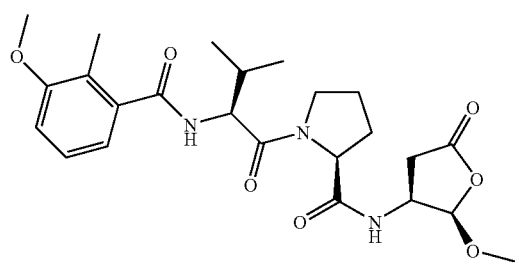

EXAMPLE I-14

(S,S,S,R)-1-[(2S)-(3-Methoxy-2-methyl-benzoylamino)-3-methyl-butyryl]-pyrrolidine-(2S)-carboxylic acid [(2R)-isopropoxy-5-oxo-tetrahydro-furan-(3S)-yl]-amide

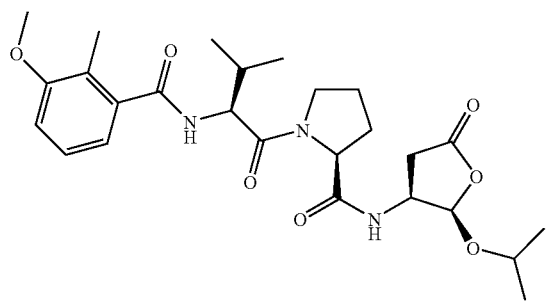

EXAMPLE I-15

(S,S,S,R)-1-[(2S)-(3-Methoxy-2-methyl-benzoylamino)-3-methyl-butyryl]-pyrrolidine-(2S)-carboxylic acid [5-oxo-(2R)-propoxy-5-tetrahydro-furan-(3S)-yl]-amide

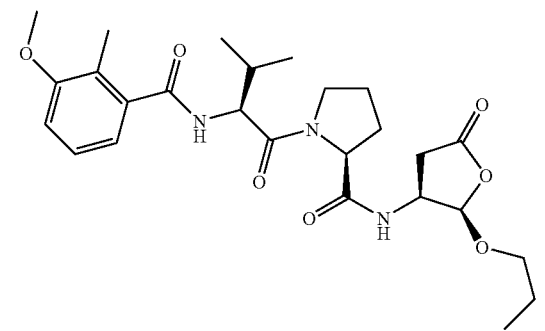

EXAMPLE I-16

(S,S,S,R)-1-[(2S)-(2-Chloro-benzoylamino)-3-methyl-butyryl]-pyrrolidine-(2S)-carboxylic acid [(2R)-ethoxy-5-oxo-tetrahydro-furan-(3S)-yl]-amide

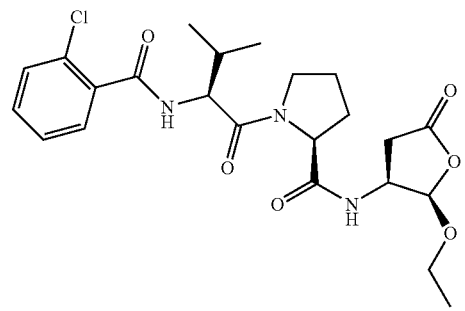

EXAMPLE I-17

(S,S,S,R)-1-[3,3-Dimethyl-(2S)-(2-methyl-benzoylamino)-butyryl]-pyrrolidine-(2S)-carboxylic acid [(2R)-ethoxy-5-oxo-tetrahydro-furan-(3S)-yl]-amide

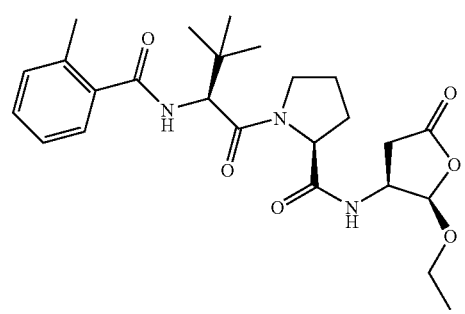

EXAMPLE I-18

(S,S,S,R)-1-[3-Methyl-2(S)-(2-trifluoromethyl-benzoylamino)-butyryl]-pyrrolidine-(2S)-carboxylic acid [(2R)-ethoxy-5-oxo-tetrahydro-furan-3(S)-yl]-amide

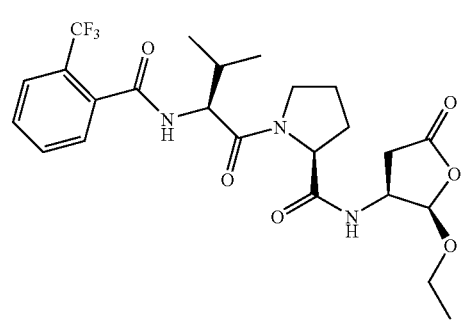

EXAMPLE I-19

(S,S,S,R)-1-[2(S)-(2-Chloro-benzoylamino)-3,3-dimethyl-butyryl]-pyrrolidine-(2S)-carboxylic acid [(2R)-methoxy-5-oxo-tetrahydro-furan-(3S)-yl]-amide

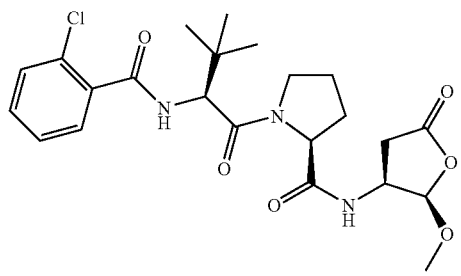

EXAMPLE I-20

(S,S,S,R)-1-[3,3-Dimethyl-(2S)-(2-trifluoromethyl-benzoylamino)-butyryl]-pyrrolidine-(2S)-carboxylic acid [(2R)-isopropoxy-5-oxo-tetrahydro-furan-(3S)-yl]-amide

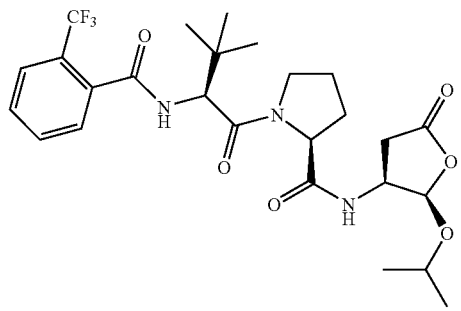

EXAMPLE I-21

(S,S,S,R)-1-[(2S)-(2-Chloro-benzoylamino)-3,3-dimethyl-butyryl]-pyrrolidine-(2S)-carboxylic acid [(2R)-ethoxy-5-oxo-tetrahydro-furan-(3S)-yl]-amide

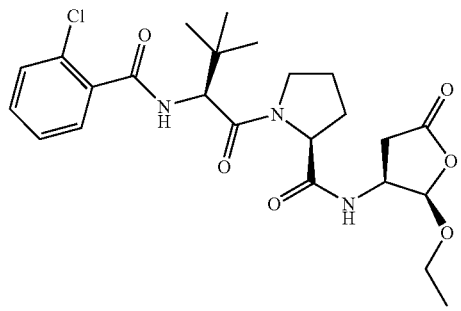

EXAMPLE I-22

(S,S,S,R)-1-[3,3-Dimethyl-(2S)-(2-trifluoromethyl-benzoylamino)-butyryl]-pyrrolidine-(2S)-carboxylic acid [(2R)-ethoxy-5-oxo-tetrahydro-furan-(3S)-yl]-amide

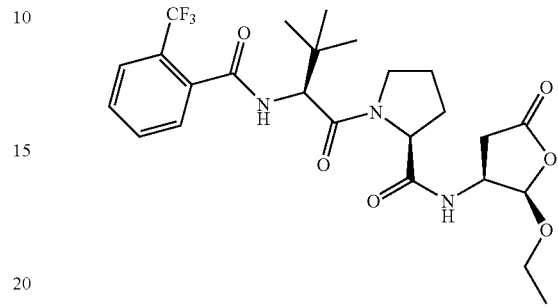

EXAMPLE I-23

(S,S,S,R)-1-[(2S)-(2-Chloro-benzoylamino)-3,3-dimethyl-butyryl]-pyrrolidine-(2S)-carboxylic acid [5-oxo-(2R)-propoxy-tetrahydro-furan-(3S)-yl]-amide

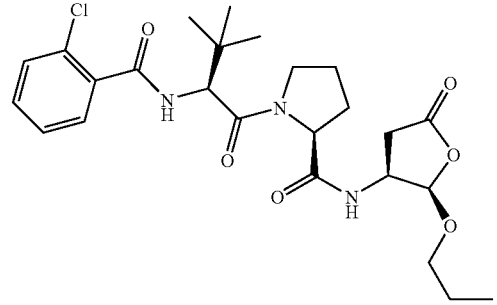

EXAMPLE I-24

(S,S,S,R)-1-[(2S)-(2-Chloro-benzoylamino)-3,3-dimethyl-butyryl]-pyrrolidine-(2S)-carboxylic acid [(2R)-butoxy-5-oxo-tetrahydro-furan-(3S)-yl]-amide

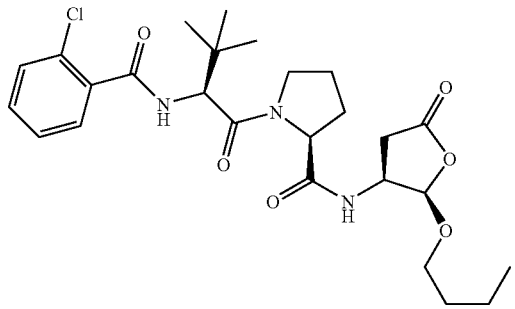

EXAMPLE I-25

(S,S,S,R)-1-[(2S)-(2-Chloro-3-trifluoromethoxy-benzoylamino)-3,3-dimethyl-butyryl]-pyrrolidine-(2S)-carboxylic acid [(2R)-ethoxy-5-oxo-tetrahydro-furan-(3S)-yl]-amide

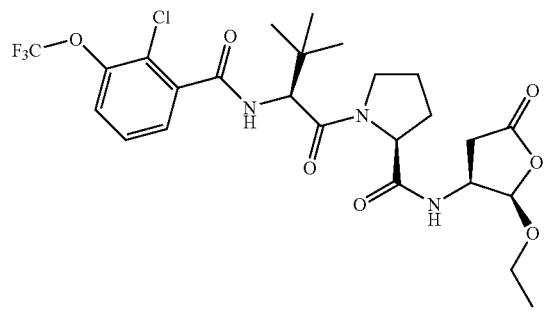

EXAMPLE I-26

(S,S,S,R)-1-[(2S)-(2-Chloro-benzoylamino)-3-methyl-butyryl]-pyrrolidine-(2S)-carboxylic acid [5-oxo-(2R)-propoxy-tetrahydro-furan-(3S)-yl]-amide

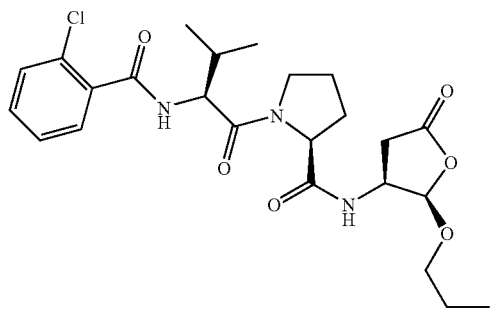

EXAMPLE I-27

(S,S,S,S)-1-[(2S)-(2-Chloro-benzoylamino)-3-methyl-butyryl]-pyrrolidine-(2S)-carboxylic acid [5-oxo-(2S)-propoxy-tetrahydro-furan-(3S)-yl]-amide

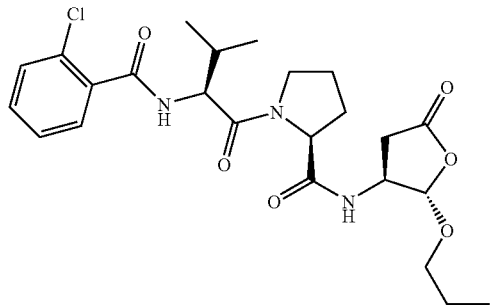

EXAMPLE I-28

(S,S,S,S)-1-[(2S)-(2-Chloro-benzoylamino)-3-methyl-butyryl]-pyrrolidine-(2S)-carboxylic acid [(2S)-ethoxy-5-oxo-tetrahydro-furan-(3S)-yl]-amide

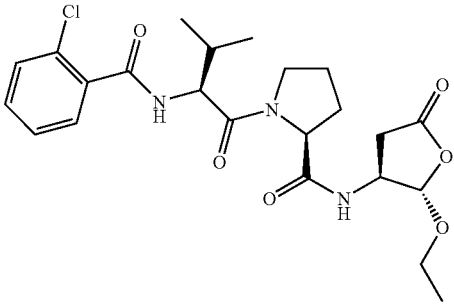

EXAMPLE I-29

(S,S,S,R)-1-[(2S)-(2-Chloro-benzoylamino)-3-methyl-butyryl]-pyrrolidine-(2S)-carboxylic acid [(2R)-butoxy-5-oxo-tetrahydro-furan-(3S)-yl]-amide

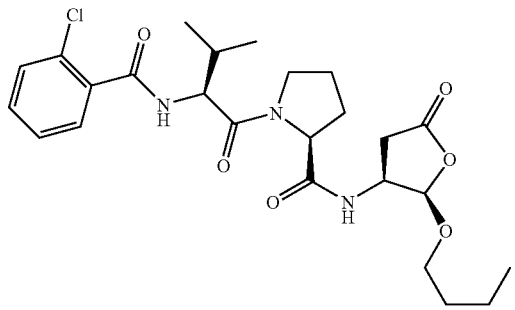

EXAMPLE I-30

(S,S,S,S)-1-[(2S)-(2-Chloro-benzoylamino)-3-methyl-butyryl]-pyrrolidine-(2S)-carboxylic acid [(2S)-butoxy-5-oxo-tetrahydro-furan-(3S)-yl]-amide

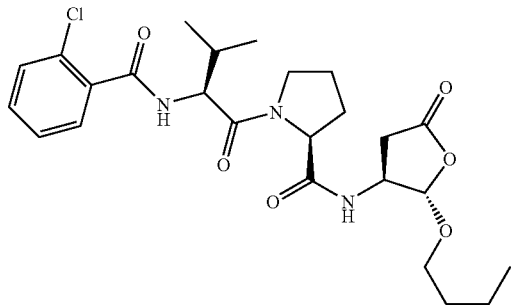

EXAMPLE I-31

(S,S,S,R)-1-[(2S)-(2-Chloro-benzoylamino)-3-methyl-butyryl]-pyrrolidine-(2S)-carboxylic acid [(2R)-isopropoxy-5-oxo-tetrahydro-furan-(3S)-yl]-amide

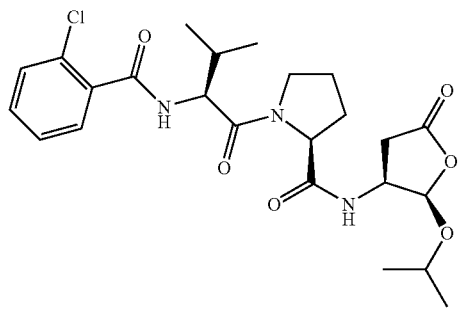

EXAMPLE I-32

(S,S,S,S)-1-[(2S)-(2-Chloro-benzoylamino)-3-methyl-butyryl]-pyrrolidine-(2S)-carboxylic acid [(2S)-isopropoxy-5-oxo-tetrahydro-furan-(3S)-yl]-amide

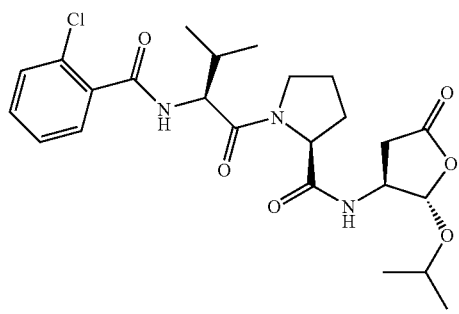

EXAMPLE I-33

(S,S,S,R)-1-[(2S)-(2-Chloro-3-cyclopropyloxy-benzoylamino)-3,3-dimethyl-butyryl]-pyrrolidine-(2S)-carboxylic acid [(2R)-ethoxy-5-oxo-tetrahydro-furan-(3S)-yl]-amide

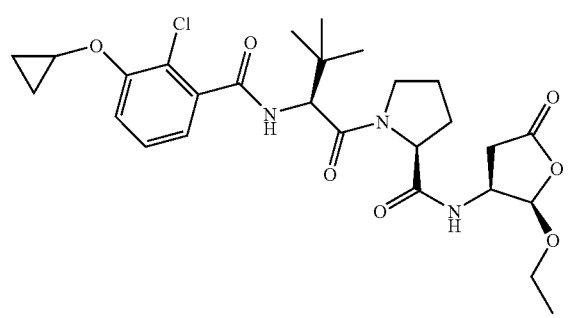

EXAMPLE I-34

(S,S,S,R)-1-[(2S)-(2-Chloro-3-methyl-benzoylamino)-3,3-dimethyl-butyryl]-pyrrolidine-(2S)-carboxylic acid [(2R)-ethoxy-5-oxo-tetrahydro-furan-(3S)-yl]-amide

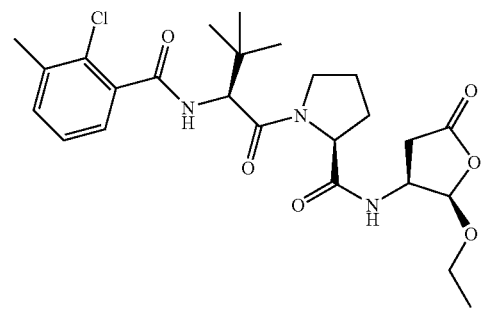

EXAMPLE I-35

(S,S,S,R)-1-[(2S)-(2-chloro-3-methoxy-benzoylamino)-3-methyl-butyryl]-pyrrolidine-(2S)-carboxylic acid [(2R)-ethoxy-5-oxo-tetrahydro-furan-(3S)-yl]-amide

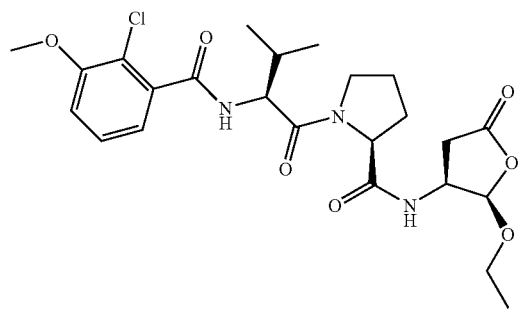

EXAMPLE I-36

(S,S,S,R)-1-[(2S)-(2-Chloro-3-ethyl-benzoylamino)-3,3-dimethyl-butyryl]-pyrrolidine-(2S)-carboxylic acid [(2R)-ethoxy-5-oxo-tetrahydro-furan-(3S)-yl]-amide

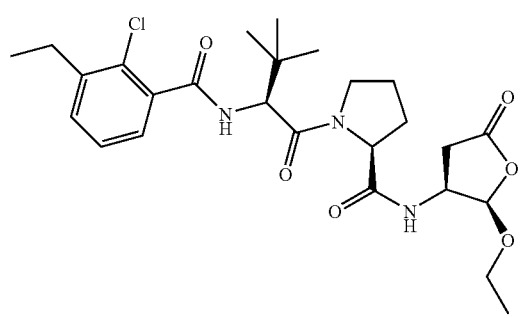

EXAMPLE I-37

(S,S,S,R)-1-[(2S)-(2-chloro-4-methoxy-benzoylamino)-3-methyl-butyryl]-pyrrolidine-(2S)-carboxylic acid [(2R)-ethoxy-5-oxo-tetrahydro-furan-(3S)-yl]-amide

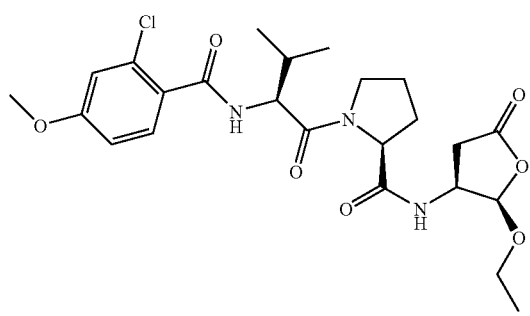

EXAMPLE I-38

(S,S,S,R)-1-[(2S)-(2-Chloro-3-cyclopropylmethyl-benzoylamino)-3,3-dimethyl-butyryl]-pyrrolidine-(2S)-carboxylic acid [(2R)-ethoxy-5-oxo-tetrahydro-furan-(3S)-yl]-amide

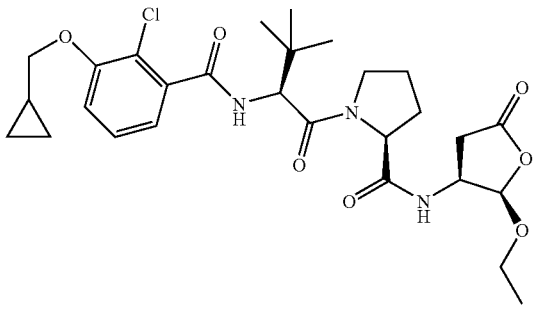

EXAMPLE I-39

(S,S,S,R)-1-[(2S)-(2-Chloro-3-hydroxy-benzoylamino)-3,3-dimethyl-butyryl]-pyrrolidine-(2S)-carboxylic acid [(2R)-ethoxy-5-oxo-tetrahydro-furan-(3S)-yl]-amide

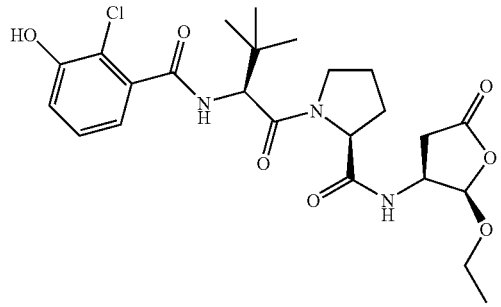

EXAMPLE I-40

(S,S,S,R)-1-[(2S)-(2-Chloro-4-acetamido-benzoylamino)-3-methyl-butyryl]-pyrrolidine-(2S)-carboxylic acid [(2R)-ethoxy-5-oxo-tetrahydro-furan-(3S)-yl]-amide

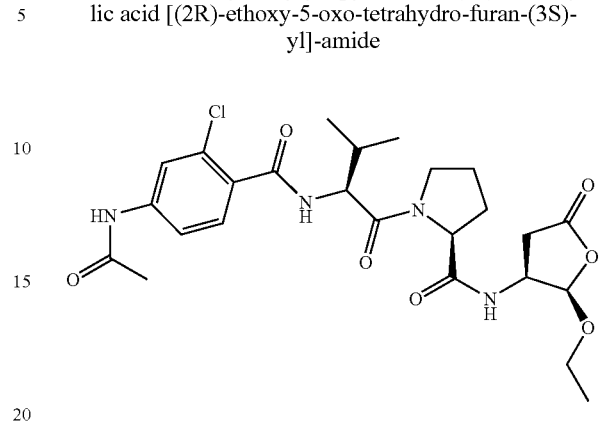

EXAMPLE I-41

(S,S,S,R)-1-[(2S)-(2-Chloro-3-acetamido-benzoylamino)-3,3-dimethyl-butyryl]-pyrrolidine-(2S)-carboxylic acid [(2R)-ethoxy-5-oxo-tetrahydro-furan-(3S)-yl]-amide

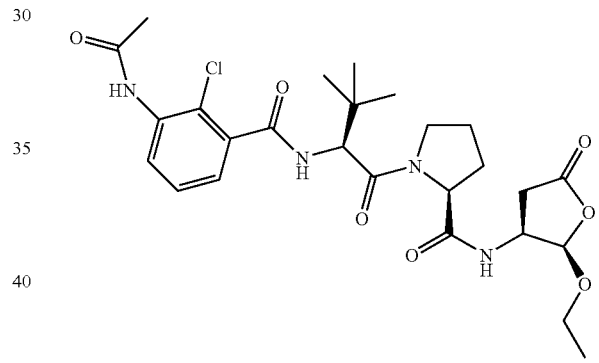

EXAMPLE I-42

(S,S,S,R)-1-[(2S)-(2-methyl-3-acetamido-benzoylamino)-3,3-dimethyl-butyryl]-pyrrolidine-(2S)-carboxylic acid [(2R)-ethoxy-5-oxo-tetrahydro-furan-(3S)-yl]-amide

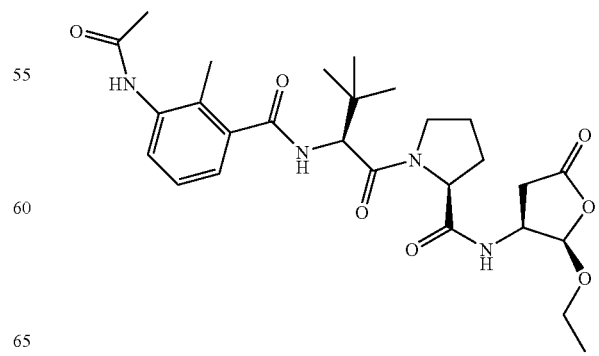

EXAMPLE I-43

(S,S,S,R)-1-[(2S)-(2-Chloro-4-acetamido-benzoylamino)-3,3-dimethyl-butyryl]-pyrrolidine-(2S)-carboxylic acid [(2R)-ethoxy-5-oxo-tetrahydro-furan-(3S)-yl]-amide

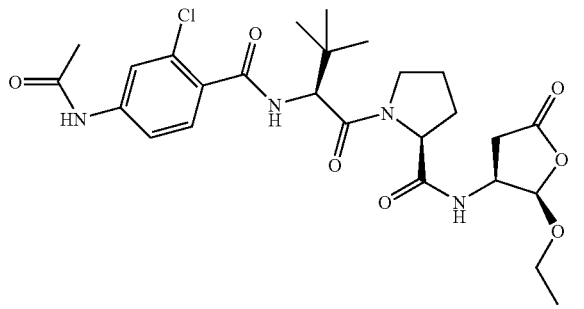

EXAMPLE I-44

(S,S,S,R)-1-[(2S)-(2-fluoro-4-acetamido-benzoylamino)-3,3-dimethyl-butyryl]-pyrrolidine-(2S)-carboxylic acid [(2R)-ethoxy-5-oxo-tetrahydro-furan-(3S)-yl]-amide

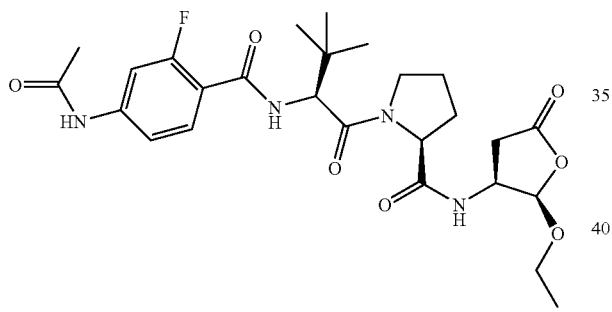

EXAMPLE I-45

(S,S,S,R)-1-[(2S)-(2-fluoro-4-acetamido-benzoylamino)-3-methyl-butyryl]-pyrrolidine-(2S)-carboxylic acid [(2R)-ethoxy-5-oxo-tetrahydro-furan-(3S)-yl]-amide

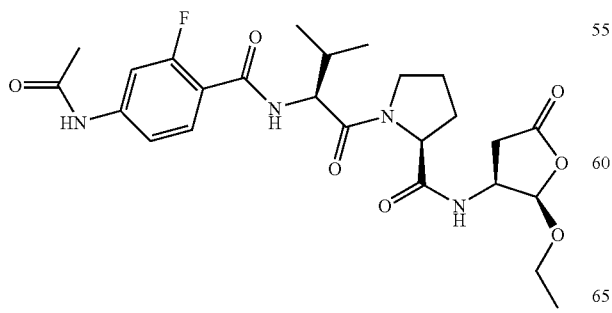

EXAMPLE I-46

(S,S,S,R)-1-[(2S)-(2-chloro-4-isopropyloxy-benzoylamino)-3-methyl-butyryl]-pyrrolidine-(2S)-carboxylic acid [(2R)-ethoxy-5-oxo-tetrahydro-furan-(3S)-yl]-amide

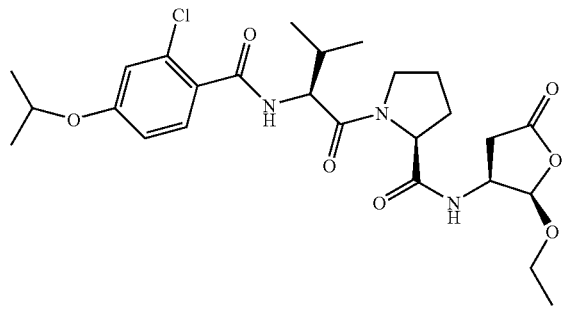

EXAMPLE I-47

(S,S,S,R)-1-[(2S)-(2-chloro-4-hydroxy-benzoylamino)-3,3-dimethyl-butyryl]-pyrrolidine-(2S)-carboxylic acid [(2R)-ethoxy-5-oxo-tetrahydro-furan-(3S)-yl]-amide

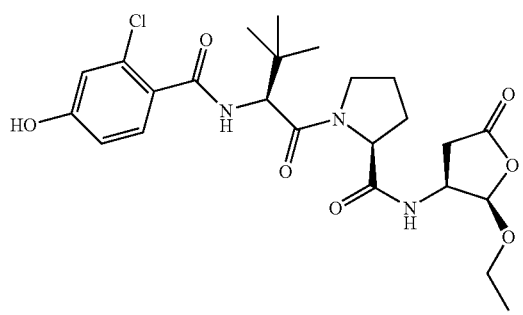

EXAMPLE I-48

(S,S,S,R)-1-[(2S)-(2-chloro-4-methoxymethyl-benzoylamino)-3,3-dimethyl-butyryl]-pyrrolidine-(2S)-carboxylic acid [(2R)-ethoxy-5-oxo-tetrahydro-furan-(3S)-yl]-amide

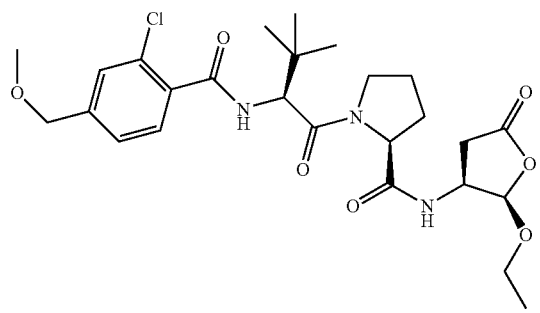

EXAMPLE I-49

(S,S,S,R)-1-[(2S)-(2-Chloro-4-isobutyrylamido-benzoylamino)-3,3-dimethyl-butyryl]-pyrrolidine-(2S)-carboxylic acid [(2R)-ethoxy-5-oxo-tetrahydro-furan-(3S)-yl]-amide

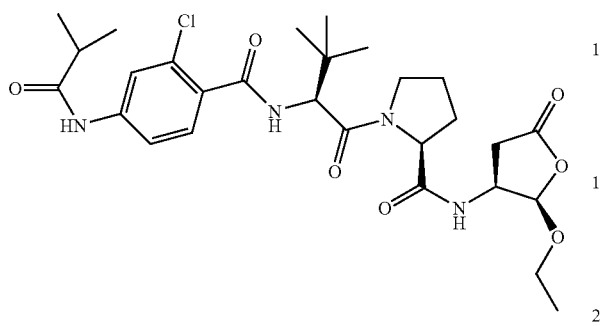

EXAMPLE I-50

(S,S,S,R)-1-[(2S)-(2-Chloro-4-acetamido-benzoylamino)-3-cyclohexyl]-pyrrolidine-(2S)-carboxylic acid [(2R)-ethoxy-5-oxo-tetrahydro-furan-(3S)-yl]-amide

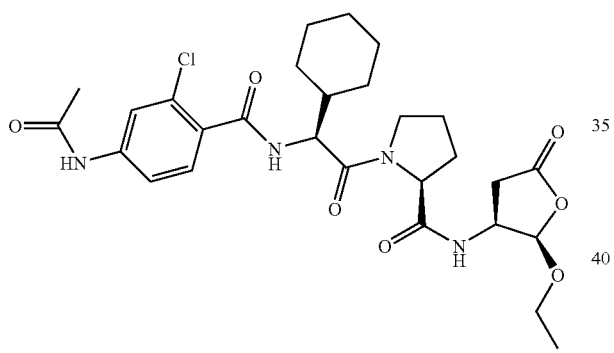

EXAMPLE I-51

(S,S,S,R)-1-[(2S)-(2-Chloro-4-methoxycarbonylamino-benzoylamino)-3,3-dimethyl-butyryl]-pyrrolidine-(2S)-carboxylic acid [(2R)-ethoxy-5-oxo-tetrahydro-furan-(3S)-yl]-amide

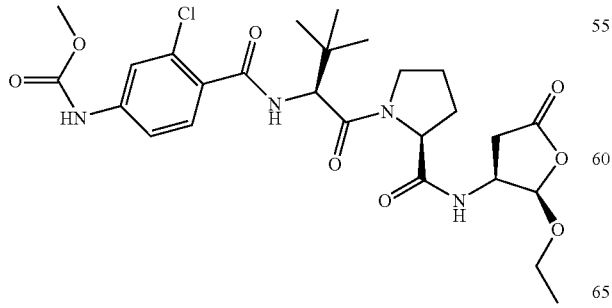

EXAMPLE I-52

(S,S,S,R)-1-[(2S)-(2-Chloro-3-phenoxy-benzoylamino)-3,3-dimethyl-butyryl]-pyrrolidine-(2S)-carboxylic acid [(2R)-ethoxy-5-oxo-tetrahydro-furan-(3S)-yl]-amide

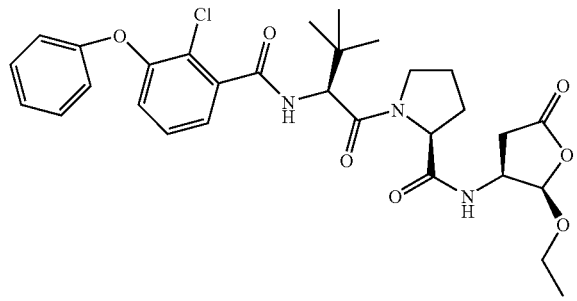

EXAMPLE I-53

(S,S,S,R)-1-[(2S)-(2-Chloro-4-thiazolylamino-benzoylamino)-3,3-dimethyl-butyryl]-pyrrolidine-(2S)-carboxylic acid [(2R)-ethoxy-5-oxo-tetrahydro-furan-(3S)-yl]-amide

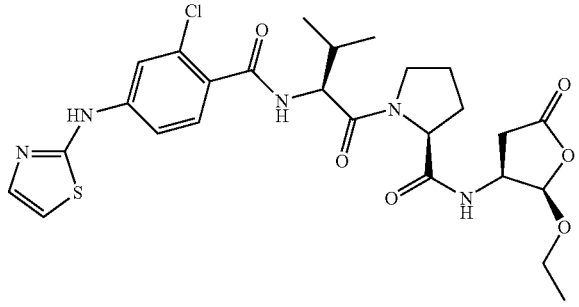

EXAMPLE I-54

(S,S,S,R)-1-[(2S)-(3-Amino-2-chloro-benzoylamino)-3-methyl-butyryl]-pyrrolidine-(2S)-carboxylic acid [(2R)-ethoxy-5-oxo-tetrahydro-furan-(3S)-yl]-amide

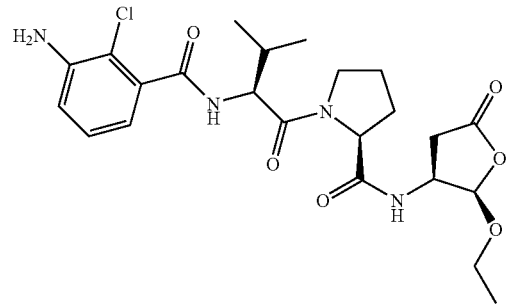

EXAMPLE I-55

(S,S,S,R)-1-[(2S)-(2-Chloro-benzoylamino)-3-thiazol-4-yl-propionyl]-pyrrolidine-(2S)-carboxylic acid [(2R)-ethoxy-5-oxo-tetrahydro-furan-(3S)-yl]-amide

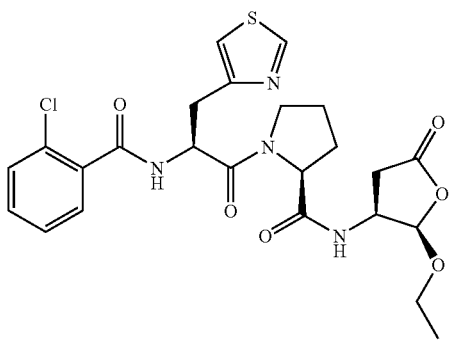

EXAMPLE I-56

(S,S,S,R)-1-[(2S)-(3-Methoxy-2-methyl-benzoylamino)-3-thiazol-4-yl-propionyl]-pyrrolidine-(2S)-carboxylic acid [(2R)-ethoxy-5-oxo-tetrahydro-furan-(3S)-yl]-amide

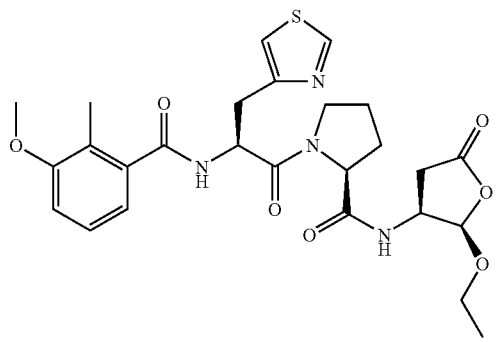

EXAMPLE I-57

(S,S,S,R)-1-[(2S)-(2-Chloro-3-methoxy-benzoylamino)-3,3-dimethyl-butyryl]-pyrrolidine-(2S)-carboxylic acid [(2R)-ethoxy-5-oxo-tetrahydro-furan-(3S)-yl]-amide

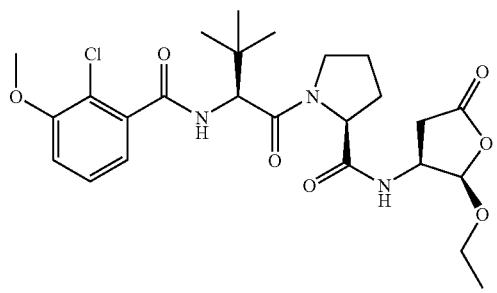

EXAMPLE I-58

(S,S,S,R)-1-[(2S)-(2-Chloro-benzoylamino)-3,3-dimethyl-butyryl]-piperidine-(2S)-carboxylic acid [(2R)-ethoxy-5-oxo-tetrahydro-furan-(3S)-yl]-amide

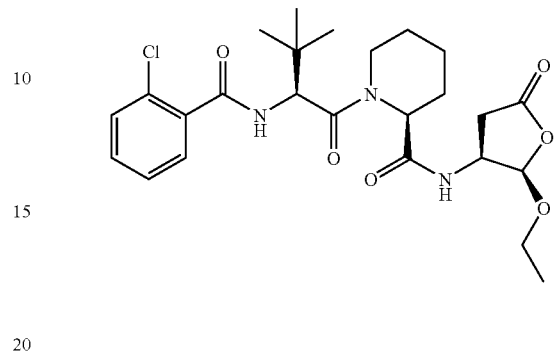

EXAMPLE I-59

2-[(2S)-(3-Methoxy-2-methyl-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

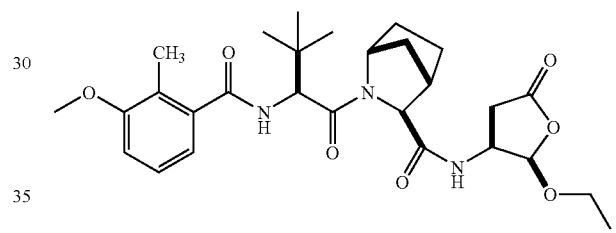

Method H (1R,3S,4S)-3((S)-2-tert-Butoxycarbonyl-1-hydroxymethyl-ethylcarbamoyl)-2-aza-bicyclo[2.2.1]heptane-2-carboxylic acid benzyl ester

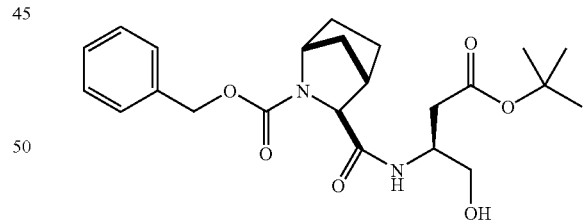

To a stirred solution of (S)-3-Amino-4-hydroxy-butyric acid tert-butyl ester (486 mg) and (1R,3S,4S)-2-Aza-bicyclo[2.2.1]heptane-2,3-dicarboxylic acid 2 benzyl ester (prepared as described in Tararov etal, *Tett. Asymm.* 2002, 13, 25-28) (767 mg) in THF (18 ml) was added 2-hydroxybenzotriazole hydrate (452 mg), DMAP (426 mg), diisopropylethylamine (631□l) and 1-(3-dimethylaminopropyl)-3-ethylcarbodiimide hydrochloride (EDC, 641 mg). The resulting mixture was stirred at ambient temperature for 18 hours then diluted with ethyl acetate. The mixture was then washed with water, saturated aqueous sodium bicarbonate solution and brine, dried over magnesium sulfate, filtered and concentrated under reduced pressure. The residue was purified by flash chromatography (60% ethyl acetate/petrol) to afford the sub-title compound as a colorless oil (1.1 g, 91%); $^1$H NMR (400 MHz, d-6 DMSO) δ 1.13-1.25 (1H, m), 1.30-1.48 (9H, m), 1.49-1.88 (6H, m), 2.20-2.52 (2H, m), 3.09-3.34 (2H, m), 3.64 (1H, d), 4.00-4.16 (2H, brm), 4.80 (1H, m), 4.90-5.15 (2H, m), 7.21-7.41 (5H, m), 7.50-7.75 (1H, m); MS ES (+) 433.37.

Method I (1R,3S,4S)-3-((S)-2-tert-Butoxycarbonyl-1-formyl-ethylcarbamoyl)-2-aza-bicyclo[2.2.1]heptane-2-carboxylic acid benzyl ester

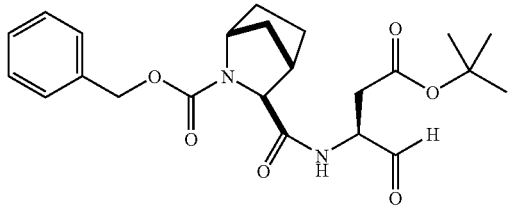

A solution of (1R,3S,4S)-3((S)-2-tert-Butoxycarbonyl-1-hydroxymethyl-ethylcarbamoyl)-2-aza-bicyclo[2.2.1]heptane-2-carboxylic acid benzyl ester (1.1 g) in DCM (10 ml) was cooled to 0° C. under nitrogen. 2,2,6,6-tetramethylpiperidinyloxy (TEMPO, 4 mg) was then added followed by trichloroisocyanuric acid (621 mg) portionwise over 30 minutes. The mixture was stirred at ambient temperature for 1 hour, then filtered through celite. The filtrate was washed with water, 1M sodium thiosulfate solution and brine. Drying over magnesium sulfate and concentration under reduced pressure gave the sub-title compound as a colorless oil (698 mg, 64%); $^1$H NMR (400 MHz, d-6 DMSO) δ 1.16-1.89 (16H, m), 2.30-2.80 (2H, m), 3.68-3.81 (1H, m), 4.19 (1H, brm), 4.39 (1H, m), 4.91-5.16 (2H, m), 7.21-7.43 (5H, m), 8.45 (0.4H, d), 8.60 (0.6, d), 9.19 (0.6H, S), 9.37 (0.4H, s).

Method J (1R,3S,4S)-3-((S)-1-tert-Butoxycarbonylmethyl-2,2-diethoxy-ethylcarbamoyl)-2-aza-bicyclo[2.2.1]heptane-2-carboxylic acid benzyl ester

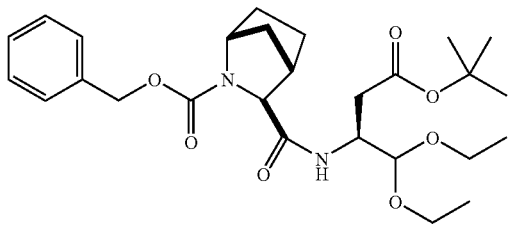

To a solution of (1R,3S,4S)-3-((S)-2-tert-Butoxycarbonyl-1-formyl-ethylcarbamoyl)-2-aza-bicyclo[2.2.1]heptane-2-carboxylic acid benzyl ester (698 mg) in dichloromethane (10 ml) was added triethyl orthoformate (720 mg) and p-toluenesulfonic acid monohydrate (6 mg). The resulting mixture was stirred at ambient temperature until no aldehyde remained by TLC. Saturated aqueous sodium bicarbonate solution was then added and the organic phase removed. This was washed with water and brine, dried (magnesium sulfate), filtered and concentrated under reduced pressure. This gave the sub-title compound as a pale yellow oil (635 mg, 78%); $^1$H NMR (400 MHz, d-6 DMSO) δ 0.96-1.15 (6H, m), 1.26-1.84 (16H, m), 2.20-2.50 (2H, m), 3.40-3.81 (5H, m), 4.10-4.28 (2H, m), 4.37 (1H, m), 4.88-5.14 (2H, m), 7.20-7.40 (5H, m), 7.65 (0.5H, d), 7.80 (0.5H, d).

Method K (1R,3S,4S)-3-((2R,3S)-2-Ethoxy-5-oxo-tetrahydro-furan-3-ylcarbamoyl)-2-aza-bicyclo[2.2.1]heptane-2-carboxylic acid benzyl ester

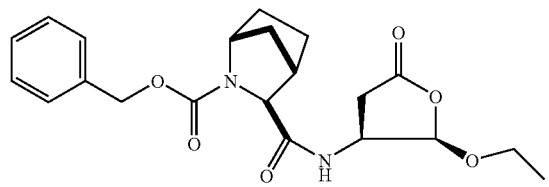

A solution of (1R,3S,4S)-3-((S)-1-tert-Butoxycarbonylmethyl-2,2-diethoxy-ethylcarbamoyl)-2-aza-bicyclo[2.2.1]heptane-2-carboxylic acid benzyl ester (635 mg) in dichloromethane (3 ml) was cooled to 0° C. under nitrogen. Trifluoroacetic acid (0.7 ml) was then added and the mixture stirred at 0° C. for 15 minutes, then warmed to ambient temperature and stirred until the reaction was complete by TLC. The mixture was then diluted with dichloromethane (10 ml) and saturated aqueous sodium bicarbonate solution (14 ml). The organic phase was then removed and washed with 1:1 saturated aqueous sodium bicarbonate/brine (8 ml), dried (magnesium sulfate), filtered and concentrated under reduced pressure. This afforded the sub-title compound as a mixture of epimers at the ketal centre. The epimers were separated on silica gel, eluting with 30% 2-butanone/petrol. Syn-isomer (oil) (115 mg, 23%); $^1$H NMR (400 MHz, d-6 DMSO) δ 0.80-1.91 (10H, m), 2.35-2.79 (2H, m), 3.56 (1H, m), 3.66-3.80 (2H, m), 4.18 (1H, m), 4.59 (1H, m), 4.94-5.11 (2H, m), 5.53 (1H, d), 7.20-7.40 (5H, m), 8.18 (0.5H, d), 8.27 (0.5H, d); MS ES+403.31 (100%), ES−401.37 (15%); Anti-isomer (oil) (103 mg, 20%); $^1$H NMR (400 MHz, d-6 DMSO) δ 0.80-1.85 (10H, m), 2.25-2.60 (1H, m), 2.95 (1H, m), 3.42 (1H, m), 3.5-3.75 (2H, m), 4.88-5.15 (3H, m), 7.21-7.40 (5H, m), 8.50 (0.4H, d), 8.59 (0.6H, d).

Method L

{(S)-1-[(1R,3S,4S)-3-((2R,3S)-2-Ethoxy-5-oxo-tetrahydro-furan-3ylcarbamoyl)-2-aza-bicyclo[2.2.1]heptane-2-carbonyl]-2,2-dimethyl-propyl}-carbamic acid benzyl ester

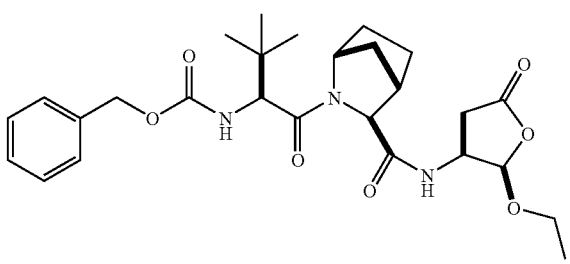

To a solution of (1R,3S,4S)-3-((2R,3S)-2-Ethoxy-5-oxo-tetrahydro-furan-3-ylcarbamoyl)-2-aza-bicyclo[2.2.1]heptane-2-carboxylic acid benzyl ester (5 g) in ethyl acetate (160 ml) and DMF (25 ml) was added triethylamine (2.5 g) followed by palladium hydroxide/carbon (20% w/w, 1 g). The mixture was stirred under an atmosphere of hydrogen until no starting material was present by TLC. The catalyst was removed by filtration through celite. To the filtrate was added (S)-2-benzyloxycarbonylamino-3,3-dimethyl-butyric acid (4.93 g), hydroxybenzotriazole hydrate (2.01 g) and 1-(3-dimethylaminopropyl)-3-ethylcarbodiimide hydrochloride (EDC, 2.85 g). The resulting mixture was stirred at ambient temperature overnight. Saturated aqueous sodium bicarbonate solution (180 ml) was then added and the organic phase removed. This was washed with saturated aqueous ammonium chloride (180 ml), then brine (180 ml), dried (magnesium sulfate), filtered and concentrated under reduced pressure. The crude product was purified on silica gel, eluting with 40-75% ethyl acetate/petrol. The sub-title compound was obtained as a white foam (5.25 g, 81%); $^1$H NMR (400 MHz, d-6 DMSO) δ 0.85-1.03 (10H, m), 1.07-1.20 (3H, t), 1.30 (1H, m), 1.40 (1H, m), 1.50-1.80 (3H, m), 1.93 (1H, m), 2.40-2.50 (1H, m), 2.78 (1H, m), 3.60 (1H, m), 3.78 (1H, m), 3.89 (1H, s), 4.26 (1H, d), 4.52 (2H, m), 4.96-5.12 (2H, m), 5.56 (1H, d), 7.10 (1H, d), 7.24-7.40 (5H, m), 8.27 (1H, d); MS ES+516.93 (100%), ES−515.05 (100%).

Method M (1R,3S,4S)-2-[(S)-2-(3-methoxy-2-methylbenzoylamino)-3,3-dimethyl-butyryl]-2-aza-bicyclo[2.2.1]heptane-3-carboxylic acid ((2R,3S)-2-ethoxy-5-oxo-tetrahydro-furan-3-yl)-amide

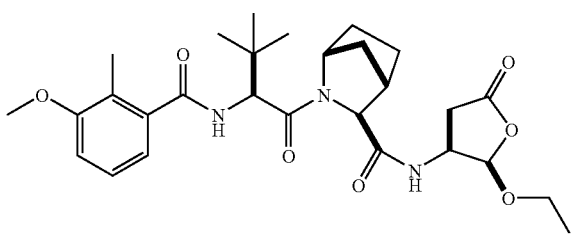

To a solution of {(S)-1-[(1R,3S,4S)-3-((2R,3S)-2-Ethoxy-5-oxo-tetrahydro-furan-3ylcarbamoyl)-2-aza-bicyclo[2.2.1]heptane-2-carbonyl]-2,2-dimethyl-propyl}-carbamic acid benzyl ester (370 mg) in ethyl acetate (20 ml) was added palladium hydroxide/carbon (20% w/w, 74 mg). The mixture was stirred under an atmosphere of hydrogen until no starting material was present by TLC. The catalyst was removed by filtration through celite and the filtrate concentrated under reduced pressure to give the amine as a brown foam (272 mg). A portion of this material (167 mg) was dissolved in THF and 3-methoxy-2-methyl benzoic acid (146 mg), diisopropylamine (191☐1), hydroxybenzotriazole hydrate (77 mg) and 1-(3-dimethylaminopropyl)-3-ethylcarbodiimide hydrochloride (EDC, 109 mg) were added. The resulting mixture was stirred at ambient temperature for 24 hours then diluted with saturated aqueous sodium bicarbonate. The organic phase was removed and washed with saturated aqueous ammonium chloride, then brine, dried (magnesium sulfate), filtered and concentrated under reduced pressure. The crude product was purified on silica gel, eluting with ethyl acetate. This gave the sub-title compound as a white solid (121 mg, 52%); $^1$H NMR (400 MHz, CDCl3) δ 1.10 (9H, s), 1.28 (3H, t), 1.43-1.56 (1H, m), 1.79-1.86 (3H, m), 1.99 (1H, brd), 2.29 (3H, s), 2.30-2.37 (1H, m), 2.83 (1H, dd), 3.02 (1H, brs), 3.66-3.74 (1H, m), 3.87 (3H, s), 3.88-3.94 (1H, m), 4.16 (1H, brs), 4.54 (1H, brs), 4.66-4.74 (1H, m), 4.97 (1H, d), 5.46 (1H, d), 6.44 (1H, brd), 6.93 (1H, d), 7.00 (1H, d), 7.22 (1H, t), 7.78 (1H, brd); IR (solid) cm$^{-1}$ 2960, 1791, 1624, 1505, 1438, 1261, 1115, 975; MS ES+530; ES−528.

Compounds of formula I-60 to I-73 have been prepared by methods substantially similar to those described in Example I-59.

EXAMPLE I-60

2-[(2S)-(2-Chloro-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

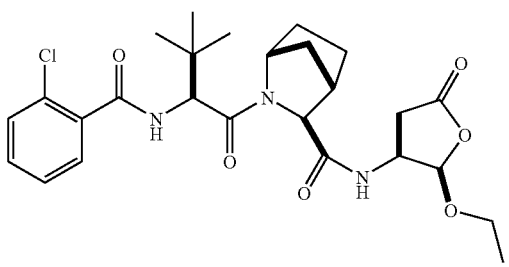

EXAMPLE I-61

2-[(2S)-(4-Acetylamino-2-chloro-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

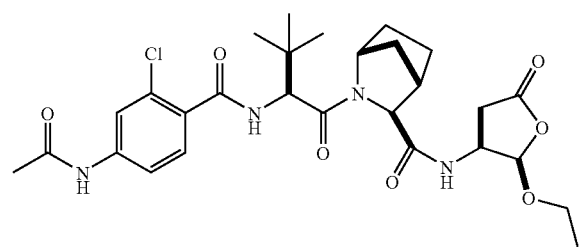

EXAMPLE I-62

2-[(2S)-(2-Chloro-4-propionylamino-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

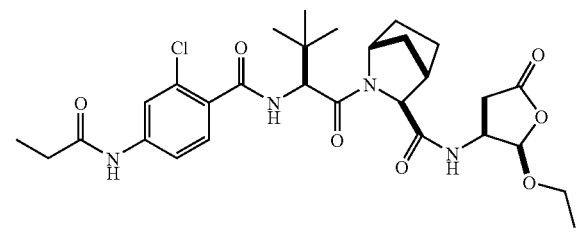

EXAMPLE I-63

2-[(2S)-(2-Chloro-3-isobutyrylamino-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

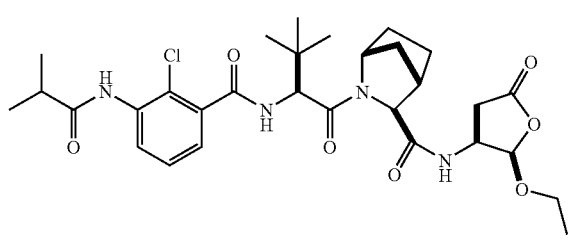

EXAMPLE I-64

2-[(2S)-(2-Fluoro-3-methoxy-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

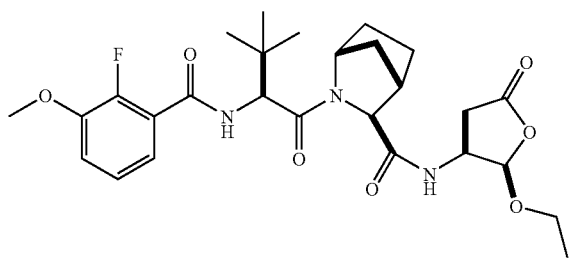

EXAMPLE I-65

2-[(2S)-(2-Fluoro-3-methoxy-benzoylamino)-3-methyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

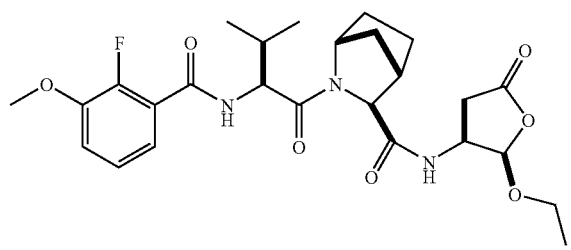

EXAMPLE I-66

2-[(2S)-(3-methoxy-2-methyl-benzoylamino)-3,3-dimethyl-butyryl]-2-(1S,4R)-aza-bicyclo[2.2.1]heptane-(3S)-carboxylic acid [(2S)-ethoxy-5-oxo-tetrahydro-furan-(3S)-yl]-amide

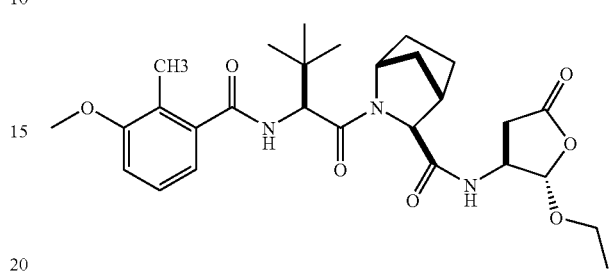

EXAMPLE I-67

2-[(2S)-(2-Chloro-benzoylamino)-3,3-dimethyl-butyryl]-2-(1S,4R)-aza-bicyclo[2.2.1]heptane-(3S)-carboxylic acid [(2S)-ethoxy-5-oxo-tetrahydro-furan-(3S)-yl]-amide

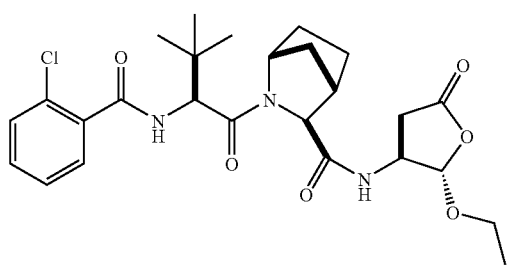

EXAMPLE I-70

2-[(2S)-(4-Acetylamino-3-chloro-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

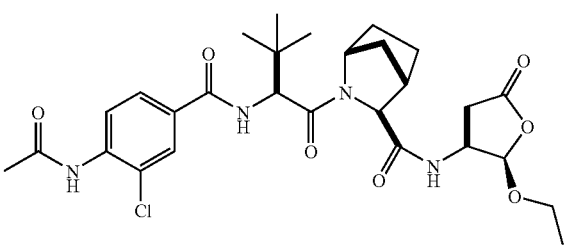

EXAMPLE I-69

2-[(2S)-(3-Chloro-4-propionylamino-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

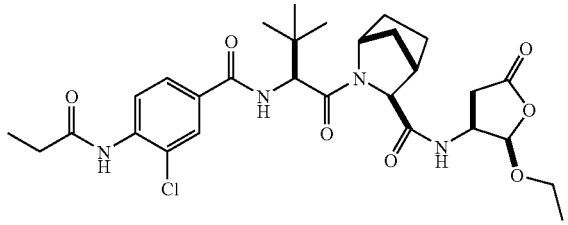

EXAMPLE I-70

2-[(2S)-(isoquinolin-1-ylcarbonylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

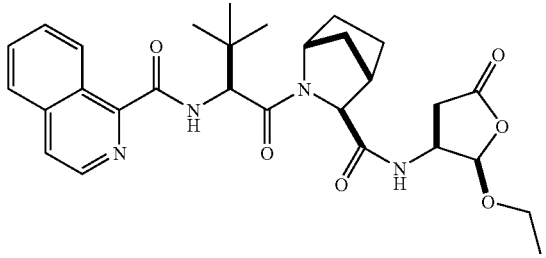

EXAMPLE I-71

2-[(2S)-(4-Amino-3-chloro-benzoylamino)-3,3-dimethyl-butyryl]-2-(1S,4R)-aza-bicyclo[2.2.1]heptane-(3S)-carboxylic acid [(2R)-ethoxy-5-oxo-tetrahydro-furan-(3S)-yl]amide

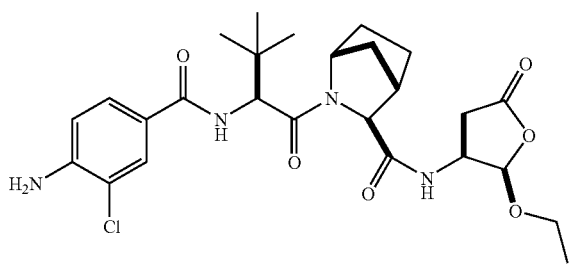

EXAMPLE I-72

2-[(2S)-(4-Amino-3-chloro-benzoylamino)-3-methyl-butyryl]-2-(1S,4R)-aza-bicyclo[2.2.1]heptane-(3S)-carboxylic acid [(2R)-ethoxy-5-oxo-tetrahydro-furan-(3S)-yl]-amide

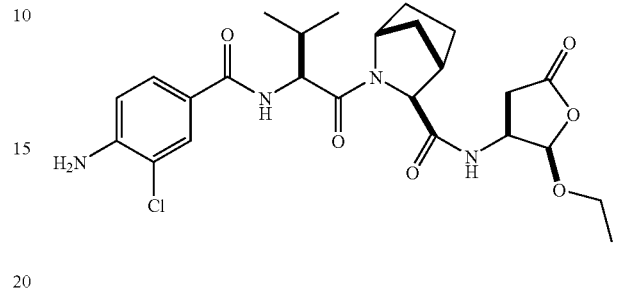

EXAMPLE I-73

2-[(2S)-(isoquinolin-1-ylcarbonylamino)-3,3-dimethyl-butyryl]-2-(1S,4R)-aza-bicyclo[2.2.1]heptane-(3S)-carboxylic acid [(2S)-ethoxy-5-oxo-tetrahydro-furan-(3S)-yl]-amide

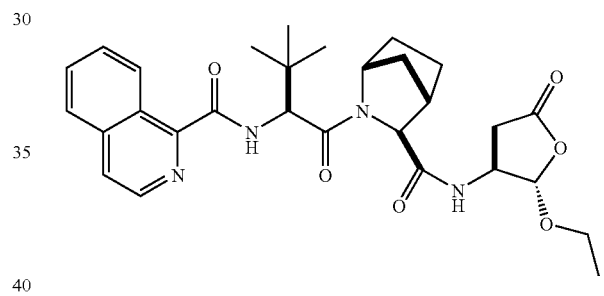

TABLE 3

Characterization Data for Selected Compounds of Formula I (by Compound Number)

| No. | M + 1 (obs) | $^1$H-NMR |
|---|---|---|
| I-1 | 490.1 | (DMSO-$d_6$) 0.94-0.95(3H, m), 0.98-0.99(3H, m), 1.13-1.16(3H, m), 1.80-2.0(4H, m), 2.10(3H, s), 2.47-2.51(2H, m), 2.73(1H, m), 3.34-3.61(2H, m), 3.73-3.77(2H, m), 3.79(3H, s), 3.90 (1H, m), 4.39(1H, m), 4.55(1H, m), 5.55(1H, d), 6.83(1H, d), 6.99(1H, d), 7.19(1H, m), 8.27(1H, d), 8.34(1H, d) |
| I-2 | 476.0 | (CDCl$_3$) 1.01-1.15(6H, m), 1.26(3H, t), 1.90-2.29(5H, m), 2.55-2.59(1H, m), 2.75-2.83(1H, m), 3.65-3.98(3H, m), 4.04(3H, s), 4.44-4.49(1H, m), 4.62-4.69(1H, m), 4.75-4.80(1H, m), 5.60(1H, d), 7.09(1H, t), 7.19(1H, d), 7.52(1H, t), 7.97(1H, d) |
| I-3 | 530.0 | (CDCl$_3$) 1.02-1.10(6H, m), 1.23-1.34(3H, m), 1.88-2.19(5H, m), 2.32-2.44(2H, m), 2.81-2.89(1H, m), 3.66-3.72(2H, m), 3.83-3.98(2H, m), 4.56-4.73(2H, m), 4.84-4.90(1H, m), 5.46(1H, d), 7.15(1H, d), 7.35-7.60(4H, m), 7.99(1H, d) |

TABLE 3-continued

Characterization Data for Selected Compounds of Formula I (by Compound Number)

| No. | M + 1 (obs) | ¹H-NMR |
|---|---|---|
| I-4 | 476.1 | (CDCl$_3$) 1.02(3H, d), 1.09(3H, d), 1.29(3H, t), 1.93-2.19(4H, m), 2.29(3H, s), 2.39(2H, dd), 2.84(1H, dd), 3.66-3.71(2H, m), 3.88-3.95(2H, m), 4.63(1H, dd), 4.68-4.74(1H, m), 4.85(1H, dd), 5.32(1H, s), 5.47(1H, d), 6.44(1H, d), 6.87(1H, d), 6.98-7.00(1H, m), 7.07-7.12(1H, m), 7.36(1H, d) |
| I-5 | 475.0 | (CDCl$_3$) 0.95-1.10(6H, m), 1.31(3H, t), 1.93-2.21(4H, m), 2.25(3H, s), 2.34-2.41(2H, m), 2.80-2.88(1H, m), 3.63-3.75(4H, m), 3.87-3.93(2H, m), 4.65-4.75(2H, m), 4.82-4.88(1H, m), 5.47(1H, d), 6.43(1H, d), 6.74(1H, d), 6.81(1H, d), 7.04(1H, t), 7.40(1H, d) |
| I-6 | 514.4 | (CDCl$_3$) 1.03-1.05(3H, m), 1.09-1.13(3H, m), 1.22-1.30(3H, m), 1.95(1H, m), 2.14-2.17(2H, m), 2.44-2.51(2H, m), 2.79(1H, m), 3.65-3.68(2H, m), 3.86-3.90(2H, m), 4.12(1H, m), 4.60-4.61(2H, m), 4.86(1H, m), 5.47(1H, m), 6.4(1H, 2×d), 7.29-7.37(3H, m), 7.54(1H, m) |
| I-7 | 461.1 | (DMSO-d$_6$) 0.95-1.01(6H, m), 1.13-1.16(3H, m), 1.80-2.10(4H, m), 2.45-2.51(5H, m), 2.74(1H, m), 3.33-3.59(2H, m), 3.68(1H, m), 3.95(1H, m), 4.38-4.44(2H, m), 4.55(1H, m), 5.55(1H, m), 7.25(1H, m), 7.62(1H, m), 8.27(1H, m), 8.48(1H, m), 8.63(1H, m) |
| I-8 | 461.1 | (CDCl$_3$) 1.02(3H, d), 1.08(3H, d), 1.28(3H, t), 1.95-2.2(4H, m), 2.4-2.5(2H, m), 2.55(3H, s), 2.8-2.9(1H, m), 3.7-3.8(2H, m), 3.85-3.95(2H, m), 4.7-4.85(2H, m), 4.9-4.95(1H, m), 5.55(1H, d), 6.6-6.65(1H, m), 7.2-7.25(1H, m), 7.35-7.4(1H, m), 8.6(1H, d), 8.7(1H, s) |
| I-9 | 465.6 | (DMSO-d$_6$) 0.93-0.95(3H, m), 0.99-1.00(3H, m), 1.13-1.16(3H, m), 1.80-2.10(4H, m), 2.40(3H, s), 2.40-2.47(2H, m), 2.73(1H, m), 3.59-3.61(2H, m), 3.73-3.75(2H, m), 4.37-4.43(2H, m), 4.55(1H, m), 5.53(1H, d), 6.97(1H, m), 7.59(1H, m), 7.81(1H, d), 8.28(1H, d) |
| I-10 | 515.0 | (CDCl$_3$) 1.01(3H, d), 1.25(3H, d), 1.27(3H, t), 1.97-2.10(2H, m), 2.14-2.26(1H, m)2.38(2H, dd), 2.84(1H, dd), 3.67-3.71(2H, m), 3.81-3.87(1H, m), 3.90-3.98(1H, m), 4.58-4.61(1H, m), 4.65-4.73(1H, m), 4.86-4.90(1H, dd), 5.47(1H, d), 6.78(1H, d), 7.23(1H, d), 7.42(1H, d), 8.40(1H, d) |
| I-11 | 515.0 | (CDCl$_3$) 1.01(3H, d), 1.14(3H, d), 1.28(3H, t), 1.96-2.12(2H, m), 2.17-2.23(2H, m), 2.38(2H, dd), 2.83(1H, dd), 3.66-3.71(2H, m), 3.82-3.95(2H, m), 4.59-4.62(1H, m), 4.65-4.71(1H, m), 4.91(1H, dd), 5.47(1H, d), 6.54(1H, br dd), 7.21(1H, br dd), 8.57(2H, s) |
| I-12 | 504.4 | (DMSO-d$_6$) 0.9-1.08(9H, s), 1.12(3H, t), 1.75-2.00(3H, m), 2.00-2.15(4H, m), 2.34-2.50(1H, m), 2.80(1H, m), 3.48-3.91(7H, m), 4.40(1H, m), 4.46-4.70(2H, m), 5.58(1H, d), 7.81(1H, d), 7.00(1H, d), 7.19(1H, dd), 8.07(1H, d), 8.27(1H, d) |
| I-13 | 476.0 | (CDCl$_3$) 0.98-1.09(6H, m), 1.90-2.05(4H, m), 2.35-2.56(2H, m), 2.70-2.85(1H, m), 3.49+3.55(3H, 2×s), 3.55-3.67(1H, m), 3.86(3H, s), 4.00-4.09(1H, m), 4.58-4.90(3H, m), 5.34-5.37(1H, m), 6.25+6.40(1H, 2×d), 6.90-7.01(2H, m), 7.18-7.25(1H, m), 7.37+7.54(1H, 2×d) |
| I-14 | 504.0 | (CDCl$_3$) 0.99-1.11(6H, m), 1.18-1.30(6H, m), 1.86-2.15(4H, m), 1.28+1.30(3H, 2×s), 2.36-2.86(3H, m), 3.56-3.68(1H, m), 3.86(3H, s), 3.87-4.05(2H, m), 4.50-4.84(3H, m), 5.55+5.59(1H, 2×d), 6.86-7.01(2H, m), 7.16-7.23(1H, m), 7.37+7.54(1H, 2×d) |
| I-15 | 504.0 | (CDCl$_3$) 0.85-1.11(9H, m), 1.55-1.73(2H, m), 1.89-2.20(4H, m), 2.28+2.29(3H, 2×s), 2.35-2.55(2H, m), 2.71-2.87(1H, m), 3.48-3.76(3H, m), 3.86(3H, s), 3.98-4.06(1H, m), 4.52-4.86(3H, m), 5.44-5.49(1H, m), 6.24+6.35(1H, 2×d), 6.88-6.99(2H, m), 7.14-7.21(1H, m), 7.41+7.55(1H, 2×d) |
| I-16 | 480.5 | (CDCl3) 1.0-1.15(6H, m), 1.3-1.4(3H, m), 1.9-2.2(4H, m), 2.4-2.5(2H, m), 2.8-2.9(1H, m), 3.7-3.8(2H, m), 3.9-4.0(2H, m), 4.65-4.75(2H, m), 4.88-4.92(1H, m), 5.5-5.52(1H, m), 6.85-6.9(1H, m), 7.4-7.55(1H, m), 7.7-7.75(1H, m) |
| I-17 | 474.6 | (DMSO-d$_6$) 1.05(9H, s), 1.15(3H, t), 1.8-2.1(4H, m), 2.3(3H, s), 2.4-2.5(1H, m), 2.7-2.8(1H, m), 3.6-3.9(4H, m), 4.4-4.45(1H, m), 4.5-4.7(2H, m), 5.55-5.6(1H, m), 7.2-7.4(4H, m), 8.1(1H, d), 8.25(1H, d) |
| I-18 | 514.5 | (DMSO-d$_6$) 0.9-1.0(6H, m), 1.15(3H, t), 1.8-2.1(4H, m), 2.4-2.5(1H, m), 2.7-2.8(1H, m), 3.6-3.85(3H, m), 3.9-3.95(1H, m), 4.4-4.6(3H, m), 5.55-5.6(1H, m), 7.4-7.45(1H, m), 7.6-7.8(3H, m), 8.22(1H, d), 8.75(1H, d) |
| I-19 | 480.5 | (CDCl$_3$) 1.13(9H, s), 1.90-2.20(3H, m), 2.35-2.44(2H, m), 2.86(1H, dd), 3.56(3H, s), 3.72-3.74(1H, m), 3.90-3.99(1H, m), 4.62-4.65(1H, m), 4.69-4.70(1H, m), 4.90(1H, d), 5.36(1H, d), 6.94(1H, d), 7.28-7.46(4H, m), 7.71(1H, dd) |
| I-20 | 542.5 | (CDCl$_3$) 1.09(9H, s), 1.27(6H, m), 1.93-2.14(3H, m), 2.34-2.42(2H, m), 2.79-2.83(1H, m), 3.71(1H, m), 3.90-3.94(1H, m), 4.01-4.04(1H, m), 4.62-4.67(2H, m), 4.88-4.91(1H, m), 5.56(1H, m), 6.46(1H, m), 7.40(1H, m), 7.54-7.62(3H, m), 7.74(1H, m) |
| I-21 | 494.5 | (CDCl$_3$) 1.12(9H, s), 1.29(3H, t), 1.90-2.20(3H, m), 2.36-2.43(2H, m), 2.85(1H, dd), 3.67-3.72(2H, m), 3.90-3.96(2H, m), 4.62-4.65(2H, m)4.91(1H, d), 5.46(1H, d), 6.95(1H, d), 7.34-7.46(4H, m), 7.71(1H, dd) |
| I-22 | 528.4 | (CDCl$_3$) 1.10(9H, s), 1.29(3H, t), 1.90-2.20(3H, m), 2.35-2.42(2H, m), 2.84(1H, dd), 3.68-3.72(2H, m), 3.90-3.95(2H, m), 4.62-4.80(2H, m), 4.89(1H, d), 5.47(1H, d), 6.45(1H, d), 7.43(1H, d), 7.54-7.61(3H, m), 7.73(1H, dd) |
| I-23 | 508.5 | (CDCl$_3$) 0.95(3H, t), 1.12(9H, s), 1.60-1.70(2H, m), 1.88-2.20(3H, m), 2.35-2.45(2H, m), 2.77-2.85(1H, m), 3.53-3.61(1H, m), 3.65-3.75(1H, m), 3.76-3.84(1H, m), 3.88-3.96(1H, m), 4.60-4.73(2H, m), 4.91(1H, d), 5.44(1H, d), 6.96(1H, d), 7.30-7.50(4H, m), 7.73(1H, d) |
| I-24 | 522.5 | (CDCl$_3$) 0.86(3H, t), 1.18(9H, s), 1.21-1.65(4H, m), 1.85-2.17(3H, m), 2.36-2.59(2H, m), 2.68-2.78(1H, m), 3.44-3.54(1H, m), 3.56-3.72(2H, m), |

TABLE 3-continued

Characterization Data for Selected Compounds of Formula I (by Compound Number)

| No. | M + 1 (obs) | $^1$H-NMR |
|---|---|---|
| I-25 | 578.3 | 3.98-4.10(1H, m), 4.56-4.85(3H, m), 5.44(1H, d), 6.95-7.02(1H, m), 7.32-7.74(5H, m) (DMSO-d$_6$) 0.99-1.21(12H, m), 1.70-2.00(3H, m), 2.01-2.17(1H, m), 2.40-2.51(1H, m), 2.70-2.80(1H, m), 3.50-3.88(4H, m), 4.40(1H, m), 4.55(1H, m), 4.65(1H, m), 5.58(1H, d), 7.36(1H, m), 7.50(1H, m), 7.61(1H, m), 8.21(1H, d), 8.70(1H, d) |
| I-26 | 494.5 | (CDCl$_3$) 0.95(3H, t), 1.05-1.15(6H, m), 1.55-1.8(3H, m), 2.0-2.25(4H, m), 2.4-2.5(1H, m), 2.6-2.9(2H, m), 3.55-3.8(3H, m), 3.85-3.95(1H, m), 4.05-4.1(1H, m), 4.7-4.85(2H, m), 5.5-5.55(1H, m), 6.85-6.9(1H, m), 7.4-7.6(3H, m), 7.7-7.8(1H, m) |
| I-27 | 494.5 | (CDCl$_3$) 0.95(3H, t), 1.05-1.15(6H, m), 1.5-1.7(3H, m), 2.0-2.2(4H, m), 2.4-2.6(2H, m), 2.9-3.1(1H, m), 3.4-3.5(1H, m), 3.55-3.7(2H, m), 4.0-4.1(1H, m), 4.35-4.5(2H, m), 4.6-4.75(1H, m), 4.8-4.9(0.5H, m), 5.35-5.38(1H, m), 6.85-6.95(1H, m), 7.4-7.55(3H, m), 7.64-7.8(1.5H, m) |
| I-28 | 480.3 | (CDCl3) 1.02-1.19(7H, m), 1.22-1.28(2H, m), 1.90-2.21(3H, m), 2.32-2.53(2H, m), 2.95(1H, 2×dd), 3.44-3.50(1H, m), 3.59-78(2H, m), 3.83-3.92(1H, m), 4.02-4.09(1H, m), 4.29-4.41(1H, m), 5.34(1H, 2×s), 6.88(1H, 2×brd d), 7.31-7.42(4H, m), 7.57(1H, 2×brd d), 7.70(1H, 2×dd) |
| I-29 | 508 | (CDCl3) 0.83-0.97(3H, m), 1.02-1.14(6H, m), 1.26-1.53(3H, m), 1.55-1.66(1H, m), 1.91-2.20(4H, m), 2.35-2.61(2H, m), 2.73-2.90(1H, m), 3.54-3.74(3H, m), 3.84-3.90(0.5H, m), 3.99-4.06(0.5H, m), 4.61-4.75(2H, m), 4.77-4.93(0.5H, m), 5.45-5.51(1H, m), 6.87(1H, brd), 7.34-7.45(4H, m), 7.55(0.5H, brd), 7.70-7.22(1H, m) |
| I-30 | 508 | (400 MHz, CDCl3) 0.87-0.97(3H, m), 0.99-1.16(6H, m), 1.27-1.40(2H, m), 1.48-1.59(1H, m), 1.91-2.19(4H, m), 2.30-2.52(2H, m), 2.90-3.07(1H, m), 3.39-3.45(0.5H, m), 3.54-3.71(2H, m), 3.78-3.82(0.5H, m), 3.86-3.92(0.5H, m), 4.04-4.09(0.5H, m), 4.31-4.35(1H, m), 4.39-4.43(1H, m), 4.56-4.59(0.5H, m), 4.66-4.68(1H, m), 4.80-4.86(0.5H, m), 5.32-5.41(1H, m), 6.87-6.91(1H, m), 7.31-7.45(4H, m), 7.55-7.76(2H, m) |
| I-31 | 494.4 | (CDCl3) 1.04-1.19(8H, m), 1.25-1.28(3H, m), 1.92-2.18(4H, m), 2.32-2.43(1H, m), 2.62-2.87(2H, m), 3.59-3.71(1H, m), 3.85-3.95(1H, m), 4.00-4.05(1H, m), 4.60-4.67(3H, m), 5.60(1H, 2×d), 6.88(1H, brd d), 7.36-7.50(4H, m), 7.52-7.56(1H, m), 7.76(1H, 2×dd) |
| I-32 | 494.3 | (CDCl3) 0.87-1.24(10H, m), 1.88-2.07(3H, m), 2.13-2.21(1H, m), 2.32-2.54(2H, m), 2.94(1H, 2×dd), 3.57-3.68(1H, m), 3.83-3.87(1H, m), 4.02-4.09(1H, m), 4.27-4.30(1H, m), 4.41(1H, dd), 4.51-4.69(1H, m), 5.43(1H, 2×s), 6.89(1h, 2×brd d), 7.30-7.45(4H, m), 7.52(1H, 2×brd d), 7.70(1H, 2×dd) |
| I-33 | 550.5 | (DMSO) 0.70(2H, m, CH2), 0.89(2H, m, CH2), 0.95-1.20(12H, m, CH3, tbutyl), 1.71-2.13(4H, m, CH2), 2.45(1H, m, asp CH2), 2.75(1H, m, asp CH2), 3.35-3.89(4H, m, CH2, CH), 3.99(1H, m, CH), 4.37(1H, m, CH), 4.51(1H, m, CH), 4.65(1H, m, CH), 5.58(1H, d, CHO), 6.90(1H, m, aryl H), 7.35(1H, m, aryl H), 7.45(1H, m, aryl H), 8.25(1H, d, NH), 8.35(1H, d, NH) |
| I-34 | 508.5 | DMSO) 0.99-1.21(12H, m, CH3, tBu), 1.75-2.14(4H, m, CH2), 2.38(3H, s, CH3), 2.40-2.51(1H, m, asp CH2), 2.70-2.82(1H, m, asp CH2), 3.37-3.90(4H, m, CH2, CH), 4.39(1H, m, CH), 4.55(1H, m, CH), 4.67(1H, m, CH), 5.58(1H, d, CH), 7.15(1H, m, aryl H), 7.28(1H, m, aryl H), 7.38(1H, m, aryl H), 8.25(1H, m, NH), 8.38(1H, m, NH) |
| I-35 | 510 | CDCl3 1.00(3H, d), 1.10(3H, d), 1.27(3H, t), 1.90-2.19(4H, m), 2.34-2.45(2H, m), 2.79-2.87(1H, m), 3.65-3.71(2H, m), 3.84-4.93(2H, m), 3.92(3H, s), 4.56-4.70(2H, m), 4.82-4.88(1H, m), 4.45(1H, d), 6.69(1H, d), 6.99(1H, d), 7.16(1H, d), 7.27(1H, t), 7.37(1H, d) |
| I-36 | 522.5 | (DMSO) 0.95-1.25(15H, m, tBu, CH3), 1.78-2.13(4H, m, CH2), 2.43(1H, m, CH2), 2.65-2.80(3H, m, CH2), 3.50-3.88(4H, m, CH2, CH), 4.42(1H, m, CH), 4.58(1H, m, CH), 4.70(1H, m, CH), 5.58(1H, d, CH), 7.15(1H, m, aryl H), 7.27(1H, m, aryl H), 7.38(1H, m, aryl H), 8.27(1H, d, NH), 8.39(1H, d, NH) |
| I-37 | 510.5 | CDCl3 1.05-1.12(6H, m), 1.25-1.3(3H, m), 1.9-2.2(2H, m), 2.4-2.5(2H, m), 2.8-2.9(1H, m), 3.65-3.75(2H, m), 3.85(3H, s), 3.9-4.0(1H, m), 4.65-4.75(2H, m), 4.85-4.9(1H, m), 6.9-6.93(1H, m), 6.98(1H, s), 7.05-7.1(1H, m), 7.4-7.45(1H, m), 7.75-7.8(1H, d) |
| I-38 | 564 | CDCl3 0.38-0.42(2H, m), 0.63-0.71(2H, m), 1.11(9H, s), 1.23-1.35(4H, m), 1.88-2.20(3H, m), 2.34-2.45(2H, m), 2.76-2.87(1H, m), 3.66-3.75(2H, m), 3.87-3.96(4H, m), 4.62-4.73(2H, m), 4.89(1H, d), 5.47(1H, d), 6.80(1H, d), 7.00(1H, m), 7.19-7.29(2H, m), 7.48(1H, d) |
| I-39 | 510 | (DMSO) 1.11(9H, s), 1.28(3H, t), 1.83-2.22(3H, m), 2.36-2.43(2H, m), 2.82-2.87(1H, m), 3.66-3.76(2H, m), 3.86-3.97(2H, m), 4.62-4.71(2H, m), 4.88(1H, d), 5.45(1H, d), 6.31(1H, S), 6.73(1H, d), 7.05-7.20(3H, m), 7.38(1H, d) |
| I-40 | 537.4 | (CDCl3) 1.06(6H, dd), 1.28-1.31(4H, m), 1.91-2.20(4H, m), 2.23(3H, s), 2.39(1H, dd), 2.84(1H, dd), 3.65-3.72(2H, m), 3.86-3.94(2H, m), 4.61-4.73(2H, m), 4.87(1H, dd), 5.46(1H, dd), 7.00-7.04(1H, m), 7.22(1H, brd s), 7.38-7.45(2H, m), 7.73(1H, d), 7.80(1H, brd s) |
| I-41 | 551.5 | (DMSO) 0.95-1.20(12H, m, tBu, CH3), 2.75-2.15(7H, m, CH2, COCH3), 2.42(1H, m, CH2), 2.77(1H, m, CH2), 3.50-3.88(4H, m, CH2, CH), 4.37(1H, m, CH), 4.55(1H, m, CH), 4.67(1H, d, CH), 5.58(1H, d, CH), 7.09(1H, m, aryl H), 7.32(1H, m, aryl H), 7.71(1H, m, aryl H), 8.26(1H, m, NH), 8.49(1H, m, NH), 9.58(1H, m, NH) |
| I-42 | 531.6 | (DMSO) 0.95-1.20(12H, m, tBu, CH3), 1.75-2.17(10H, m, CH3, COCH3, CH2), 2.45(1H, m, CH2), 2.77(1H, m, CH2), 3.48-3.91(4H, m, CH2, CH), 4.31-4.70(3H, m, CH), 5.55(1H, d, CH), 7.04(1H, |

TABLE 3-continued

Characterization Data for Selected Compounds of Formula I (by Compound Number)

| No. | M + 1 (obs) | ¹H-NMR |
|---|---|---|
|  |  | m, aryl H), 7.18(1H, m, aryl H), 7.41(1H, m, aryl H), 8.20(1H, d, NH), 8.27(1H, d, NH), 9.39(1H, brs, NH) |
| I-43 | 551.4 | DMSO) 1.04(9H, s), 1.12-1.17(3H, m), 1.78-1.95(4H, m), 2.06(3H, s), 2.45(1H, dd), 2.72(1H, dd), 3.52-3.81(4H, m), 4.36-4.39(1H, m), 4.47-4.54(1H, m), 4.64(1H, d), 5.54(1H, dd), 7.33-7.35(1H, m), 7.43-7.46(1H, m), 7.81(1H, brd s), 8.21-8.25(2H, m), 10.23(1H, brd s) |
| I-44 | 535.4 | (DMSO) 1.02(9H, s), 1.14(3H, t), 1.78-1.98(4H, m), 2.08(3H, s), 2.48(1H, dd), 2.79(1H, dd), 3.51-3.82(4H, m), 4.36-4.39(1H, m), 4.49-4.58(1H, m), 4.71(1H, d), 5.54(1H, d), 7.31-7.34(1H, m), 7.65-7.72(3H, m), 8.49(1H, d), 10.38(1H, s) |
| I-45 | 521.4 | (DMSO) 0.95(6H, dd), 1.12-1.16(4H, m), 1.72-1.97(4H, m), 2.07(3H, s), 2.48(1H, dd), 2.73(1H, dd), 3.51-3.62(2H, m), 3.71-3.83(2H, m), 4.35-4.38(1H, m), 4.48-4.59(2H, m), 5.53(1H, d), 7.29-7.31(1H, m), 7.59-7.67(2H, m), 8.01-8.05(1H, m), 8.28(1H, d), 10.35(1H, s) |
| I-46 | 538.5 | (CDCl3 1.1-1.12(6H, m), 1.3(3H, m), 1.4(6H, d), 2.0-2.2(2H, m), 2.4-2.5(2H, m), 2.8-2.9(1H, m), 3.7-3.75(2H, m), 3.9-4.0(1H, m), 4.6-4.75(3H, m), 4.85-4.95(1H, m), 6.85-6.9(1H, m), 6.95(1H, s), 7.05-7.1(1H, m), 7.4-7.45(1H, m), 7.8(1H, d) |
| I-47 | 510.5 | (CDCl3) 1.15(9H, m), 1.25(3H, t), 2.0-2.2(4H, m), 2.4-2.5(2H, m), 2.8-2.9(1H, m), 3.7-3.85(2H, m), 3.9-4.0(1H, m), 4.05-4.1(1H, m), 4.7-4.8(1H, m), 4.85(1H, d), 5.5(1H, m), 6.5(1H, d), 6.8(1H, s), 7.2(1H, d), 7.4(1H, d), 7.55(1H, d) |
| I-48 | 538.5 | (CDCl3) 1.12(9H, s), 1.29(3H, t), 1.90-2.20(3H, m), 2.36-2.43(2H, m), 2.85(1H, m), 3.42(3H, s), 3.68-3.74(2H, m), 3.91-3.95(2H, m), 4.48(2H, s), 4.62-4.75(2H, m), 4.90(1H, m), 5.47(1H, m), 7.00(1H, m), 7.31(1H, m), 7.43-7.54(2H, m), 7.72(1H, m) |
| I-49 | 579.5 | (CDCl3) 1.12(9H, s), 1.28-1.31(9H, m), 1.90-2.20(3H, m), 2.36-2.43(2H, m), 2.54(1H, m), 2.85(1H, m), 3.68-3.72(2H, m), 3.91-3.95(2H, m), 4.62-4.69(2H, m), 4.88(1H, d), 5.47(1H, m), 7.14(1H, m), 7.27(1H, m), 7.41(1H, m), 7.50(1H, d), 7.78(1H, d), 7.87(1H, m) |
| I-50 | 577.3 | (DMSO) 1.12-1.16(7H, m), 1.58-1.81(5H, m), 1.83-1.92(5H, m), 2.04-2.08(4H, m), 2.50(1H, dd), 2.75(1H, dd), 3.57-3.66(2H, m), 3.72-3.78(1H, m), 3.82-3.91(1H, m), 4.33-4.36(1H, m), 4.46(1H, t), 4.52-4.61(1H, m), 5.54(1H, d), 7.32(1H, d), 7.43(1H, dd), 7.81(1H, d), 8.25(1H, d), 8.47(1H, d), 10.22(1H, s) |
| I-51 | 567.4 | (DMSO) 0.98-1.25(12H, m, tBu, CH3), 1.78-2.14(4H, m, CH2), 2.44(1H, m, CH2), 2.78(1H, m, CH2), 3.50-3.88(7H, m, CH3, CH2, CH), 4.38(1H, m, CH), 4.55(1H, m, CH), 4.67(1H, d, CH), 5.58(1H, d, CH), 7.30-7.42(2H, m, aryl H), 7.60(1H, brs, NH), 8.21(2H, m, aryl H, NH), 9.99(1H, brs, NH). |
| I-52 | 586.4 | (DMSO) 0.95-1.24(12H, m, tBu, CH3), 1.70-2.13(4H, m, CH2), 2.44(1H, m, CH2), 2.75(1H, m, CH2), 3.45-3.90(4H, m, CH2, CH), 4.37(1H, m, CH), 4.55(1H, m, CH), 4.70(1H, d, CH), 5.57(1H, d, CH), 6.91(2H, d, aryl H), 7.06-7.19(3H, m, aryl H), 7.30-7.45(3H, m, aryl H), 8.20(1H, d, NH), 8.55(1H, d, NH) |
| I-53 | 578.5 | (DMSO) 0.9-1.0(6H, m), 1.18(3H, t), 1.8-2.15(4H, m), 2.4-2.5(1H, m), 2.7-2.8(1H, m), 3.6-3.85(4H, m), 4.4-4.6(3H, m), 5.55(1H, d), 7.05(1H, d), 7.3-7.35(2H, m), 7.98(1H, s), 8.3(1H, d), 8.45(1H, d), 10.7(1H, s) |
| I-54 | 495.0 | (DMSO) 0.94-0.98(6H, m), 1.13-1.18(3H, m), 1.80-2.10(5H, m), 2.50(1H, m), 2.73(1H, m), 3.58-3.61(2H, m), 3.74(1H, m), 3.9(1H, m), 4.38-4.41(2H, m), 4.60(1H, m), 5.46(2H, s), 5.54(1H, m), 6.48(1H, m), 6.80(1H, m), 7.04(1H, m), 8.27(1H, d), 8.40(1H, d) |
| I-55 | 535.0 | (CDCl3) 1.25(3H, t), 1.99-2.01(3H, s), 2.30-2.39(1H, m), 2.68(1H, dd), 2.79(1H, dd), 3.21-3.27(2H, m), 3.39(1H, dd), 3.47-3.51(2H, m), 3.65-3.75(1H, m), 3.88-3.94(1H, m), 4.64-4.68(1H, m), 4.70-4.78(1H, m), 5.56(1H, d), 7.31-7.35(5H, m), 7.63-7.65(1H, m), 8.00(1H, d), 8.76(1H, d) |
| I-56 | 545.0 | (CDCl3) 1.25(3H, t), 2.01-2.03(3H, m), 2.25(3H, s), 2.30-2.37(1H, m), 2.65(1H, dd), 2.80(1H, dd), 3.27-3.41(2H, m), 3.47(1H, dd), 3.65-3.79(2H, m), 3.85(3H, s), 3.86-3.90(1H, m), 4.64-4.67(1H, m), 4.71-4.80(1H, m), 5.18-5.22(1H, m), 5.54(1H, d), 6.83(1H, d), 6.90-6.97(2H, m), 7.19(1H, t), 7.24-7.28(1H, m), 7.90(1H, d), 8.77(1H, d) |
| I-57 | 524.0 | (CDCl3) 1.12(9H, s), 1.31(3H, t), 1.93-2.20(3H, m), 2.35-2.46(2H, m), 2.79-2.86(1H, m), 3.65-3.74(2H, m), 3.87-3.96(2H, m), 3.95(3H, s), 4.65-4.74(2H, m), 4.89(1H, d), 5.47(1H, d), 6.76(1H, d), 7.03(1H, d), 7.30(1H, t), 7.48(1H, d) |
| I-58 | 530.4 | (CDCl3) 1.10(9H, s), 1.28(3H, t), 1.43-1.56(1H, m), 1.79-1.86(3H, m), 1.99(1H, brd), 2.29(3H, s), 2.30-2.37(1H, m), 2.83(1H, dd), 3.02(1H, brs), 3.66-3.74(1H, m), 3.87(3H, s), 3.88-3.94(1H, m), 4.16(1H, brs), 4.54(1H, brs), 4.66-4.74(1H, m), 4.97(1H, d), 5.46(1H, d), 6.44(1H, brd), 6.93(1H, d), 7.00(1H, d), 7.22(1H, t), 7.78(1H, brd) |
| I-59 | 520.5 | (CDCl3) 1.13(9H, s), 1.29(3H, t), 1.76-1.90(3H, m), 2.00(1H, brd), 2.35(1H, dd), 2.83(1H, dd), 3.66-3.74(1H, m), 3.87-3.94(1H, m), 4.15(1H, s), 4.54(1H, brs), 4.62-4.78(1H, m), 4.99(1H, d), 5.46(1H, d), 6.92(1H, brd), 7.33-7.46(3H, m), 7.69(1H, brdd), 7.77(1H, brd) |
| I-60 | 577.5 | (CDCl3) 1.12(9H, s), 1.26-1.31(3H, m), 1.43-1.45(1H, m), 1.83(3H, brs), 1.99(1H, brd), 2.06(1H, m), 2.23(3H, s), 2.34(1H, brdd), 2.83(1H, brdd), 3.01(1H, brs), 3.66-3.74(1H, m), 3.87-3.95(1H, m), 4.12-4.19(1H, m), 4.53(1H, brs), 4.65-4.76(1H, m), 4.98(1H, d), 5.45-5.47(1H, m), 7.08(1H, brd), 7.30(1H, m), 7.37(1H, brd), 7.73-7.75(1H, m), 7.80-7.82(2H, m) |
| I-61 | 591.5 | (CDCl3) 1.14(9H, s), 1.22-1.30(6H, m), 1.54-1.57(1H, m), 1.77-1.85(3H, |

TABLE 3-continued

Characterization Data for Selected Compounds of Formula I (by Compound Number)

| No. | M + 1 (obs) | ¹H-NMR |
|---|---|---|
| | | m), 1.97(1H, d), 2.30-2.45(3H, m), 2.75-2.84(1H, m), 3.00(1H, s), 3.63-3.72(1H, m), 3.84-3.93(1H, m), 4.10-4.16(1H, m), 4.51(1H, s), 4.64-4.71(1H, m), 4.96(1H, d), 5.45(1H, d), 7.05(1H, d), 7.26(1H, s), 7.36(1H, d), 7.73(1H, d), 7.80(1H, d), 7.82(1H, s) |
| I-62 | 605.6 | (CDCl3) 1.15(9H, s), 1.3(3H, t), 1.35(6H, d), 1.4-1.55(3H, m), 1.8-1.95(3H, m), 2.0-2.1(1H, m), 2.3-2.4(1H, m), 2.65-2.75(1H, m), 2.8-2.9(1H, m), 3.05(1H, s), 3.7-3.8(1H, m), 3.9-4.0(1H, m), 4.2(1H, s), 4.55(1H, s), 4.7-4.8(1H, m), 5.0(1H, d), 5.5(1H, d), 6.6(1H, d), 7.3-7.45(2H, m), 7.75(1H, d), 7.85(1H, s), 8.55(1H, d) |
| I-63 | 534.4 | (CDCl3) 1.13(9H, s), 1.31(3H, t), 1.42-1.48(1H, m), 1.56(1H, brs), 1.77-1.83(3H, m), 1.99(1H, brd), 2.35(1H, dd), 2.83(1H, dd), 3.01(1H, brs), 3.67-3.76(1H, m), 3.88-3.99(4H, m), 4.14(1H, brs), 4.52(1H, brs), 4.65-4.73(1H, m), 5.00(1H, dd), 5.47(1H, d), 7.10-7.21(2H, m), 7.34-7.39(1H, m), 7.56-7.61(1H, m), 7.89(1H, d) |
| I-64 | 520.5 | (CDCl3) 1.03(3H, d), 1.10(3H, d), 1.32(3H, t), 1.50(1H, m), 1.59(1H, m), 1.812-1.84(3H, m), 2.0(1H, m), 2.15(1H, m), 2.36(1H, m), 2.83(1H, m), 3.02(1H, br s), 3.69(1H, m), 3.90-3.95(4H, m), 4.13(1H, br s), 4.40(1H, br s), 4.67(1H, m), 4.97(1H, m), 5.47(1H, d), 7.12-7.21(2H, m), 7.28(1H, m), 7.59(1H, m), 7.80(1H, m) |
| I-65 | 530.9 | (DMSO) 0.91-2.40(23H, m), 2.95-3.40(2H, m), 3.51-3.81(5H, m), 4.00-4.71(3H, m), 5.29(1H, m), 6.80(1H, d), 7.00(1H, d), 7.19(1H, t), 7.94(1H, d), 8.48(1H, d) |
| I-66 | 522.8 | (DMSO) 0.95-1.20(12H, m), 1.24-1.40(2H, m), 1.41-2.40(6H, m), 3.05(1H, m), 3.50-3.80(3H, m), 4.15(1H, m), 4.60(1H, m), 4.70(1H, d), 5.30(1H, s), 7.28-7.50(4H, m), 8.35(1H, d), 8.48(1H, d) |
| I-67 | 577.5 | ᶜCDCl3) δ 1.10(9H, s), 1.26-1.33(3H, m), 1.43-1.45(1H, m), 1.74-1.83(2H, m), 2.01(1H, brd), 2.06(1H, m), 2.30(3H, s), 2.37(1H, brdd), 2.85(1H, brdd), 2.99(1H, brs), 3.69-3.76(1H, m), 3.89-3.97(1H, m), 4.11-4.31(2H, m), 4.53(1H, brs), 4.65-4.76(1H, m), 4.95(1H, d), 5.45-5.47(1H, m), 6.75(1H, brd), 7.67-7.69(2H, m), 7.78(1H, brs), 7.92(1H, m), 8.55(1H, brd) |
| I-68 | 577.5 | (CDCl3) 1.10(9H, s), 1.26-1.33(3H, m), 1.43-1.45(1H, m), 1.74-1.83(2H, m), 2.01(1H, brd), 2.06(1H, m), 2.30(3H, s), 2.37(1H, brdd), 2.85(1H, brdd), 2.99(1H, brs), 3.69-3.76(1H, m), 3.89-3.97(1H, m), 4.11-4.31(2H, m), 4.53(1H, brs), 4.65-4.76(1H, m), 4.95(1H, d), 5.45-5.47(1H, m), 6.75(1H, brd), 7.67-7.69(2H, m), 7.78(1H, brs), 7.92(1H, m), 8.55(1H, brd) |
| I-69 | 591.5 | (CDCl3) 1.10(9H, s), 1.26-1.33(6H, m), 1.42-1.16(1H, m), 1.55-1.83(4H, m), 2.01(1H, brd), 2.36(1H, dd), 2.53(2H, q), 2.83(1H, dd), 2.99(1H, brs), 3.69-3.76(1H, m), 3.89-3.96(1H, m), 4.11(1H, s), 4.53(1H, brs), 4.66-4.77(1H, m), 4.95(1H, d), 5.48(1H, d), 6.76(1H, d), 7.67-7.74(2H, m), 8.80(1H, s), 7.90(1H, d), 8.58(1H, d) |
| I-70 | 537.4 | (CDCl3) 1.12(9H, s), 1.23-1.30(3H, m), 1.36-1.41(1H, m), 1.73-1.84(3H, m), 1.98-2.03(1H, m), 2.33-2.41(1H, m), 2.75-2.83(1H, m), 2.96(1H, brs), 3.65-3.73(1H, m), 3.84-3.93(1H, m), 4.11(1H, brs), 4.56(1H, s), 4.63-4.71(1H, m), 4.96-4.99(1H, m), 5.43-5.46(1H, m), 7.64-7.72(2H, m), 7.79-7.87(3H, m), 8.48-8.52(1H, m), 8.90(1H, brd), 9.51(1H, d) |
| I-71 | 535.6 | (CDCl3) 1.09(9H, s), 1.32(3H, t), 1.41-1.71(5H, m), 1.76-1.87(3H, m), 2.00(1H, brd), 2.37(1H, dd), 2.83(1H, dd), 2.98(1H, brs), 3.68-3.77(1H, m), 3.89-3.97(1H, m), 4.11(1H, s), 4.54(1H, brs), 4.67-4.74(1H, m), 4.95(1H, d), 5.48(1H, d), 6.64(1H, brd), 6.78(1H, d), 7.54(1H, dd), 7.71(1H, brd), 7.78(1H, d) |
| I-72 | 521.5 | (CDCl3) 1.05(3H, d), 1.15(3H, d), 1.35(3H, t), 1.5-1.6(1H, m), 1.6-1.7(1H, m), 1.8-1.9(2H, s), 2.0-2.05(1H, m), 2.15-2.25(1H, m), 2.35-2.45(1H, m), 2.8-2.9(1H, m), 2.95(1H, s), 3.7-3.8(1H, m), 3.9-4.0(1H, m), 4.1(1H, s), 4.45(3H, s), 4.7-4.8(1H, m), 4.9-4.95(1H, m), 5.55(1H, d), 6.7(1H, d), 6.85(1H, d), 7.65(1H, d), 7.75(1H, d), 7.82(1H, s) |
| I-73 | 537.4 | (CDCl3) 1.14(9H, s), 1.25(3H, t), 1.40-1.46(1H, m), 1.77-1.89(3H, m), 1.98-2.02(1H, m), 2.34(1H, dd), 2.99-3.05(1H, m), 3.62-3.69(1H, m), 3.83-3.91(1H, m), 4.12(1H, s), 4.29-4.34(1H, m), 4.59(1H, s), 4.99(1H, d), 5.38(1H, s), 7.67-7.76(2H, m), 7.86(2H, dd), 8.13(1H, d), 8.56(1H, d), 8.96(1H, d), 9.56(1H, d) |

EXAMPLE II-1

(S,S,S)-(3S)-({1-[(2S)-(3-Methoxy-2-methyl-benzoylamino)-3-methyl-butyryl]-pyrrolidine-(2S)-carbonyl}-amino)-4-oxo-butyric acid Method I (S,S,S,R)-1-[(2S)-(3-Methoxy-2-methyl-benzoylamino)-3-methyl-butyryl]-pyrrolidine-(2S)-carboxylic acid [(2R)-ethoxy-5-oxo-tetrahydro-furan-(3S)-yl]-amide (97.6 mg, 0.20 mmol) was dissolved in a mixture of 2M HCl (2 ml) and MeCN (2 ml). The reaction mixture was stirred at room temperature for 2.5 hours. The resulting crude mixture was diluted with EtOAc and washed with water. The aqueous layer was extracted twice with EtOAc. The combined organic extracts were washed with brine, dried over magnesium sulfate, filtered and concentrated in vacuo. The residue was co-evaporated with DCM/Petrol to afford the title compound as a white solid (81.3 mg, 88% yield).

Compounds of formula II-2 to II-61 have been prepared by methods substantially similar to those described in Example II-1.

EXAMPLE II-2

(S,S,S)-(3S)-({1-[(2S)-(2-Chloro-benzoylamino)-3-methyl-butyryl]-pyrrolidine-(2S)-carbonyl}-amino)-4-oxo-butyric acid

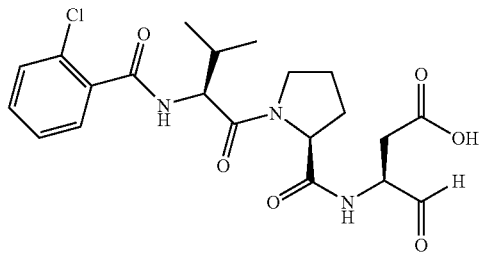

EXAMPLE II-3

(S,S,S)-(3S)-({1-[3-Methyl-(2S)-(2-methyl-benzoylamino)-butyryl]-pyrrolidine-(2S)-carbonyl}-amino)-4-oxo-butyric acid

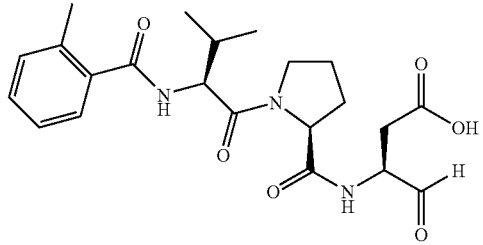

EXAMPLE II-4

(S,S,S)-(3S)-({1-[(2S)-(2-methoxy-benzoylamino)-3-methyl-butyryl]-pyrrolidine-(2S)-carbonyl}-amino)-4-oxo-butyric acid

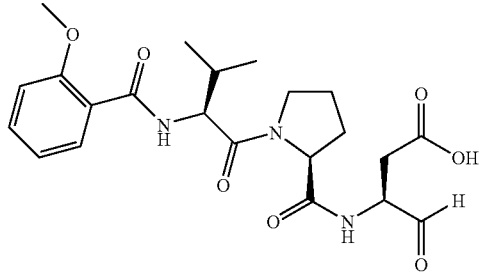

EXAMPLE II-5

(S,S,S)-(3S)-({1-[3-Methyl-(2S)-(2-trifluoromethoxy-benzoylamino)-butyryl]-pyrrolidine-(2S)-carbonyl}-amino)-4-oxo-butyric acid

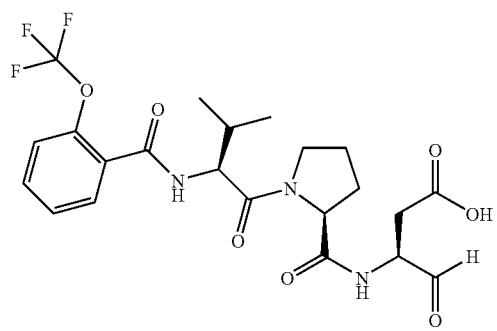

EXAMPLE II-6

(S,S,S)-(3S)-({1-[(2S)-(3-Hydroxy-2-methyl-benzoylamino)-3-methyl-butyryl]-pyrrolidine-(2S)-carbonyl}-amino)-4-oxo-butyric acid

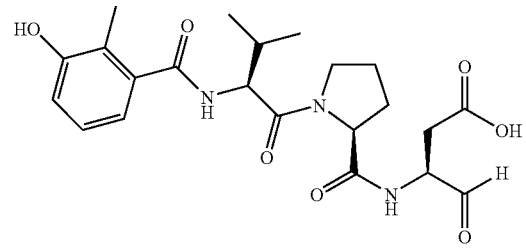

EXAMPLE II-7

(S,S,S)-(3S)-({1-[(2S)-(3-Amino-2-methyl-benzoylamino)-3-methyl-butyryl]-pyrrolidine-(2S)-carbonyl}-amino)-4-oxo-butyric acid

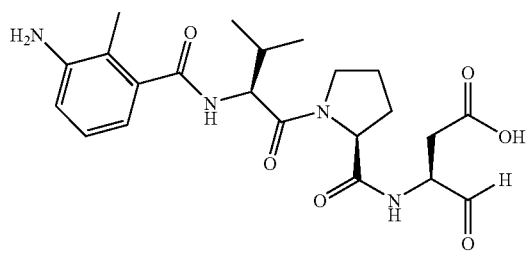

EXAMPLE II-8

(S,S,S)-(3S)-({1-[(2S)-(2,3-Dichloro-benzoylamino)-3-methyl-butyryl]-pyrrolidine-(2S)-carbonyl}-amino)-4-oxo-butyric acid

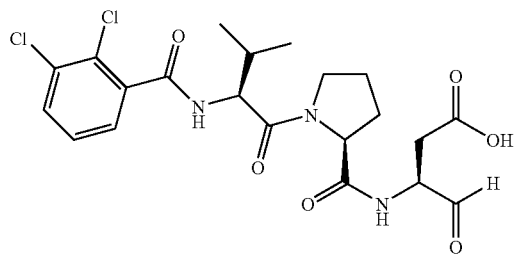

EXAMPLE II-9

(S,S,S)-(3S)-({1-[(2S)-(2-Chloro-3-trifluoromethyl-benzoylamino)-3-methyl-butyryl]-pyrrolidine-(2S)-carbonyl}-amino)-4-oxo-butyric acid

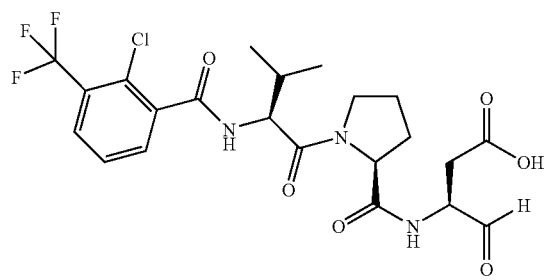

EXAMPLE II-10

(S,S,S)-(3S)-({1-[(2S)-(3-Chloro-2-methyl-benzoylamino)-3-methyl-butyryl]-pyrrolidine-(2S)-carbonyl}-amino)-4-oxo-butyric acid

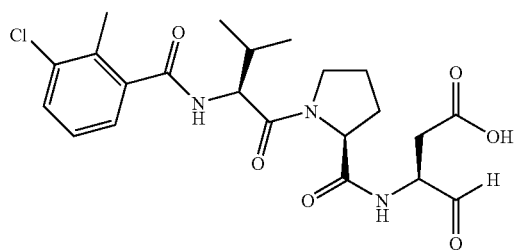

EXAMPLE II-11

(S,S,S)-(3S)-({1-[(2S)-(2,4-Dichloro-benzoylamino)-3-methyl-butyryl]-pyrrolidine-(2S)-carbonyl}-amino)-4-oxo-butyric acid

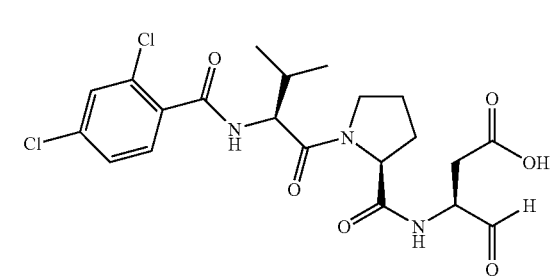

EXAMPLE II-12

(S,S,S)-(3S)-({1-[(2S)-(2,5-Dichloro-benzoylamino)-3-methyl-butyryl]-pyrrolidine-(2S)-carbonyl}-amino)-4-oxo-butyric acid

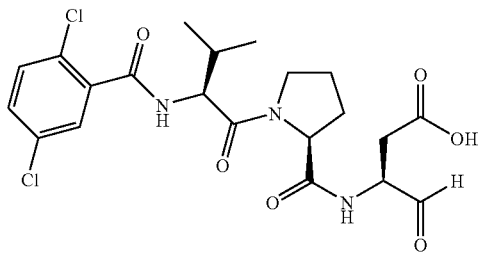

EXAMPLE II-13

(S,S,S)-(3S)-({1-[(2S)-(2,6-Dichloro-benzoylamino)-3-methyl-butyryl]-pyrrolidine-(2S)-carbonyl}-amino)-4-oxo-butyric acid

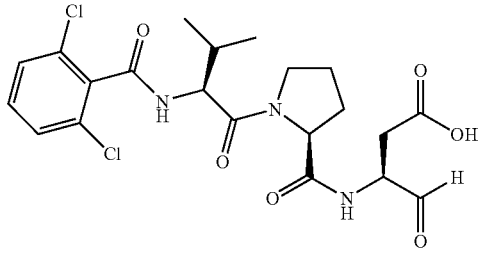

EXAMPLE II-14

(S,S,S)-(3S)-({1-[(2S)-(2,6-Methyl-benzoylamino)-3-methyl-butyryl]-pyrrolidine-(2S)-carbonyl}-amino)-4-oxo-butyric acid

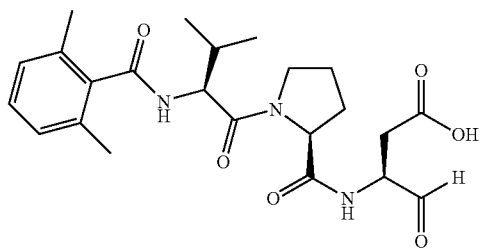

EXAMPLE II-15

(S,S,S)-(3S)-[(1-{3-Methyl-(2S)-[(2-methyl-pyridine-3-carbonyl)-amino]-butyryl}-pyrrolidine-(2S)-carbonyl)-amino]-4-oxo-butyric acid

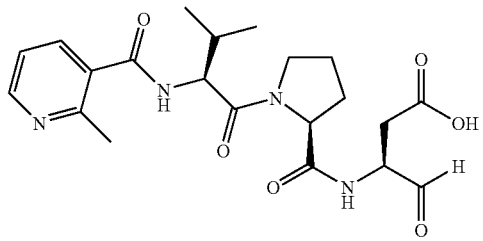

EXAMPLE II-16

(S,S,S)-(3S)-[(1-{3-Methyl-(2S)-[(4-methyl-pyridine-3-carbonyl)-amino]-butyryl}-pyrrolidine-(2S)-carbonyl)-amino]-4-oxo-butyric acid

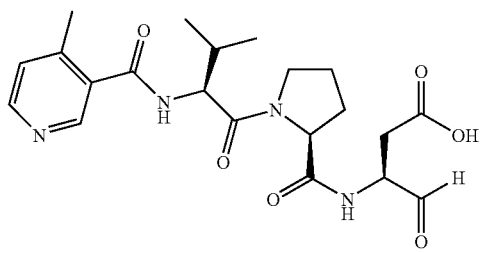

EXAMPLE II-17

(S,S,S)-(3S)-[(1-{3-Methyl-(2S)-[(3-methyl-thiophene-2-carbonyl)-amino]-butyryl}-pyrrolidine-(2S)-carbonyl)-amino]-4-oxo-butyric acid

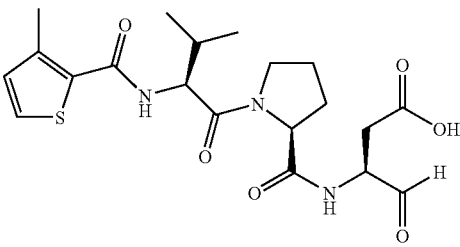

EXAMPLE II-18

(S,S,S)-(3S)-[(1-{(2S)-[(2,3-Dichloro-pyridine-4-carbonyl)-amino]-3-methyl-butyryl}-pyrrolidine-(2S)-carbonyl)-amino]-4-oxo-butyric acid

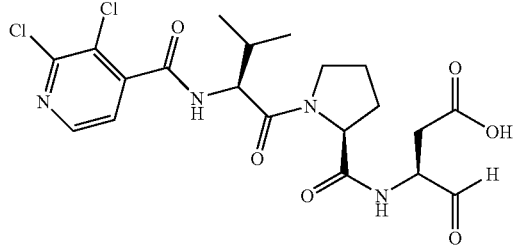

EXAMPLE II-19

(S,S,S)-(3S)-[(1-{(2S)-[(3,5-Dichloro-pyridine-4-carbonyl)-amino]-3-methyl-butyryl}-pyrrolidine-(2S)-carbonyl)-amino]-4-oxo-butyric acid

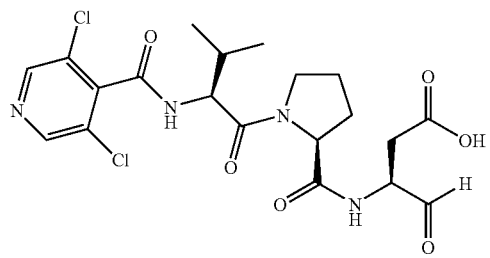

EXAMPLE II-20

(S,S,S)-(3S)-({1-[(2S)-(3-Methoxy-2-methyl-benzoylamino)-3,3-dimethyl-butyryl]-pyrrolidine-(2S)-carbonyl}-amino)-4-oxo-butyric acid

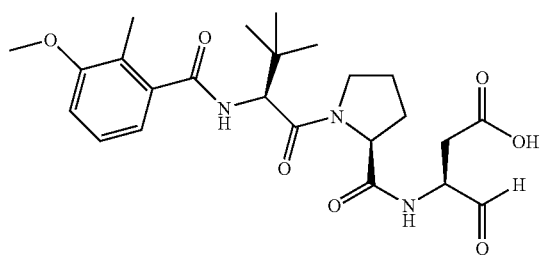

EXAMPLE II-21

(S,S,S)-4-Oxo-(3S)-({1-[4,4,4-trifluoro-(2S)-(2-methyl-3-methoxy-benzoylamino)-butyryl]-pyrrolidine-(2S)-carbonyl}-amino)-butyric acid

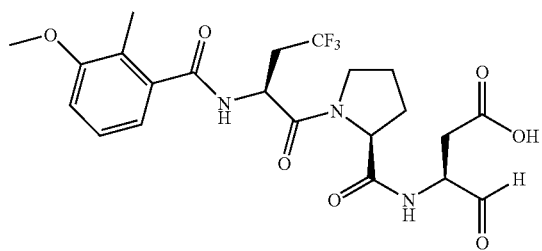

EXAMPLE II-22

(S,S,S)-(3S)-({1-[(2S)-(5-Methoxy-2-methyl-benzoylamino)-3-methyl-butyryl]-pyrrolidine-(2S)-carbonyl}-amino)-4-oxo-butyric acid

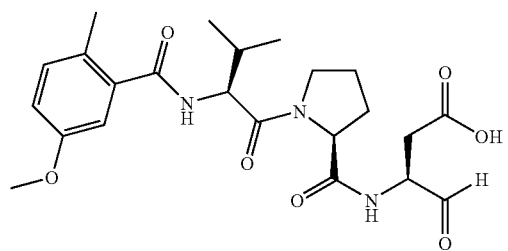

EXAMPLE II-23

(S,S,S)-(3S)-({1-[(2S)-(3-Methoxy-2-methyl-benzoylamino)-3-thiazol-4-yl-propionyl]-pyrrolidine-(2S)-carbonyl}-amino)-4-oxo-butyric acid

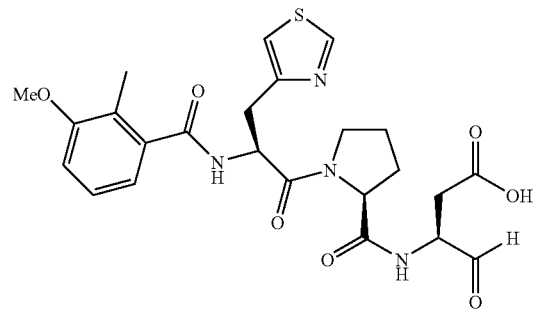

EXAMPLE II-24

(S,S,S)-(3S)-({1-[(2S)-(2-Chloro-benzoylamino)-4,4,4-trifluoro-butyryl]-pyrrolidine-(2S)-carbonyl}-amino)-4-oxo-butyric acid

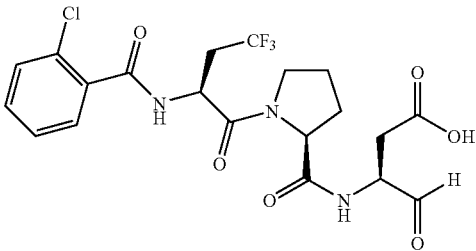

EXAMPLE II-25

(S,S,S)-(3S)-({1-[(2S)-(2-Chloro-benzoylamino)-3-thiazol-4-yl-propionyl]-pyrrolidine-(2S)-carbonyl}-amino)-4-oxo-butyric acid

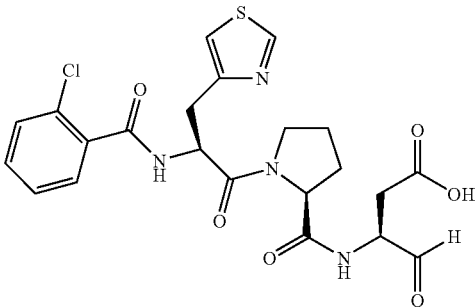

EXAMPLE II-26

(S,S,S)-(3S)-({1-[3,3-Dimethyl-(2S)-(2-methyl-benzoylamino)-butyryl]-pyrrolidine-(2S)-carbonyl}-amino)-4-oxo-butyric acid

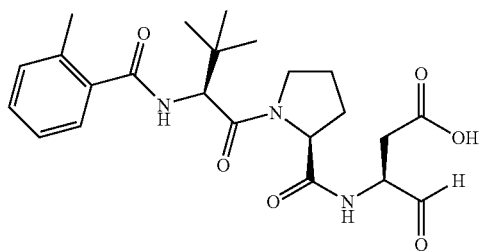

EXAMPLE II-27

(S,S,S)-(3S)-({1-[3-Methyl-(2S)-(2-trifluoromethyl-benzoylamino)-butyryl]-pyrrolidine-(2S)-carbonyl}-amino)-4-oxo-butyric acid

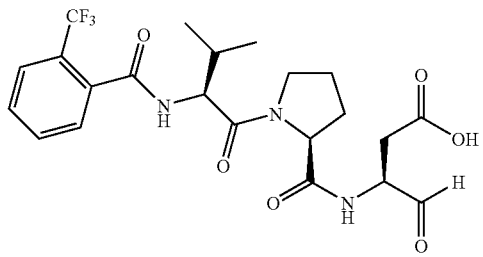

EXAMPLE II-28

(S,S,S)-(3S)-({1-[(2S)-(2-Chloro-benzoylamino)-3,3-dimethyl-butyryl]-pyrrolidine-(2S)-carbonyl}-amino)-4-oxo-butyric acid

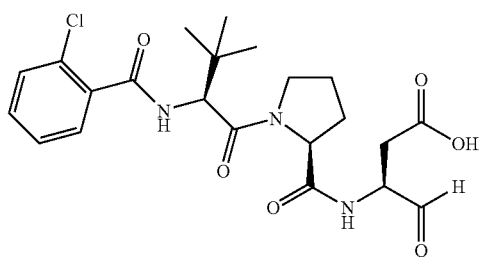

EXAMPLE II-29

(S,S,S)-(3S)-({1-[3,3-Dimethyl-(2S)-(2-trifluoromethyl-benzoylamino)-butyryl]-pyrrolidine-(2S)-carbonyl}-amino)-4-oxo-butyric acid

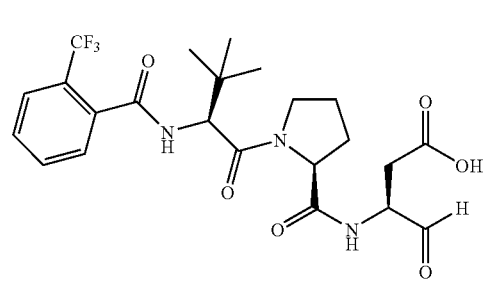

EXAMPLE II-30

(S,S,S)-(3S)-({1-[(2S)-(2-Chloro-3-methoxy-benzoylamino)-3,3-dimethyl-butyryl]-pyrrolidine-(2S)-carbonyl}-amino)-4-oxo-butyric acid

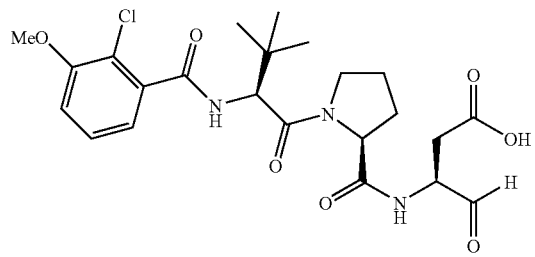

EXAMPLE II-31

(S,S,S)-(3S)-({1-[(2S)-(2-Fluoro-3-methoxy-benzoylamino)-3,3-dimethyl-butyryl]-pyrrolidine-(2S)-carbonyl}-amino)-4-oxo-butyric acid

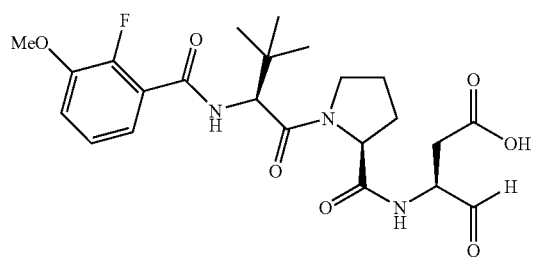

EXAMPLE II-32

(S,S,S)-(3S)-({1-[(2S)-(2-Chloro-3-trifluoromethoxy-benzoylamino)-3,3-dimethyl-butyryl]-pyrrolidine-(2S)-carbonyl}-amino)-4-oxo-butyric acid

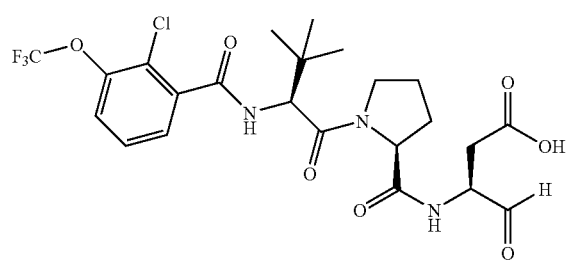

EXAMPLE II-33

(S,S,S)-(3S)-({1-[(2S)-(2-Chloro-3-cyclopropyloxy-benzoylamino)-3,3-dimethyl-butyryl]-pyrrolidine-(2S)-carbonyl}-amino)-4-oxo-butyric acid

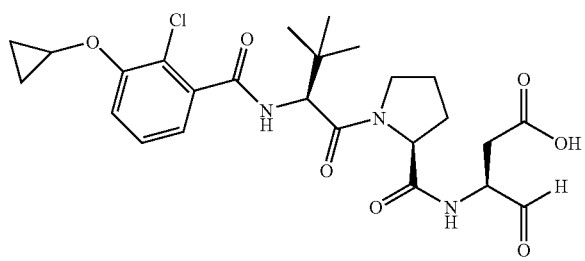

EXAMPLE II-34

(S,S,S)-(3S)-({1-[(2S)-(2-Chloro-3-methyl-benzoylamino)-3,3-dimethyl-butyryl]-pyrrolidine-(2S)-carbonyl}-amino)-4-oxo-butyric acid

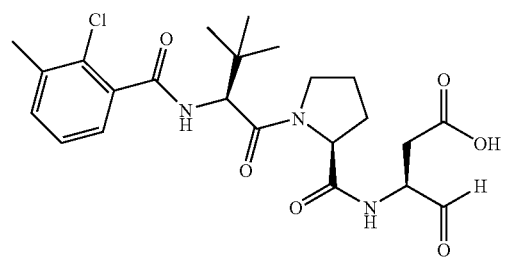

EXAMPLE II-35

(S,S,S)-(3S)-({1-[(2S)-(2-chloro-3-methoxy-benzoylamino)-3-methyl-butyryl]-pyrrolidine-(2S)-carbonyl}-amino)-4-oxo-butyric acid

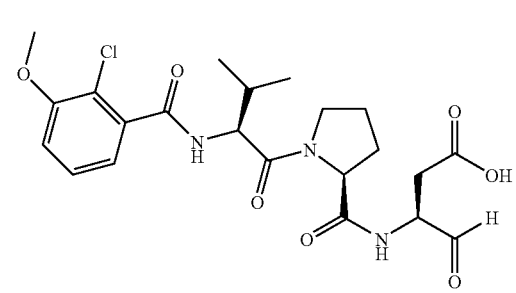

EXAMPLE II-36

(S,S,S)-(3S)-({1-[(2S)-(2-Chloro-3-ethyl-benzoylamino)-3,3-dimethyl-butyryl]-pyrrolidine-(2S)-carbonyl}-amino)-4-oxo-butyric acid

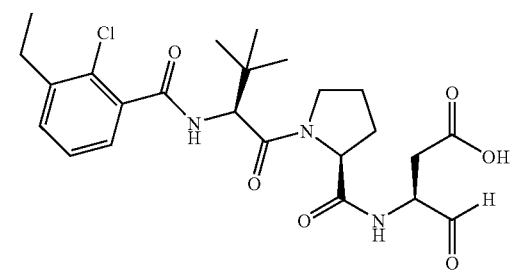

EXAMPLE II-37

(S,S,S)-(3S)-({1-[(2S)-(2-chloro-4-methoxy-benzoylamino)-3-methyl-butyryl]-pyrrolidine-(2S)-carbonyl}-amino)-4-oxo-butyric acid

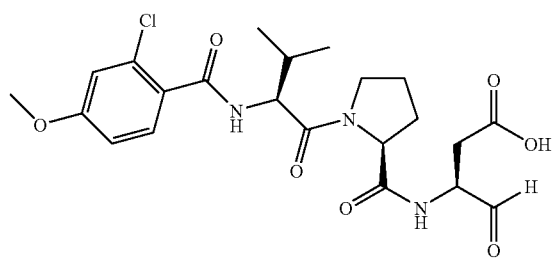

EXAMPLE II-38

(S,S,S)-(3S)-({1-[(2S)-(2-Chloro-3-cyclopropyl-methoxy-benzoylamino)-3,3-dimethyl-butyryl]-pyrrolidine-(2S)-carbonyl}-amino)-4-oxo-butyric acid

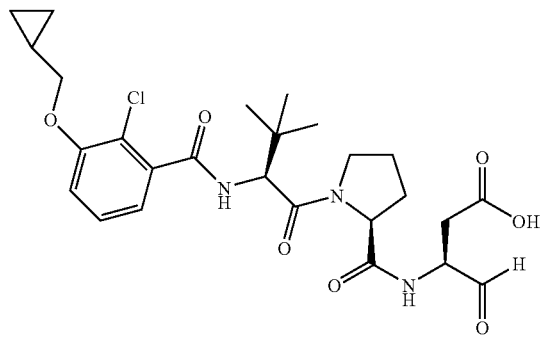

EXAMPLE II-39

(S,S,S)-(3S)-({1-[(2S)-(2-Chloro-3-hydroxy-benzoylamino)-3,3-dimethyl-butyryl]-pyrrolidine-(2S)-carbonyl}-amino)-4-oxo-butyric acid

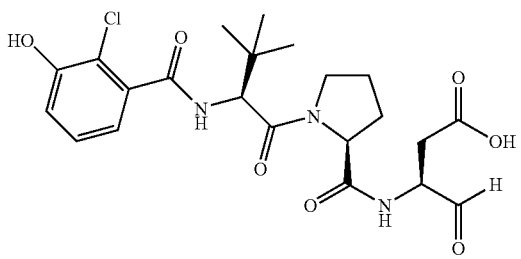

EXAMPLE II-40

(S,S,S)-(3S)-({1-[(2S)-(2-chloro-4-acetamido-benzoylamino)-3-methyl-butyryl]-pyrrolidine-(2S)-carbonyl}-amino)-4-oxo-butyric acid

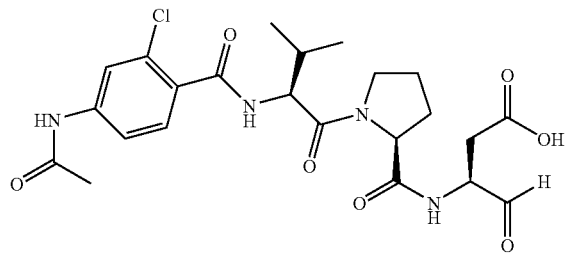

EXAMPLE II-41

(S,S,S)-(3S)-({1-[(2S)-(2-Chloro-3-acetamido-benzoylamino)-3,3-dimethyl-butyryl]-pyrrolidine-(2S)-carbonyl}-amino)-4-oxo-butyric acid

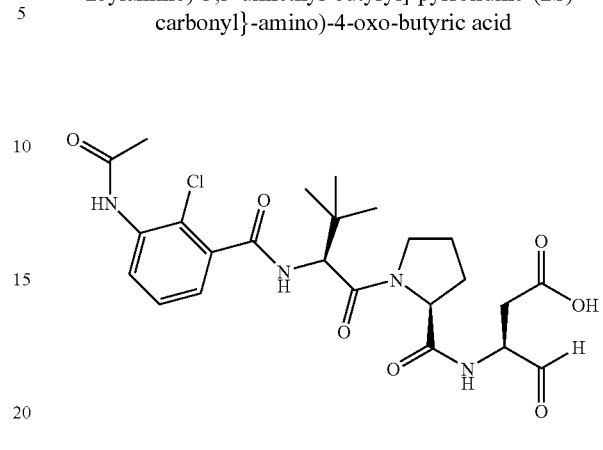

EXAMPLE II-42

(S,S,S)-(3S)-({1-[(2S)-(2-methyl-3-acetamido-benzoylamino)-3,3-dimethyl-butyryl]-pyrrolidine-(2S)-carbonyl}-amino)-4-oxo-butyric acid

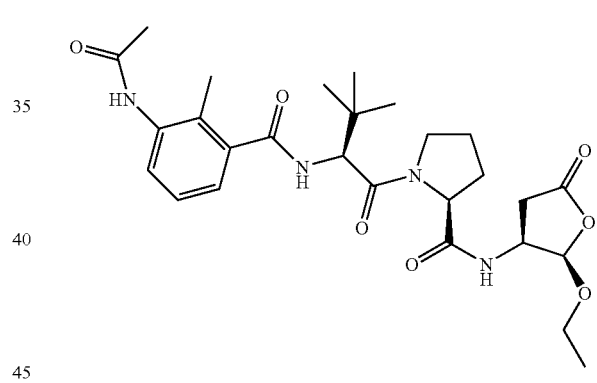

EXAMPLE II-43

(S,S,S)-(3S)-({1-[(2S)-(2-chloro-4-acetamido-benzoylamino)-3,3-dimethyl-butyryl]-pyrrolidine-(2S)-carbonyl}-amino)-4-oxo-butyric acid

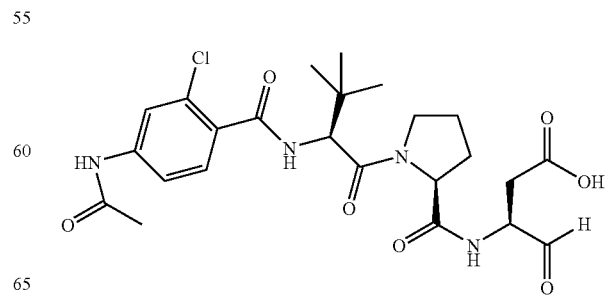

EXAMPLE II-44

(S,S,S)-(3S)-({1-[(2S)-(2-fluoro-4-acetamido-benzoylamino)-3,3-dimethyl-butyryl]-pyrrolidine-(2S)-carbonyl}-amino)-4-oxo-butyric acid

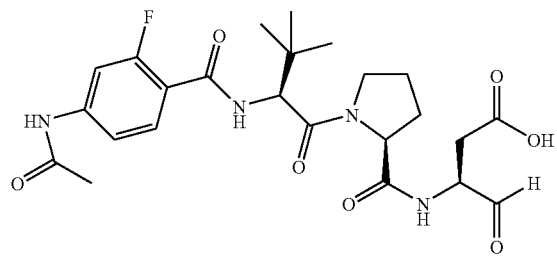

EXAMPLE II-45

(S,S,S)-(3S)-({1-[(2S)-(2-fluoro-4-acetamido-benzoylamino)-3-methyl-butyryl]-pyrrolidine-(2S)-carbonyl}-amino)-4-oxo-butyric acid

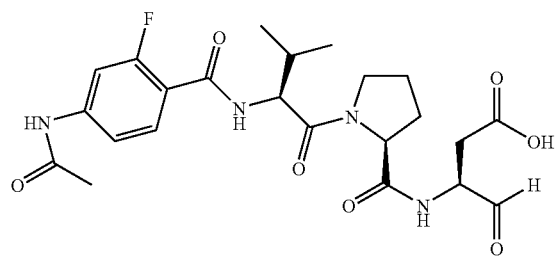

EXAMPLE II-46

(S,S,S)-(3S)-({1-[(2S)-(2-chloro-4-isopropyloxy-benzoylamino)-3-methyl-butyryl]-pyrrolidine-(2S)-carbonyl}-amino)-4-oxo-butyric acid

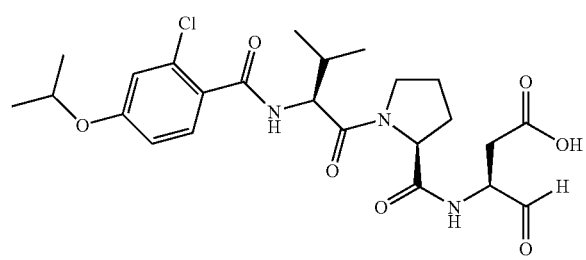

EXAMPLE II-47

(S,S,S)-(3S)-({1-[(2S)-(2-chloro-4-hydroxy-benzoylamino)-3,3-dimethyl-butyryl]-pyrrolidine-(2S)-carbonyl}-amino)-4-oxo-butyric acid

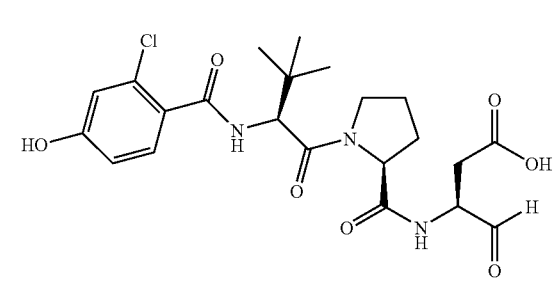

EXAMPLE II-48

(S,S,S)-(3S)-({1-[(2S)-(2-chloro-4-methoxymethyl-benzoylamino)-3,3-dimethyl-butyryl]-pyrrolidine-(2S)-carbonyl}-amino)-4-oxo-butyric acid

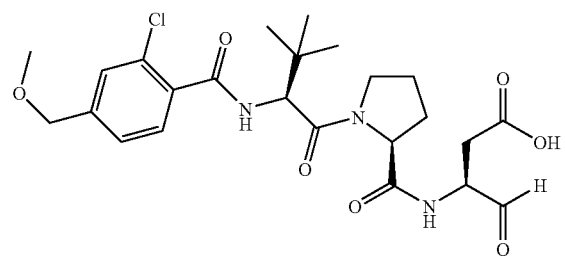

EXAMPLE II-49

(S,S,S)-(3S)-({1-[(2S)-(2-chloro-4-isobutyrylamido-benzoylamino)-3,3-dimethyl-butyryl]-pyrrolidine-(2S)-carbonyl}-amino)-4-oxo-butyric acid

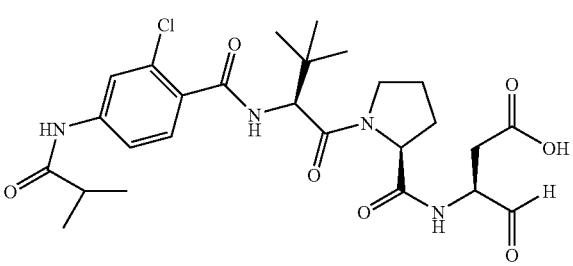

EXAMPLE II-50

(S,S,S)-(3S)-({1-[(2S)-(2-chloro-4-acetamido-benzoylamino)-3-cyclohexyl]-pyrrolidine-(2S)-carbonyl}-amino)-4-oxo-butyric acid

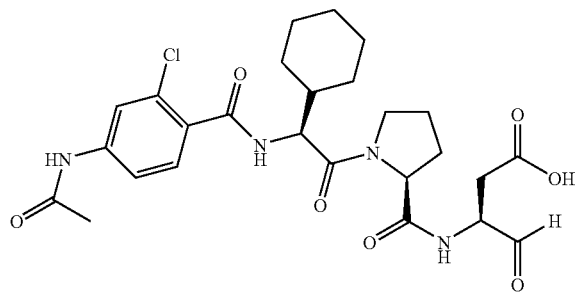

EXAMPLE II-51

(S,S,S)-(3S)-({1-[(2S)-(2-chloro-4-methoxycarbonylamino-benzoylamino)-3,3-dimethyl-butyryl]-pyrrolidine-(2S)-carbonyl}-amino)-4-oxo-butyric acid

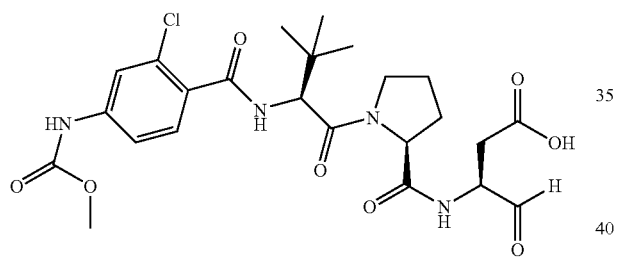

EXAMPLE II-52

(S,S,S)-(3S)-({1-[(2S)-(2-chloro-3-phenoxy-benzoylamino)-3,3-dimethyl-butyryl]-pyrrolidine-(2S)-carbonyl}-amino)-4-oxo-butyric acid

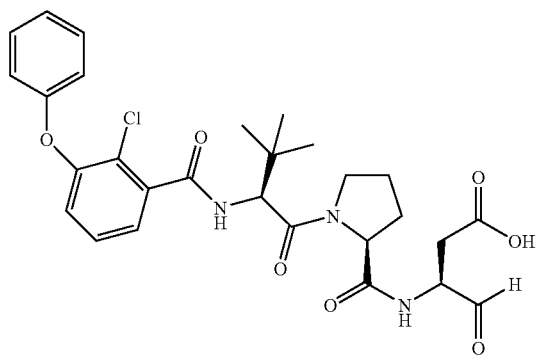

EXAMPLE II-53

(S,S,S)-(3S)-({1-[(2S)-(2-chloro-6-amino-benzoylamino)-3-methyl-butyryl]-pyrrolidine-(2S)-carbonyl}-amino)-4-oxo-butyric acid

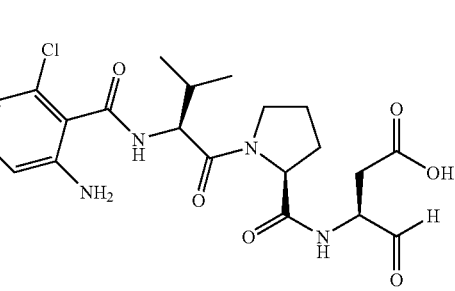

EXAMPLE II-54

(S,S,S)-(3S)-({1-[(2S)-(2-chloro-benzoylamino)-3,3-dimethyl-butyryl]-piperidine-(2S)-carbonyl}-amino)-4-oxo-butyric acid

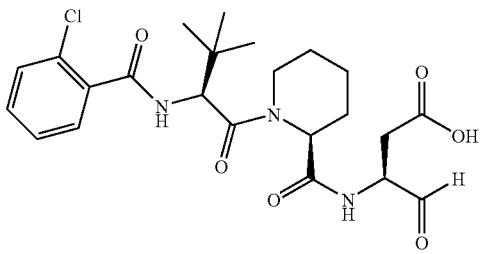

EXAMPLE I-55

(3S)-({2-[(2S)-(3-Methoxy-2-methyl-benzoylamino)-3,3-dimethyl-butyryl]-2-(1S,4R)-aza-bicyclo[2.2.1]heptane-(3S)-carbonyl}-amino)-4-oxo-butyric acid

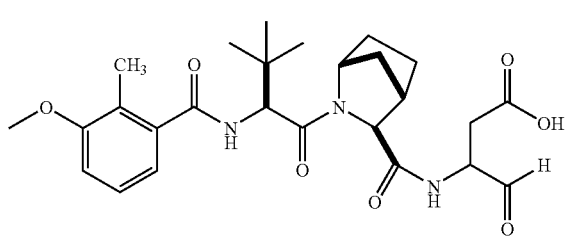

EXAMPLE II-56

(3S)-({2-[(2S)-(2-Chloro-benzoylamino)-3,3-dimethyl-butyryl]-2-(1S,4R)-aza-bicyclo[2.2.1]heptane-(3S)-carbonyl}-amino)-4-oxo-butyric acid

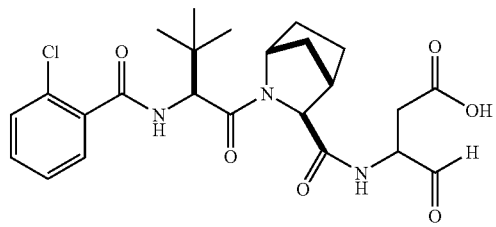

EXAMPLE II-57

(3S)-({2-[(2S)-(4-Acetylamino-2-chloro-benzoylamino)-3,3-dimethyl-butyryl]-2-(1S,4R)-aza-bicyclo[2.2.1]heptane-(3S)-carbonyl}-amino)-4-oxo-butyric acid

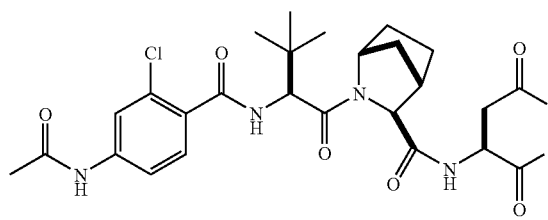

EXAMPLE II-58

(3S)-({2-[(2S)-(2-Chloro-4-propionylamino-benzoylamino)-3,3-dimethyl-butyryl]-2-(1S,4R)-aza-bicyclo[2.2.1]heptane-(3S)-carbonyl}-amino)-4-oxo-butyric acid

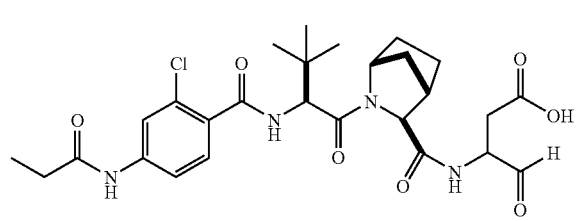

EXAMPLE II-59

(3S)-({2-[(2S)-(2-Chloro-3-isobutyrylamino-benzoylamino)-3,3-dimethyl-butyryl]-2-(1S,4R)-aza-bicyclo[2.2.1]heptane-(3S)-carbonyl}-amino)-4-oxo-butyric acid

EXAMPLE II-60

(3S)-({2-[(2S)-(2-Fluoro-3-methoxy-benzoylamino)-3,3-dimethyl-butyryl]-2-(1S,4R)-aza-bicyclo[2.2.1]heptane-(3S)-carbonyl}-amino)-4-oxo-butyric acid

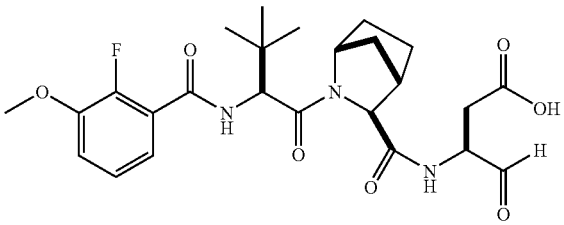

EXAMPLE II-61

(3S)-({2-[(2S)-(2-Fluoro-3-methoxy-benzoylamino)-3-methyl-butyryl]-2-(1S,4R)-aza-bicyclo[2.2.1]heptane-(3S)-carbonyl}-amino)-4-oxo-butyric acid

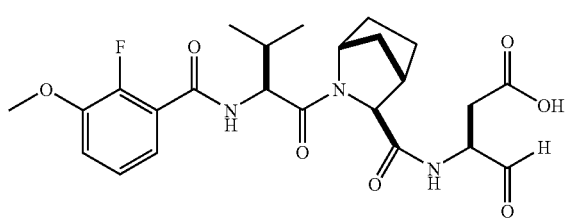

EXAMPLE II-62

(3S)-({2-[(2S)-(4-Acetylamino-3-chloro-benzoylamino)-3,3-dimethyl-butyryl]-2-(1S,4R)-aza-bicyclo[2.2.1]heptane-(3S)-carbonyl}-amino)-4-oxo-butyric acid

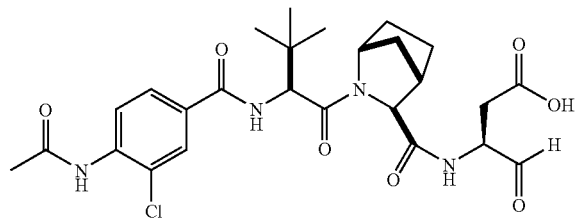

EXAMPLE II-63

(3S)-({2-[(2S)-(3-Chloro-4-propionylamino-benzoylamino)-3,3-dimethyl-butyryl]-2-(1S,4R)-aza-bicyclo[2.2.1]heptane-(3S)-carbonyl}-amino)-4-oxo-butyric acid

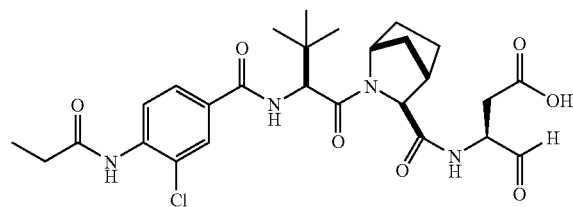

EXAMPLE II-64

(3S)-({2-[(2S)-(Isoquinolin-1-ylcarbonylamino)-3,3-dimethyl-butyryl]-2-(1S,4R)-aza-bicyclo[2.2.1]heptane-(3S)-carbonyl}-amino)-4-oxo-butyric acid

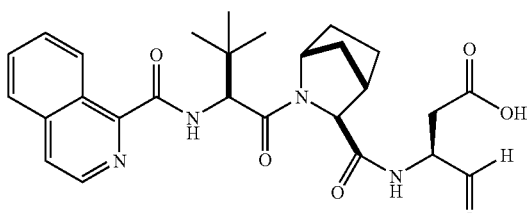

EXAMPLE II-65

(3S)-({2-[(2S)-(4-Amino-3-chloro-benzoylamino)-3,3-dimethyl-butyryl]-2-(1S,4R)-aza-bicyclo[2.2.1]heptane-(3S)-carbonyl}-amino)-4-oxo-butyric acid

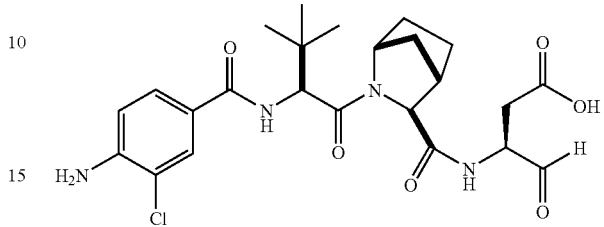

EXAMPLE II-66

(3S)-({2-[(2S)-(4-Amino-3-chloro-benzoylamino)-3-methyl-butyryl]-2-(1S,4R)-aza-bicyclo[2.2.1]heptane-(3S)-carbonyl}-amino)-4-oxo-butyric acid

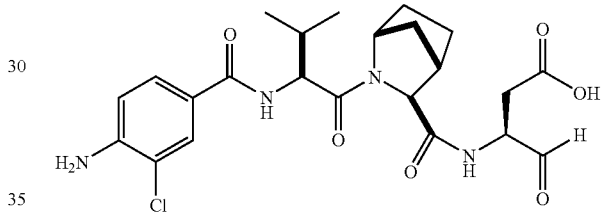

The characterization data for compounds II-1 to II-66 is summarized in Table 4 below and includes HPLC, LC/MS (observed) and $^1$H NMR data. $^1$H NMR data was obtained at 400 MHz, and was found to be consistent with structure.

TABLE 4

Characterization Data for Selected Compounds of Formula II (According to Compound Number)

| No. | M + 1 (obs) | $^1$H-NMR |
|---|---|---|
| II-1 | 462.1 | (DMSO-$d_6$) 0.82-0.98(6H, m), 1.89-2.07(5H, m), 2.10(3H, s), 3.0(1H, m), 3.63(1H, m), 3.79(3H, s), 3.88(1H, m), 4.00(1H, m), 4.25(1H, m), 4.40-4.44(2H, m), 5.45(1H, br s), 6.83(1H, d), 7.00(1H, d), 7.19(1H, t), 7.77(1H, br s), 8.32-8.50(2H, m) |
| II-2 | 452.0 | (DMSO-$d_6$) 0.95-0.99(6H, m), 1.87-2.09(5H, m), 3.00(1H, m), 3.64(1H, m), 3.85(1H, m), 4.04(1H, m), 4.25(1H, m), 4.40(1H, m), 4.47(1H, m), 5.45(1H, m), 7.34-7.49(4H, m), 7.78(1H, m), 8.40(1H, m), 8.64(1H, m) |
| II-3 | 432.1 | (DMSO-$d_6$) 0.94-0.99(6H, m), 1.87-2.09(5H, m), 2.30(3H, s), 2.90(1H, m), 3.64(1H, m), 3.88(1H, m), 4.03(1H, m), 4.30(1H, m), 4.44(1H, m), 5.45(1H, m), 7.19-7.33(4H, m), 7.77(1H, br s), 8.35-8.40(2H, m) |
| II-4 | 448.0 | (CD$_3$OD) 1.05-1.18(6H, m), 2.00-2.30(5H, m), 2.52-2.75(2H, m), 3.66-3.83(1H, m), 3.92-4.03(1H, m), 4.26-4.35(1H, |

TABLE 4-continued

Characterization Data for Selected Compounds of Formula II (According to Compound Number)

| No. | M + 1 (obs) | ¹H-NMR |
|---|---|---|
| | | m), 4.45-4.55(1H, m), 4.61-4.70(1H, m), 4.78-4.85(1H, m), 7.13(1H, t), 7.21(1H, d), 7.57(1H, t), 8.00(1H, d), 8.69(1H, d) |
| II-5 | 502.0 | (CD₃OD) 0.98-1.15(6H, m), 1.95-2.26(5H, m), 2.54-2.76(2H, m), 3.73-3.84(1H, m), 3.99-4.06(1H, m), 4.21-4.32(1H, m), 4.45-4.53(1H, m), 4.60-4.70(2H, m), 7.30-4.47(2H, m), 7.54-7.64(2H, m) |
| II-6 | 448.1 | (DMSO-d₆) 0.92-0.98(6H, m), 1.85-2.04(5H, m), 2.07(3H, s), 3.00(1H, m), 3.63(1H, m), 3.87(1H, m), 4.03(1H, m), 4.25(1H, m), 4.41(1H, m), 5.45(1H, m), 6.68(1H, m), 6.82(1H, m), 7.01(1H, m), 7.81(1H, m), 8.25(1H, d), 8.40(1H, m), 9.5(1H, m) |
| II-7 | 447.0 | (CD₃OD) 1.02-1.18(6H, m), 1.88-2.28(5H, m), 2.39(3H, s), 2.50-2.78(2H, m), 3.75-3.83(1H, m), 4.00-4.10(1H, m), 4.21-4.32(1H, m), 4.45-4.52(1H, m), 4.60-4.65(2H, m), 7.39-7.54(3H, m) |
| II-8 | 446.0 | (DMSO-d₆) 0.94-0.99(6H, m), 1.71-2.12(4H, m), 2.33(1H, br s), 2.67(1H, br S), 2.94-3.07(1H, m), 3.61-3.69(1H, m), 3.82-3.87(1H, m), 4.03-4.10(1H, m), 4.19-4.28(1H, m), 4.30-4.43(2H, m), 5.42-5.47(1H, m), 7.28-7.30(1H, m), 7.37-7.40(1H, m), 7.68-7.82(2H, m), 8.77(1H, d) |
| II-9 | 519.9 | (DMSO-d₆) 0.94-0.99(6H, m), 1.86-2.09(5H, m), 3.00(1H, m), 3.65(1H, m), 3.84(1H, m), 4.05(1H, m), 4.24(1H, m), 4.40(1H, m), 4.51(1H, m), 5.45(1H, m), 7.57-7.62(2H, m), 7.77(1H, d), 7.90(1H, m), 8.40(1H, d), 8.87(1H, d) |
| II-10 | 466.0 | (DMSO-d₆) 0.93-0.99(6H, 2×d), 1.77-2.19(5H, m), 2.29(3H, s), 2.97(1H, br S), 3.62-3.65(1H, m), 3.85-3.88(1H, m), 4.00-4.32(2H, br m), 4.41-4.53(2H, m), 5.45(1h, br s), 7.18-7.27(2H, m), 7.45-7.50(1H, m), 7.85(1h, br d), 8.41(1H, br d), 8.57(1H, d) |
| II-11 | 485.9 | (DMSO-d₆) 0.82-0.86(3H, m), 0.93-0.98(3H, m), 1.87-2.08(5H, m), 3.00(1H, m), 3.64(1H, m), 3.82(1H, m), 4.10(1H, m), 4.30(1H, m), 4.45(1H, m), 4.47(1H, m), 5.44(1H, d), 7.37(1H, m), 7.47(1H, m), 7.65(1H, m), 7.77(1H, m), 8.40(1H, m), 8.72(1H, m) |
| II-12 | 485.9 | (DMSO-d₆) 0.94-0.99(6H, m), 1.91-2.09(5H, m), 3.00(1H, m), 3.64(1H, m), 3.83(1H, m), 4.03(1H, m), 4.20(1H, m), 4.40(1H, m), 4.47(1H, m), 5.45(1H, m), 7.37(1H, s), 7.50-7.52(2H, m), 7.78(1H, m), 8.44(1H, m), 8.79(1H, m) |
| II-13 | 486.3 | (DMSO-d₆) 0.82-0.86(3H, m), 0.92-0.99(3H, m), 1.80-1.87(2H, m), 1.99-2.02(4H, m), 2.48(0.5 H, m), 2.95(0.5 H, m), 3.51(1H, m), 3.80-4.56(4H, m), 5.00 and 5.47(1H, 2×m), 7.37-7.48(3H, m), 7.76-8.32(1H, m), 8.95-9.39(1H, 3×dd) |
| II-14 | 446.0 | (DMSO-d₆) 0.93-0.99(6H, m), 1.80-2.09(5H, m)2.17(6H, d), 2.95(1H, br s), 3.63-3.65(1H, m), 3.96-3.99(1H, m), 4.10(1H, br s), 4.30(1H, br s), 4.44(1H, t), 5.48(1H, br s), 7.00(2H, d), 7.14(1H, t), 7.78(1H, br s), 8.50(1H, br s), 8.55(1H, d) |
| II-15 | 433.1 | (DMSO-d₆) 0.91-1.02(6H, m), 1.80-2.20(5H, m), 2.66-2.68(3H, s), 3.00(1H, m), 3.62-3.85(3H, m), 4.10(1H, m), 4.24(1H, m), 4.51(1H, m), 5.72(1H, m), 7.73-7.76(2H, m), 8.19(1H, m), 8.52(1H, m), 8.75(1H, d), 8.90(1H, m) |
| II-16 | 433.1 | (DMSO-d₆) 0.9-1.05(6H, m), 1.8-2.2(6H, m), 2.3-2.4(1H, m), 2.7-2.75(1H, m), 2.9-3.0(1H, m), 3.65-3.75(1H, m), 3.8-3.9(1H, m), 4.1-4.15(1H, m), 4.3-4.4(1H, m), 4.45-4.65(1H, m), 7.8-7.9(1H, m), 8.7-8.8(2H, d), 8.9-8.95(1H, m) |
| II-17 | 438.0 | (DMSO-d₆) 0.83-0.99(6H, m), 1.80-2.20(5H, m), 2.40(3H, s), 3.00(1H, m), 3.61(1H, m), 3.81(1H, m), 4.10(1H, m), 4.25(1H, m), 4.42-4.46(2H, m), 5.44(1H, br s), 6.97(1H, m), 7.34(1H, m), 7.59(1H, m), 7.81(1H, m), 8.49(1H, m) |
| II-18 | 487.0 | (DMSO-d₆) 0.92-1.00(6H, m), 1.75-2.08(5H, m), 2.30-2.34(1H, m), 2.99(1H, dd), 3.62-3.67(1H, m), 3.78-3.82(1H, m), 3.78-3.82(1H, m), 4.05-4.26(1H, m), 4.38-4.54(2H, m), 5.44-5.72(1H, m), 7.37-7.41(1H, m), 8.41-8.43(2H, m), 8.97-9.00(1H, d) |
| II-19 | 487.0 | (DMSO-d₆) 0.94-1.00(6H, m), 1.77-2.15(5H, m), 3.02(1H, dd), 3.61-3.70(1H, m), 3.80-3.90(1H, m), 4.03-4.08(1H, m), 4.52-4.56(1H, m), 4.95(2H, br s), 5.45(1H, s), 8.42(1H, d), 8.67(2H, s), 9.17(1H, d) |
| II-20 | 476.4 | (DMSO-d₆) 0.91-1.11(9H, m), 1.70-2.14(7H, m), 2.31(1H, m), 3.01(1H, m), 3.50-3.97(5H, m), 4.00-4.62(3H, m), 5.50(1H, m), 6.77(1H, d), 7.00(1H, d), 7.18(1H, dd), 7.50-8.50(3H, m) |
| II-21 | 502.1 | (DMSO-d₆) 1.80-2.00(3H, m), 2.11(4H, overlapping s and m), 2.60-2.80(2H, m), 3.64-3.69(1H, m), 3.80(3H, s), 4.10(1H, vbrs), 4.30(1H, vbrs), 5.00(1H, m), 6.86(1H, d), 7.03(1H, d), 7.22(1H, t), 8.45(1H, vbrs), 8.81(1H, d) |
| II-22 | 462.4 | (DMSO-d₆) 0.93-1.00(6H, m), 1.70-2.15(5H, m), 2.22(3H, s), 2.33(1H, d), 2.99(1H, dd), 3.60-3.65(2H, m), 3.74(3H, s), 4.04-4.08(1H, m), 4.21-4.27(1H, m), 4.40-4.58(2H, m), 5.46(1H, brd d), 6.78-6.81(1H, m), 6.85-6.91(1H, m), 7.09-7.14(1H, m), 8.37(2H, 2×brd d) |
| II-23 | 517.0 | (DMSO-d₆) 1.77-2.19(5H, m), 2.95-3.28(3H, m), 3.60(1H, brd d), 3.71-3.78(4H, m), 4.10-4.42(6H, m), 4.97(1H, brd s), 5.45-72(1H, m), 6.74(1H, d), 6.97(1H, d), 7.10-7.22(1H, m), 7.44(1H, m), 8.37-8.68(2H, m), 9.05(1H, brd s) |
| II-24 | 492.0 | (DMSO-d₆) 1.75-1.98(3H, m), 2.08-2.13(1H, m), 2.64-2.77(2H, m), 2.99(0.5H, dd), 3.63-3.73(2H, m), 4.08(0.5H, brt), 4.20(0.5H, dd), 4.23-4.49(3 multiplets, 1H total), 5.00-5.10(1H, m), 5.42(0.5H, s), 7.36-7.52(4H, m), 7.77(1H, m), 8.30(0.5H, d), 9.09(1H, d) |
| II-25 | 507.0 | (DMSO-d₆) 1.79-1.96(5H, m), 2.94-3.28(3H, m), 3.58(1H, brd d), 3.73(1H, brd d), 4.04-4.59(2H, m), 4.98-5.02(1h, m), 5.54-5.74(2H, m), 7.26-7.46(5H, m), 8.43(1H, m), 8.82(1H, d), 9.39(1H, brd s) |

TABLE 4-continued

Characterization Data for Selected Compounds of
Formula II (According to Compound Number)

| No. | M + 1 (obs) | ¹H-NMR |
|---|---|---|
| II-26 | 446.6 | (DMSO-d₆) 1.05(9H, s), 1.15(3H, t), 1.8-2.1(4H, m), 2.3(3H, s), 2.4-2.5(1H, m), 2.9-3.0(1H, m), 3.7-3.75(1H, m), 3.8-3.85(1H, m), 4.1-4.15(0.5H, m), 4.25-4.3(1H, m), 4.4-4.5(0.5H, m), 4.7-4.75(1H, m), 5.55-5.6(1H, m), 7.2-7.4(4H, m), 7.7-7.75(1H, m), 8.1-8.15(1H, m), 8.35-8.4(1H, m) |
| II-27 | 486.5 | (DMSO-d₆) 0.95-1.05(6H, m), 1.8-2.1(4H, m), 2.4-2.5(1H, m), 3.0-3.1(1H, m), 3.7-3.75(1H, m), 3.8-3.85(1H, m), 4.1-4.15(0.5H, m), 4.25-4.3(1H, m), 4.4-4.5(0.5H, m), 5.55-5.6(1H, m), 7.4-7.45(1H, m), 7.6-7.8(3H, m), 8.4-8.45(1H, m), 8.75-8.8(1H, m) |
| II-28 | 466.1 | (CDCl₃) 1.11-1.16(9H, m), 1.94-2.22(4H, m), 2.38-2.50(2H, m), 2.77-2.87(1H, m), 3.71-3.79(1H, m), 3.96-4.06(1H, m), 4.56-4.67(2H, m), 4.85-4.91(1H, m), 6.99-7.02(1H, m), 7.28-7.45(3H, m), 7.60-7.84(2H, m) |
| II-29 | 500.2 | (CDCl₃) 1.07(9H, s), 1.85-2.19(2H, m), 2.37-2.40(2H, m), 2.81-3.07(1H, m), 3.37(1H, brs), 4.01(1H, brs), 4.46-4.67(2H, m), 4.87(1H, d), 5.73(1H, brs), 6.68(1H, brs), 7.38-7.74(5H, m) |
| II-30 | 496.2 | (CD₃OD) 1.15(9H, s), 1.85-2.20(4H, m), 2.46-2.72(2H, m), 3.74-3.81(1H, m), 3.92(3H, s), 3.93-4.03(1H, m), 4.20-4.31(1H, m), 4.45-4.52(1H, m), 4.60-4.75(1H, m), 4.83(1H, d), 7.00(1H, d), 7.15(1H, d), 7.33(1H, t) |
| II-31 | 480.5 | (DMSO-d₆) 1.05(9H, s), 1.8-2.1(4H, m), 2.4-2.5(1H, m), 3.75-3.8(1H, m), 3.8-3.85(1H, m), 3.9(3H, s), 4.1-4.3(1H, m), 4.7(1H, d), 5.3-5.5(0.5H, br s), 7.1-7.3(3H, m), 7.7-7.8(1H, m), 8.0-8.1(1H, m), 8.35-8.45(1H, m) |
| II-32 | 550.3 | (DMSO-d₆) 0.91-1.10(9H, m), 1.70-2.15(5H, m), 2.60-3.08(1H, m), 3.60-3.90(2H, m), 3.98-4.71(3H, m), 5.40-5.80(1H, m), 7.30-7.91(3H, m), 8.30-8.80(3H, m) |
| II-33 | 523.3 | (DMSO) 0.60-0.90(4H, m, cyclopropyl CH2), 0.92-1.10(9H, m, tBu), 1.71-2.21(5H, m, CH2), 2.65-3.10(1H, brm, CH2), 3.36-3.50(1H, m, CH), 3.60-4.75(6H, m, CH), 6.92(1H, d, aryl H), 7.36(1H, m, aryl H), 7.45(1H, m, aryl H), 7.65-8.60(3H, m, NH, OH) |
| II-34 | 480.3 | (DMSO) 0.99-1.10(9H, m, tBu), 1.70-2.12(5H, m, CH2), 2.35(3H, s, CH3), 2.60-3.08(1H, m, CH2), 3.58-3.87(2H, m, CH), 4.00-4.70(3H, m, CH), 5.38-5.79(1H, m, CH), 7.12(1H, d, aryl H), 7.24(1H, m, aryl H), 7.38(1H, m, aryl H), 7.69-8.55(3H, m, NH, OH) |
| II-35 | 482 | CD3OD 1.01-1.15(6H, m), 1.95-2.22(5H, m), 2.48-2.69(2H, m), 3.73-3.80(1H, m), 4.92(3H, s), 3.99-4.19(1H, m), 4.20-4.30(1H, m), 4.58-4.67(2H, m), 7.00(1H, d), 7.14(1H, d), 7.31(1H, t) |
| II-36 | 494.4 | (DMSO) 0.94-1.08(9H, s, tBu), 1.19(3H, t, CH3), 1.70-2.40(5H, m, CH2), 2.60-3.08(3H, m, CH2), 3.69(1H, m, CH), 3.81(1H, m, CH), 4.04-4.71(3H, m, CH), 5.40-5.80(1H, m, CH), 7.14(1H, m, aryl H), 7.31(1H, m, aryl H), 7.39(1H, m, aryl H), 7.70-8.50(3H, m, NH, OH) |
| II-37 | 482.5 | (DMSO) 0.9-1.0(6H, m), 1.85-2.3(4H, m), 3.0-3.1(1H, m), 3.65-3.7(1H, m), 3.78(3H, s), 3.8-3.85(1H, m), 4.1-4.15(0.5H, m), 4.25-4.3(0.5H, m), 4.5-4.55(1H, m), 5.5-5.55(1H, m), 6.93(1H, d), 6.98(1H, s), 7.35(1H, d), 7.75-7.8(1H, m), 8.45(1H, d) |
| II-38 | 536 | (CD3OD) 0.34-0.40(2H, m), 0.60-0.67(2H, m), 1.16(9H, s), 1.25-1.32(1H, m), 1.93-2.22(4H, m), 2.50-2.66(2H, m), 3.74-3.84(1H, m), 3.91-4.03(3H, m), 4.22-4.32(1H, m), 4.45-4.54(1H, m), 4.61-4.69(1H, m), 4.82(1H, d), 6.99(1H, d), 7.12(1H, d), 7.32(1H, t), 8.40(1H, d) |
| II-39 | 482 | (CD3OD) 1.12(9H, s), 1.90-2.22(4H, m), 2.51-2.70(2H, m), 3.75-3.83(1H, m), 3.97-4.05(1H, m), 4.23-4.30(1H, m), 4.46-4.54(1H, m), 4.63-4.70(1H, m), 4.83(1H, d), 6.91(1H, d), 6.99(1H, d), 7.17(1H, t), 8.36(1H, d) |
| II-40 | 509.3 | (DMSO) 0.93-0.98(6H, m)1.71-2.09(10H, m), 2.35-2.45(1H, m), 3.61-3.64(1H, m), 4.02-4.04(1H, m), 4.06-4.35(2H, m), 4.43-4.46(1H, m), 7.33(1H, d), 7.43-7.46(1H, m), 7.80(1H, brd s), 8.28-8.49(2H, m), 10.25(1H, brd s) |
| II-41 | 523.3 | (DMSO) 0.95-1.08(9H, s, tBu), 1.70-2.38(8H, m, COCH3, CH2), 2.58-3.08(1H, m, CH2), 3.65(1H, m, CH), 3.82(1H, m, CH0), 3.95-4.69(3H, m, CH), 5.40-5.60(1H, m, CH), 7.09(1H, m, aryl H), 7.31(1H, m, aryl H), 7.64-8.60(4H, m, aryl H, NH), 9.55(1H, m, CH) |
| II-42 | 503.4 | (DMSO) 0.91-1.08(9H, s, tBu), 1.70-2.40(11H, m, CH3, COCH3, CH2), 2.60-3.08(1H, m, CH2), 3.66(1H, m, CH), 3.87(1H, m, CH), 4.00-4.65(3H, m, CH), 5.40-5.78(1H, m, CH), 7.04(1H, m, aryl H), 7.18(1H, m, aryl H), 7.38(1H, m, aryl H), 7.65-7.88(1H, m, NH), 8.07-8.70(2H, m, NH), 9.34(1H, m, CH) |
| II-43 | 523.3 | (DMSO) 1.03(9H, s), 1.71-2.00(3H, m), 2.07(3H, s), 2.55-2.73(1H, m), 2.97(1H, dd), 3.60-3.67(1H, m), 3.75-3.82(1H, m), 3.98-4.04(1H, m), 4.19-4.24(1H, m), 4.37-4.45(1H, m), 4.63(1H, d), 5.45(1H, d), 7.33-7.35(1H, m), 7.43-7.45(1H, d), 7.76-7.83(2H, m), 8.25-8.28(1H, m), 8.41-8.58(1H, m), 10.27(1H, s) |
| II-44 | 507.4 | (DMSO) 1.01(9H, 2xs), 1.72-1.99(4H, m), 2.05-2.09(4H, m), 2.35-2.57(2H, m), 2.71-3.00(1H, brd m), 3.60-3.65(1H, m), 3.71-3.80(1H, m), 4.08-4.37(2H, brd m), 4.70(1H, d), 7.32(1H, dd), 7.65-7.80(3H, m), 8.33-8.52(1H, brd m), 10.37(1H, s) |
| II-45 | 493.4 | (DMSO) 0.94(6H, dd), 1.72-1.99(10H, m), 2.36-2.52(2H, m), 3.57-3.68(1H, m), 3.76-3.88(1H, m), 4.20-4.43(2H, m), 4.51-4.55(1H, m), 7.30(1H, dd), 7.58-7.77(3H, m), 8.00-8.04(1H, m), 10.34(1H, s) |
| II-46 | 510.5 | (DMSO) 0.95-1.0(6H, m), 1.25(6H, d), 1.85-2.2(4H, m), 3.0-3.1(1H, m), 3.9-4.0(3H, m), 4.2-4.3(0.5H, m), 4.4-4.5(0.5H, m), 4.7-4.8(1H, m), 6.9-6.95(1H, d), 6.99(1H, s), 7.3(1H, d), 8.3-8.4(1H, m) |
| II-47 | 482.5 | (DMSO) 1.05(9H, m), 1.8-2.1(4H, m), 2.6-2.7(1H, m), 2.9-3.0(2H, m), 3.6-3.7(2H, m), 3.8-3.9(1H, m), 4.0-4.1(1H, |

TABLE 4-continued

Characterization Data for Selected Compounds of Formula II (According to Compound Number)

| No. | M + 1 (obs) | 1H-NMR |
|---|---|---|
| | | m), 4.2-4.3(1H, m), 4.6-4.65(1H, m), 5.5-5.55(1H, m), 6.75-6.85(2H, m), 7.35(1H, d), 7.75(1H, d), 8.0-8.1(1H, m), 8.35(1H, m), 10.25(1H, s) |
| II-48 | 510.5 | (DMSO) 1.03(9H, s), 1.80-2.10(4H, m), 3.00(1H, br s), 3.30(3H, s), 3.66(1H, m), 3.81(1H, m), 4.06(1H, m), 4.25(1H, m), 4.44(2H, s), 4.65(1H, d), 5.46 1H, br s), 7.29-7.39(3H, m), 7.77(1H, br s), 8.43(1H, m) |
| II-49 | 551.5 | (DMSO) 1.03(9H, s), 1.09(3H, m), 1.11(3H, m), 1.79-2.15(4H, m), 2.32(1H, m), 2.98(1H, m), 3.51(1H, m), 3.79(1H, m), 4.10(1H, m), 4.23(1H, m), 4.40-4.65(2H, m), 5.45-5.73(1H, m), 7.35(1H, m), 7.49(1H, m), 7.76-7.84(2H, m), 8.23-8.60(2H, m), 10.11(1H, s) |
| II-50 | 493.3 | (DMSO) 0.92-1.19(4H, m), 1.49-1.90(9H, m), 1.91-1.99(2H, m), 2.06(4H, brd s), 2.49-2.52(2H, m), 3.57-3.68(1H, m), 3.80-3.90(1H, m), 4.01-4.28(2H, m), 4.46(1H, t), 7.32(1H, d), 7.43(1H, dd), 7.81(2H, brd s), 8.31-8.78(1H, m), 8.46(1H, d), 10.22(1H, s) |
| II-51 | 539.3 | (DMSO) 0.90-1.07(9H, s, tBu), 1.70-2.40(4H, brm, CH2), 2.54-3.07(1H, m, CH2), 3.52-3.88(5H, m, CH3, CH), 4.00-4.65(3H, m, CH), 5.40-5.80(1H, m, CH), 7.30-7.44(2H, m, aryl H), 7.60(1H, m, aryl H), 7.67(1H, br, NH), 8.10-8.70(2H, m, NH), 10.00(1H, m, CH) |
| II-52 | 558.3 | (DMSO) 0.91-1.11(9H, s, tBu), 1.70-2.41(4H, m, CH2), 2.56-3.09(1H, m, CH2), 3.60-3.90(2H, m, CH), 4.14-4.72(3H, m, CH), 5.38-5.80(1H, m, CH), 6.98(2H, m, aryl H), 7.07-7.20(3H, m, aryl H), 7.31-7.46(3H, m, aryl H), 7.66-8.67(3H, m, NH, OH) |
| II-53 | 467 | (DMSO) 0.83-1.04(6H, m), 1.81-2.08(5H, m), 3.34-3.63(1H, m), 3.84-3.90(1H, m), 4.00-4.60(3H, m), 5.29-5.75(2H, m), 6.53-6.59(1H, m), 6.70-6.90(1H, m), 7.20-7.35(0.5H, m), 7.78(0.5H. brs), 8.43-8.60(2H, m) |
| II-55 | 502.6 | (DMSO) 0.96(1H, s). 1.03(9H, s), 1.30-1.39(2H, m), 1.68-1.71(2H, m), 1.79-1.82(1H, m), 1.97(1H, brd), 2.11(3H, s), 3.79(3H, s), 3.84(1H, vbrs), 4.09(1H, vbrs), 4.56-4.58(1H, m), 4.67(1H, d), 6.81(1H, d), 7.00(1H, d), 7.19(1H, t), 7.79(0.5H, vbrs), 7.93(1H, brd), 8.42(0.5H, vbrs) |
| II-56 | 492.5 | (CDCl3) 1.08-1.14(9H, m), 1.85-2.05(4H, m), 2.32-2.45(1H, m), 2.79-2.85(1H, m), 3.01-3.07(1H, m), 4.13-4.17(1H, m), 4.53-4.70(1H, m), 4.98(1H, t), 5.70 and 5.81(1H total, brs and brd), 6.91-7.00(1H, m), 7.34-7.44(3H, m), 7.67-7.75(1H, m) |
| II-57 | 549.5 | (DMSO) 1.03(9H, s), 1.31-1.38(2H, m), 1.62-1.74(3H, m), 1.98(1H, brt), 2.07(3H, s), 2.36(1H, vbrs), 2.83(1H, vbrs), 3.84(1H, brs), 4.17(1H, vbrs), 4.54-4.57(1H, m), 4.70(1H, d), 7.34(1H, d), 7.42-7.45(1H, m), 8.16(1H, t), 8.37(1H, brs), 10.23(1H, s) |
| II-58 | 563.5 | (CD3OD) 1.17(9H, s), 1.21(3H, t), 1.41-1.55(2H, m), 1.75-1.90(3H, m), 2.03-2.19(1H, m), 2.37-2.50(3H, m), 2.58-2.78(2H, m), 3.87-4.02(1H, m), 4.20-4.30(1H, m), 4.55-4.70(2H, m), 4.91(1H, obscured), 7.45(1H, d), 7.51(1H, d), 7.85(1H, s), 8.29(1H, d) |
| II-59 | 577.5 | (DMSO) 1.05(9H, s), 1.15(6H, d), 1.35-1.5(2H, m), 1.75-1.9(3H, m), 2.0-2.1(1H, m), 2.3-2.45(1H, m), 2.7-2.9(1H, m), 4.05-4.15(1H, m), 4.65(1H, s), 4.7-4.75(1H, m), 7.15(1H, d), 7.35(1H, t), 7.7(1H, d), 8.4-8.55(2H, m), 9.5(1H, s) |
| II-60 | 506.5 | (DMSO) 1.03(9H, s), 1.31-1.38(2H, m), 1.68(3H, m), 2.30-2.33(2H, m), 2.67(0.5H, brs), 2.99(0.5H, brs), 3.34(0.5H, brs), 3.76(3H, s), 4.04(0.5H, m), 4.58(1H, s), 4.72(1H, d), 7.09-7.12(1H, m), 7.16-7.20(1H, m), 7.26-7.30(1H, m), 7.78(0, 5H, vbrs), 8.02(1H, brs), 8.42(0.5H, vbrs) |
| II-61 | 492.8 | (DMSO) 0.95(3H, d), 0.10(3H, d), 1.17(1H, m), 1.32(1H, m), 1.64-1.80(3H, m), 2.00(1H, m), 2.30(1H, br s), 2.67(0.5H, br s), 2.99(0.5H, br s), 3.75(0.5H, br s), 3.85(3H, s), 4.06(0.5H, m), 4.50-4.55(2H, m), 5.42(1H, br s), 7.07(1H, m), 7.17(1H, m), 7.26(1H, m), 7.80(1H, br s), 8.35(1H, m) |
| II-62 | 549.5 | DMSO) δ 1.04(9H, s), 1.29-1.34(2H, m), 1.59-1.67(3H, m), 1.91-1.97(1H, m), 2.13(3H, s), 2.96(1H, vbrs), 3.77(1H, vbrs), 4.10(1H, vbrs), 4.72(1H, s), 4.76(1H, d), 7.80-7.83(1H, m), 7.88-7.91(1H, m), 8.00-8.02(1H, m), 8.18-8.24(12H, m), 8.39(1H, vbrs), 9.62(1H, s) |
| II-63 | 563.5 | (DMSO) 1.05(9H, s,)1.09(3H, t), 1.19-1.37(3H, m), 1.47-1.77(3H, m), 1.91-1.99(1H, m), 2.28(0.5H, brdd), 2.48(2H, q), 2.63-2.74(1H, m), 3.01(0.5H, dd), 3.63(0.5H, s), 3.78-4.37(2H, total, m), 4.42-4.59(1H. m), 4.75(1H, d), 5.42(0.5H, d), 7.76(0.5H, a), 7.80-7.83(1H, m), 7.87(1H, d), 8.01(1H, m), 8.08-8.15(1H, m), 8.36(0.5H, d), 9.53(1H, s) |
| II-64 | 509.5 | (DMSO) 1.07(9H, s), 1.34-1.37(2H, m), 1.64-1.72(3H, m), 1.95-2.04(1H, m), 2.31-2.35(1H, m), 2.65-2.70(1H, m), 3.01-3.03(1H, m), 3.99(0.5H, m), 4.26-4.28(0.5H, m), 4.68(1H, s), 4.82(1H, d), 5.45(0.5H, s), 7.73-7.86(3H, m), 8.05-8.08(2H, m), 8.49(0.5H, d), 8.57-8.59(1H, m), 8.69(0.5H, d), 9.15(1H, d) |
| II-65 | 507.5 | (DMSO) 1.02(9H, s), 1.28-1.34(2H, m), 1.57-1.64(3H, m), 1.90-1.96(1H, m), 3.72-3.80(1H, m), 4.50(1H, brs), 4.72-4.74(1H, m), 5.91(1H, s), 6.76(1H, d), 7.58-7.61(1H, m), 7.81-7.83(1H, m) |
| II-66 | 493.5 | / |

EXAMPLE III

Biological Methods

Compounds of this invention may be tested using the methods described below. Table 5 lists caspase-1 and caspase-8 enzyme inhibition data for compounds II-1-II-25. In the Table, compounds with a Ki of <10 are assigned category A, compounds with a Ki of 10-20 are assigned category B, and compounds with a Ki of 21-30 are assigned category C.

In Vitro Assays Enzyme Inhibition

Ki values for test compounds with caspase-1 and caspase-8 were obtained by the method of Margolin et al. (*J. Biol. Chem.*, 272 pp. 7223-7228 (1997)). Other caspases may be assayed similarly (see, e.g., WO 99/47545). Assays were performed in 10 mM Tris (Sigma Corp, St Louis Mo.) pH 7.5, 1 mM Dithiothreitol (DTT, Research Organic INC, Cleveland, Ohio) and 0.1% CHAPS (Pierce, Rockford Ill.) at 37° C. For caspase-3, a solution of 8% glycerol was added to the assay buffer to improve enzyme stability. A 65 μL aliquot of the assay buffer and 5 μL aliquot of the appropriate dilutions of inhibitor in DMSO where pipetted into a 96 well plate, treated with 10 μL of caspase, then diluted in assay buffer (0.5-40 nM active protein by active site titration). A control containing DMSO but no compound was included for each determination. The plates were then incubated for 15 minutes at 37° C., before addition of the appropriate substrate (20 μL, final concentration 1-4×$K_M$, final assay volume 100 μL) to initiate the reaction. Reaction rates were measured at 37° C. either by following the time dependant increase in absorbance at 405 nM (for the pNA substrates) or in fluorescence (Ex 390, Em 460) (for the AMC substrates). The rates obtained were plotted against inhibitor concentration and the data fit to the Morrison tight-binding equation for competitive inhibitors (Morrison, J. F., *Biochem. Biophys. Acta,* 185 pp. 269-286 (1969)). The substrates used for the individual assays were as follows:

Caspase-1 Suc-YVAD-pNA (Bachem, King of Prussia, Pa.) (final concentration in the assay 80 μM);

Caspase-8 Ac-DEVD-pNA (Bachem, King of Prussia, Pa.) (final concentration in assay 80 μM).

TABLE 5

Caspase-1 (C1) and caspase-8 (c8) inhibition data.

| Compound | Ki C1 (nM) | Ki C8 (nM) |
| --- | --- | --- |
| II-1 | A | A |
| II-2 | A | A |
| II-3 | A | A |
| II-4 | A | B |
| II-5 | A | B |
| II-6 | A | A |
| II-7 | A | B |
| II-8 | A | B |
| II-9 | A | B |
| II-10 | A | B |
| II-11 | A | C |
| II-12 | A | B |
| II-13 | B | B |
| II-14 | B | A |
| II-15 | A | C |
| II-16 | A | C |
| II-17 | A | A |
| II-18 | A | B |
| II-19 | B | A |
| II-20 | A | A |
| II-21 | A | C |
| II-22 | A | C |
| II-23 | A | C |
| II-24 | A | C |
| II-25 | A | C |
| II-26 | A | A |
| II-27 | A | A |
| II-28 | A | A |
| II-29 | A | A |
| II-30 | A | A |
| II-31 | A | A |
| II-32 | A | A |
| II-33 | A | A |
| II-34 | A | A |
| II-35 | A | A |
| II-36 | A | A |
| II-37 | A | B |
| II-38 | A | A |
| II-39 | A | A |
| II-40 | A | B |
| II-41 | A | A |
| II-42 | A | B |
| II-43 | A | A |
| II-44 | A | A |
| II-45 | A | A |
| II-46 | A | C |
| II-47 | A | A |
| II-48 | A | A |
| II-49 | A | A |
| II-50 | A | C |
| II-51 | A | A |
| II-52 | A | A |
| II-53 | A | C |
| II-55 | A | A |
| II-56 | A | A |
| II-57 | A | A |
| II-58 | A | A |
| II-59 | A | A |
| II-60 | A | A |
| II-61 | A | A |
| II-62 | A | B |
| II-63 | A | B |
| II-64 | B | B |
| II-65 | A | A |
| II-66 | B | A |

PBMC Cell Assay

IL-1β Assay with a Mixed Population of Human Peripheral Blood Mononuclear Cells (PBMC) or Enriched Adherent Mononuclear Cells Processing of pre-IL-1β by ICE may be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure:

An initial dilution series of test compound in DMSO or ethanol is prepared, with a subsequent dilution into RPMI-10% FBS media (containing 2 mM L-glutamine, 10 mM HEPES, 50 U and 50 ug/ml pen/strep) respectively to yield drugs at 4× the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

Generally 5-6 compound dilutions are tested and the cellular component of the assay is performed in duplicate, with duplicate ELISA determinations on each cell culture supernatant.

PBMC Isolation and IL-1 Assay:

Buffy coat cells isolated from one pint human blood (yielding 40-45 ml final volume plasma plus cells) are diluted with media to 80 ml and LeukoPREP separation tubes (Becton Dickinson) are each overlaid with 10 ml of cell suspension. After 15 min centrifugation at 1500-1800×g, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300×g for 15 min. The PBMC pellet is resuspended in a small volume of media, the cells are counted and adjusted to $6 \times 10^6$ cells/ml.

For the cellular assay, 1.0 ml of the cell suspension is added to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16-18 hr at 37° C. in the presence of 5% $CO_2$.

At the end of the incubation period, cells are harvested and transferred to 15 ml conical centrifuge tubes. After centrifugation for 10 min at 200×g, supernatants are harvested and transferred to 1.5 ml Eppendorf tubes. It may be noted that the cell pellet may be utilized for a biochemical evaluation of pre-IL-1β and/or mature IL-1β content in cytosol extracts by Western blotting or ELISA with pre-IL-1β specific antisera.

Isolation of Adherent Mononuclear Cells:

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5-3.0 \times 10^5$ cells per well. The addition of test compounds, LPS, cell incubation conditions and processing of supernatants proceeds as described above.

ELISA:

Quantikine kits (R&D Systems) may be used for the measurement of mature IL-1β. Assays are performed according to the manufacturer's directions. Mature IL-1β levels of about 1-3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

The skilled practitioner realizes that values obtained in cell assays may depend on multiple factors. The values may not necessarily represent fine quantitative results.

Selected compounds of this invention have been tested for inhibition of IL-1β release from PBMCs with IC50 values between 300 nM and 4 μM.

Whole Blood Assay for IL-1β Production

Whole blood assay $IC_{50}$ values for compounds of this invention may be obtained using the method described below:

Purpose:

The whole blood assay is a simple method for measuring the production of IL-1β (or other cytokines) and the activity of potential inhibitors. The complexity of this assay system, with its full complement of lymphoid and inflammatory cell types, spectrum of plasma proteins and red blood cells is an ideal in vitro representation of human in vivo physiologic conditions.

Materials:
Pyrogen-free syringes (~30 cc)
Pyrogen-free sterile vacuum tubes containing lyophilized $Na_2EDTA$ (4.5 mg/10 ml tube)
Human whole blood sample (~30-50 cc)
1.5 ml Eppendorf tubes
Test compound stock solutions (~25 mM in DMSO or other solvent)
Endotoxin-free sodium chloride solution (0.9%) and HBSS
Lipopolysaccharide (Sigma; Cat.# L-3012) stock solution at 1 mg/ml in HBSS
IL-1β ELISA Kit (R & D Systems; Cat # DLB50)
TNFα ELISA Kit (R & D Systems; Cat # DTA50)
Water bath or incubator Whole Blood Assay Experimental Procedure:

Set incubator or water bath at 30° C. Aliquot 0.25 ml of blood into 1.5 ml eppendorf tubes. Note: be sure to invert the whole blood sample tubes after every two aliquots. Differences in replicates may result if the cells sediment and are not uniformly suspended. Use of a positive displacement pipette will also minimize differences between replicate aliquots.

Prepare drug dilutions in sterile pyrogen-free saline by serial dilution. A dilution series which brackets the apparent $K_i$ for a test compound determined in an ICE inhibition assay is generally used for the primary compound screen. For extremely hydrophobic compounds, prepare compound dilutions in fresh plasma obtained from the same blood donor or in PBS-containing 5% DMSO to enhance solubility.

Add 25 μl test compound dilution or vehicle control and gently mix the sample. Then add 5.0 μl LPS solution (250 ng/ml stocked prepared fresh: 5.0 ng/ml final concentration LPS), and mix again. Incubate the tubes at 30° C. in a water bath for 16-18 hr with occasional mixing. Alternatively, the tubes can be placed in a rotator set at 4 rpm for the same incubation period. This assay should be set up in duplicate or triplicate with the following controls: negative control—no LPS; positive control—no test inhibitor; vehicle control—the highest concentration of DMSO or compound solvent used in the experiment. Additional saline is added to all control tubes to normalize volumes for both control and experimental whole blood test samples.

After the incubation period, whole blood samples are centrifuged for 10 minutes at ~2000 rpm in the microfuge, plasma is transferred to a fresh microfuge tube and centrifuged at 1000×g to pellet residual platelets if necessary. Plasma samples may be stored frozen at −70° C. prior to assay for cytokine levels by ELISA.

ELISA:

R & D Systems (614 McKinley Place N.E. Minneapolis, Minn. 55413) Quantikine kits may be used for measurement of IL-1β and TNF-α. The assays are performed according to the manufacturer's directions. IL-1β levels of ~1-5 ng/ml in positive controls among a range of individuals may be observed. A 1:200 dilution of plasma for all samples is usually sufficient for experiments for ELISA results to fall on the linear range of the ELISA standard curves. It may be necessary to optimize standard dilutions if you observe differences in the whole blood assay. Nerad, J. L. et al., *J. Leukocyte Biol.*, 52, pp. 687-692 (1992).

Selected compounds of this invention have been tested for inhibition of IL-1β release from whole blood with IC50 values between 1 μM and 40 μM.

In Vivo Assays

Compounds of this invention may be tested in in vivo assays such as those described in WO 99/47545.

WO 99/47545 and all the other documents cited herein are hereby incorporated by reference.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

We claim:
1. A compound of formula I:

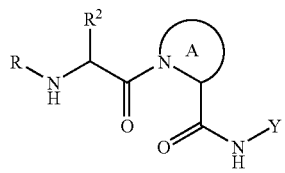

I wherein:
Y is

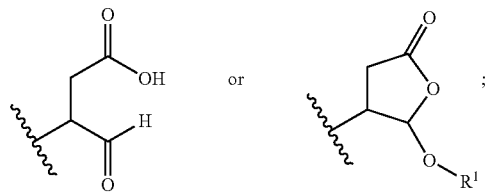

R[1] is H, $C_{1-12}$aliphatic, $C_{3-10}$cycloaliphatic, $C_{6-10}$aryl, 5-10 membered heterocyclyl, 5-10 membered heteroaryl, ($C_{3-10}$cycloalkyl)-($C_{1-12}$aliphatic)-, cycloalkenyl-($C_{1-12}$aliphatic)-, ($C_{6-10}$aryl)-($C_{1-12}$aliphatic)-, (5-10 membered heterocyclyl)-($C_{1-12}$aliphatic)-, or (5-10 membered heteroaryl)-($C_{1-12}$aliphatic)-, wherein any hydrogen atom is optionally and independently replaced by R[8] and any set of two hydrogen atoms bound to the same atom is optionally and independently replaced by carbonyl;
Ring A is:

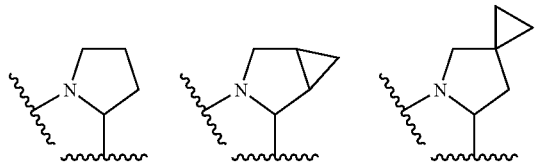

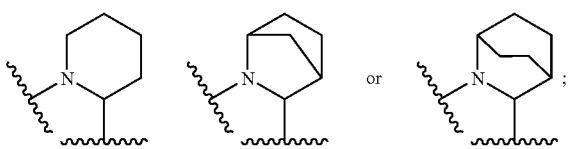

wherein, in each ring, any hydrogen atom is optionally and independently replaced by R[4] and any set of two hydrogen atoms bound to the same atom is optionally and independently replaced by carbonyl;
when Ring A is

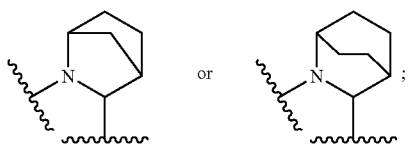

then
R is $R^3C(O)$—, HC(O), $R^3SO_2$—, $R^3OC(O)$, $(R^3)_2NC(O)$, $(R^3)(H)NC(O)$, $R^3C(O)C(O)$—, $R^3$—, $(R^3)_2NC(O)C(O)$, $(R^3)(H)NC(O)C(O)$, or $R^3OC(O)C(O)$—; and
R[3] is $C_{1-12}$aliphatic, $C_{3-10}$cycloaliphatic, $C_{6-10}$aryl, 5-10 membered heterocyclyl, 5-10 membered heteroaryl, ($C_{3-10}$cycloaliphatic)-($C_{1-12}$aliphatic)-, ($C_{6-10}$aryl)-($C_{1-12}$aliphatic)-, (5-10 membered heterocyclyl)-($C_{1-12}$aliphatic)-, or (5-10 membered heteroaryl)-($C_{1-12}$aliphatic)-; or two R[3] groups bound to the same atom form together with that atom a 3-10 membered aromatic or nonaromatic ring; wherein any ring is optionally fused to an $C_{6-10}$aryl, 5-10 membered heteroaryl, $C_{3-10}$cycloalkyl, or 5-10 membered heterocyclyl; wherein up to 3 aliphatic carbon atoms may be replaced by a group selected from O, N, NR[9], S, SO, and $SO_2$, wherein R[3] is substituted with up to 6 substituents independently selected from R[8'];
when Ring A is

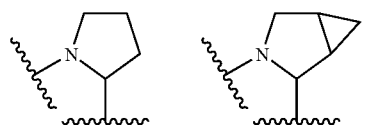

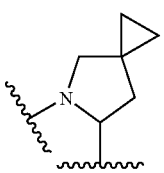

then
R is $R^3C(O)$—, as shown in formula II,

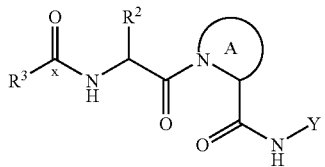

and R³ is phenyl, thiophene, or pyridine, wherein each ring is optionally substituted with up to 5 groups independently selected from R⁸', and wherein at least one position on the phenyl, thiophene, or pyridine adjacent to bond x is substituted by R¹², wherein R¹² has no more than 5 straight-chained atoms;

R⁴ is halogen, —OR⁹, —NO₂, —CN, —CF₃, —OCF₃, —R⁹, 1,2-methylenedioxy, 1,2-ethylenedioxy, —N(R⁹)₂, —SR⁹, —SOR⁹, —SO₂R⁹, —SO₂N(R⁹)₂, —SO₃R⁹, —C(O)R⁹, —C(O)C(O)R⁹, —C(O)C(O)OR⁹, —C(O)C(O)N(R⁹)₂, —C(O)CH₂C(O)R⁹, —C(S)R⁹, —C(S)OR⁹, —C(O)OR⁹, —OC(O)R⁹, —C(O)N(R⁹)₂, —OC(O)N(R⁹)₂, —C(S)N(R⁹)₂, —(CH₂)₀₋₂NHC(O)R⁹, —N(R⁹)N(R⁹)COR⁹, —N(R⁹)N(R⁹)C(O)OR⁹, —N(R⁹)N(R⁹)CON(R⁹)₂, —N(R⁹)SO₂R⁹, —N(R⁹)SO₂N(R⁹)₂, —N(R⁹)C(O)OR⁹, —N(R⁹)C(O)R⁹, —N(R⁹)C(S)R⁹, —N(R⁹)C(O)N(R⁹)₂, —N(R⁹)C(S)N(R⁹)₂, —N(COR⁹)COR⁹, —N(OR⁹)R⁹, —C(=NH)N(R⁹)₂, —C(O)N(OR⁹)R⁹, —C(=NOR⁹)R⁹, —OP(O)(OR⁹)₂, —P(O)(R⁹)₂, —P(O)(OR⁹)₂, or —P(O)(H)(OR⁹);

R² is —C(R⁵)(R⁶)(R⁷), C₆₋₁₀aryl, 5-10 membered heteroaryl, or C₃₋₇ cycloalkyl;

R⁵ is H or a C₁₋₆ straight-chained or branched alkyl;

R⁶ is H or a C₁₋₆ straight-chained or branched alkyl;

R⁷ is —CF₃, —C₃₋₇cycloalkyl, C₆₋₁₀aryl, 5-10 membered heteroaryl, heterocycle, or a C₁₋₆ straight-chained or branched alkyl, wherein each carbon atom of the alkyl is optionally and independently substituted with R¹⁰;

or R⁵ and R⁷ taken together with the carbon atom to which they are attached form a 3-10 membered cycloaliphatic;

R⁸ and R⁸' are each independently halogen, —OR⁹, —NO₂, —CN, —CF₃, —OCF₃, —R⁹, 1,2-methylenedioxy, 1,2-ethylenedioxy, —N(R⁹)₂, —SR⁹, —SOR⁹, —SO₂R⁹, —SO₂N(R⁹)₂, —SO₃R⁹, —C(O)R⁹, —C(O)C(O)R⁹, —C(O)C(O)OR⁹, —C(O)C(O)N(R⁹)₂, —C(O)CH₂C(O)R⁹, —C(S)R⁹, —C(S)OR⁹, —C(O)OR⁹, —OC(O)R⁹, —C(O)N(R⁹)₂, —OC(O)N(R⁹)₂, —C(S)N(R⁹)₂, —(CH₂)₀₋₂NHC(O)R⁹, —N(R⁹)N(R⁹)COR⁹, —N(R⁹)N(R⁹)C(O)OR⁹, —N(R⁹)N(R⁹)CON(R⁹)₂, —N(R⁹)SO₂R⁹, —N(R⁹)SO₂N(R⁹)₂, —N(R⁹)C(O)OR⁹, —N(R⁹)C(O)R⁹, —N(R⁹)C(S)R⁹, —N(R⁹)C(O)N(R⁹)₂, —N(R⁹)C(S)N(R⁹)₂, —N(COR⁹)COR⁹, —N(OR⁹)R⁹, —C(=NH)N(R⁹)₂, —C(O)N(OR⁹)R⁹, —C(=NOR⁹)R⁹, —OP(O)(OR⁹)₂, —P(O)(R⁹)₂, —P(O)(OR⁹)₂, and —P(O)(H)(OR⁹);

R⁹ is hydrogen, C₁₋₁₂aliphatic, C₃₋₁₀cycloaliphatic, C₆₋₁₀aryl, 5-10 membered heterocyclyl, 5-10 membered heteroaryl, (C₃₋₁₀cycloaliphatic)-(C₁₋₁₂aliphatic)-, (C₆₋₁₀aryl)-(C₁₋₁₂aliphatic)-, (5-10 membered heterocyclyl)-(C₁₋₁₂aliphatic)-, or heteroaryl-(C₁₋₁₂aliphatic)-; wherein any hydrogen atom is optionally and independently replaced by R⁸ and any set of two hydrogen atoms bound to the same atom is optionally and independently replaced by carbonyl;

R¹⁰ is halogen, —OR¹¹, —NO₂, —CN, —CF₃, —OCF₃, —R¹¹, or —SR₁₁; wherein R¹¹ is C₁₋₄-aliphatic-;

R¹¹ is C₁₋₄-aliphatic-;

R¹² is halogen, —OR¹¹, —NO₂, —CN, —CF₃, —OCF₃, —R¹¹, or —SR⁹;

R¹³ is —OR¹⁴, —NO₂, —CN, —CF₃, —OCF₃, —R¹⁴, 1,2-methylenedioxy, 1,2-ethylenedioxy, —N(R¹⁴)₂, —SR¹⁴, —SOR¹⁴, —SO₂R¹⁴, —SO₂N(R¹⁴)₂, —SO₃R¹⁴, —C(O)R¹⁴, —C(O)C(O)R¹⁴, —C(O)C(O)OR¹⁴, —C(O)C(O)N(R¹⁴)₂, —C(O)CH₂C(O)R¹⁴—C(S)R¹⁴, —C(S)R¹⁴, —C(O)OR¹⁴, —OC(O)R¹⁴, —C(O)N(R¹⁴)₂, —OC(O)N(R¹⁴)₂, —C(S)N(R¹⁴)₂, —(CH₂)₀₋₂NHC(O)R¹⁴, —N(R¹⁴)N(R¹⁴)COR¹⁴, —N(R¹⁴)N(R¹⁴)C(O)OR¹⁴, —N(R¹⁴)N(R¹⁴)CON(R¹⁴)₂, —N(R¹⁴)SO₂R¹⁴, —N(R¹⁴)SO₂N(R¹⁴)₂, —N(R¹⁴)C(O)OR¹⁴, —N(R¹⁴)C(O)R¹⁴, —N(R¹⁴)C(S)R¹⁴, —N(R¹⁴)C(O)N(R¹⁴)₂, —N(R¹⁴)C(S)N(R¹⁴)₂, —N(COR¹⁴)COR¹⁴, —N(OR¹⁴)R¹⁴, —C(=NH)N(R¹⁴)₂, —C(O)N(OR¹⁴)R¹⁴, —C(=NOR¹⁴)R¹⁴, —OP(O)(OR⁻)₂, —P(O)(R¹⁴)₂, —P(O)(OR¹⁴)₂, and —P(O)(H)(OR¹⁴);

R¹⁴ is hydrogen, C₁₋₁₂aliphatic, C₃₋₁₀cycloaliphatic, C₆₋₁₀aryl, 5-10 membered heterocyclyl, 5-10 membered heteroaryl, (C₃₋₁₀cycloaliphatic)-(C₁₋₁₂aliphatic)-, (C₆₋₁₀aryl)-(C₁₋₁₂aliphatic)-, (5-10 membered heterocyclyl)-(C₁₋₁₂aliphatic)-, or heteroaryl-(C₁₋₁₂aliphatic)-.

2. The compound according to claim 1 wherein R is R³C(O)—; and R³ is C₆₋₁₀aryl or 5-10 membered heteroaryl, wherein any hydrogen atom of R³ is optionally and independently substituted by R⁸'.

3. The compound of claim 1, as represented by formula II:

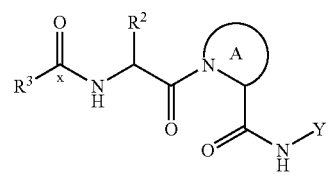

wherein R³ is phenyl, thiophene, or pyridine, wherein each ring is optionally substituted with up to 5 groups independently selected from R⁸', and wherein at least one position on the phenyl, thiophene, or pyridine adjacent to bond x is substituted by R¹², wherein R¹² has no more than 5 straight-chained atoms.

4. The compound according to any one of claims 1-3 wherein Y is

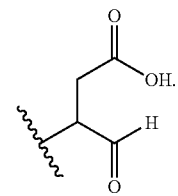

5. The compound according to claim 3 wherein ring A is:

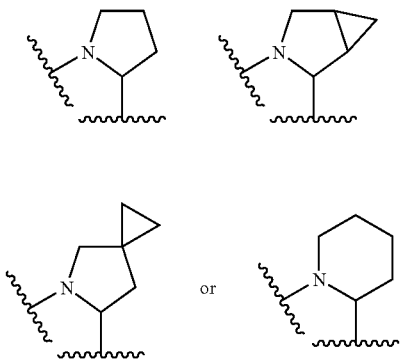

optionally substituted by $R^4$.

6. The compound according to claim 5, wherein ring A is:

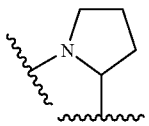

optionally substituted by $R^4$.

7. The compound according to claim 5, wherein $R^4$ is halogen, —$OR^9$, —$CF_3$, —$OCF_3$, —$R^9$, or —$SR^9$.

8. The compound according to claim 7, wherein $R^4$ is H.

9. The compound according to claim 7 wherein $R^2$ is a $C_{3-4}$ branched alkyl group.

10. The compound according to claim 9 wherein $R^5$ is H or —$CH_3$, $R^6$ —$CH_3$, and $R^7$ is —$CH_3$.

11. The compound according to claim 7 wherein $R^{12}$ has no more than 4 straight-chained atoms.

12. The compound according to claim 11 wherein $R^{12}$ has no more than 3 straight-chained atoms.

13. The compound according to claim 12, wherein $R^{12}$ has no more than 2 straight-chained atoms and is selected from —$OCF_3$, —$OCH_3$, —$CF_3$, —$CH_3$, —$CH_2CH_3$, —Cl, or —F.

14. The compound according to claim 13, wherein $R^{12}$ is —$CF_3$, —$CH_3$, —Cl, or —F.

15. The compound according to claim 14, wherein $R^{12}$ is —$CH_3$, —Cl, or —F.

16. The compound according to any one of claim 15 wherein each $R^{8'}$ is independently halogen, —$OR^9$, —$NO_2$, —CN, —$CF_3$, —$OCF_3$, —$R^9$, 1,2-methylenedioxy, 1,2-ethylenedioxy, —$N(R^9)_2$, —$SR^9$, —$SOR^9$, —$SO_2R^9$, —$SO_2N(R^9)_2$, —$C(O)R^9$, —$C(O)C(O)N(R^9)_2$, —$C(O)N(R^9)_2$, —$OC(O)N(R^9)_2$, —$(CH_2)_{0-2}NHC(O)R^9$, —$N(R^9)SO_2R^9$, —$N(R^9)SO_2N(R^9)_2$, —$N(R^9)C(O)OR^9$, —$N(R^9)C(O)R^9$, or —$N(R^9)C(O)N(R^9)_2$.

17. The compound according to claim 16 wherein each $R^{8'}$ is independently —$NH_2$, —$N(R^9)_2$, —$N(R^9)C(O)R^9$, —$OCF_3$, —$OR^9$, —$CF_3$, —$R^9$, —$SR^9$, or halo.

18. A compound selected from

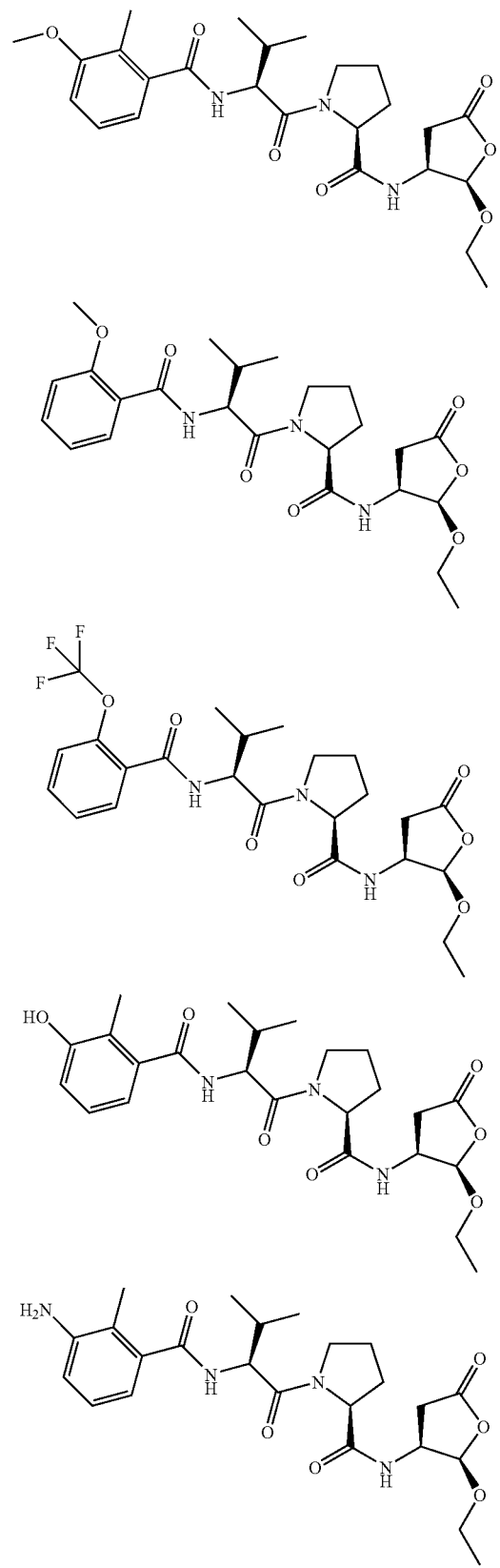

-continued
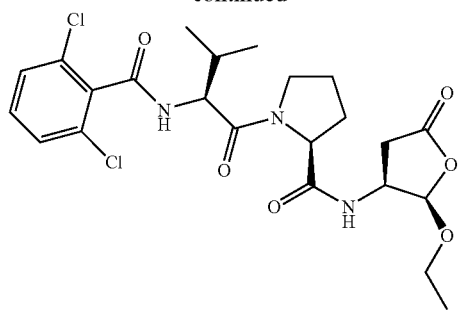
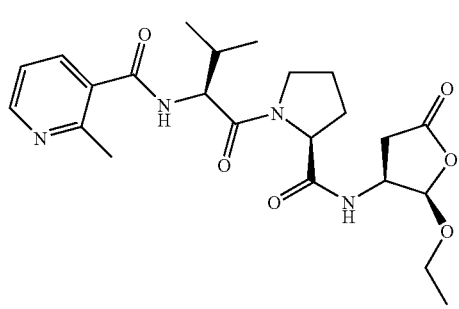
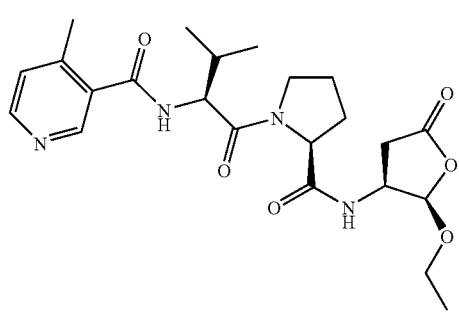
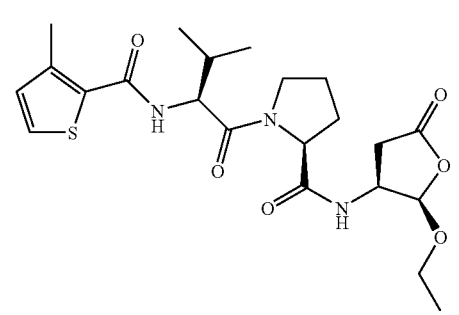
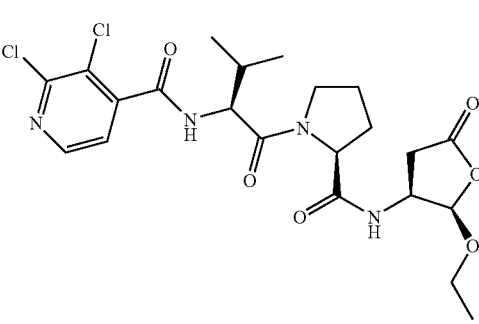
-continued
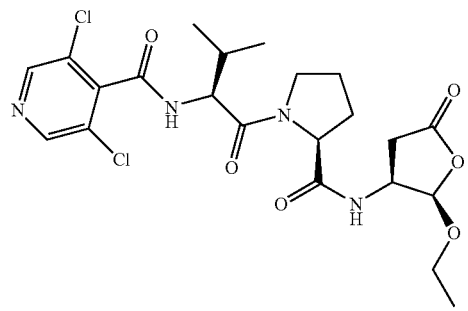
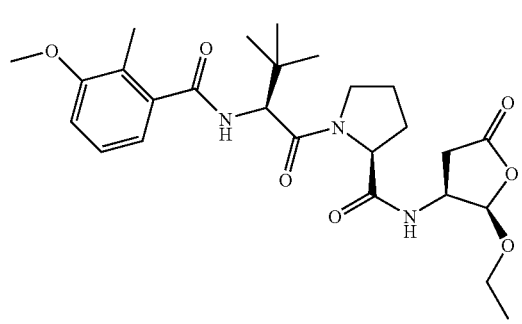
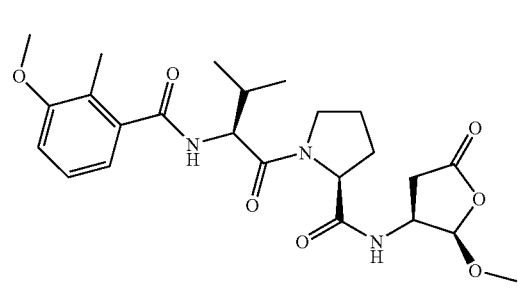
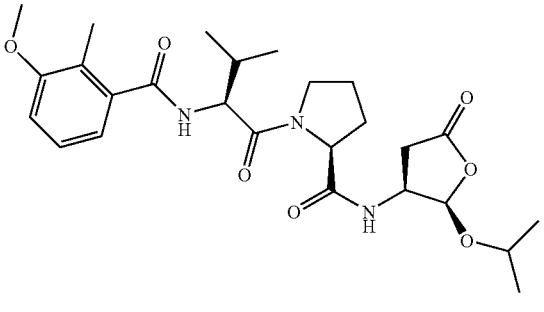
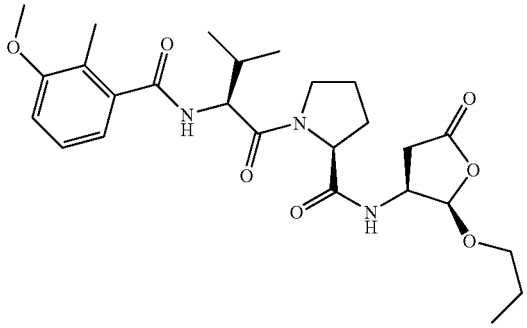

-continued
175
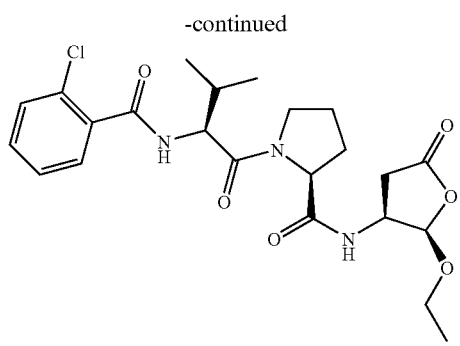
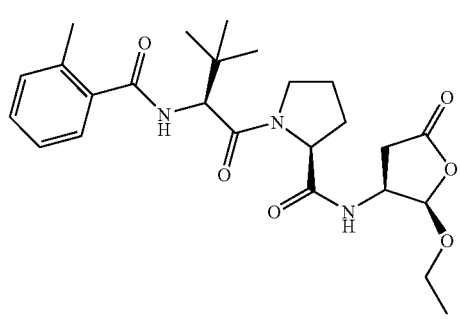
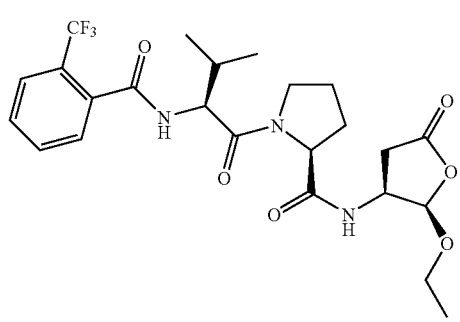
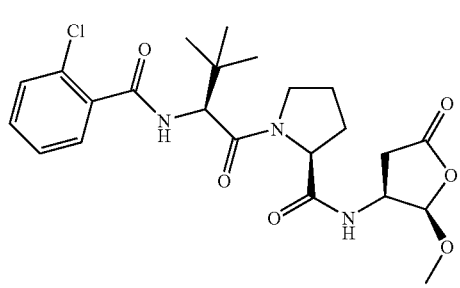
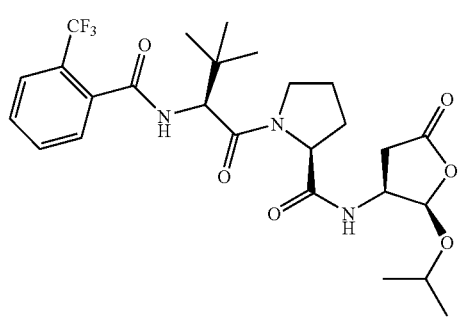
176
-continued
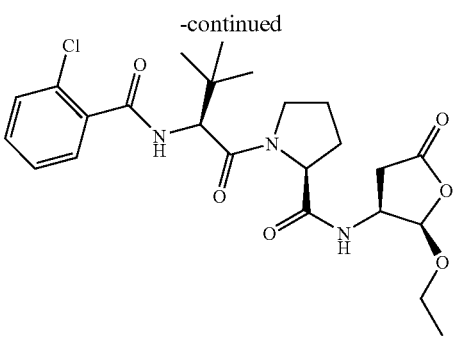
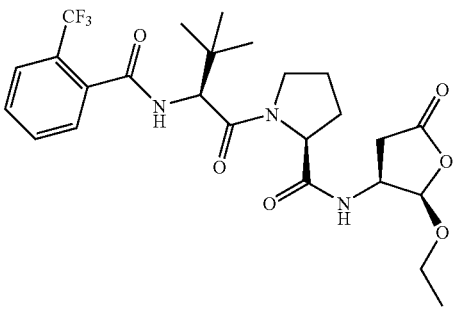
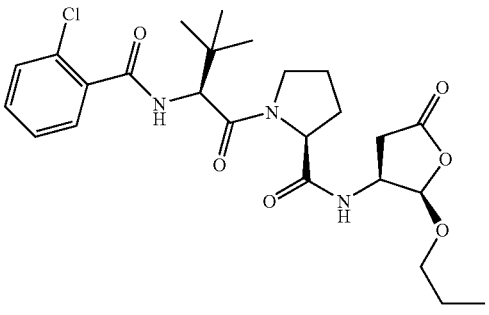
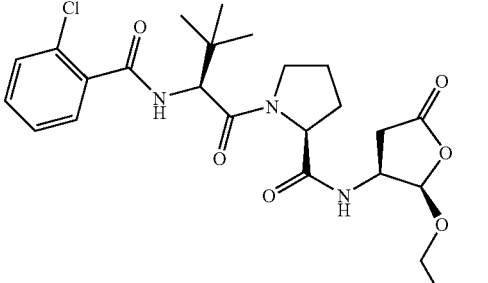
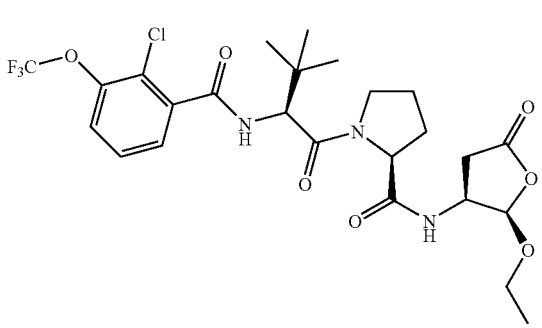

177
-continued
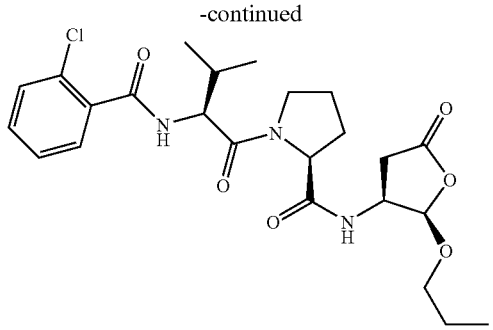
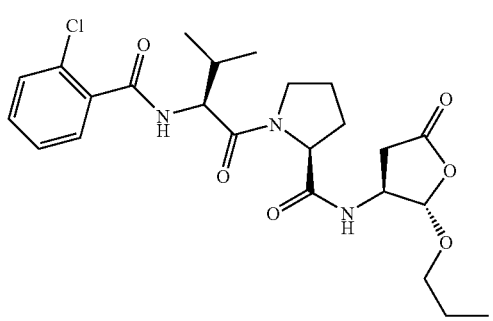
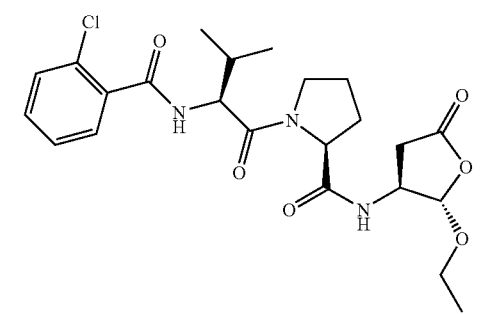
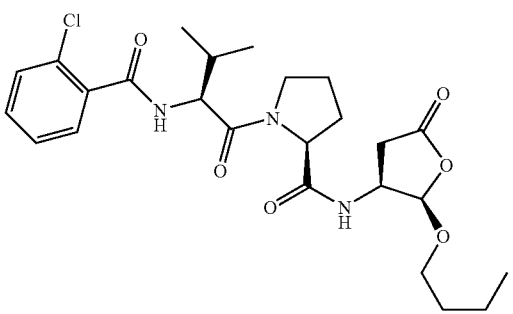
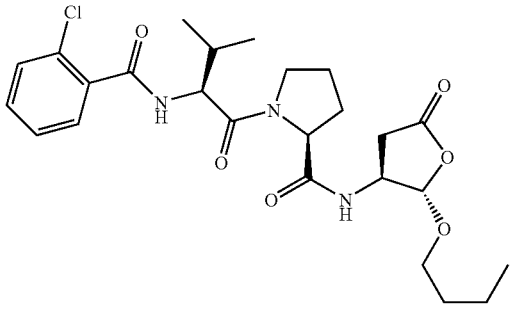
178
-continued
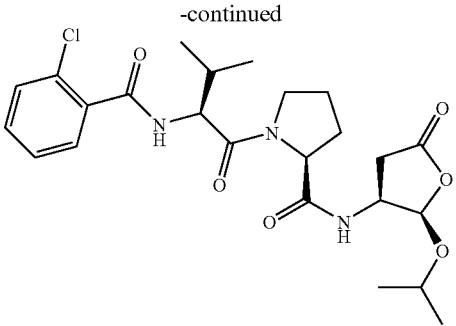
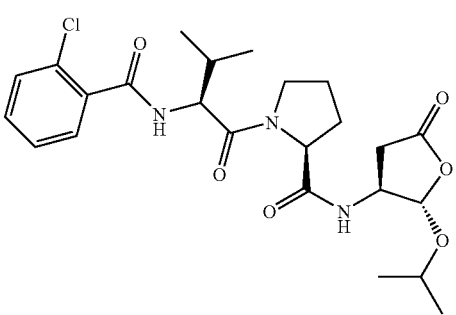
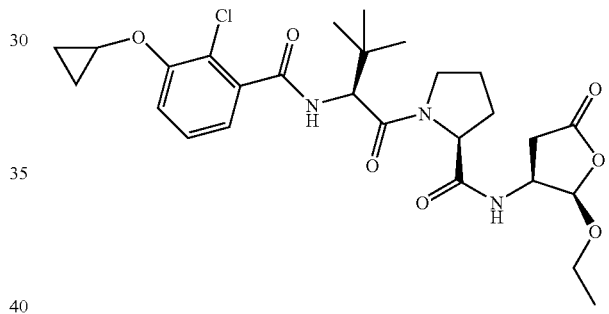
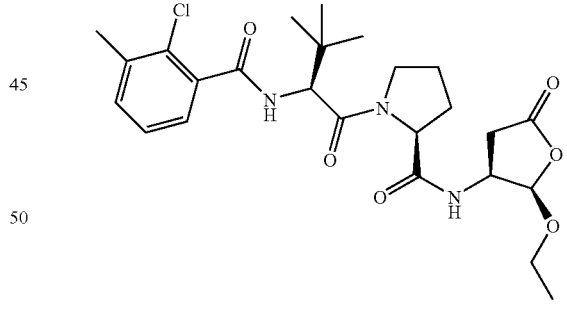
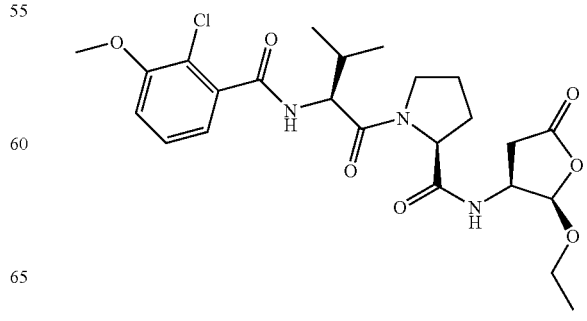

| 179 | 180 |
|---|---|
| -continued | -continued |
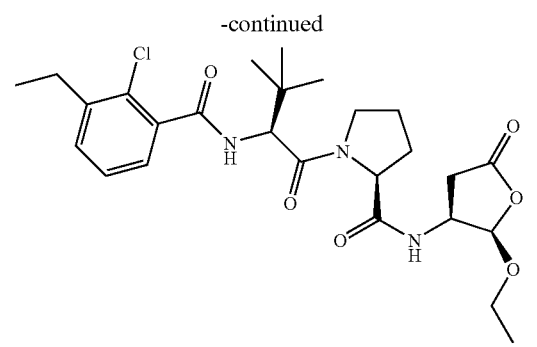
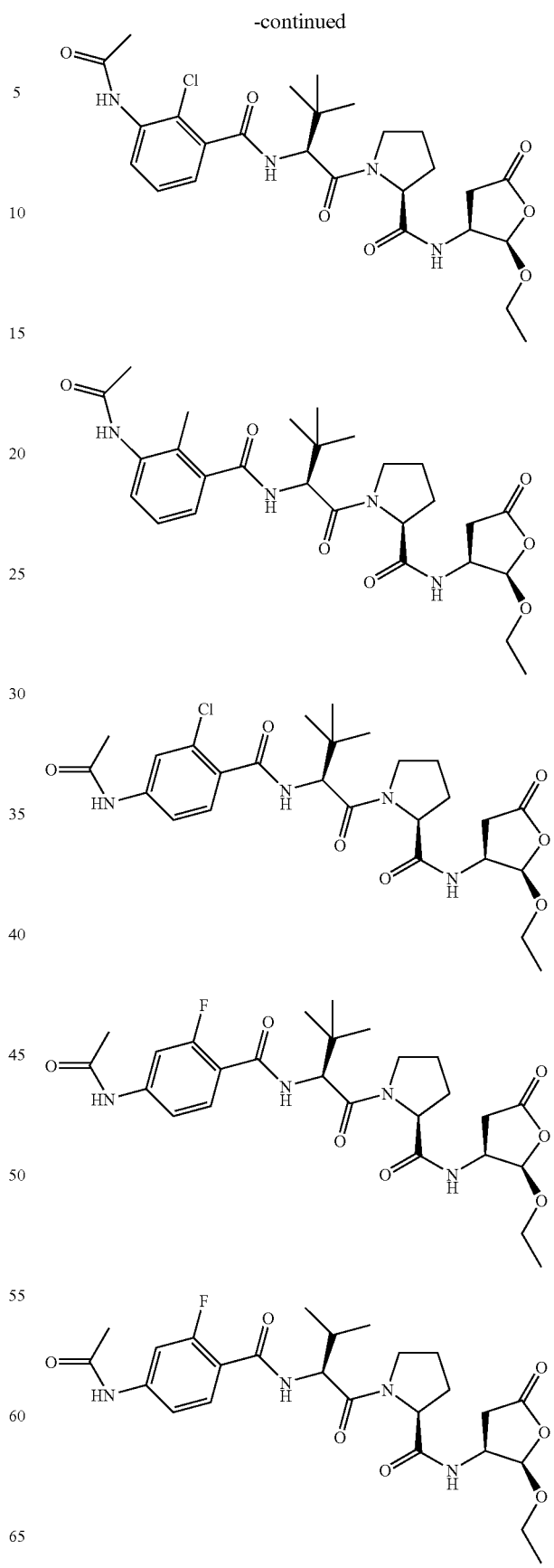

181
-continued
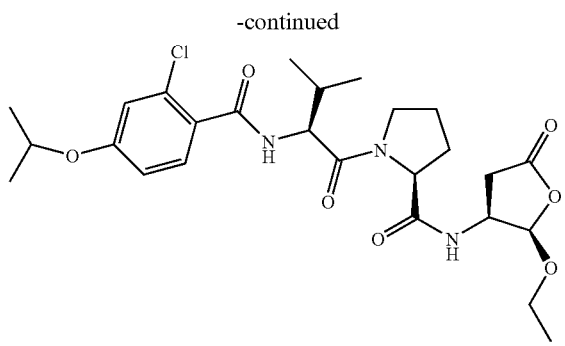
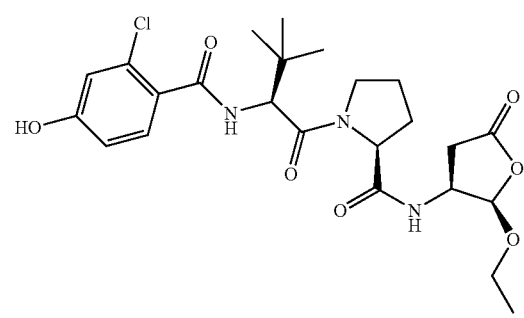
182
-continued
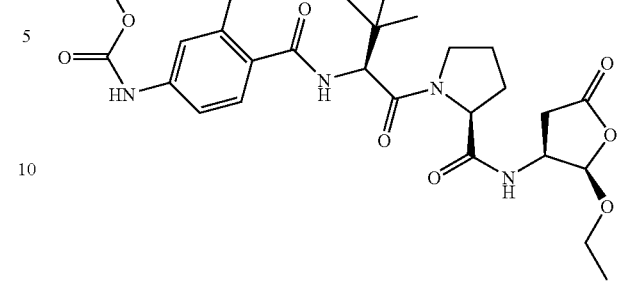
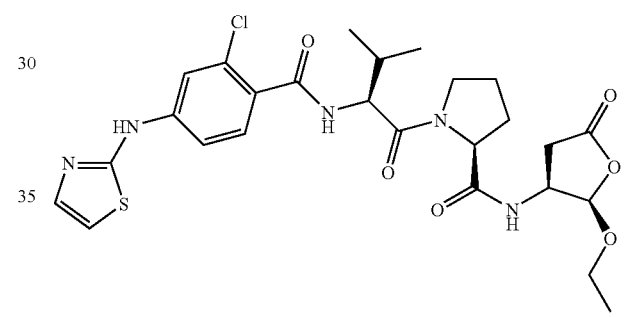
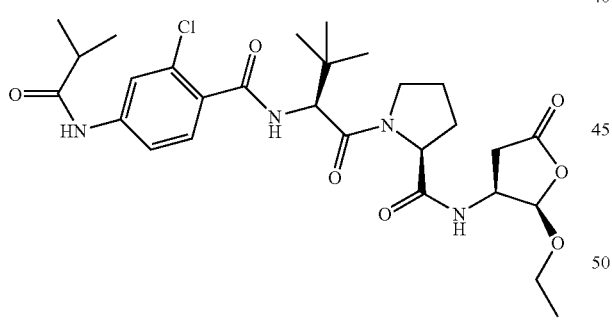
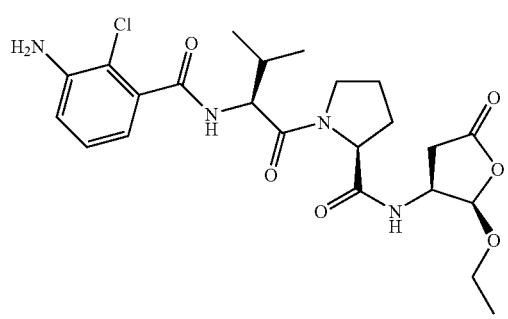
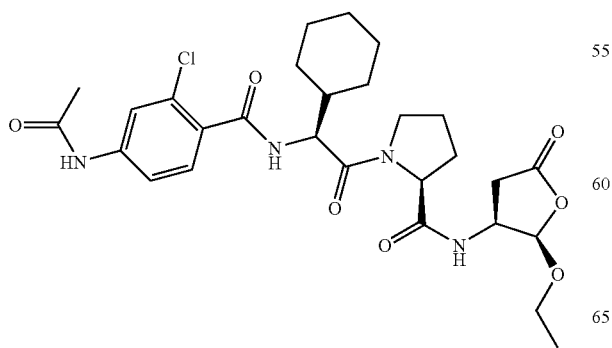
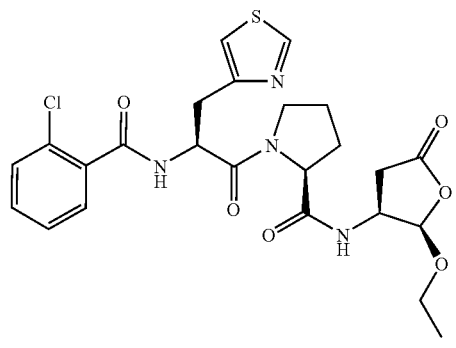

183
-continued
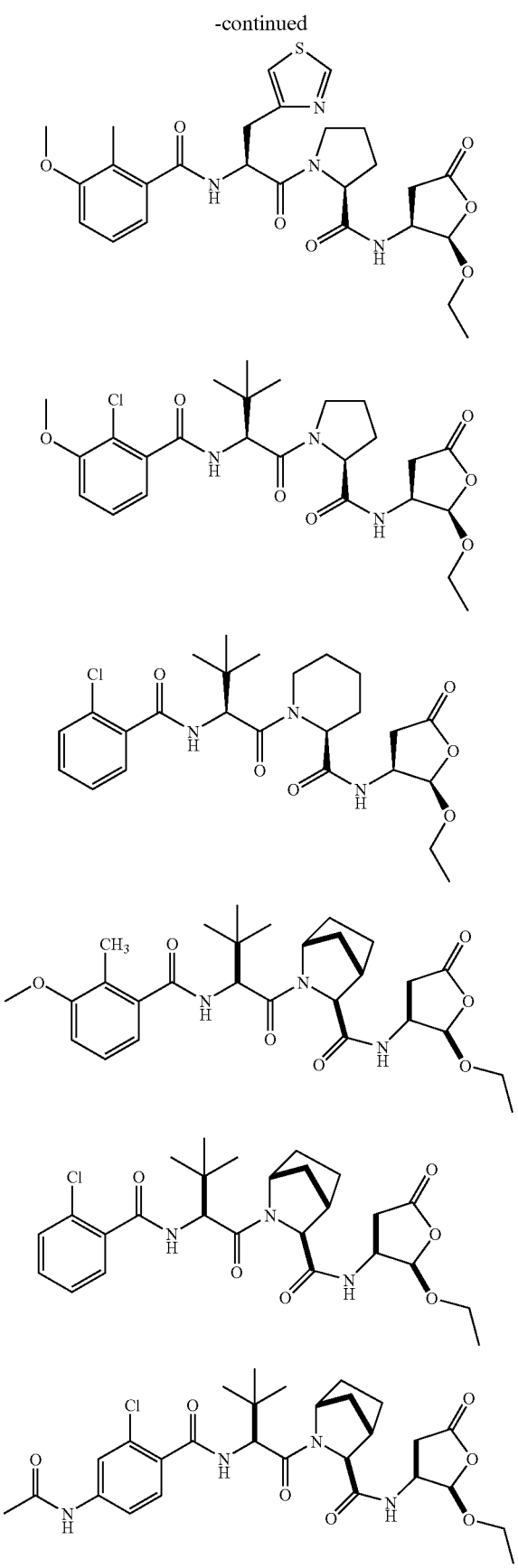
184
-continued
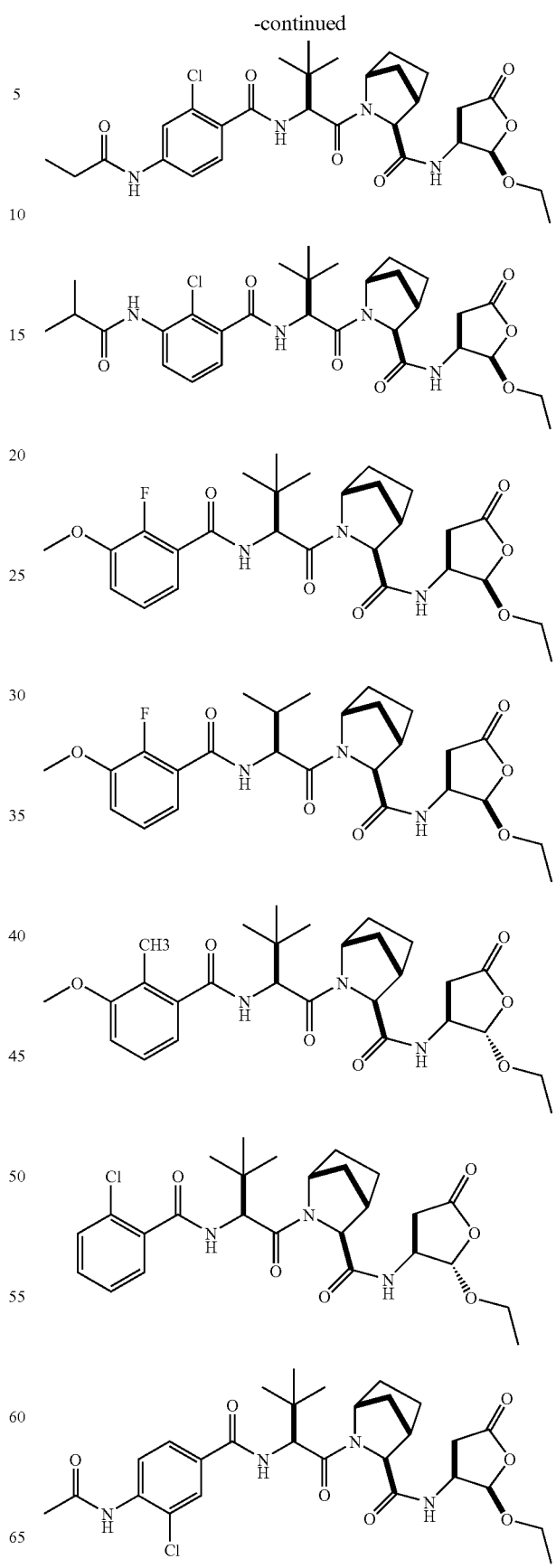

185
-continued
186
-continued
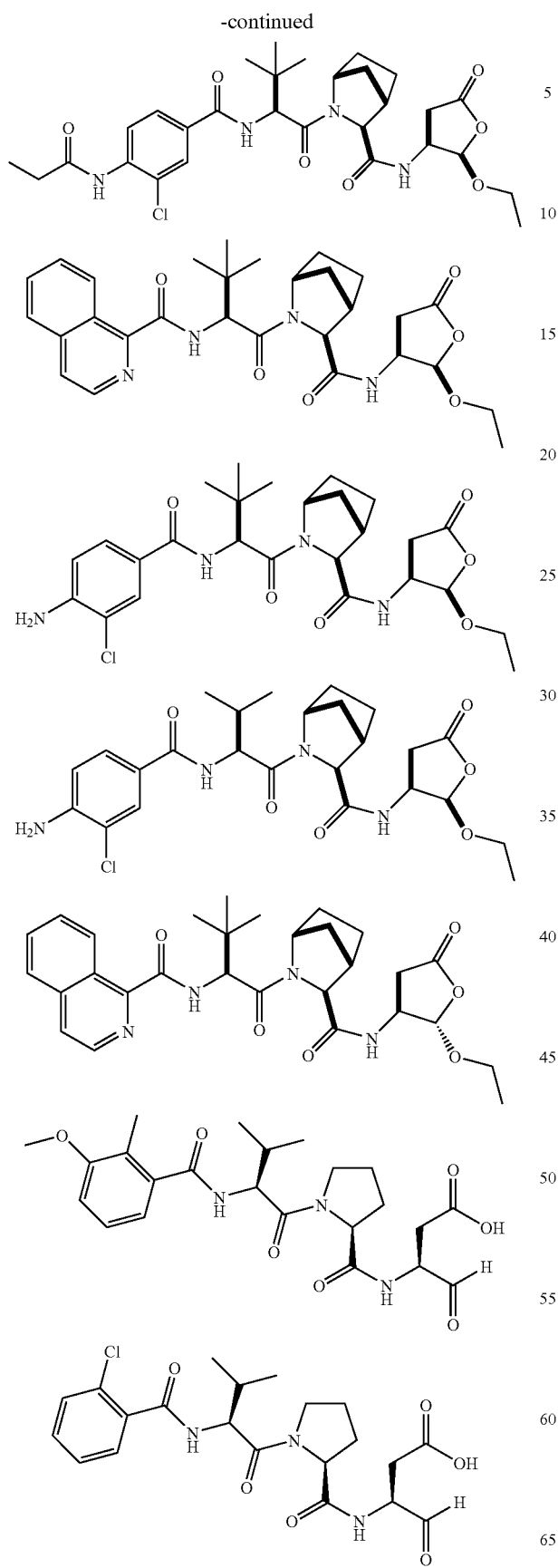
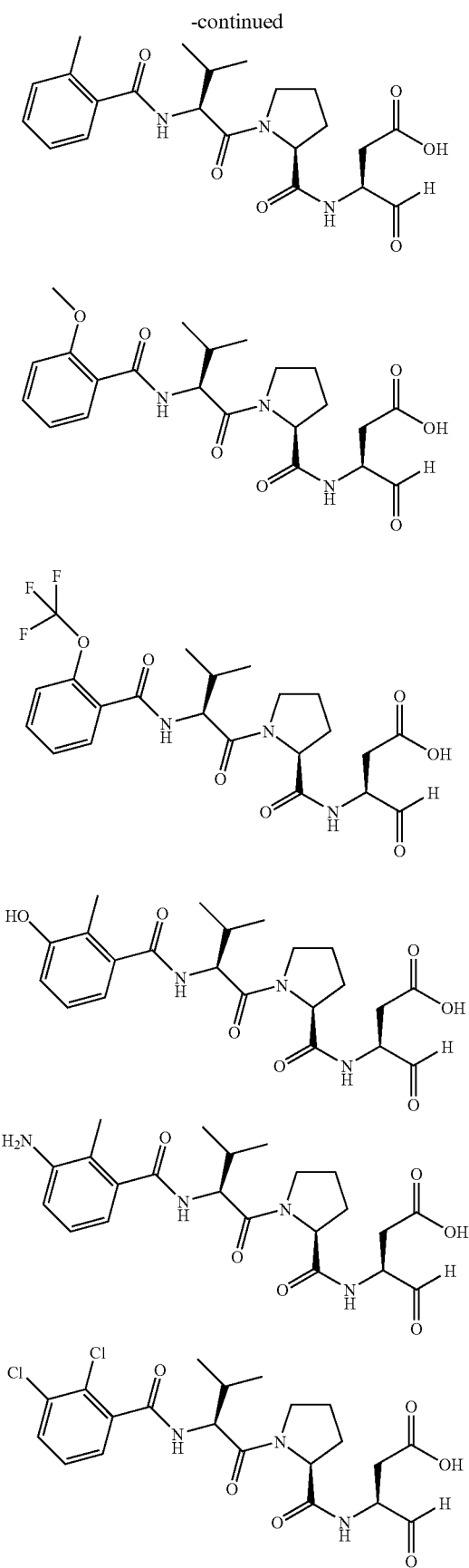

187
-continued
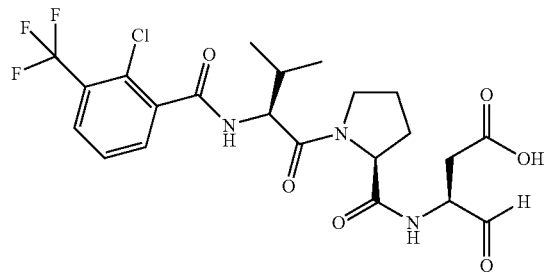
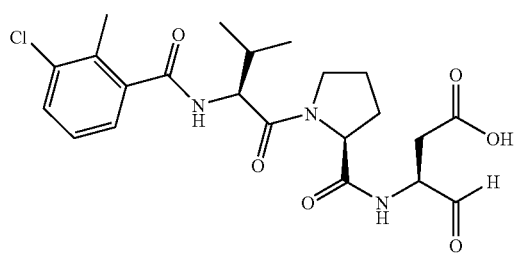
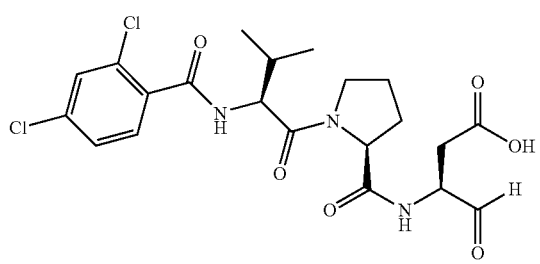
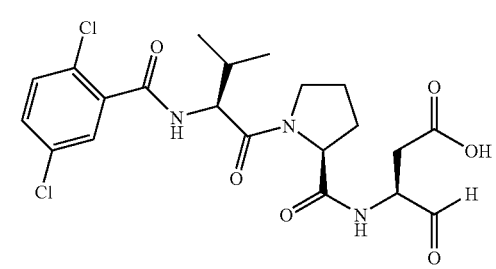
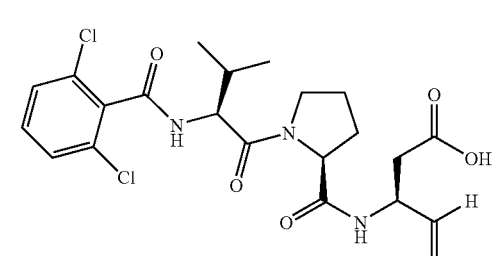
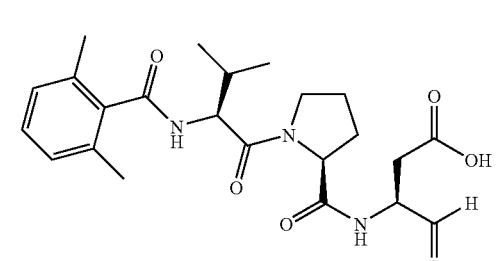
188
-continued
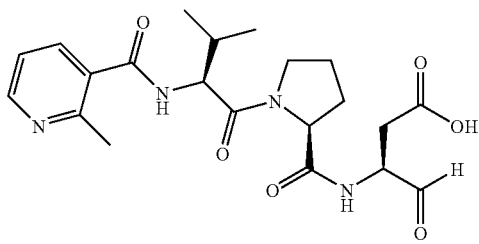
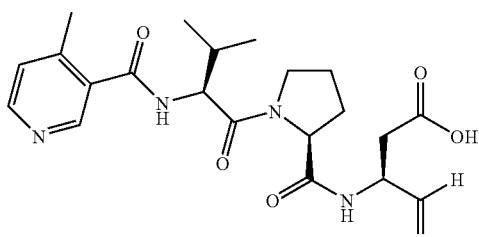
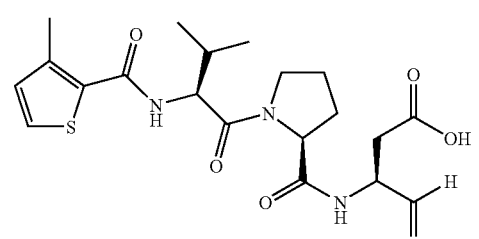
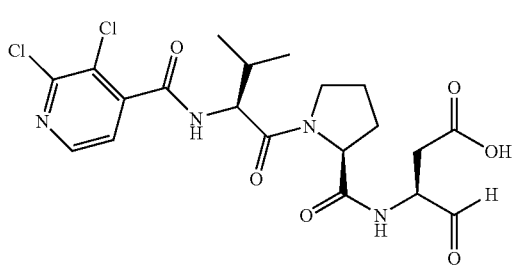
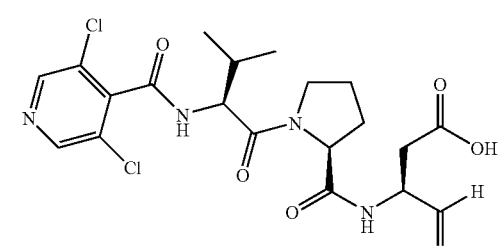
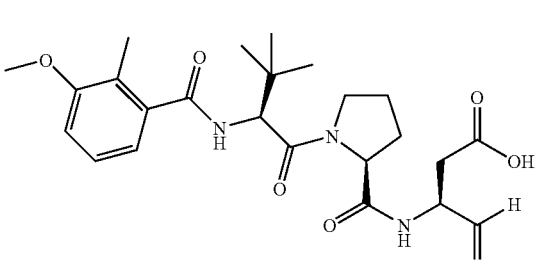

189
-continued
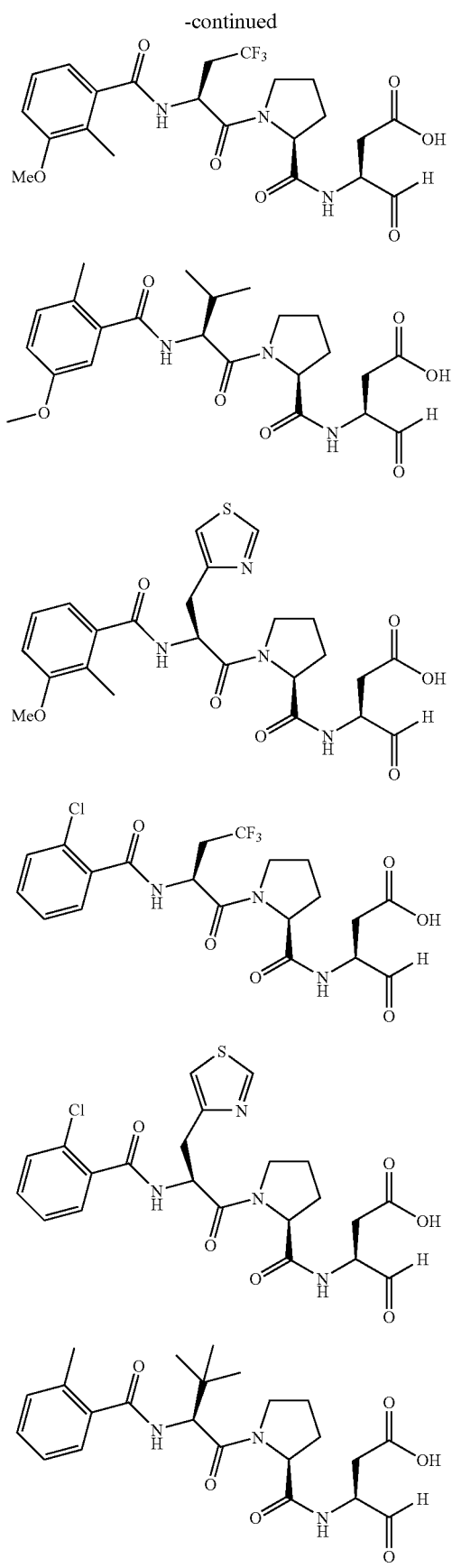
190
-continued
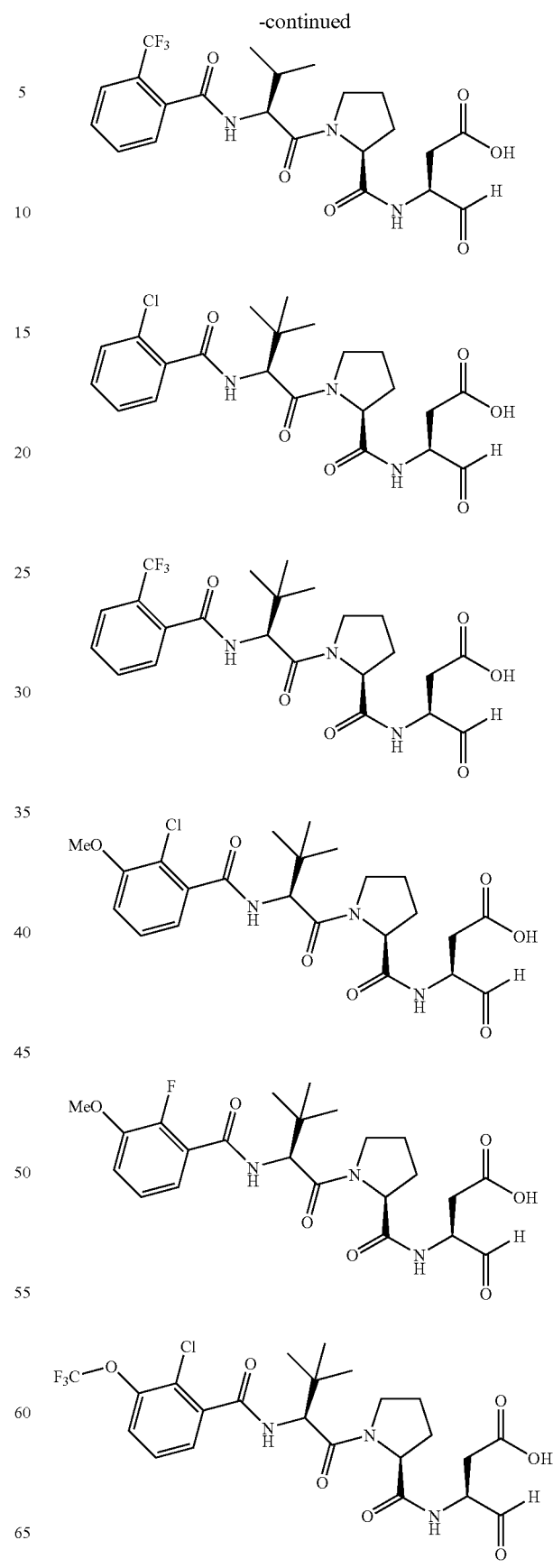

191
-continued
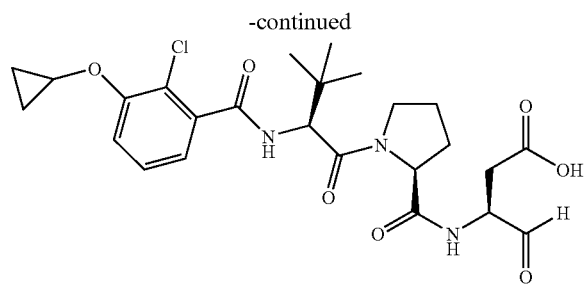
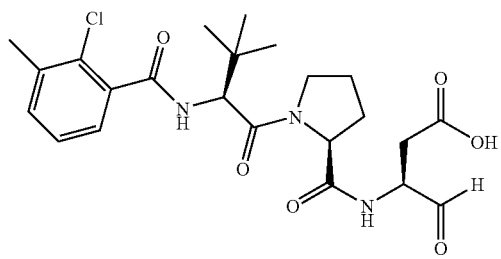
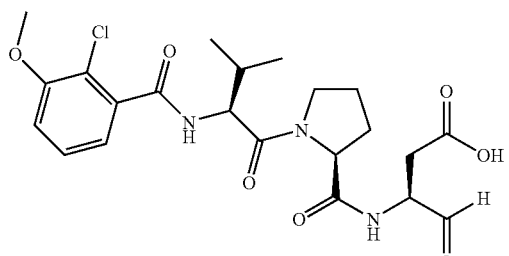
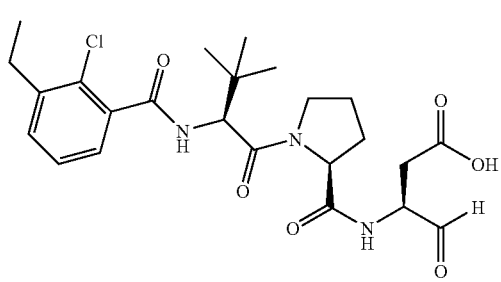
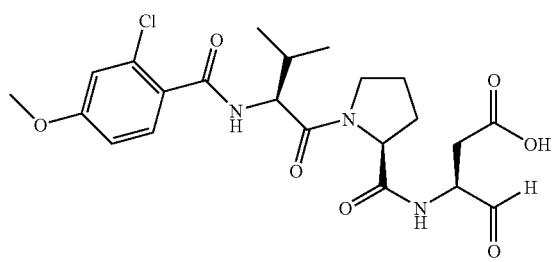
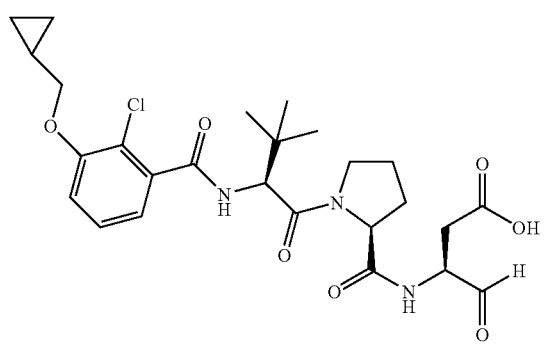
192
-continued
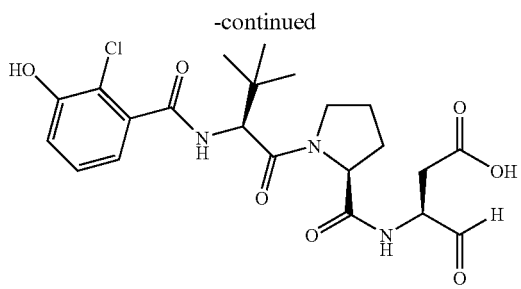
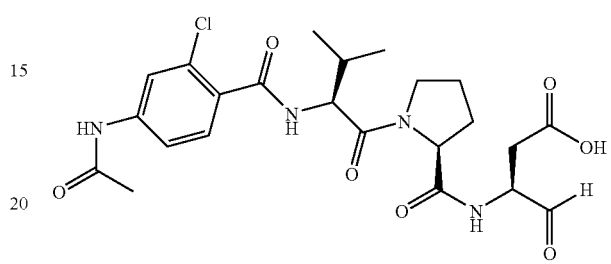
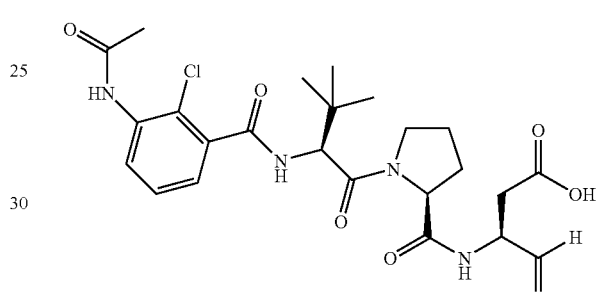
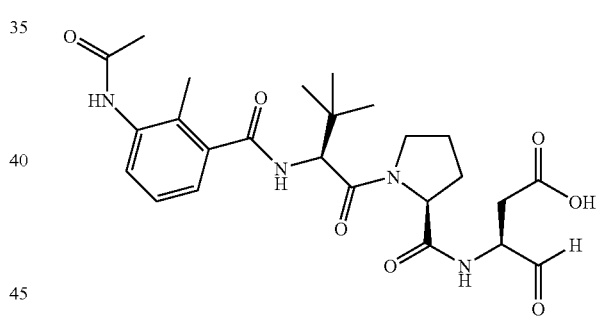
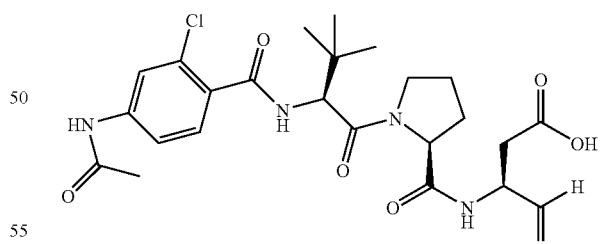
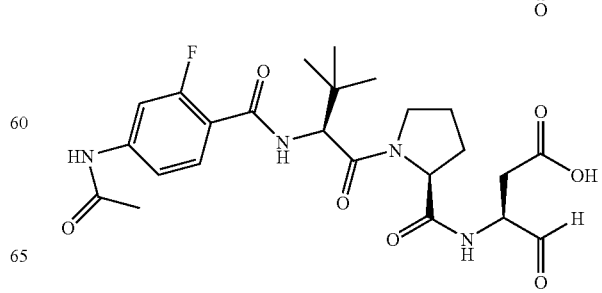

-continued
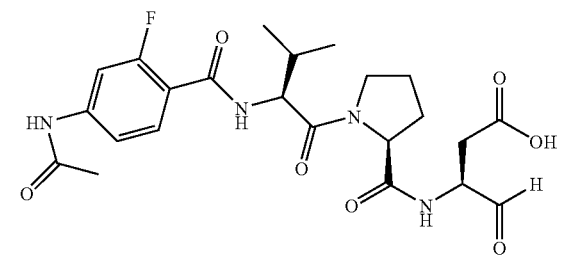
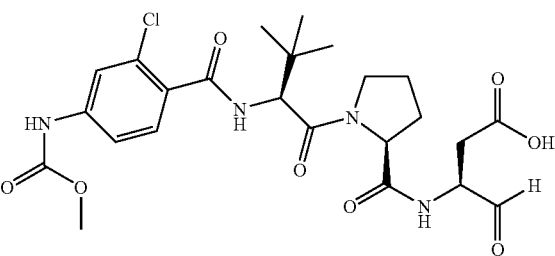
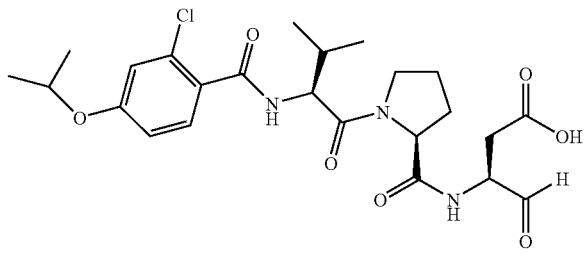
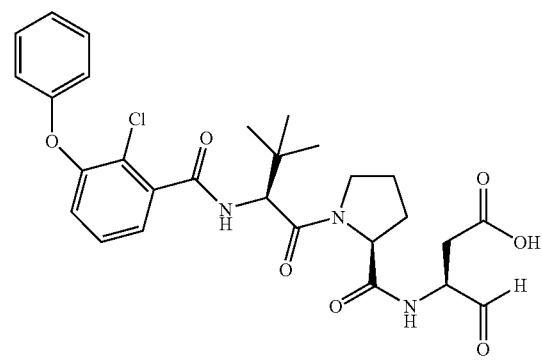
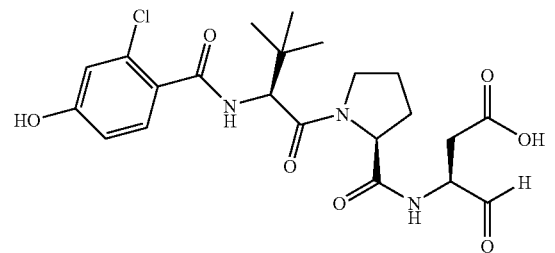
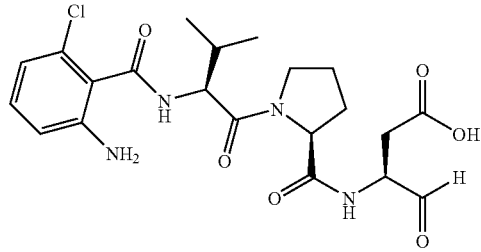
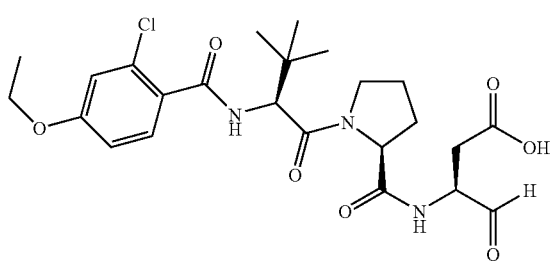
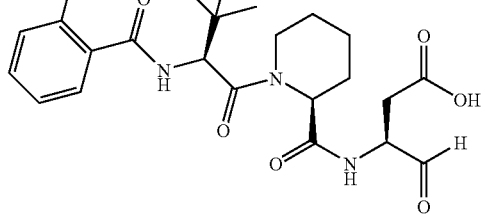
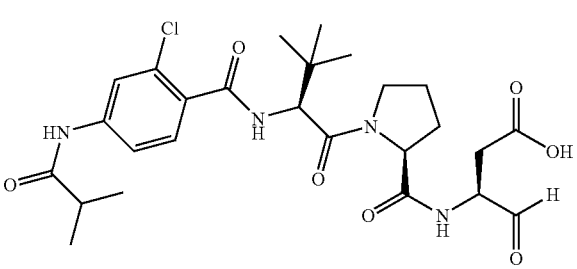
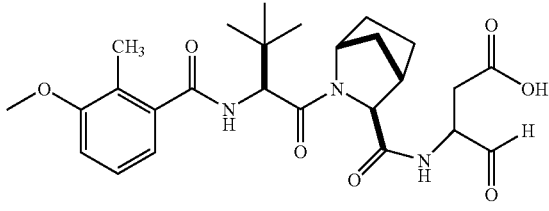
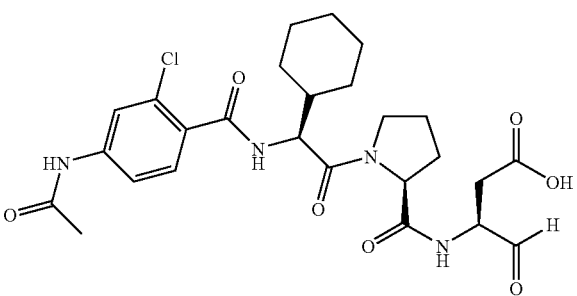
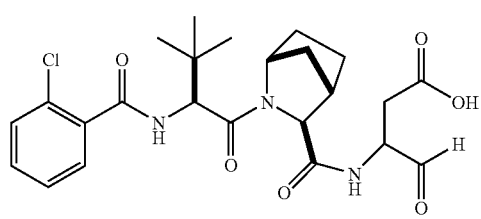

-continued
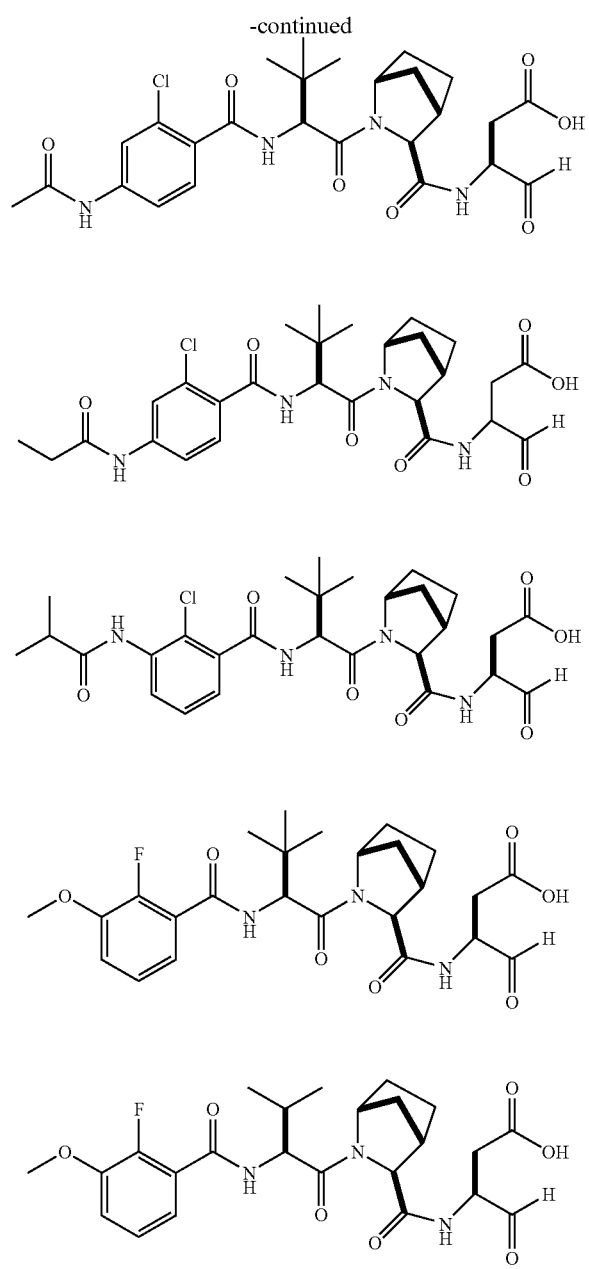
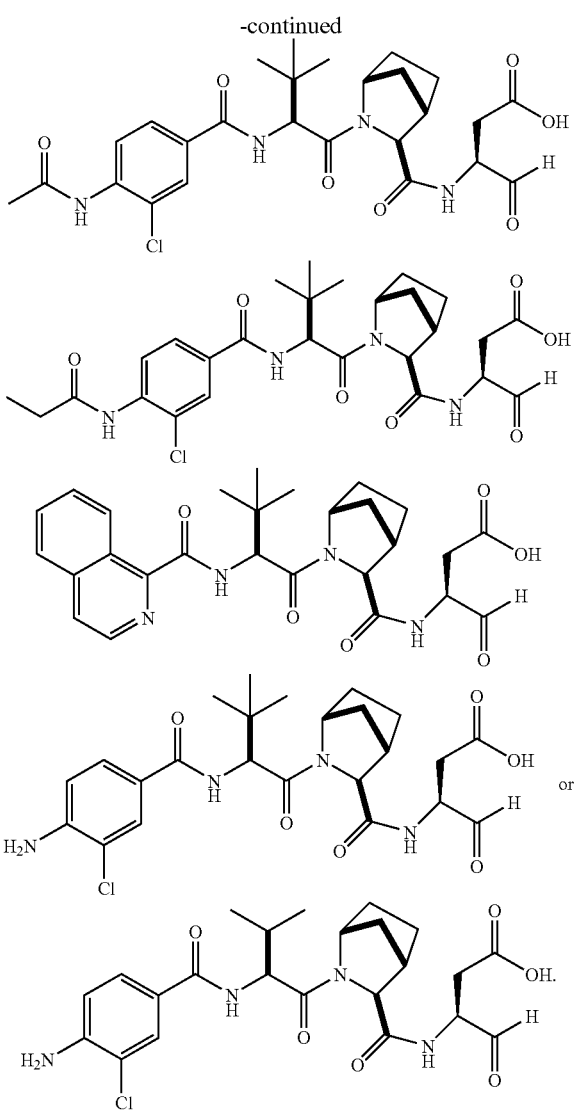
19. A pharmaceutical composition comprising:
a) a compound according to claim 1; and
b) a pharmaceutically acceptable carrier, adjuvant or vehicle.
* * * * *

UNITED STATES PATENT AND TRADEMARK OFFICE
CERTIFICATE OF CORRECTION

PATENT NO. : 7,652,153 B2
APPLICATION NO. : 11/069895
DATED : January 26, 2010
INVENTOR(S) : Jean-Damien Charrier et al.

It is certified that error appears in the above-identified patent and that said Letters Patent is hereby corrected as shown below:

At column 170, line 10, add "," after -- —C(O)CH2C(O)R14--.

At column 170, line 11, replace "—C(S)R14" with "C(S)OR14".

Signed and Sealed this
Sixteenth Day of October, 2012

David J. Kappos
*Director of the United States Patent and Trademark Office*